US012780778B2

(12) United States Patent
Chan et al.

(10) Patent No.: US 12,780,778 B2
(45) **Date of Patent: *Nov. 3, 2026**

(54) CREATINE PRODRUGS, COMPOSITIONS AND METHODS OF USE THEREOF

(71) Applicant: Ultragenyx Pharmaceutical Inc., Novato, CA (US)

(72) Inventors: Yiumo Chan, Novato, CA (US); Emil D. Kakkis, Novato, CA (US); Alexandra Trotier-Faurion, Novato, CA (US); William F. Brubaker, Novato, CA (US); Arjun Natesan, Novato, CA (US); Paul Lee, Novato, CA (US); Sharyl Fyffe-Maricich, Novato, CA (US); David Lapointe, Oakland, CA (US); Mike E. Lizarzaburu, Pacifica, CA (US)

(73) Assignee: Ultragenyx Pharmaceutical Inc., Novato, CA (US)

(*) Notice: Subject to any disclaimer, the term of this patent is extended or adjusted under 35 U.S.C. 154(b) by 528 days.

This patent is subject to a terminal disclaimer.

(21) Appl. No.: 18/352,959

(22) Filed: Jul. 14, 2023

(65) Prior Publication Data

US 2024/0092731 A1 Mar. 21, 2024

Related U.S. Application Data

(60) Continuation of application No. 17/706,283, filed on Mar. 28, 2022, now Pat. No. 11,753,369, which is a division of application No. 16/764,969, filed as application No. PCT/US2018/063580 on Dec. 3, 2018, now Pat. No. 11,332,438.

(60) Provisional application No. 62/593,731, filed on Dec. 1, 2017.

(51) Int. Cl.

| | |
|---|---|
| ***C07C 279/22*** | (2006.01) |
| ***A61K 31/155*** | (2006.01) |
| ***A61K 31/16*** | (2006.01) |
| ***A61K 31/395*** | (2006.01) |
| ***A61K 45/06*** | (2006.01) |
| ***A61P 9/10*** | (2006.01) |
| ***A61P 25/28*** | (2006.01) |
| ***C07B 59/00*** | (2006.01) |
| ***C07D 213/82*** | (2006.01) |
| ***C07D 273/02*** | (2006.01) |
| ***C07D 317/40*** | (2006.01) |
| ***C07D 498/10*** | (2006.01) |

(52) U.S. Cl.

CPC .......... *C07C 279/22* (2013.01); *C07B 59/001* (2013.01); *C07B 59/002* (2013.01); *C07D 213/82* (2013.01); *C07D 273/02* (2013.01); *C07D 498/10* (2013.01); *C07B 2200/05* (2013.01)

(58) Field of Classification Search

None

See application file for complete search history.

(56) References Cited

U.S. PATENT DOCUMENTS

| | | | | |
|---|---|---|---|---|
| 6,008,252 | A | 12/1999 | Beale | |
| 7,319,157 | B1 | 1/2008 | Chaudhuri et al. | |
| 8,350,077 | B2 | 1/2013 | Burov et al. | |
| 8,354,105 | B2 | 1/2013 | Wu et al. | |
| 9,233,099 | B2 | 1/2016 | Clark et al. | |
| 9,617,230 | B2 | 4/2017 | Brubaker | |
| 10,344,007 | B2 | 7/2019 | Brubaker | |
| 11,021,501 | B2 | 6/2021 | Brubaker | |
| 11,332,438 | B2 * | 5/2022 | Chan | C07D 273/02 |
| 11,407,722 | B2 | 8/2022 | Brubaker | |
| 11,753,369 | B2 * | 9/2023 | Chan | C07D 273/02<br>514/355 |
| 2003/0013767 | A1 | 1/2003 | Bessman | |
| 2003/0108596 | A1 | 6/2003 | Sung | |
| 2004/0120983 | A1 | 6/2004 | Connolly | |
| 2006/0004099 | A1 | 1/2006 | Roe | |
| 2007/0105899 | A1 | 5/2007 | Suzuki et al. | |
| 2007/0281909 | A1 | 12/2007 | Zerangue et al. | |
| 2007/0281996 | A1 | 12/2007 | Gao et al. | |
| 2008/0051371 | A1 | 2/2008 | Zerangue et al. | |
| 2008/0103202 | A1 | 5/2008 | Ferguson et al. | |
| 2008/0200705 | A1 | 8/2008 | Chaudhuri et al. | |
| 2011/0201558 | A1 | 8/2011 | Roe et al. | |
| 2011/0269986 | A1 | 11/2011 | Burov et al. | |
| 2012/0065261 | A1 | 3/2012 | Nivaggioli et al. | |
| 2014/0377245 | A9 | 12/2014 | Annunziata et al. | |
| 2015/0238453 | A1 | 8/2015 | Owoc | |
| 2016/0289175 | A1 | 10/2016 | Jungles et al. | |
| 2017/0273950 | A1 | 9/2017 | Cantrell, Jr. et al. | |
| 2019/0337909 | A1 | 11/2019 | Brubaker | |

FOREIGN PATENT DOCUMENTS

| | | | |
|---|---|---|---|
| AR | 091857 | A1 | 3/2015 |
| EP | 2269980 | A1 | 1/2011 |
| JP | H0718000 | B2 | 3/1995 |

(Continued)

OTHER PUBLICATIONS

Burov, et al., Creatinyl amino acids—new hybrid compounds with neuroprotective activity, Journal of Peptide Science, Sep. 2011, 620-6.

(Continued)

*Primary Examiner* — Sun Jae Yoo

(74) *Attorney, Agent, or Firm* — COOLEY LLP

(57) ABSTRACT

The present disclosure provides creatine prodrug analogs and their compositions useful for the treatment of creatine deficiencies.

18 Claims, 3 Drawing Sheets

(56) References Cited

FOREIGN PATENT DOCUMENTS

| | | | |
|---|---|---|---|
| JP | 2013028562 | A | 2/2013 |
| JP | 2016534201 | A | 11/2016 |
| JP | 2016536372 | A | 11/2016 |
| JP | 2017525748 | A | 9/2017 |
| WO | WO-03097604 | A1 | 11/2003 |
| WO | WO-03101402 | A2 | 12/2003 |
| WO | WO-2005108370 | A1 | 11/2005 |
| WO | WO-2007146086 | A1 | 12/2007 |
| WO | WO-2008101309 | A1 | 8/2008 |
| WO | WO-2008101310 | A1 | 8/2008 |
| WO | WO-2008101313 | A1 | 8/2008 |
| WO | WO-2009143630 | A1 | 12/2009 |
| WO | WO-2010005692 | A2 | 1/2010 |
| WO | WO-2011159634 | A1 | 12/2011 |
| WO | WO-2013043580 | A2 | 3/2013 |
| WO | WO-2014018570 | A1 | 1/2014 |
| WO | WO-2014019855 | A1 | 2/2014 |
| WO | WO-2014097335 | A1 | 6/2014 |
| WO | WO-2015031712 | A1 | 3/2015 |
| WO | WO-2015069699 | A1 | 5/2015 |
| WO | WO-2015097660 | A1 | 7/2015 |
| WO | WO-2016036699 | A1 | 3/2016 |
| WO | WO-2016106284 | A2 | 6/2016 |
| WO | WO-2016110822 | A1 | 7/2016 |
| WO | WO-2016160885 | A1 | 10/2016 |
| WO | WO-2019109067 | A2 | 6/2019 |

OTHER PUBLICATIONS

Extended European Search Report for European Application No. 15874283.3, mailed Sep. 5, 2018, 8 pages.
Extended European Search Report for European Application No. 18883842, mailed Jun. 30, 2021, 11 pages.
Extended European Search Report for European Application No. 20184803.3, mailed Nov. 4, 2020, 10 pages.
Extended European Search Report for European Application No. 20184803.3, mailed Oct. 6, 2021, 7 pages.
Garbati, et al., A new method to synthesize creatine derivatives, Amino Acids, Oct. 2013, pp. 821-833.
Gavezzotti, et al., Are Crystal Structures Predictable? Acc. Chem. Res., Dipartimento di Chimica Fisica ed Elettrochimica, Univesita di Milano, Milano, Italy; May 16, 1994, pp. 309-314.
Hecker, et al. Prodrugs of phosphates and phosphonates, Journal of medicinal chemistry, Apr. 2008, pp. 2328-2345.
International Preliminary Report on Patentability for International Patent Application No. PCT/US2014/064028, mailed May 10, 2016, 7 pages.
International Search Report and Written Opinion for International Application No. PCT/US2014/064028, mailed Jan. 21, 2015, 10 pages.
International Search Report and Written Opinion for International Patent Application No. PCT/US2015/067283, mailed Aug. 19, 2016, 11 pages.
International Search Report and Written Opinion for International Patent Application No. PCT/US2016/024845, mailed Jul. 26, 2016, 9 pages.
International Search Report and Written Opinion issued on Apr. 22, 2019 for International Patent Application No. PCT/US2018/063580, 9 pages.
Meinig, et al. Targeting fatty-acid amide hydrolase with prodrugs for CNS-selective therapy, ACS chemical neuroscience, Nov. 2017, pp. 2468-2476.
Partial Supplementary European Search Report and Opinion for European Application No. 15874283.3, mailed Jun. 4, 2018, 9 pages.
Patani, et al., Bioisosterism: A Rational Approach in Drug Design, Chemical Reviews, Dec. 1996, pp. 3147-3176.
Rautio, et al. Prodrugs: design and clinical Applications, Nature Reviews, Drug Discovery, Mar. 2008, pp. 255-270.
Samain, et al., Structure of Scopafungin, a Potent Nonpolyene Antifungal Antibiotic, Journal of the American Chemical Society, Jul. 1982, pp. 4129-4141.
STN Registry RN 1002719-42-6, entered STN Dec. 26, 2007, 1 page.
STN Registry RN 1002719-94-9, entered STN Feb. 11, 2008, 1 page.
STN Registry RN 1071430-27-7, entered STN Nov. 7, 2008, 1 page.
STN Registry RN 1071430-29-9, entered STN Nov. 7, 2008, 1 page.
STN Registry RN 1075221-05-4, entered STN Nov. 24, 2008, 1 page.
Supplementary European Search Report for European Application No. 14859445.0, mailed May 22, 2017, 9 pages.
Supplementary Partial European Search Report for European Application No. 18883842, mailed Jun. 2, 2021, 12 pages.
Trotier-Faurion, et al., Synthesis and Biological Evaluation of New Creatine Fatty Esters Revealed Dodecyl Creatine Ester as a Promising Drug Candidate for the Treatment of the Creatine Transporter Deficiency, Journal of Medicinal Chemistry, May 2013, pp. 5173-5181.
CoNCERT Pharmaceuticals, Inc., “Precision Deuterium Chemistry Backgrounder,” 2007, 6 pages.
Mallinson, J. et al., “Macrocycles In New Drug Discovery,” Future Medicinal Chemistry, Jul. 2012, vol. 4, No. 11, pp. 1409-1438.
Yu, X. et al., “Macrocyclic drugs and synthetic methodologies toward macrocycles,” Molecules, May 2013, vol. 18, No. 6, pp. 6230-6268.

* cited by examiner

CREATINE PRODRUGS, COMPOSITIONS AND METHODS OF USE THEREOF

CROSS-REFERENCE TO RELATED APPLICATIONS

This application is a continuation of U.S. application Ser. No. 17/706,283, filed Mar. 28, 2022, now U.S. Pat. No. 11,753,369, which is a division of U.S. application Ser. No. 16/764,969, filed May 18, 2020, now U.S. Pat. No. 11,332,438, which is a U.S. National Stage Application under 35 U.S.C. § 371 of International Application No. PCT/US2018/063580, filed Dec. 3, 2018, which claims priority to U.S. Provisional Application No. 62/593,731, filed Dec. 1, 2017, each of which is hereby incorporated by reference in its entireties for all purposes.

FIELD OF THE DISCLOSURE

This disclosure describes membrane permeable creatine prodrugs, or pharmaceutically acceptable salts, solvates, tautomers or stereoisomers thereof, pharmaceutical compositions comprising said creatine prodrugs, and methods of treating diseases, including but not limited to, ischemia, heart failure, neurodegenerative disorders and genetic disorders affecting the creatine kinase system. In some embodiments this disclosure describes treating a genetic disease affecting the creatine kinase system, such as, for example, a creatine transporter disorder or a creatine synthesis disorder comprising administering creatine prodrugs, or a pharmaceutically acceptable salt, solvate, tautomer or stereoisomer thereof or pharmaceutical compositions thereof.

BACKGROUND OF THE DISCLOSURE

Creatine, a naturally occurring amino acid derivative, plays an important part in cellular energy metabolism. Creatine, when phosphorylated by creatine kinase with an adenosine triphosphate (ATP), forms a high-energy phosphocreatine (creatine phosphate), which is a significant cellular energy reserve, and an adenosine diphosphate (ADP). Phosphorylation by creatine kinase is reversible, thus phosphocreatine helps to supply energy to cells in the body by increasing the formation of ATP as needed. This interaction maintains the ATP concentration at a constant level at the moments of its intense consumption. For example, during cellular work, it is of vital importance to replenish ATPs as rapidly as possible. Approximately >95% of the human body's total creatine is located in skeletal muscle and brain.

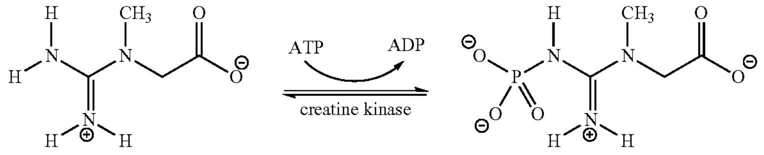

creatine phosphocreatine

The creatine kinase system has a dual role in intracellular energy metabolism-functioning as an energy buffer to restore depleted ATP levels at sites of high ATP hydrolysis, and to transferring energy in the form of phosphocreatine from the mitochondria to other parts of the cell by a process involving intermediate energy carriers, several enzymatic reactions, and diffusion through various intracellular structures.

It is known that dysfunction in energy metabolism can cause many diseases. Particularly, the loss of cellular ATP due to oxygen and glucose deprivation during ischemia is a cause of tissue death. Phosphocreatine represents a reserve of macroergic phosphate in maintaining the membrane potential, activation of metabolites or contractive activity of a cell. It maintains the ATP level along with an increasing of energy consumption in a cell, i.e. restores an ortho-phosphate residue on ADP. Phosphocreatine and creatine are also allosteric regulators of cell processes. The creatine kinase system is a key biochemical mechanism that prevents ATP depletion in mammalian cells. The level of phosphocreatine in a cell is an important predictor of resistance to ischemic insult, and remaining stores of creatine phosphate are correlated with the extent of tissue damage. Thus, creatine can be used for treating cardiac and brain ischemia, neuronal degeneration (e.g., Parkinson's disease, Alzheimer's disease, and Huntington's disease), developmental disorders associated with creatine deficiency, organ transplant viability, and muscle fatigue and other diseases related to creatine deficiency. There are now significant clinical improvements in the treatment of creatine biosynthesis defects but not creatine transport defects since uptake of creatine, especially in brain is highly dependent on the creatine transporter. In the literature, the creatine transporter is believed to play multiple roles: uptake of creatine at the BBB, uptake and transfer of creatine in and between brain cells and uptake and re-uptake of the creatine at the neuronal synapses. Due to challenges in gastro-intestinal absorption and uptake to the brain and into the brain cells, the treatment of the biosynthesis disorders requires high doses of creatine. For the effective use of creatine, compositions produced at the present time require consumption in an amount of up to 20 g per day. Such high doses of creatine may lead to negative consequences for the organism, such as disturbance of nitrogen exchange, gastrointestinal disorders, diarrhea, etc. Some clinical studies based on the use of creatine supplemented by amino acids such as L-arginine and L-glycine showed no improvement of clinical features in long-term follow-up of patients with creatine transporter defect. This supplementation of the amino acids precursors of the synthesis may also lead to accumulation of the intermediate guanidinoacetic acid that may be neurotoxic. This could also contribute to the lack of improvement of the clinical features upon treatment. In the creatine transporter deficiency, creatine and/or phosphocreatine can not access the brain through the BBB and once in the brain, can not be taken up by the brain cells. Thus, successful therapeutic strategies still need to be discovered in order to treat the creatine transporter defect.

Creatine supplementation increases intracellular creatine phosphate levels (Harris et al., Clinical Sci 1992, 83, 367-74). Creatine readily crosses the blood-brain barrier in healthy individuals via the active creatine transporter, SLC6A8 and brain creatine levels can be increased via oral administration (Dechent et al., Am J Physiol 1999, 277, R698-704). Prolonged creatine supplementation can elevate the cellular pools of creatine phosphate and increase resistance to tissue ischemia and muscle fatigue.

Some clinical evidence is available that creatine replacement is efficacious for autosomal recessive disorders of creatine synthesis. Patients with arginine:glycine amidinotransferase (AGAT) deficiency and guanidinoacetate methyltransferase (GAMT) deficiency treated with creatine or ornithine supplementation showed improvement in seizures, intellectual disability, and developmental outcomes (see: Stockler-Ipsiroglu et al. *Mol. Genet. Metab.* 2014, 111, 16-25 and Bianchi, et al. 2007, both herein incorporated in their entirety for all purposes).

Thus, although administration of creatine may have some therapeutic usefulness, a modified creatine molecule that is more stable and is more permeable to barrier tissues and cellular membranes independent of creatine transporter would have enhanced therapeutic value, especially for patients with creatine transporter defect.

SUMMARY OF THE DISCLOSURE

Creatine prodrugs of the present disclosure are designed to enter cells by either passive diffusion or active transport independent of creatine transporter, and to release creatine into the cellular cytoplasm. Such prodrugs can also cross important barrier tissues such as the intestinal mucosa, the blood-brain barrier, and the blood-placental barrier. Because of the ability to pass through biological membranes, creatine prodrugs can restore and maintain energy homeostasis in ATP depleted cells via the creatine kinase system, and rapidly restore ATP levels to protect tissues from further ischemic stress. Creatine prodrugs of the present disclosure can also be used to deliver sustained systemic concentrations of creatine.

In one embodiment, a compound of the present disclosure has the structure of Formula (I):

(I)

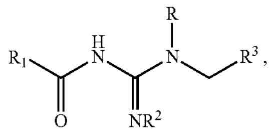

or a pharmaceutically acceptable salt or solvate thereof; wherein:

R is —$CH_3$, —$CH_2D$, —$CHD_2$, or —$CD_3$;

$R^1$ is linear or branched alkyl, linear or branched alkenyl, aryl or heteroaryl, wherein $R^1$ is optionally substituted with $R^4$;

$R^2$ is hydrogen, —C(O)$NHR^5$, —C(O)$R^1$ or —C(O)$OR^5$;

$R^3$ is —C(O)$OR^6$, or -alkyl(OH);

or alternatively, $R^2$ and $R^3$ together is an alkylene group which with the atoms which they are each bonded to, forms a 5 to 6 membered ring wherein the 5 to 6 membered ring is optionally substituted with oxo;

$R^4$ is halogen, —OH, —$OR^5$, oxo, —$NH_2$, —$NHR^5$, —$N(R^5)_2$, —$NO_2$, —$CF_3$, —$C_1$-$C_6$ alkyl, or —$C_1$-$C_6$ haloalkyl;

$R^5$ is linear or branched alkyl; and $R^6$ is H, linear or branched alkyl,

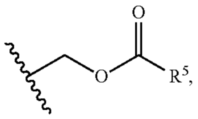
or
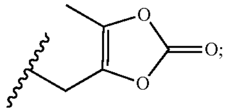

or alternatively, $R^6$ and $R^1$ together is an alkylene group or an alkenylene group which with the atoms which they are each bonded to, forms a 12 to 25 membered ring, wherein 1, 2, 3, or 4 —$CH_2$— units making up the alkylene group or the alkenylene group is optionally replaced with a heteroatom selected from —O—, —S—, or —N—, provided that no adjacent —$CH_2$— is replaced; wherein the alkylene group or the alkenylene group is optionally substituted with one or more $R^4$;

wherein, two $R^4$ on the same or adjacent carbon can form a 3 to 6 membered fused or spiro cycloalkyl ring or a 3 to 6 membered fused or spiro heterocyclic ring.

In one embodiment of the compound of Formula (I), R is —$CH_3$ or —$CD_3$.

In one embodiment of the compound of Formula (I), $R^1$ is —$C_6$-$C_{20}$ alkyl or —$C_6$-$C_{20}$ alkenyl. In some embodiments, $R^1$ is —$C_6$-$C_{18}$ alkyl or —$C_6$-$C_{18}$ alkenyl. In other embodiments, $R^1$ is pyridyl.

In one embodiment of the compound of Formula (I), $R^2$ is hydrogen. In some embodiments, $R^2$ is —C(O)$OR^5$.

In one embodiment of the compound of Formula (I), $R^5$ is linear or branched —$C_1$-$C_6$ alkyl.

In one embodiment of the compound of Formula (I), $R^3$ is —C(O)$OR^6$. In one embodiment of the compound of Formula (I), $R^6$ is H or linear or branched $C_1$-$C_8$ alkyl.

In one embodiment of the compound of Formula (I), $R^6$ and $R^1$ together is an alkylene group or an alkenylene group which with the atoms which they are each bonded to, forms a 12 to 25 membered ring, wherein 1, 2, 3, or 4 —$CH_2$— units making up the alkylene group or the alkenylene group is optionally replaced with a heteroatom selected from —O—, —S—, or —N—, provided that no adjacent —$CH_2$— is replaced; wherein the alkylene group or the alkenylene group is optionally substituted with one or more $R^4$. In one embodiment, $R^6$ and $R^1$ together is an unsubstituted alkylene group or an unsubstituted alkenylene group with the atoms which they are each bonded to, forms a 13 to 24 membered ring.

In one embodiment of the compound of Formula (I), the compound is a pharmaceutically acceptable salt selected from the sodium salt, potassium salt, lithium salt, hydrochloric acid salt, formic acid salt, trifluoroacetic acid salt, acetic acid salt or trichloroacetic acid/2 lithium salt.

In one embodiment of the compound of Formula (I), the compound has the structure of Formula (II):

(II)

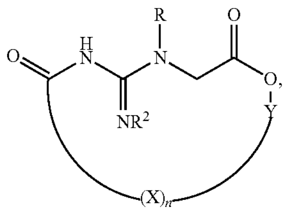

or a pharmaceutically acceptable salt or solvate thereof; wherein:

R is $—CH_3$, $—CH_2D$, $—CHD_2$, or $—CD_3$;

$R^2$ is hydrogen, $—C(O)NHR^5$, $—C(O)R^5$ or $—C(O)OR^5$;

$R^1$ is linear or branched alkyl, or linear or branched alkenyl, wherein $R^1$ is optionally substituted with $R^4$;

$R^4$ is halogen, —OH, $—OR^5$, oxo, $—NH_2$, $—NHR^5$, $—N(R^5)_2$, $—NO_2$, $—CF_3$, $—C_1$-$C_6$ alkyl, or $—C_1$-$C_6$ haloalkyl;

X at each occurrence is each independently $—C(R^{5a})_2—C(R^{5a})_2—$, $—CH(R^{5a})—CH(R^{5a})—$, $—C(R^{5a})═C(R^{5a})—$, $—O—C(R^{5a})_2—$, $—O—CH(R^{5a})—$, $—C(R^{5a})_2—O—$, or $—CH(R^{5a})—O—$;

Y is $—C(R^{5a})_2—$, $—CH(R^{5a})—$, $—C(R^{5a})_2—C(R^{5a})_2—$, $—CH(R^{5a})—CH(R^{5a})—$, $—C(R^{5a})═C(R^{5a})—$, $—C(R^{5a})_2—O—$, or $—CH(R^{5a})—O—$;

n is 2, 3, 4, 5, 6, 7, or 8, wherein when n is 2, Y is $—C(R^{5a})_2—C(R^{5a})_2—$, $—CH(R^{5a})—CH(R^{5a})—$, $—C(R^{5a})═C(R^{5a})—$, $—C(R^{5a})_2—O—$, or $—CH(R^{5a})—O—$;

$R^5$ is H or linear or branched alkyl; and $R^{5a}$ is H, halogen, —OH, $—OR^5$, $—NH_2$, $—NHR^5$, $—N(R^5)_2$, $—NO_2$, $—CF_3$, $—C_1$-$C_6$ alkyl, or $—C_1$-$C_6$ haloalkyl;

wherein, two $R^{5a}$ on the same or adjacent carbon can form a 3 to 6 membered fused or spiro cycloalkyl ring or a 3 to 6 membered fused or spiro heterocyclic ring.

In one embodiment of the compound of Formula (II), at least one of X is $—C(R^{5a})_2—C(R^{5a})_2—$, $—CH(R^{5a})—CH(R^{5a})—$, or $—C(R^{5a})═C(R^{5a})—$, wherein $R^{5a}$ is H or $—C_1$-$C_6$ alkyl; and wherein, two $R^{5a}$ on the same or adjacent carbon can form a 3 to 6 membered fused or spiro cycloalkyl ring or a 3 to 6 membered fused or spiro heterocyclic ring. In one embodiment, X is $—CH_2CH_2—$, $—CH═CH—$, $—O—CH_2—$, or $—CH_2—O—$.

In one embodiment of the compound of Formula (II), Y is $—C(R^{5a})_2—$, $—CH(R^{5a})—$, $C(R^{5a})_2—C(R^{5a})_2—$, $—CH(R^{5a})—CH(R^{5a})—$, or $—C(R^{5a})═C(R^{5a})—$, wherein $R^{5a}$ is H or $—C_1$-$C_6$ alkyl; and wherein, two $R^{5a}$ on the same or adjacent carbon can form a 3 to 6 membered fused or spiro cycloalkyl ring or a 3 to 6 membered fused or spiro heterocyclic ring. In one embodiment, Y is $—C(R^{5a})_2—$, $—CH(R^{5a})—$; $—C(R^{5a})_2—C(R^{5a})_2—$, $—CH(R^{5a})—CH(R^{5a})—$, $—CH_2—$, $—CH_2CH_2—$, $—CH═CH—$,

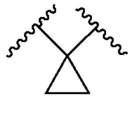, 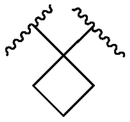, 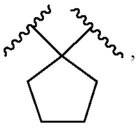, 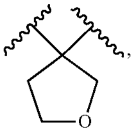, 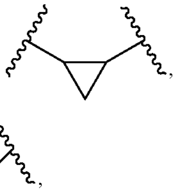, 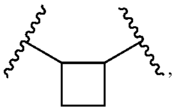, or 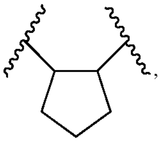, wherein, $R^{5a}$ is linear or branched $—C_1$-$C_6$ alkyl.

In one embodiment of the compound of Formula (II), R is $—CH_3$ or $—CD_3$.

In one embodiment of the compound of Formula (II), $R^2$ is hydrogen.

In one embodiment of the compound of Formula (II), the compound is a pharmaceutically acceptable salt selected from the sodium salt, potassium salt, lithium salt, hydrochloric acid salt, formic acid salt, trifluoroacetic acid salt, acetic acid salt or trichloroacetic acid/2 lithium salt.

In one embodiment of the compound of Formula (I), the compound has the structure of Formula (I-A):

(I-A)

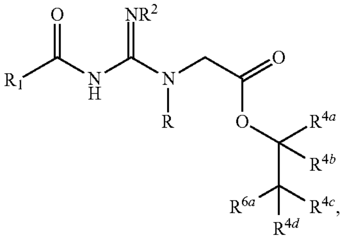, or a pharmaceutically acceptable salt or solvate thereof; wherein:

R is $—CH_3$, $—CH_2D$, $—CHD_2$, or $—CD_3$;

$R^2$ is hydrogen, $—C(O)NHR^5$, $—C(O)R^5$ or $—C(O)OR^5$;

$R^3$ is $—C(O)OR^6$, or -alkyl(OH);

or alternatively, $R^2$ and $R^3$ together is an alkylene group which with the atoms which they are each bonded to, forms a 5 to 6 membered ring wherein the 5 to 6 membered ring is optionally substituted with oxo;

$R^4$ is halogen, —OH, $—OR^3$, oxo, $—NH_2$, $—NHR^5$, $—N(R^5)_2$, $—NO_2$, $—CF_3$, $—C_1$-$C_6$ alkyl, or $—C_1$-$C_6$ haloalkyl;

$R^{4a}$, $R^{4b}$, $R^{4c}$, and $R^{4d}$, each independently, is H, halogen, —OH, $—OR^5$, oxo, $—NH_2$, $—NHR^5$, $—N(R)_2$, $—NO_2$, $—CF_3$, $—C_1$-$C_6$ alkyl, or $—C_1$-$C_6$ haloalkyl;

$R^5$ is linear or branched alkyl; and $R^{6a}$ and $R^1$ together is an alkylene group or an alkenylene group which with the atoms which they are each bonded to, forms a 12 to 25 membered ring, wherein 1, 2, 3, or 4 $—CH_2—$ units making up the alkylene group or the alkenylene group is optionally replaced with a heteroatom selected from —O—, —S—, or —N—, provided that no adjacent $—CH_2—$ is replaced; wherein the alkylene group or the alkenylene group is optionally substituted with one or more $R^4$;

wherein, $R^{4a}$ and $R^{4b}$ or $R^{4c}$ and $R^{4d}$ together can form a 3 to 6 membered spiro cycloalkyl ring or a 3 to 6 membered spiro heterocyclic ring; or wherein $R^{4b}$ and $R^{4c}$ together can form a 3 to 6 membered fused cycloalkyl ring or a 3 to 6 membered fused heterocyclic ring.

In one embodiment of the compound of Formula (I-A), $R^{4a}$ is $—C_1$-$C_6$ alkyl. In one embodiment of the compound of Formula (I-A), $R^{4b}$ is $—C_1$-$C_6$ alkyl. In one embodiment of the compound of Formula (I-A), $R^{4c}$ is $—C_1$-$C_6$ alkyl. In one embodiment of the compound of Formula (I-A), $R^{4b}$, $R^{4c}$, and $R^{4d}$ is H. In one embodiment of the compound of Formula (I-A), $R^{4b}$ and $R^{4d}$ is H.

In one embodiment of the compound of Formula (I-A), $R^{4a}$ and $R^{4b}$ together form a 3 to 6 membered spiro cycloalkyl ring or a 3 to 6 membered spiro heterocyclic ring. In some embodiments, $R^{4a}$ and $R^{4b}$ together form

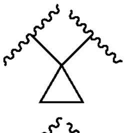, 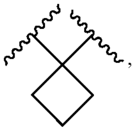, 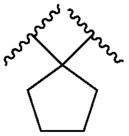, or

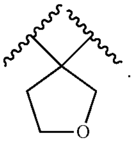.

In one embodiment of the compound of Formula (I-A), $R^{4b}$ and $R^{4c}$ together form a 3 to 6 membered fused cycloalkyl ring or a 3 to 6 membered fused heterocyclic ring. In some embodiments, $R^{4b}$ and $R^{4c}$ together form

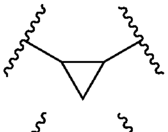, 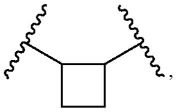, or

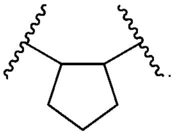.

In one embodiment of the compound of Formula (I-A), R is $—CH_3$ or $—CD_3$.

In one embodiment of the compound of Formula (I-A), $R^2$ is hydrogen.

In one embodiment of the compound of Formula (I-A), the compound is a pharmaceutically acceptable salt selected from the sodium salt, potassium salt, lithium salt, hydrochloric acid salt, formic acid salt, trifluoroacetic acid salt, acetic acid salt or trichloroacetic acid/2 lithium salt.

In one embodiment of the compound of Formula (I), the compound has the structure of Formula (III):

(III-A)

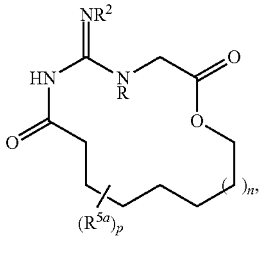

or a pharmaceutically acceptable salt or solvate thereof; wherein:

R is $CH_3$, $CH_2D$, $CHD_2$, or $CD_3$;

$R^1$ is linear or branched alkyl, or linear or branched alkenyl;

$R^2$ is hydrogen, $—C(O)NHR^5$, $—C(O)R^1$ or $—C(O)OR^5$;

$R^5$ is H or linear or branched alkyl;

$R^{5a}$ is halogen, —OH, $—OR^5$, oxo, $—NH_2$, $—NHR^5$, $—N(R^5)_2$, $—NO_2$, $—CF_3$, $—C_1\text{-}C_6$ alkyl, or $—C_1\text{-}C_6$ haloalkyl, wherein, two $R^{5a}$ on the same or adjacent carbon can form a 3 to 6 membered fused or spiro cycloalkyl ring or a 3 to 6 membered fused or spiral heterocyclic ring;

n is 0, 1, 2, 3, 4, 5, 6, 7, 8, 9, 10, or 11; and p is 0, 1, 2, 3, 4, 5, 6, 7, or 8.

In one embodiment of the compound of Formula (III-A), R is $—CH_3$ or $—CD_3$.

In one embodiment of the compound of Formula (III-A), $R^2$ is H.

In one embodiment of the compound of Formula (III-A), n is 0, 1, 2, 3, 4, 5, 6, or 7.

In one embodiment of the compound of Formula (III-A), p is 0, 1, or 2.

In one embodiment of the compound of Formula (III-A), $R^{5a}$ is $—C_1\text{-}C_6$ alkyl.

In one embodiment of the compound of Formula (I), the compound is selected from Table A, or a pharmaceutically acceptable salt thereof. In one embodiment of the compound of Formula (I), the compound is selected from Table B, or a pharmaceutically acceptable salt thereof. In one embodiment of the compound of Formula (I), the compound is selected from Table C, or a pharmaceutically acceptable salt thereof. In one embodiment of the compound of Formula (I), (I-A), (II), (III), and/or (III-A), the compound is selected from Table D, or a pharmaceutically acceptable salt thereof. In one embodiment of the compound of Formula (I), (I-A), (II), (III), and/or (III-A), the compound is selected from Table E. In one embodiment of the compound of Formula (I), the compound is selected from Table S1. In one embodiment of the compound of Formula (I), the compound is selected from Table S2.

In one embodiment of the compound of Formula (I), (I-A), (II), (III), and/or (III-A), the compound is selected from.

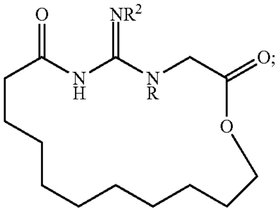

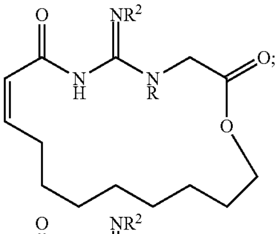

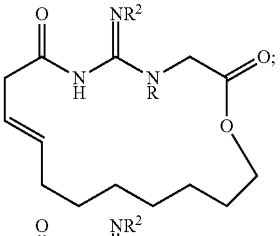

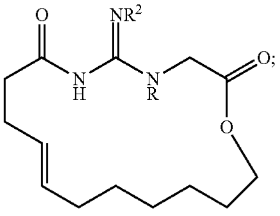

-continued

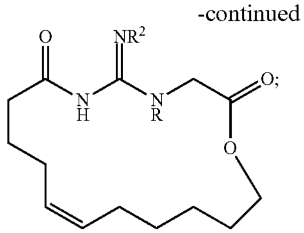

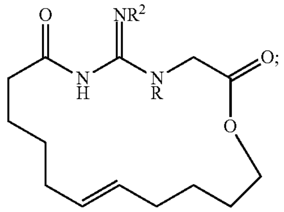

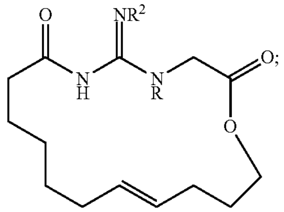

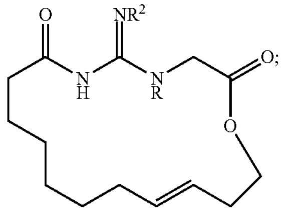

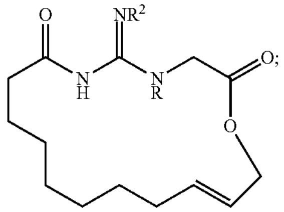

or

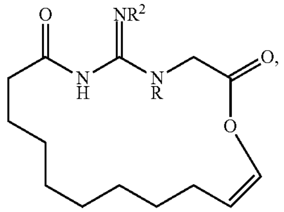

or a pharmaceutically acceptable salt thereof, wherein R is $—CH_3$ or $—CD_3$ and $R^2$ is H.

In one embodiment of the present disclosure, a pharmaceutical composition comprising a creatine analog or a creatine prodrug of the present disclosure is provided. In one embodiment, the creatine analog or the creatine prodrug is a compound of Formula (I), (I-A), (II), (III), and/or (III-A), or a pharmaceutically acceptable salt or solvate thereof, and a pharmaceutically acceptable carrier.

In one embodiment of the present disclosure, a method of delivering creatine or deuterated creatine to a patient in need thereof is provided. In the method disclosed herein, a therapeutically effective amount of a compound of Formula (I), (I-A), (II), (III), and/or (III-A), or a pharmaceutically acceptable salt or solvate thereof is administered to a patient in need thereof.

In one embodiment of the present disclosure, a method of treating creatine deficiency in a patient in need thereof is provided. In the method disclosed herein, a therapeutically effective amount of a compound of Formula (I), (I-A), (II), (III), and/or (III-A), or a pharmaceutically acceptable salt or solvate thereof is administered to a patient in need thereof.

In one embodiment, the creatine deficiency comprises a disease or condition associated with creatine transporter dysfunction. In another embodiment, the creatine deficiency comprises a disease or condition associated with creatine synthesis disorder.

In one embodiment of the present disclosure, a method of treating a disease in a patient in need thereof is provided. In the method disclosed herein, a therapeutically effective amount of a compound of Formula (I), (I-A), (II), (III), and/or (III-A), or a pharmaceutically acceptable salt or solvate thereof is administered to a patient in need thereof, wherein the disease is ischemia, oxidative stress, a neuro-degenerative disease, ischemic reperfusion injury, a cardio-vascular disease, a genetic disease affecting the creatine kinase system, multiple sclerosis, a psychotic disorder or muscle fatigue. In one embodiment, the genetic disease affecting the creatine kinase system is a creatine transporter disorder or a creatine synthesis disorder.

In one embodiment of the present disclosure, a method of enhancing muscle strength in a patient comprising administering to a patient in need of such enhancement a therapeutically effective amount of a compound of Formula (I), (I-A), (II), (III), and/or (III-A), or a pharmaceutically acceptable salt or solvate thereof.

DETAILED DESCRIPTIONS OF THE DISCLOSURE

Definitions

Figure 1:
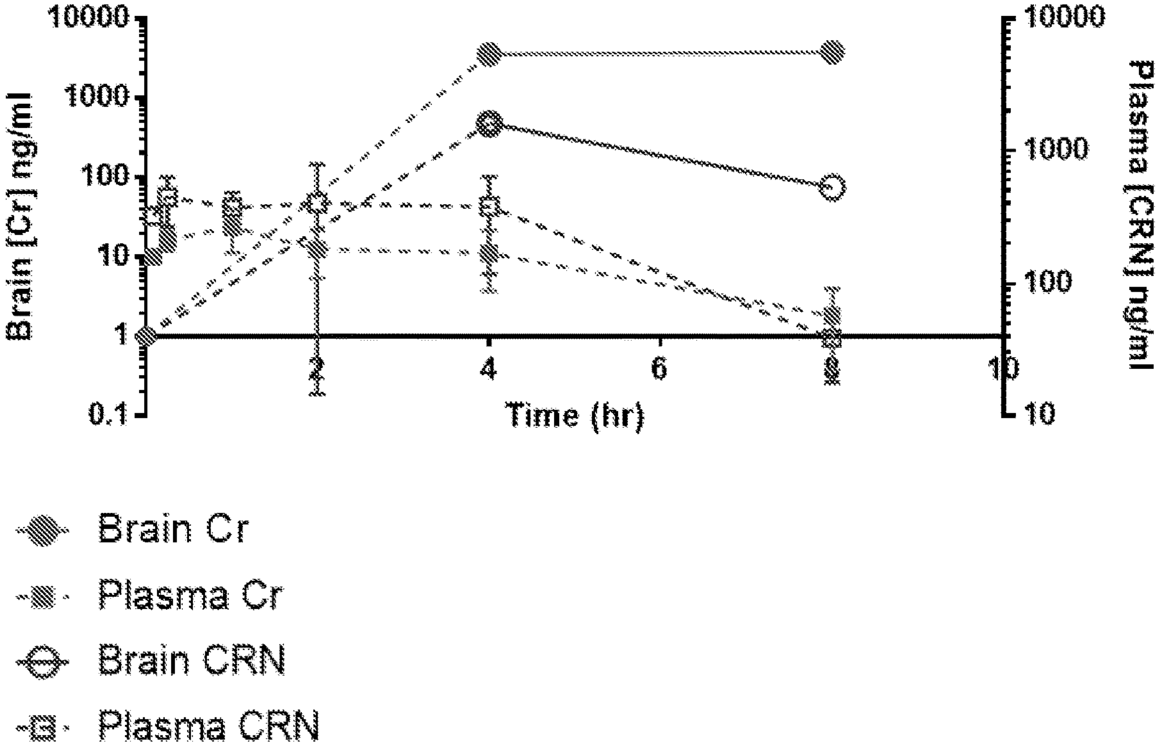
FIG. 1 is a graph of the data from a single-dose study comparing d3-creatine and d3-creatinine levels in the plasma and brain of CrT KO mice treated with compound 15 and measured over 8 h. Cr=d3-creatine; CRN=d3-creatinine.

The terms "a" and "an" do not denote a limitation of quantity, but rather denote the presence of at least one of the referenced item. The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The term "about" and/or "approximately" can be used in conjunction with numerical values and/or ranges. The term "about" is understood to mean those values near to a recited value. For example, "about 40 [units]" can mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" can be used interchangeably.

The term "present compound(s)" or "compound(s) of the present disclosure" refers to compounds encompassed by structural formulae disclosed herein and includes any subgenus and specific compounds within these formulae whose structure is disclosed herein. Compounds may be identified either by their chemical structure and/or chemical name. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the disclosure include, but are not limited to, $^{2}H$, $^{3}H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

Compounds of the disclosure may also exist in several tautomeric forms, and the depiction herein of one tautomer is for convenience only, and is also understood to encompass other tautomers of the form shown. The term "tautomer" as used herein refers to isomers that change into one another with great ease so that they can exist together in equilibrium. Accordingly, the chemical structures depicted herein encompass all possible tautomeric forms of the illustrated compounds.

A dash ("-") that is not between two letters or symbols is used to indicate a point of attachment for a moiety or substituent. For example, —$CONH_2$ is attached through the carbon atom.

"Alkyl," by itself or as part of another substituent, refers to a saturated branched, straight-chain or cyclic monovalent hydrocarbon radical derived by the removal of one hydrogen atom from a single carbon atom of a parent alkane. The term "alkyl" includes "cycloalkyl" as defined herein below. Typical alkyl groups include, but are not limited to, methyl; ethyl; propyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). $C_1$-$C_6$ alkyl is also known as "lower alkyl".

It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. In some embodiments, an alkylene group comprises from 1 to 20 carbon atoms ($C_1$-$C_2$M alkylene). In other embodiments, an alkylene group comprises from 1 to 10 carbon atoms ($C_1$-$C_{10}$ alkylene). In still other embodiments, an alkylene group comprises from 1 to 6 carbon atoms ($C_1$-$C_6$ alkylene).

"Alkenyl," by itself or as part of another substituent, refers to an unsaturated branched, straight-chain or cyclic monovalent hydrocarbon radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —C(O)$R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. That is, arylalkyl can also be considered as an alkyl substituted by aryl. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkyl, arylalkenyl and/or arylalkynyl is used. In some embodiments, an arylalkyl group is ($C_6$-$C_{30}$) arylalkyl, e.g., the alkyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkyl, alkenyl or alkynyl moiety of the arylalkyl group is ($C_1$-$C_5$) alkyl and the aryl moiety is ($C_6$-$C_{10}$) aryl.

"Carbocyclic," or "Carbocyclyl," by itself or as part of another substituent, refers to a saturated or partially saturated, buy not aromatic, cyclic monovalent hydrocarbon radical, including cycloalkyl, cycloalkenyl, and cycloalkynyl as defined herein. Typical carbocyclyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The carbocyclyl may be further substituted by one or more heteroatoms including, but not limited to, N, P, O, S, and Si, which attach to the carbon atoms of the cycloalkyl via monovalent or multivalent bond.

"Heteroalkyl," by themselves or as part of other substituents, refer to alkyl groups, in which one or more of the carbon atoms, are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl group. Typical heteroatomic groups which can be included in these groups include, but are not limited to, —O—, —S—, —O—O—, —S—S—, —O—S—, —N$R^{201}R^{202}$—, =N—N=, —N=N—, —N=N—N$R^{203}R^{204}$, —P$R^{205}$—, —P(O)$_2$—, —PO$R^{206}$—, —O—P(O)$_2$—, —SO—, —SO$_2$—, —Sn$R^{207}R^{208}$— and the like, where $R^{201}$, $R^{202}$, $R^{203}$, $R^{204}$, $R^{205}$, $R^{206}$, $R^{207}$ and $R^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heterocyclic," or "Heterocyclyl," by itself or as part of another substituent, refers to a carbocyclic radical in which one or more carbon atoms are independently replaced with the same or different heteroatom. The heterocyclyl may be further substituted by one or more heteroatoms including, but not limited to, N, P, O, S, and Si, which attach to the carbon atoms of the heterocyclyl via monovalent or multivalent bond. Typical heteroatoms to replace the carbon atom(s) include, but are not limited to, N, P, O, S, Si, etc. Typical heterocyclyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the heterocyclyl group comprises from 3 to 10 ring atoms (3-10 membered heterocyclyl). In other embodiments, the heterocyclyl group comprise from 5 to 7 ring atoms (5-7 membered heterocyclyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl, and N-methyl-pyrrolidinyl are included within the definition of"heterocyclyl." A heterocyclyl group may be attached to the remainder of the molecule via a ring carbon atom or a ring heteroatom. As used herein, heterocyclyl includes a glucose residue, a nucleoside residue, and an ascorbic acid residue.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkyl, heteroarylalkenyl and/or heteroarylalkynyl is used. In some embodiments, the heteroarylalkyl group is a 6-21 membered heteroarylalkyl, e.g., the alkyl, alkenyl or alkynyl moiety of the heteroarylalkyl is $(C_1-C_6)$ alkyl and the heteroaryl moiety is a 5-15-membered heteroaryl. In other embodiments, the heteroarylalkyl is a 6-13 membered heteroarylalkyl, e.g., the alkyl, alkenyl or alkynyl moiety is $(C_1-C_3)$ alkyl and the heteroaryl moiety is a 5-10 membered heteroaryl.

An "amide" refers to an organic compound that contains the functional group consisting of a carbonyl group linked to a nitrogen atom. For example, an amide group can be represented by the following structural formula:

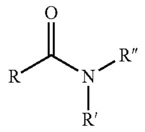

R is an optionally substituted hydrocarbon moiety;

R' and R" are independently hydrogen or optionally substituted hydrocarbon moiety.

A "lactam" group is a cyclic amide. That is, a lactam is an amide with the above structural formula where R and R' or R and R", taken together with the carbon and nitrogen atoms to which they are attached, form an optionally substituted cyclic group.

An "ester" refers to an organic compound derived by reacting/condensing an oxoacid with a hydroxyl compound. For example, an amide group can be represented by the following structural formula:

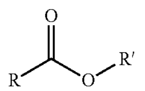

R and R' are independently hydrogen or optionally substituted hydrocarbon moiety.

A "lactone" group is a cyclic ester. That is, a lactone is an ester with the above structural formula where R and R', taken together with the carbon and oxygen atoms to which they are attached, form an optionally substituted cyclic group which can be saturated, unsaturated, or aromatic.

A "urea" or "carbamide" refers to an organic compound having the following structural formula:

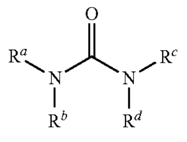

$R^a$, $R^b$, $R^c$, and $R^d$ are independently hydrogen or optionally substituted hydrocarbon moiety.

A cyclic urea is a urea with the above structural formula where any two of $R^a$, $R^b$, $R^c$, and $R^d$, taken together with the carbon and nitrogen atoms to which they are attached, form an optionally substituted cyclic group which can be saturated, unsaturated, or aromatic.

A "carbonate" refers to an organic compound having the following structural formula:

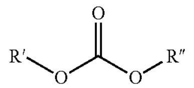

R' and R" are independently hydrogen or optionally substituted hydrocarbon moiety.

A cyclic carbonate is a carbonate with the above structural formula where R' and R", taken together with the carbon and oxygen atoms to which they are attached, form an optionally substituted cyclic group which can be saturated, unsaturated, or aromatic.

A "carbamate" refers to an organic compound having the following structural formula:

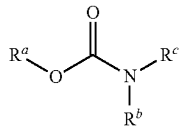

$R^a$, $R^b$, and $R^c$ are independently hydrogen or optionally substituted hydrocarbon moiety.

A cyclic carbamate is a carbamate with the above structural formula where any two of $R^a$ and $R^b$, or $R^a$ and $R^c$, taken together with the carbon and nitrogen/oxygen atoms to which they are attached, form an optionally substituted cyclic group which can be saturated, unsaturated, or aromatic.

"Hydrocarbon" refers to an organic compound consisting of hydrogen and carbon. Hydrocarbons can be straight, branched, or cyclic; and include arenes, alkanes, alkenes, cycloalkanes, alkynes, and etc. The term "substituted hydrocarbon" refers to a hydrocarbon where a carbon or hydrogen atom is replaced by an atom which is not carbon or hydrogen. The substituted hydrocarbons include substituted arenes, substituted alkanes, heteroalkanes, substituted alkenes, heteroalkenes, substituted cycloalkanes, heterocycloalkanes, substituted alkynes, and etc.

"Prodrug" refers to a derivative of a therapeutically active agent that will be converted to the active agent in vivo. That is, a prodrug is a precursor of a drug.

As used herein, "creatine analog" includes "creatine prodrug," which is a prodrug of creatine.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as formic acid, acetic acid, trifluoroacetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion (e.g., lithium, sodium, potassium), an alkaline earth ion (e.g., calcium, magnesium), or an aluminum ion; or coordinates with an organic base such as ethanolamine, diethanolamine, triethanolamine, N-methylglucamine and the like. In some embodiments, salts include $Na_2PO_4H$ salt.

"Solvate" means a compound formed by solvation (the combination of solvent molecules with molecules or ions of the solute), or an aggregate that consists of a solute ion or molecule, i.e., a compound of the present disclosure, with one or more solvent molecules. When water is the solvent, the corresponding solvate is "hydrate".

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"N-oxide", also known as amine oxide or amine-N-oxide, means a compound that derives from a compound of the present disclosure via oxidation of an amine group of the compound of the present disclosure. An N-oxide typically contains the functional group $R_3N^+—O^-$ (sometimes written as $R_3N═O$ or $R_3N\rightarrow O$).

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halogen groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, arylalkyl or heteroarylalkyl groups, arylalkoxy or heteroarylalkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$C_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof. In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art.

The term "optionally substituted" denotes the presence or absence of the substituent group. For example, optionally substituted alkyl includes both unsubstituted alkyl and substituted alkyl. The substituents used to substitute a specified group can be further substituted, typically with one or more of the same or different groups selected from the various groups specified above.

Substituent groups useful for substituting saturated carbon atoms in the specified group or radical include, but are not limited to —$R^a$, halo, —O—, ═O, —$OR^b$, —$SR^b$, —S; ═S, —$NR^cR^c$, ═$NR^b$, ═N—$OR^b$, trihalomethyl, —$CF_3$, —CN, —OCN, —SCN, —NO, —$NO_2$, ═$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR)(O^-)$, —$P(O)(OR^b)(OR^b)$, —$C(O)R^b$, —$C(S)R^b$, —$C(NR^b)R^b$, —$C(O)O^-$, —$C(O) OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-$C(O)OR^b$, -alkylene-$C(O)NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS (O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C (S)R^b$, —$C(NR^b)R^b$, —$C(O)O^-$, —$C(O)OR^b$, —$C(S)OR^b$, —$C(O)NR^cR^c$, —$C(NR^b)NR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)$ $OR^b$, $—NR^bC(S)OR^b$, $—NR^bC(O)NR^cR^c$, $—NR^bC(NR^b)R^b$ and $—NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, $—R^a$, $—O^-$, $—OR^b$, $—SR^b$, $—S^-$, $—NR^cR^c$, trihalomethyl, $—CF_3$, —CN, —NO, $—NO_2$, $—S(O)_2R^b$, $—S(O)_2O^-$, $—S(O)_2OR^b$, $—OS(O)_2R^b$, $—OS(O)_2O^-$, $—OS(O)_2OR^b$, $—P(O)(O^-)_2$, $—P(O)(OR^b)(O^-)$, $—P(O)(OR^b)(OR^b)$, $—C(O)R^b$, $—C(S)R^b$, $—C(NR^b)R^b$, $—C(O)OR^b$, $—C(S)OR^b$, $—C(O)NR^cR^c$, $—C(NR^b)NR^cR^c$, $—OC(O)R^b$, $—OC(S)R^b$, $—OC(O)OR^b$, $—OC(S)OR^b$, $—NR^bC(O)R^b$, $—NR^bC(S)R^b$, $—NR^bC(O)OR^b$, $—NR^bC(S)OR^b$, $—NR^bC(O)NR^cR^c$, $—NR^bC(NR^b)R^b$ and $—NR^bC(NR^b)NR^cR^c$, where $R^a$, $R^b$ and $R^c$ are as previously defined.

The term "amino acid" refers to an organic compounds that contains an amino group ($NH_2$), a carboxyl group (COOH), and any of various side groups. For example, the twenty two amino acids that are naturally incorporated into polypeptides (a.k.a. natural amino acids or naturally occurring amino acids) have the structural formula $NH_2CHRCOOH$, wherein R is a moiety including hydrogen, optionally substituted hydrocarbon moiety, etc. It is commonly known that certain amino acids have two stereoisomers designated as L and D amino acids. Amino acids as mentioned herein include L isomer, D isomer, or a mixture thereof. Furthermore, any of the L, D, or mixed amino acids may further contain additional stereoisomeric center(s) in their structures. The amino and carboxyl groups may be located at alpha, beta, gamma, delta, or other positions. Amino acids suitable for the present disclosure can be naturally occurring amino acid or non-naturally occurring (e.g., synthetic) amino acid. Examples of the amino acids include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, selenocysteine, pyrrolysine, pyroglutamate and any derivatives thereof.

The term "peptidyl group", as used herein, denotes an organic moiety derived from one or more amino acid(s) by removal of a hydrogen atom from the $NH_2$ and/or OH group of the amino acid(s). When the peptidyl group is derived from a single amino acid, it is a monopeptidyl group. When the peptidyl group is derived from a molecule of multiple amino acids, it is a multipeptidyl group, e.g., dipeptidyl or tripeptidyl. The amino acids in a multipeptidyl group are linked with each other via amide bond(s). The term "dipeptide", as used herein, denotes a molecule containing two amino acids joined by a single amide bond, while the term "tripeptide", as used herein, denotes a molecule containing three amino acids joined by two amide bonds.

"Leaving group" refers to an atom or a group capable of being displaced by a nucleophile and includes halogen, such as chloro, bromo, fluoro, and iodo, alkoxycarbonyl (e.g., acetoxy), aryloxycarbonyl, mesyloxy, tosyloxy, trifluoromethanesulfonyloxy, aryloxy (e.g., 2,4-dinitrophenoxy), methoxy, N,O-dimethylhydroxylamino, and the like.

"Creatine kinase system" includes, but is not limited to the creatine transporter, creatine, creatine kinase, creatine phosphate, and the intracellular energy transport of creatine, creatine kinase, and/or creatine phosphate. The creatine kinase system includes mitochondrial and cytoplasmic creatine kinase systems. Affecting the creatine kinase system refers to the transport, synthesis, metabolism, translocation, and the like, of the compounds and proteins comprising the creatine kinase system.

By "immediate release" or "instant release", it is meant a conventional or non-modified release in which greater than or equal to about 75% of the active agent is released within two hours of administration, specifically within one hour of administration.

By "sustained release", it is meant a dosage form in which the release of the active agent is controlled or modified over a period of time. Sustained can mean, for example, extended-, controlled-, delayed-, timed-, or pulsed-release at a particular time. Alternatively, controlled can mean that the release of the active agent is extended for longer than it would be in an immediate-release dosage form, e.g., at least over several hours.

By "effective amount" or "therapeutically effective amount" it is meant the amount of the present compound that, when administered to a patient for treating a disease, such as one related to Creatine Transporter Deficiency, is sufficient to effect such treatment for the disease. The "effective amount" or "therapeutically effective amount" will vary depending on the active agent, the disease and its severity, and the age, weight, and other conditions of the patient to be treated.

The terms "treating" and "treatment", as used herein, refer to an approach for obtaining beneficial or desired results including clinical results. For purposes of this disclosure, beneficial or desired clinical results include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, increasing production, uptake and retention of Creatine, phosphocreatine (e.g., increasing intracellular production of Creatine) and restoring the levels of creatine/phosphocreatine, intracellular ATP and other proteins in regulating creatine/phosphocreatine levels in body, especially in brain, skeletal muscles and heart, decreasing the dose of one or more other medications required to treat the disease, and/or increasing the quality of life. "Treating" a patient with a compound or composition described herein includes management of an individual to inhibit or cause regression of a disease or condition.

"Prophylaxis" or "prophylactic treatment" "or preventive treatment" refers to prevention of the occurrence of symptoms and/or their underlying cause, for example, prevention of a disease or condition in a patient susceptible to developing a disease or condition (e.g., at a higher risk, as a result of genetic predisposition, environmental factors, predisposing diseases or disorders, or the like). Prophylaxis includes, for example GNE myopathy, arginine:glycine amidinotransferase (AGAT) deficiency, and guanidinoacetate methyltransferase (GAMT) deficiency, in which chronic disease changes in the muscles are irreversible and for which animal model data suggests treatment benefit in prophylaxis.

"Disease" refers to a disease, disorder, condition, symptom or indication.

"Pharmaceutical composition" refers to at least one compound of the disclosure and at least one pharmaceutically acceptable vehicle, with which the at least one compound of the disclosure is administered to a patient, contacted with a tissue or organ or contacted with a cell. "Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, e.g., an alkali metal ion, an alkaline earth ion or an aluminum ion; or coordinates with an organic base such as ethanolamine, diethanolamine, triethanolamine, N-methylglucamine, and the like. In certain embodiments, a pharmaceutically acceptable salt is the hydrochloride salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier or a combination of any of the foregoing with which a compound of the disclosure may be administered to a patient and which does not destroy the pharmacological activity thereof and which is non-toxic when administered in doses sufficient to provide a therapeutically effective amount of the compound.

"Carrier" refers to a diluent, adjuvant, excipient or vehicle with which a compound is administered.

The term "patient" refers to an animal, for example, a mammal and includes, but is not limited to, human, bovine, horse, feline, canine, rodent, or primate. Preferably, the patient is a human.

"AUC" is the area under a curve representing the concentration of a compound or metabolite thereof in a biological fluid in a patient as a function of time following administration of the compound to the patient. In certain embodiments, the compound can be a prodrug and the metabolite can be a drug. Examples of biological fluids include plasma and blood. The AUC may be determined by measuring the concentration of a compound or metabolite thereof in a biological fluid such as the plasma or blood using methods such as liquid chromatography-tandem mass spectrometry (LC-MS/MS), at various time intervals, and calculating the area under the plasma concentration-versus-time curve. Suitable methods for calculating the AUC from a drug concentration-versus-time curve are well known in the art. As relevant to the disclosure, an AUC for a drug or metabolite thereof may be determined by measuring over time the concentration of the drug in the plasma, blood or other biological fluid or tissue of a patient following administration of a corresponding compound of the disclosure to the patient.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"$C_{max}$" is the maximum concentration of a drug in the plasma or blood of a patient following administration of a dose of the drug or prodrug to the patient.

"$T_{max}$" is the time to the maximum (peak) concentration ($C_{max}$) of a drug in the plasma or blood of a patient following administration of a dose of the drug or prodrug to the patient.

Embodiments of the Compounds

Creatine transporter defect (CTD) is an inborn error of creatine metabolism in which creatine is not properly transported to the brain and muscles due to defective creatine transporters. CTD is an X-linked recessive disorder caused by mutations in the SLC6A8 gene. It is estimated that there a 50,000 patients with CTD in the developed world, with females having the mild to severe phenotype. Typical clinical characteristics include CNS deficits such as seizures, progressive intellectual disability, autism, speech/language delays, gross motor delays, and behavioral problems. Non-CNS deficits include muscle hypotonia and hypotrophy.

To address CTD and the plethora of often grave associated conditions, creatine prodrugs of the present disclosure have been designed to cross important barrier tissues such as the intestinal mucosa, the blood-brain barrier, and the blood-placental barrier. Because of the ability to pass through biological membranes, creatine prodrugs can restore and maintain energy homeostasis in ATP depleted cells via the creatine kinase system, and rapidly restore ATP levels to protect tissues from further ischemic stress. Accordingly, without being bound to any theory, the creatine prodrugs of the present disclosure would have a higher free energy or lower affinity for creatine kinase, and will be able to regenerate ATP under more severe conditions of energy depletion. Creatine prodrugs of the present disclosure can also be used to deliver sustained systemic concentrations of creatine. Thus, the prodrugs disclosed herein can be effective in treating CTD and the associated conditions brought about by dysfunction in energy metabolism.

In one aspect, the present disclosure is directed to creatine analogs which are converted, at least in part, to creatine upon administration to a patient. The present disclosure is directed, in some aspects, to deuterated creatine analogs which will release in part, to deuterated creatine upon administration to a patient. The present disclosure encompasses creatine analogs or creatine prodrugs that can be deuterated or non-deuterated. In one embodiment, the deuterated creatine analogs or deuterated creatine prodrugs have comparable in vivo and in vitro activity to that of the corresponding non-deuterated creatine analogs or non-deuterated creatine prodrugs. The deuteration of the creatine analogs or the creatine prodrugs is particularly useful in quantifying and analyzing the analog or the prodrug's in vivo activity and its fate due to the ability of separating their effect from the endogenous non-deuterated creatine and creatinine. Thus, in some embodiments, the deuteration of the compound of the present disclosure is to enhance detection and quantification of the compound's effect and not necessarily to modify and/or enhance efficacy of the compound.

In one embodiment of the present disclosure, creatine analogs comprise a fatty acid amide chain, which can be referred to as fatty acid amide creatine or denoted as FAA-Cr.

In one embodiment, the compounds of the present disclosure are chemically and metabolically stable in circulation. In another embodiment, the compounds of the present disclosure are capable of crossing blood-brain barrier. In some embodiments, the compounds of the present disclosure can enter into neurons, glial cells, astrocytes, and/or oligodendrites in brain and release creatine or deuterated creatine. In one embodiment, the compounds of the present disclosure do not substantially cyclize into creatinine upon administration to a patient in need thereof. In one embodiment, the compound of the present disclosure produces less creatinine in vivo by cyclization when compared to in vitro conditions.

In one embodiment, the compounds of the present disclosure favors the release of creatine in the brain over cyclization to creatinine. In some embodiments, the compounds of the present disclosure releases higher amounts of creatine in the brain when compared to previously known creatine prodrugs, when administered in the same molar equivalence. In some embodiments, the compounds of the present disclosure provides smaller amounts of cyclized creatinine byproduct when administered to a subject in need thereof, compared to previously known creatine prodrugs, when administered in the same molar equivalence. In one embodiment, the compounds of the present disclosure releases more creatine in the brain than the amount of creatinine released in the brain. In one embodiment, the compounds of the present disclosure provides higher creatine concentration in the brain than the concentration of creatinine in the brain. In one embodiment, the compounds of the present disclosure provides higher creatine concentration in the plasma than the concentration of creatinine in the plasma.

Without being bound by any particular theory, it has been discovered that administration of the compounds of the present disclosure favors release of creatine in the brain of a subject undergoing treatment. This desired pathway is highly dominant over the undesirable cyclizing side reaction that leads to the formation of creatinine. As such, the prodrug compounds described herein are believed to be effective in the treatment of CTD.

In one embodiment, a compound of the present disclosure has the structure of Formula (I):

(I)

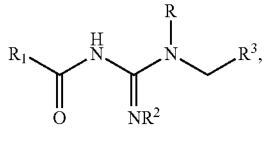

or a pharmaceutically acceptable salt or solvate thereof; wherein:

R is —$CH_3$, —$CH_2D$, —$CHD_2$, or —$CD_3$;

$R^1$ is linear or branched alkyl, linear or branched alkenyl, aryl or heteroaryl, wherein $R^1$ is optionally substituted with $R^4$;

$R^2$ is hydrogen, —C(O)NHR$^5$, —C(O)R$^1$ or —C(O)OR$^5$;

$R^3$ is —C(O)OR$^6$, or -alkyl(OH);

or alternatively, $R^2$ and $R^3$ together is an alkylene group which with the atoms which they are each bonded to, forms a 5 to 6 membered ring wherein the 5 to 6 membered ring is optionally substituted with oxo;

$R^4$ is halogen, —OH, —OR$^5$, oxo, —$NH_2$, —NHR$^5$, —N(R$^5$)$_2$, —$NO_2$, —$CF_3$, —$C_1$-$C_6$ alkyl, or —$C_1$-$C_6$ haloalkyl;

$R^5$ is linear or branched alkyl; and $R^6$ is H, linear or branched alkyl,

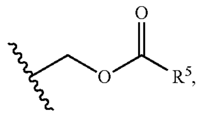

or

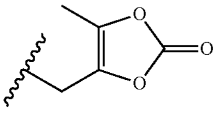

;

or alternatively, $R^6$ and $R^1$ together is an alkylene group or an alkenylene group which with the atoms which they are each bonded to, forms a 12 to 25 membered ring, wherein 1, 2, 3, or 4 —$CH_2$— units making up the alkylene group or the alkenylene group is optionally replaced with a heteroatom selected from —O—, —S—, or —N—, provided that no adjacent —$CH_2$— is replaced; wherein the alkylene group or the alkenylene group is optionally substituted with one or more $R^4$; and wherein, two $R^4$ on the same or adjacent carbon can form a 3 to 6 membered fused or spiro cycloalkyl ring or a 3 to 6 membered fused or spiro heterocyclic ring.

In one embodiment of the compound of Formula (I), R is —$CH_3$ or —$CD_3$.

In one embodiment of the compound of Formula (I), $R^1$ is $C_6$-$C_{20}$ alkyl or $C_6$-$C_{20}$ alkenyl. In some embodiments, $R^1$ is $C_6$-$C_{18}$ alkyl or $C_6$-$C_{18}$ alkenyl. In other embodiments, $R^1$ is pyridyl.

In one embodiment of the compound of Formula (I), $R^2$ is hydrogen. In some embodiments, $R^2$ is —C(O)OR$^5$.

In one embodiment of the compound of Formula (I), $R^5$ is linear or branched $C_1$-$C_6$ alkyl.

In one embodiment of the compound of Formula (I), $R^3$ is —C(O)OR$^6$. In one embodiment of the compound of Formula (I), $R^6$ is H or linear or branched $C_1$-$C_8$ alkyl.

In one embodiment of the compound of Formula (I), $R^6$ and $R^1$ together is an alkylene group or an alkenylene group which with the atoms which they are each bonded to, forms a 12 to 25 membered ring, wherein 1, 2, 3, or 4 —$CH_2$— units making up the alkylene group or the alkenylene group is optionally replaced with a heteroatom selected from —O—, —S—, or —N—, provided that no adjacent —$CH_2$— is replaced; wherein the alkylene group or the alkenylene group is optionally substituted with one or more $R^4$. In one embodiment, $R^6$ and $R^1$ together is an unsubstituted alkylene group or an unsubstituted alkenylene group which forms a 13 to 24 membered ring with the atoms which they are each bonded to.

In one embodiment of the compound of Formula (I), $R^4$ is halogen, —OH, —O($C_1$-$C_6$ alkyl), oxo, —$NH_2$, —NH($C_1$-$C_6$ alkyl), —N($C_1$-$C_6$ alkyl)$_2$, —$NO_2$, —$CF_3$, —$C_1$-$C_6$ alkyl, or —$C_1$-$C_6$ haloalkyl. In some embodiments, $R^4$ is halogen, —OH, —$C_1$-$C_6$ alkyl, or —$C_1$-$C_6$ haloalkyl. In some embodiments, $R^4$ is linear or branched —$C_1$-$C_6$ alkyl.

In one embodiment of the compound of Formula (I), two $R^4$ on the same carbon form a 3 to 6 membered spiro cycloalkyl ring or a 3 to 6 membered spiro heterocyclic ring.

In one embodiment of the compound of Formula (I), two $R^4$ on the adjacent carbon form a 3 to 6 membered fused cycloalkyl ring or a 3 to 6 membered fused heterocyclic ring.

In one embodiment of the compound of Formula (I), the compound is a pharmaceutically acceptable salt selected from sodium salt, potassium salt, lithium salt, $Na_2PO_4H$ salt, hydrochloric acid salt, formic acid salt, trifluoroacetic acid salt, acetic acid salt or trichloroacetic acid/2 lithium salt. In one embodiment, the pharmaceutically acceptable salt of Formula (I) can be a hydrate.

In one embodiment, R is $CH_3$. In another embodiment, R is $CD_3$.

In one embodiment, $R^1$ is C1-C20 alkyl or C2-C20 alkenyl. In one embodiment, $R^1$ is C6-C20 alkyl or C6-C20 alkenyl. In one embodiment, $R^1$ is a C6-C20 alkyl. In one embodiment, $R^1$ is a linear or branched, optionally substituted alkyl selected from C6-alkyl, C7-alkyl, C8-alkyl, C9-alkyl, C10-alkyl, C11-alkyl, C12-alkyl, C13-alkyl, C14-alkyl, C15-alkyl, C16-alkyl, C17-alkyl, C18-alkyl, C19-alkyl or C20-alkyl. In one embodiment, $R^1$ is a linear alkyl selected from C6-alkyl, C7-alkyl, C8-alkyl, C9-alkyl, C10-alkyl, C11-alkyl, C12-alkyl, C13-alkyl, C14-alkyl, C15-alkyl, C16-alkyl, C17-alkyl, C18-alkyl, C19-alkyl or C20-alkyl. In other embodiments, $R^1$ is an unsubstituted linear alkyl selected from C6-alkyl, C7-alkyl, C8-alkyl, C9-alkyl, C10-alkyl, C11-alkyl, C12-alkyl, C13-alkyl, C14-alkyl, C15-alkyl, C16-alkyl, C17-alkyl, C18-alkyl, C19-alkyl or C20-alkyl.

In one embodiment, $R^1$ is a C6-C20 alkenyl. In one embodiment, $R^1$ is a linear or branched, optionally substituted alkenyl selected from C6-alkenyl, C7-alkenyl, C8-alkenyl, C9-alkenyl, C10-alkenyl, C11-alkenyl, C12-alkenyl, C13-alkenyl, C14-alkenyl, C15-alkenyl, C16-alkenyl, C17-alkenyl, C18-alkenyl, C19-alkenyl or C20-alkenyl. In another embodiment, $R^1$ is a linear alkenyl selected from C6-alkenyl, C7-alkenyl, C8-alkenyl, C9-alkenyl, C10-alkenyl, C11-alkenyl, C12-alkenyl, C13-alkenyl, C14-alkenyl, C15-alkenyl, C16-alkenyl, C17-alkenyl, C18-alkenyl, C19-alkenyl or C20-alkenyl. In other embodiments, $R^1$ is an unsubstituted linear alkenyl selected from C6-alkenyl, C7-alkenyl, C8-alkenyl, C9-alkenyl, C10-alkenyl, C11-alkenyl, C12-alkenyl, C13-alkenyl, C14-alkenyl, C15-alkenyl, C16-alkenyl, C17-alkenyl, C18-alkenyl, C19-alkenyl or C20-alkenyl.

In some embodiments, when $R^1$ is alkenyl, the alkenyl can contain 1 to 10 double bonds. In one embodiment, when $R^1$ is alkenyl, the alkenyl can contain 1, 2, 3, or 4 double bonds. In one embodiment, when $R^1$ is alkenyl containing multiple double bonds can take the E or Z form or a mixture thereof. In some embodiments, when $R^1$ is alkenyl containing multiple double bonds, all of the double bonds are in Z orientation.

In one embodiment, $R^1$ is an aryl or a heteroaryl. In one embodiment, $R^1$ is an aryl. In one embodiment, $R^1$ is an phenyl optionally substituted with $R^4$.

In one embodiment, $R^1$ is a heteroaryl. In some embodiments, $R^1$ is a 5- or 6-membered heteroaryl containing at least one nitrogen atom. In one embodiment, $R^1$ is a pyridyl optionally substituted with $R^4$. In another embodiment, $R^1$ is selected from

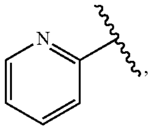,
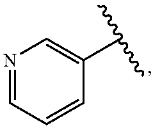, or
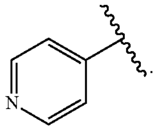.

In one embodiment, $R^1$ is

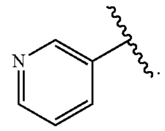 [SMILES: *c1cccnc1].

In one embodiment, $R^2$ is hydrogen. In another embodiment, $R^2$ is —C(O)NHR$^5$, —C(O)R$^1$ or —C(O)OR$^5$.

In one embodiment, $R^2$ is —C(O)OR$^5$. In another embodiment, $R^2$ is —C(O)OR$^5$ where $R^5$ is linear or branched $C_1$-$C_6$ alkyl. In some embodiments, $R^2$ is —C(O)OC$(CH_3)_3$.

In one embodiment, $R^2$ is —C(O)NHR$^5$. In another embodiment, $R^2$ is —C(O)NHR$^5$ where $R^5$ is linear or branched $C_1$-$C_6$ alkyl.

In one embodiment, $R^2$ is —C(O)R$^1$. In one embodiment $R^2$ is —C(O)R$^1$ where $R^1$ is C6-C20 alkyl or C6-C20 alkenyl. In one embodiment, $R^2$ is —C(O)R$^1$ where $R^1$ is a C6-C20 alkyl. In one embodiment, $R^2$ is —C(O)R$^1$ where $R^1$ is a linear or branched, optionally substituted alkyl selected from C6-alkyl, C7-alkyl, C8-alkyl, C9-alkyl, C10-alkyl, C11-alkyl, C12-alkyl, C13-alkyl, C14-alkyl, C15-alkyl, C16-alkyl, C17-alkyl, C18-alkyl, C19-alkyl or C20-alkyl. In one embodiment, $R^2$ is —C(O)R$^1$ where $R^1$ is a linear alkyl selected from C6-alkyl, C7-alkyl, C8-alkyl, C9-alkyl, C10-alkyl, C11-alkyl, C12-alkyl, C13-alkyl, C14-alkyl, C15-alkyl, C16-alkyl, C17-alkyl, C18-alkyl, C19-alkyl or C20-alkyl. In other embodiments, $R^2$ is —C(O)R$^1$ where $R^1$ is an unsubstituted linear alkyl selected from C6-alkyl, C7-alkyl, C8-alkyl, C9-alkyl, C10-alkyl, C11-alkyl, C12-alkyl, C13-alkyl, C14-alkyl, C15-alkyl, C16-alkyl, C17-alkyl, C18-alkyl, C19-alkyl or C20-alkyl.

In one embodiment, $R^2$ is —C(O)R$^1$ where $R^1$ is a C6-C20 alkenyl. In one embodiment, $R^2$ is —C(O)R$^1$ where $R^1$ is a linear or branched, optionally substituted alkenyl selected from C6-alkenyl, C7-alkenyl, C8-alkenyl, C9-alkenyl, C10-alkenyl, C11-alkenyl, C12-alkenyl, C13-alkenyl, C14-alkenyl, C15-alkenyl, C16-alkenyl, C17-alkenyl, C18-alkenyl, C19-alkenyl or C20-alkenyl. In another embodiment, $R^2$ is —C(O)R$^1$ where $R^1$ is a linear alkenyl selected from C6-alkenyl, C7-alkenyl, C8-alkenyl, C9-alkenyl, C10-alkenyl, C11-alkenyl, C12-alkenyl, C13-alkenyl, C14-alkenyl, C15-alkenyl, C16-alkenyl, C17-alkenyl, C18-alkenyl, C19-alkenyl or C20-alkenyl. In other embodiments, $R^2$ is —C(O)R$^1$ where $R^1$ is an unsubstituted linear alkenyl selected from C6-alkenyl, C7-alkenyl, C8-alkenyl, C9-alkenyl, C10-alkenyl, C11-alkenyl, C12-alkenyl, C13-alkenyl, C14-alkenyl, C15-alkenyl, C16-alkenyl, C17-alkenyl, C18-alkenyl, C19-alkenyl or C20-alkenyl.

In some embodiments, $R^2$ is —C(O)R$^1$ where $R^1$ is alkenyl and $R^1$ contain 1 to 10 double bonds. In one embodiment, $R^2$ is —C(O)R$^1$ where $R^1$ is alkenyl and $R^1$ can contain 1, 2, 3, or 4 double bonds. In one embodiment, $R^2$ is —C(O)R$^1$ where $R^1$ is alkenyl containing multiple double bonds, each are in E or Z form or a mixture thereof. In some embodiments, $R^2$ is —C(O)R$^1$ where $R^1$ is alkenyl containing multiple double bonds, all of the double bonds are in Z orientation.

In one embodiment, $R^3$ is —C(O)OR$^6$. In another embodiment, $R^3$ is —C(O)OR, where $R^6$ is H or a straight or branched alkyl. In one embodiment, $R^3$ is —C(O)OR$^6$, where $R^6$ is H. In some embodiments, $R^3$ is —C(O)OR$^6$, where $R^6$ is a straight or branched alkyl. In some embodiments, $R^3$ is —C(O)$OR^6$, where $R^6$ is a straight or branched C1-C10 alkyl. In one embodiment, $R^3$ is —C(O)$OR^6$, where $R^6$ is a straight or branched C1-C8 alkyl. In some embodiments, $R^6$ is a straight alkyl selected from C1-alkyl, C2-alkyl, C3-alkyl, C4-alkyl, C5-alkyl, C6-alkyl, C7-alkyl, C8-alkyl, C9-alkyl, or C10-alkyl. In one embodiment, $R^3$ is —C(O)$OR^6$, where $R^6$ is a branched alkyl selected from C3-alkyl, C4-alkyl, C5-alkyl, C6-alkyl, C7-alkyl, C8-alkyl, C9-alkyl, or C10-alkyl. In one embodiment, $R^3$ is —C(O)$OR^6$, where $R^6$ is methyl, ethyl, propyl, isopropyl, n-butyl, t-butyl, n-pentyl, n-hexyl, n-heptyl, or n-octyl.

In one embodiment, $R^3$ is —C(O)$OR^6$, where $R^6$ is a

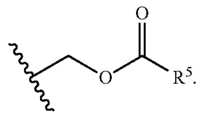

In another embodiment, $R^3$ is —C(O)$OCH_2OC$(O)$R^5$, where $R^5$ is a linear or branched C1-C6 alkyl. In another embodiment, $R^3$ is —C(O)$OCH_2OC$(O)$R^5$, where $R^5$ is a linear alkyl selected from C1 alkyl, C2-alkyl, C3-alkyl, C4-alkyl, C5-alkyl, or C6-alkyl. In one embodiment, $R^3$ is —C(O)$OCH_2OC$(O)$R^5$, where $R^5$ is methyl. In another embodiment, $R^3$ is —C(O)$OCH_2OC$(O)$R^5$, where $R^5$ is a branched alkyl selected from C3-alkyl, C4-alkyl, C5-alkyl, or C6-alkyl.

In one embodiment, $R^3$ is —C(O)$OR^6$, where $R^6$ is a

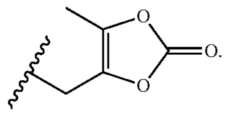 [SMILES: *Cc1oc(=O)oc1C]

In another embodiment, $R^3$ is -alkylene-(OH). In one embodiment, $R^3$ is —(C1-C10 alkylene)-(OH). In one embodiment, $R^3$ is —(C1 alkylene)-(OH), —(C2 alkylene)-(OH), —(C3 alkylene)-(OH), —(C4 alkylene)-(OH), —(C5 alkylene)-(OH), —(C6 alkylene)-(OH), —(C7 alkylene)-(OH), —(C8 alkylene)-(OH), —(C9 alkylene)-(OH), or —(C10 alkylene)-(OH). In one embodiment, R3 is -methylene-(OH).

In one embodiment, $R^2$ and $R^3$ are alkylene groups and together form a 5 to 6 membered ring optionally substituted with oxo. In one embodiment, $R^2$ and $R^3$ are alkylene groups and together form a 5-membered ring optionally substituted with oxo. In another embodiment, $R^2$ and $R^3$ are alkylene groups and together forms a 6-membered ring optionally substituted with oxo. In one embodiment, $R^2$ and $R^3$ together form

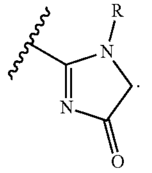

In one embodiment, the compounds of Formula (I) are present as pharmaceutically acceptable salts. In one embodiment, the compounds of Formula (I) are sodium salts. In another embodiment, the compounds of Formula (I) are lithium salts. In another embodiment, the compounds of Formula (I) are hydrochloric acid salts. In another embodiment, the compounds of Formula (I) are trichloroacetic acid two lithium salts (TCA/2Li salt).

In one embodiment of the compound of Formula (I), the compound has the structure of Formula (II):

(II)

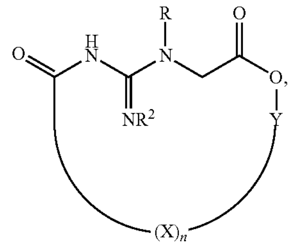

or a pharmaceutically acceptable salt or solvate thereof; wherein:

R is $CH_3$, $CH_2D$, $CHD_2$, or $CD_3$;

$R^2$ is hydrogen, —C(O)$NHR^5$, —C(O)$R^1$ or —C(O)$OR^5$;

$R^1$ is linear or branched alkyl, or linear or branched alkenyl, wherein $R^1$ is optionally substituted with $R^4$;

$R^4$ is halogen, —OH, —$OR^5$, oxo, —$NH_2$, —$NHR^5$, —$N(R^5)_2$, —$NO_2$, —$CF_3$, —$C_1$-$C_6$ alkyl, or —$C_1$-$C_6$ haloalkyl;

X at each occurrence is independently —$C(R^{5a})_2$—$C(R^{5a})_2$—, —$CH(R^{5a})$—$CH(R^{5a})$—, —$C(R^{5a})$=$C(R^{5a})$—, —O—$C(R^{5a})_2$—, —O—$CH(R^{5a})$—, —$C(R^{5a})_2$—O—, or —$CH(R^{5a})$—O—;

Y is —$C(R^{5a})_2$—; —$CH(R^{5a})$—; —$C(R^{5a})_2$—$C(R^{5a})_2$—, —$CH(R^{5a})$—$CH(R^{5a})$—, —$C(R^{5a})$=$C(R^{5a})$—, —$C(R^{5a})_2$—O—, or —$CH(R^{5a})$—O—;

n is 3, 4, 5, or 6, wherein when n is 3, Y is —$CH(R^{5a})$—$CH(R^{5a})$—, —$C(R^{5a})$=$C(R^{5a})$—, or —$CH(R^{5a})$—O—;

$R^5$ is H or linear or branched alkyl;

$R^{5a}$ is H, halogen, —OH, —$OR^5$, —$NH_2$, —$NHR^5$, —$N(R^5)_2$, —$NO_2$, —$CF_3$, —$C_1$-$C_6$ alkyl, or —$C_1$-$C_6$ haloalkyl; and wherein, two $R^{5a}$ on the same or adjacent carbon can form a 3 to 6 membered fused or spiro cycloalkyl ring or a 3 to 6 membered fused or spiro heterocyclic ring.

In one embodiment of the compound of Formula (II), at least one of X is —$C(R^{5a})_2$—$C(R^{5a})_2$—, —$CH(R^{5a})$—$CH(R^{5a})$—, or —$C(R^{5a})$=$C(R^{5a})$—, wherein $R^{5a}$ is H or —C1-C6 alkyl; and wherein, two $R^{5a}$ on the same or adjacent carbon can form a 3 to 6 membered fused or spiro cycloalkyl ring or a 3 to 6 membered fused or spiro heterocyclic ring In some embodiments, X is —$CH_2CH_2$—, —CH=CH—, —O—$CH_2$—, or —$CH_2$—O—.

In one embodiment of the compound of Formula (II), Y is —$C(R^{5a})_2$—, —$CH(R^{5a})$—; —$C(R^{5a})_2$—$C(R^{5a})_2$—, —$CH(R^{5a})$—$CH(R^{5a})$—, or —$C(R^{5a})$=$C(R^{5a})$—, wherein $R^{5a}$ is H or —$C_1$-$C_6$ alkyl; and wherein, two $R^{5a}$ on the same or adjacent carbon can form a 3 to 6 membered fused or spiro cycloalkyl ring or a 3 to 6 membered fused or spiro heterocyclic ring. In some embodiments, Y is —$CH_2$—, —$CH_2CH_2$—, or —CH=CH—. In other embodiments, Y is —$C(R^{5a})_2$—, —$CH(R^{5a})$—; —$C(R^{5a})_2$—$C(R^{5a})_2$—, —$CH(R^{5a})$—$CH(R^{5a})$—, —$CH_2$—, —$CH_2CH_2$—, —CH=CH—,

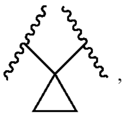,

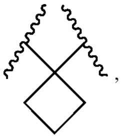,

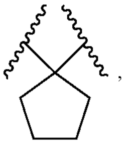,

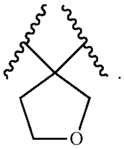.

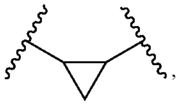,

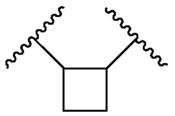, or

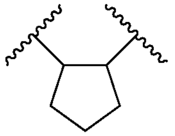;

wherein, $R^{5a}$ is linear or branched $—C_1$-$C_6$ alkyl.

In one embodiment of the compound of Formula (II), R is $—CH_3$ or $—CD_3$.

In one embodiment of the compound of Formula (II), $R^2$ is hydrogen.

In one embodiment of the compound of Formula (II), the compound is a pharmaceutically acceptable salt selected from sodium salt, potassium salt, lithium salt, $Na_2PO_4H$ salt, hydrochloric acid salt, formic acid salt, trifluoroacetic acid salt, acetic acid salt or trichloroacetic acid/2 lithium salt. In one embodiment, the pharmaceutically acceptable salt of Formula (II) can be a hydrate.

In one embodiment of the compound of Formula (I), the compound has the structure of Formula (I-A):

(I-A)

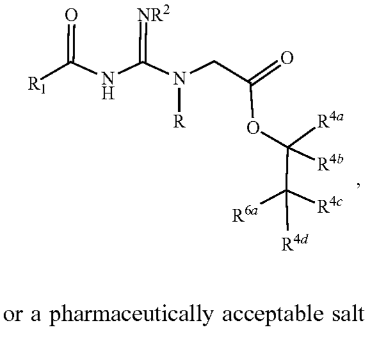, or a pharmaceutically acceptable salt or solvate thereof;

wherein:

R is $—CH_3$, $—CH_2D$, $—CHD_2$, or $—CD_3$;

$R^2$ is hydrogen, $—C(O)NHR^5$, $—C(O)R^1$ or $—C(O)OR^5$;

$R^3$ is $—C(O)OR^6$, or -alkyl(OH);

or alternatively, $R^2$ and $R^3$ together is an alkylene group which with the atoms which they are each bonded to, forms a 5 to 6 membered ring wherein the 5 to 6 membered ring is optionally substituted with oxo;

$R^4$ is halogen, —OH, $—OR^5$, oxo, $—NH_2$, $—NHR^5$, $—N(R^5)_2$, $—NO_2$, $—CF_3$, $—C_1$-$C_6$ alkyl, or $—C_1$-$C_6$ haloalkyl;

$R^{4a}$, $R^{4b}$, $R^{4c}$, and $R^{4d}$, each independently, is H, halogen, —OH, $—OR^5$, oxo, $—NH_2$, $—NHR^5$, $—N(R^5)_2$, $—NO_2$, $—CF_3$, $—C_1$-$C_6$ alkyl, or $—C_1$-$C_6$ haloalkyl;

$R^5$ is linear or branched alkyl; and $R^{6a}$ and $R^1$ together is an alkylene group or an alkenylene group which with the atoms which they are each bonded to, forms a 12 to 25 membered ring, wherein 1, 2, 3, or 4 $—CH_2—$ units making up the alkylene group or the alkenylene group is optionally replaced with a heteroatom selected from —O—, —S—, or —N—, provided that no adjacent $—CH_2—$ is replaced; wherein the alkylene group or the alkenylene group is optionally substituted with one or more $R^4$;

wherein, $R^{4a}$ and $R^{4b}$ or $R^{4c}$ and $R^{4d}$ together can form a 3 to 6 membered spiro cycloalkyl ring or a 3 to 6 membered spiro heterocyclic ring; or wherein $R^{4b}$ and $R^{4c}$ together can form a 3 to 6 membered fused cycloalkyl ring or a 3 to 6 membered fused heterocyclic ring.

As described herein, any one of the embodiments described for Formula (I) can be applied to the compound of Formula (I-A).

In one embodiment of the compound of Formula (I-A), $R^{4a}$ is $—C_1$-$C_6$ alkyl. In some embodiments, $R^{4a}$ is $—C_1$-$C_6$ alkyl and $R^{4b}$, $R^{4c}$, and $R^{4d}$ is H. In other embodiments, $R^{4a}$ and $R^{4b}$ is $—C_1$-$C_6$ alkyl and $R^{4c}$ and $R^{4d}$ is H. In another embodiment, $R^{4a}$ and $R^{4c}$ is $—C_1$-$C_6$ alkyl and $R^{4b}$ and $R^{4d}$ is H.

In one embodiment of the compound of Formula (I-A), $R^{4b}$ is $—C_1$-$C_6$ alkyl. In some embodiments, $R^{4b}$ is $—C_1$-$C_6$ alkyl and $R^{4a}$, $R^{4c}$, and $R^{4d}$ is H. In one embodiment, $R^{4a}$, $R^{4b}$, $R^{4c}$, and $R^{4d}$, each independently, is H.

In one embodiment of the compound of Formula (I-A), $R^{4a}$ and $R^{4b}$ together form a 3 to 6 membered spiro cycloalkyl ring or a 3 to 6 membered spiro heterocyclic ring. In some embodiments, $R^{4a}$ and $R^{4b}$ together form

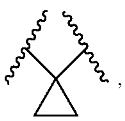,

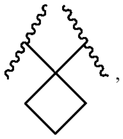,

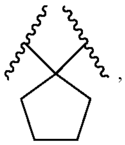, or

-continued

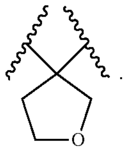

In one embodiment of the compound of Formula (I-A), $R^{4b}$ and $R^{4c}$ together form a 3 to 6 membered fused cycloalkyl ring or a 3 to 6 membered fused heterocyclic ring. In some embodiments, $R^{4b}$ and $R^{4c}$ together form

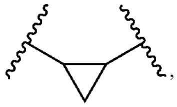, 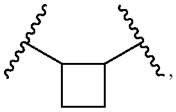, or

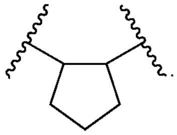.

In one embodiment of the compound of Formula (I-A), R is $—CH_3$ or $—CD_3$.

In one embodiment of the compound of Formula (I-A), $R^2$ is hydrogen.

In one embodiment of the compound of Formula (I-A), the compound is a pharmaceutically acceptable salt selected from the sodium salt, potassium salt, lithium salt, hydrochloric acid salt, formic acid salt, trifluoroacetic acid salt, acetic acid salt or trichloroacetic acid/2 lithium salt. In one embodiment of the compound of Formula (I-A), the compound is a pharmaceutically acceptable salt selected from sodium salt, lithium salt, hydrochloric acid salt, formic acid salt, trifluoroacetic acid salt, acetic acid salt or trichloroacetic acid/2 lithium salt.

In one embodiment of the compound of Formula (I), the compound has the structure of Formula (III):

(III)

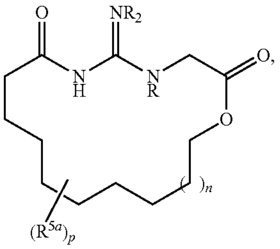

or a pharmaceutically acceptable salt or solvate thereof; wherein:

R is $CH_3$, $CH_2D$, $CHD_2$, or $CD_3$;

$R^1$ is linear or branched alkyl, or linear or branched alkenyl;

$R^2$ is hydrogen, $—C(O)NHR^5$, $—C(O)R^1$ or $—C(O)OR^5$;

$R^5$ is H or linear or branched alkyl;

$R^{5a}$ is halogen, —OH, $—OR^3$, oxo, $—NH_2$, $—NHR^5$, $—N(R^5)_2$, $—NO_2$, $—CF_3$, $—C_1$-$C_6$ alkyl, or $—C_1$-$C_6$ haloalkyl;

n is 0, 1, 2, 3, 4, or 5; and p is 0, 1, 2, 3, 4, 5, 6, 7, or 8.

In one embodiment of the compound of Formula (III), R is $CH_3$ or $CD_3$.

In one embodiment of the compound of Formula (III), $R^2$ is H.

In one embodiment of the compound of Formula (III), n is 1. In some embodiments, n is 2. In one embodiment, n is 3.

In one embodiment of the compound of Formula (III), p is 0, 1, or 2.

In one embodiment of the compound of Formula (I), the compound has the structure of Formula (III-A):

(III-A)

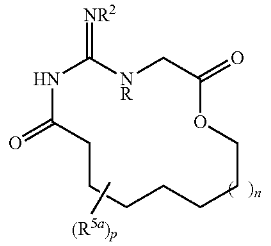, or a pharmaceutically acceptable salt or solvate thereof; wherein:

R is $—CH_3$, $—CH_2D$, $—CHD_2$, or $—CD_3$;

$R^1$ is linear or branched alkyl, or linear or branched alkenyl;

$R^2$ is hydrogen, $—C(O)NHR^5$, $—C(O)R^1$ or $—C(O)OR^5$;

$R^5$ is H or linear or branched alkyl;

$R^{5a}$ is halogen, —OH, $—OR^5$, oxo, $—NH_2$, $—NHR^5$, $—N(R^5)_2$, $—NO_2$, $—CF_3$, $—C_1$-$C_6$ alkyl, or $—C_1$-$C_6$ haloalkyl, wherein, two $R^{5a}$ on the same or adjacent carbon can form a 3 to 6 membered fused or spiro cycloalkyl ring or a 3 to 6 membered fused or spiral heterocyclic ring;

n is 0, 1, 2, 3, 4, 5, 6, 7, 8, 9, 10, or 11; and p is 0, 1, 2, 3, 4, 5, 6, 7, or 8.

In one embodiment of the compound of Formula (III-A), R is $—CH_3$ or $—CD_3$.

In one embodiment of the compound of Formula (III-A), $R^2$ is H.

In one embodiment of the compound of Formula (III-A), n is 0, 1, 2, 3, 4, 5, 6, 7, 8, 9, or 10. In some embodiments, n is 0, 1, 2, 3, 4, 5, 6, 7, 8, or 9. In other embodiments, n is 0, 1, 2, 3, 4, 5, 6, 7, or 8. In one embodiment, n is 0, 1, 2, 3, 4, 5, 6, or 7.

In one embodiment of the compound of Formula (III-A), p is 0, 1, 2, 3, or 4. In one embodiment, p is 0, 1, or 2.

In one embodiment of the compound of Formula (Ill-A), $R^5$ is linear or branched $—C_1$-$C_6$ alkyl.

In one embodiment of the compound of Formula (III-A), $R^{5a}$ is halogen, —OH, $—O(C_1$-$C_6$ alkyl), oxo, $—NH_2$, $—NH(C_1$-$C_6$ alkyl), $—N(C_1$-$C_6$ alkyl$)_2$, $—NO_2$, $—CF_3$, $—C_1$-$C_6$ alkyl, or $—C_1$-$C_6$ haloalkyl. In some embodiments, $R^{5a}$ is halogen, —OH, $—C_1$-$C_6$ alkyl, or $—C_1$-$C_6$ haloalkyl. In other embodiments, $R^{5a}$ is $—C_1$-$C_6$ alkyl. In some embodiments, $R^{5a}$ is linear or branched $—C_1$-$C_6$ alkyl.

In one embodiment of the compound of Formula (I), (I-A), (II), (III), and/or (III-A), the compound is selected from:

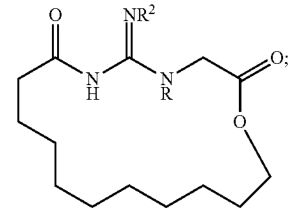

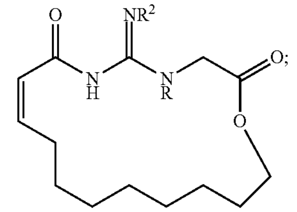

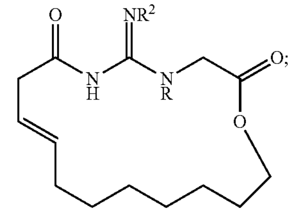

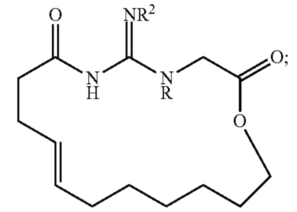

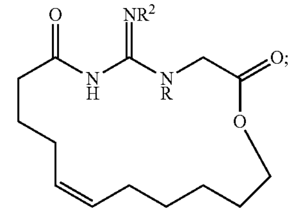

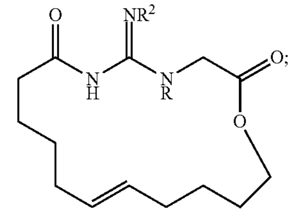

-continued

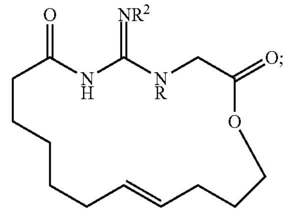

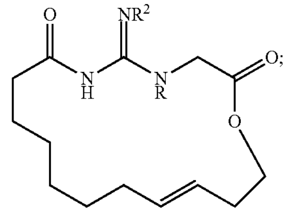

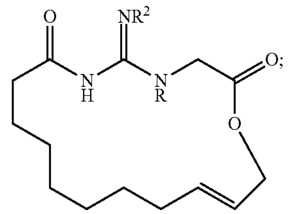

or

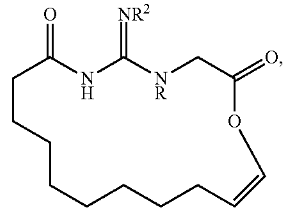

or a pharmaceutically acceptable salt thereof, wherein R is —$CH_3$ or —$CD_3$ and $R^2$ is H.

In one embodiment of the compound of Formula (III) or (III-A), the compound is a pharmaceutically acceptable salt selected from sodium salt, potassium salt, lithium salt, $Na_2PO_4H$ salt, hydrochloric acid salt, formic acid salt, trifluoroacetic acid salt, acetic acid salt or trichloroacetic acid/2 lithium salt. In one embodiment, the pharmaceutically acceptable salt of Formula (III) or (III-A) can be a hydrate.

In one embodiment of Formula (I), the compound is selected from Table A, or a pharmaceutically acceptable salt thereof:

TABLE A

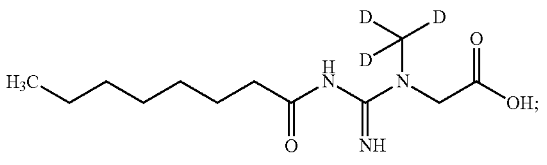 [SMILES: [2H]C([2H])([2H])N(CC(=O)O)C(=N)NC(=O)CCCCCCC]

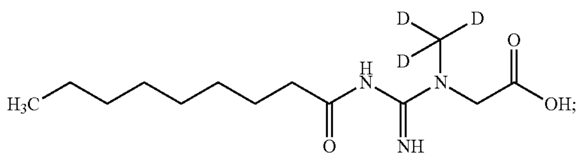 [SMILES: [2H]C([2H])([2H])N(CC(=O)O)C(=N)NC(=O)CCCCCCCC]

TABLE A-continued
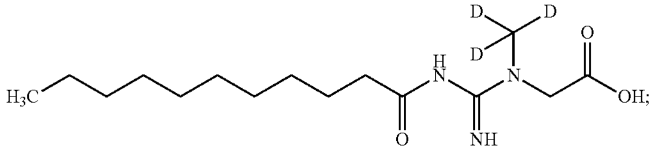 [SMILES: [2H]C([2H])([2H])N(CC(=O)O)C(=N)NC(=O)CCCCCCCCCC]
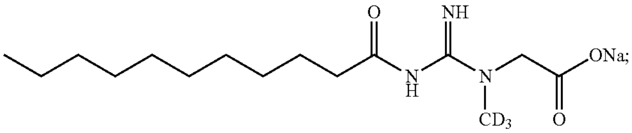
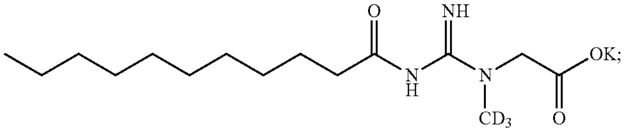
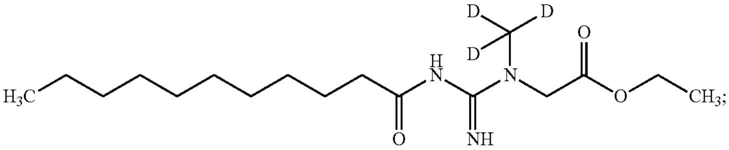 [SMILES: [2H]C([2H])([2H])N(CC(=O)OCC)C(=N)NC(=O)CCCCCCCCCC]
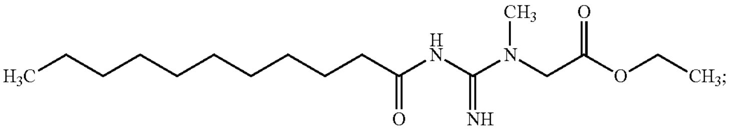 [SMILES: CCCCCCCCCCC(=O)NC(=N)N(C)CC(=O)OCC]
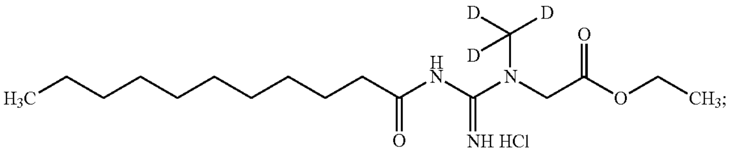
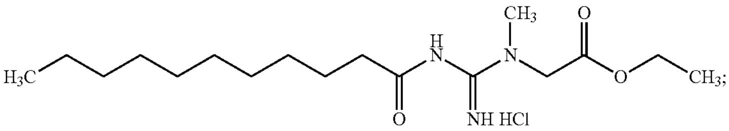
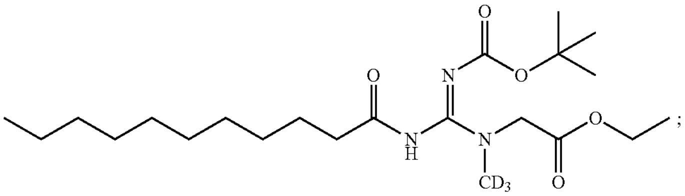 [SMILES: [2H]C([2H])([2H])N(CC(=O)OCC)/C(=N\C(=O)OC(C)(C)C)NC(=O)CCCCCCCCCC]
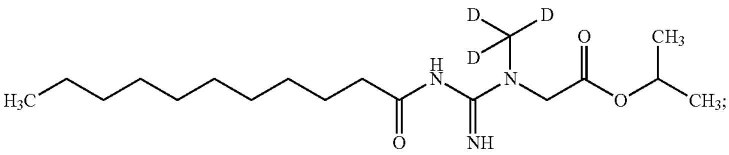 [SMILES: [2H]C([2H])([2H])N(CC(=O)OC(C)C)C(=N)NC(=O)CCCCCCCCCC]
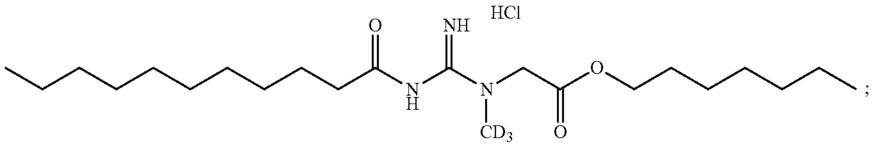 [SMILES: Cl ; [2H]C([2H])([2H])N(CC(=O)OCCCCCCC)C(=N)NC(=O)CCCCCCCCCC]

TABLE A-continued
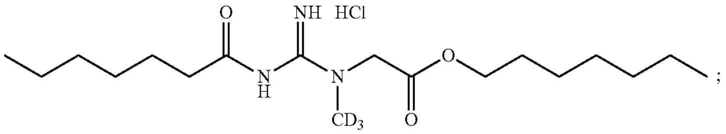 [SMILES: Cl ; [2H]C([2H])([2H])N(CC(=O)OCCCCCCC)C(=N)NC(=O)CCCCCC]
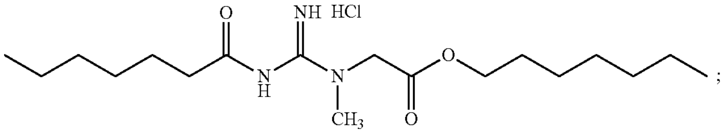 [SMILES: Cl ; CCCCCCCOC(=O)CN(C)C(=N)NC(=O)CCCCCC]
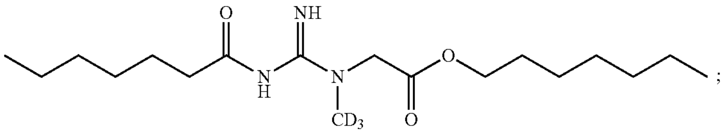
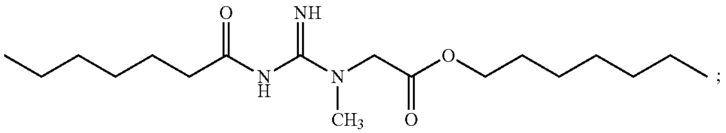 [SMILES: [2H]C([2H])([2H])N(CC(=O)OCCCCCCC)C(=N)NC(=O)CCCCCC]
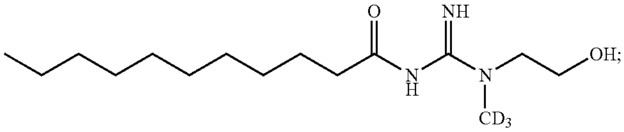 [SMILES: [2H]C([2H])([2H])N(CCO)C(=N)NC(=O)CCCCCCCCCC]
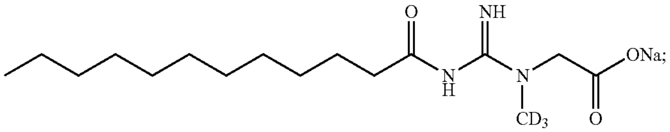
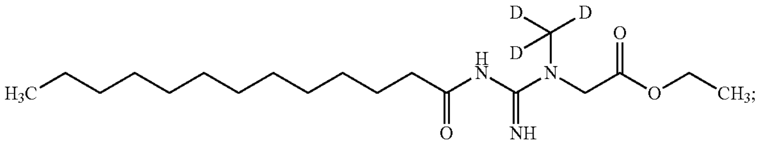 [SMILES: [2H]C([2H])([2H])N(CC(=O)OCC)C(=N)NC(=O)CCCCCCCCCCCC]
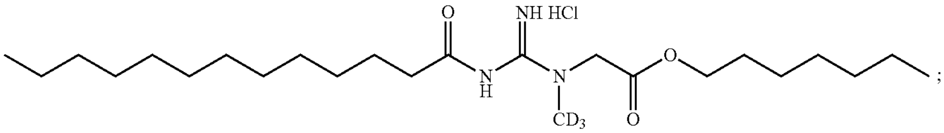
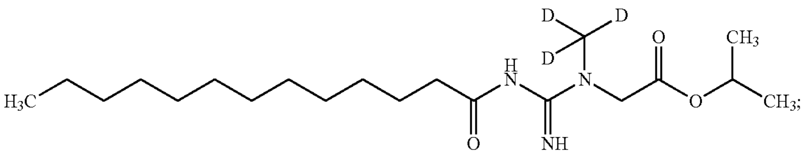 [SMILES: [2H]C([2H])([2H])N(CC(=O)OC(C)C)C(=N)NC(=O)CCCCCCCCCCCC]
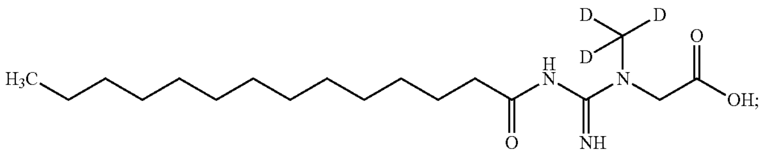 [SMILES: [2H]C([2H])([2H])N(CC(=O)O)C(=N)NC(=O)CCCCCCCCCCCCC]

TABLE A-continued
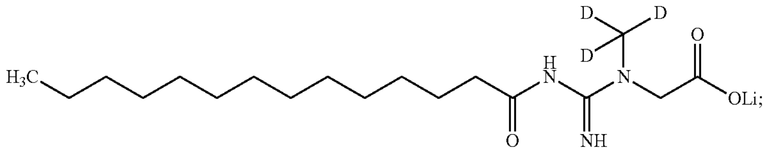
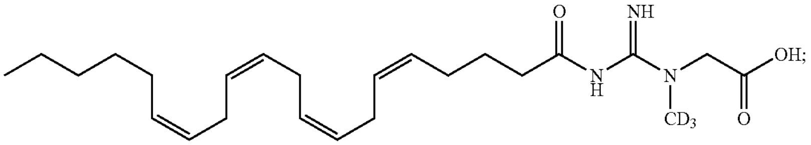 [SMILES: [2H]C([2H])([2H])N(CC(=O)O)C(=N)NC(=O)CCC/C=C\C/C=C\C/C=C\C/C=C\CCCCC]
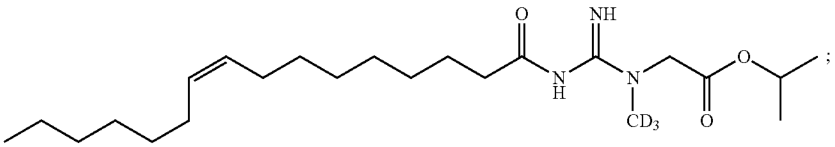 [SMILES: [2H]C([2H])([2H])N(CC(=O)OC(C)C)C(=N)NC(=O)CCCCCCC/C=C\CCCCCC]
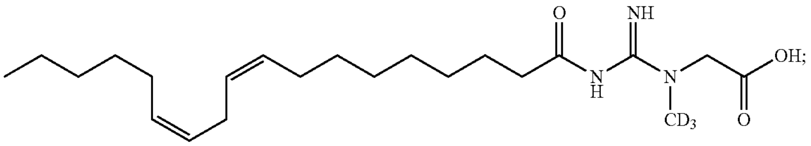 [SMILES: [2H]C([2H])([2H])N(CC(=O)O)C(=N)NC(=O)CCCCCCC/C=C\C/C=C\CCCCC]
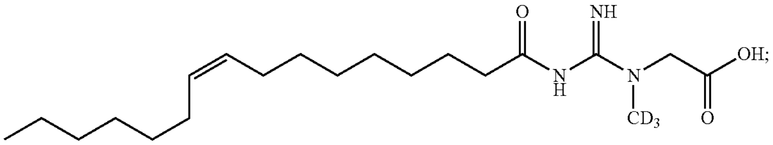 [SMILES: [2H]C([2H])([2H])N(CC(=O)O)C(=N)NC(=O)CCCCCCC/C=C\CCCCCC]
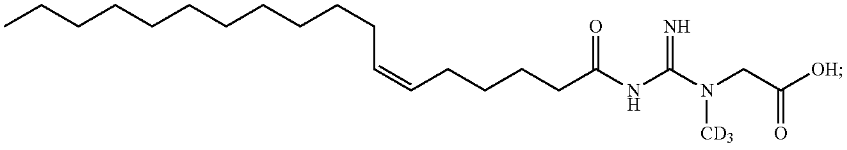 [SMILES: [2H]C([2H])([2H])N(CC(=O)O)C(=N)NC(=O)CCCC/C=C\CCCCCCCCCCC]
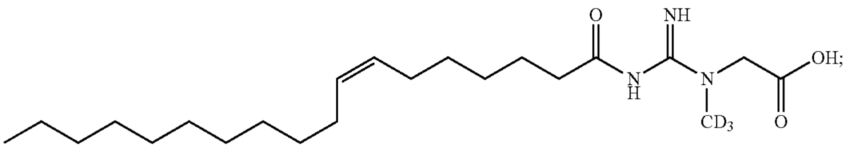 [SMILES: [2H]C([2H])([2H])N(CC(=O)O)C(=N)NC(=O)CCCCC/C=C\CCCCCCCCCC]
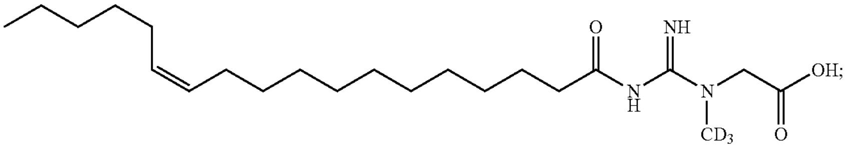 [SMILES: [2H]C([2H])([2H])N(CC(=O)O)C(=N)NC(=O)CCCCCCCCCC/C=C\CCCCC]
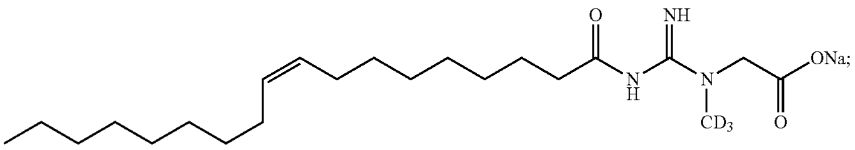
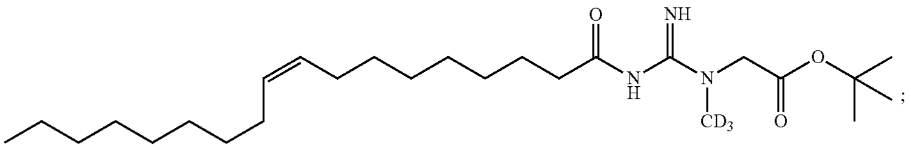 [SMILES: [2H]C([2H])([2H])N(CC(=O)OC(C)(C)C)C(=N)NC(=O)CCCCCCC/C=C\CCCCCCCC]

TABLE A-continued
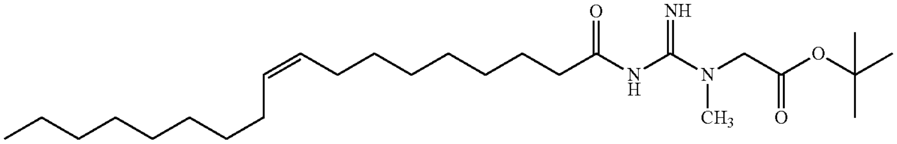
;
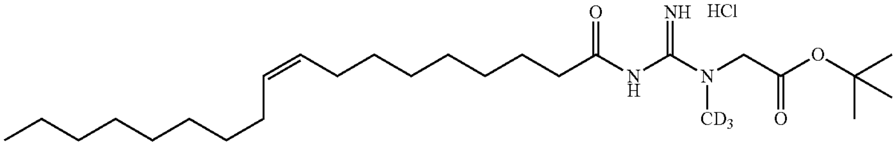
;
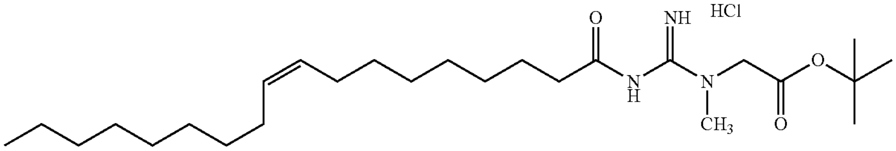
;
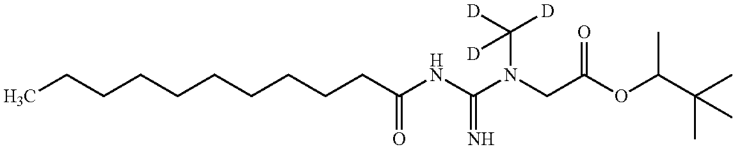
;
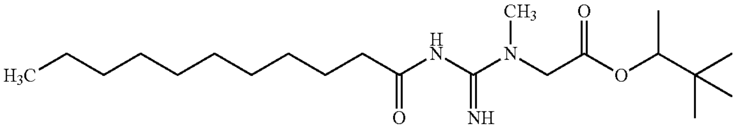
;
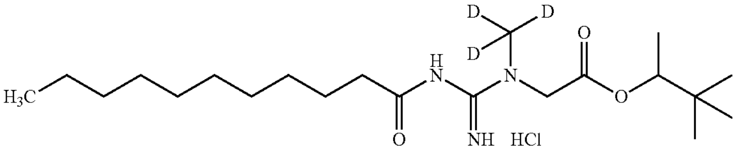
;
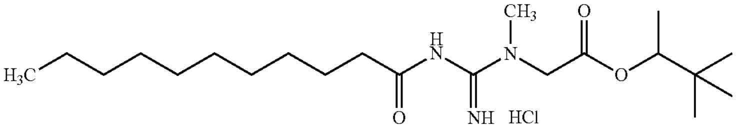
;
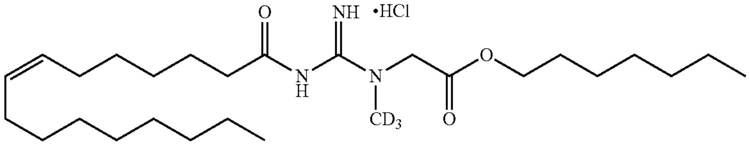
;
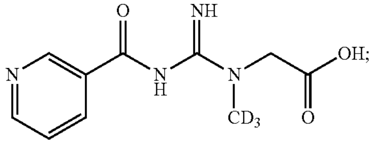 [SMILES: [2H]C([2H])([2H])N(CC(=O)O)C(=N)NC(=O)c1cccnc1]
;
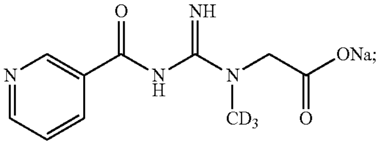
;

TABLE A-continued
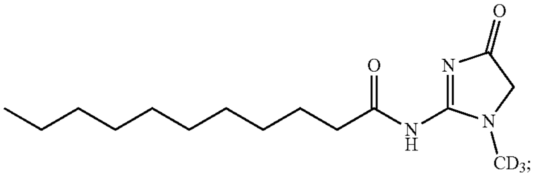 [SMILES: [2H]C([2H])([2H])N1CC(=O)N=C1NC(=O)CCCCCCCCCC]
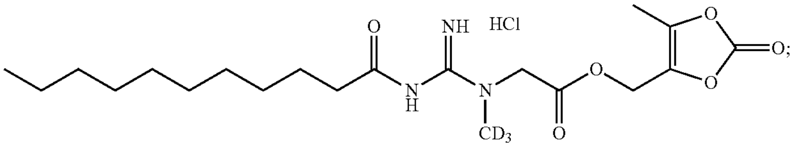 [SMILES: [2H]C([2H])([2H])N(CC(=O)OCc1oc(=O)oc1C)C(=N)NC(=O)CCCCCCCCCC ; Cl]
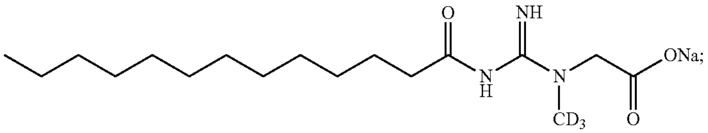
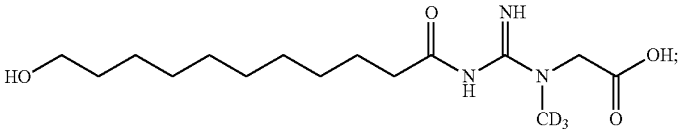
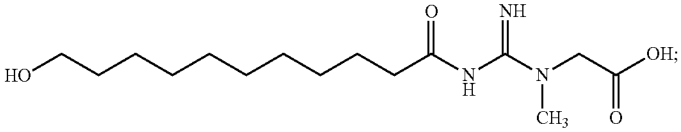 [SMILES: CN(CC(=O)O)C(=N)NC(=O)CCCCCCCCCCO]
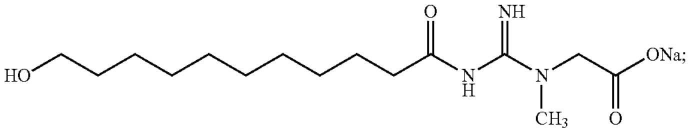
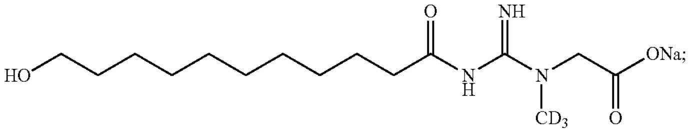
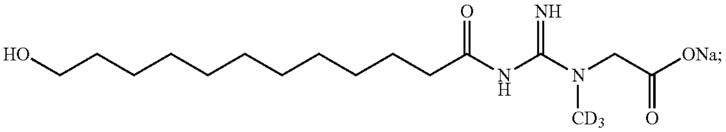
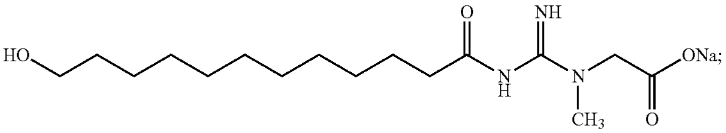
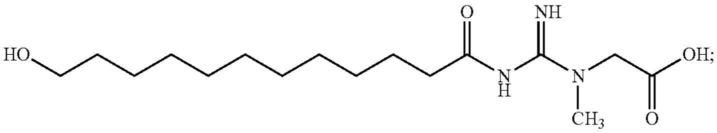 [SMILES: CN(CC(=O)O)C(=N)NC(=O)CCCCCCCCCCCO]

TABLE A-continued
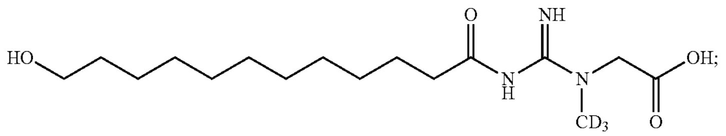 [SMILES: [2H]C([2H])([2H])N(CC(=O)O)C(=N)NC(=O)CCCCCCCCCCCO]
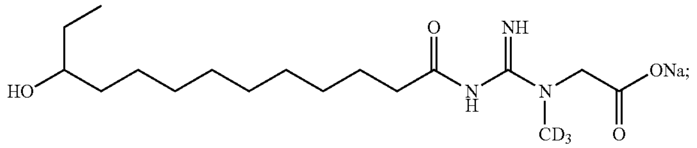
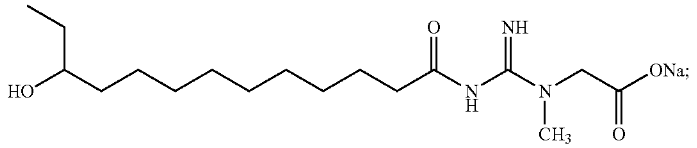
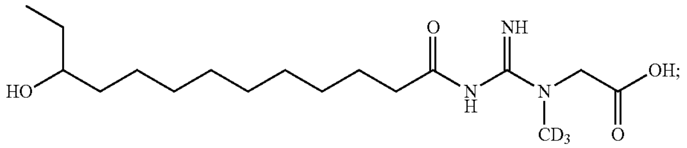
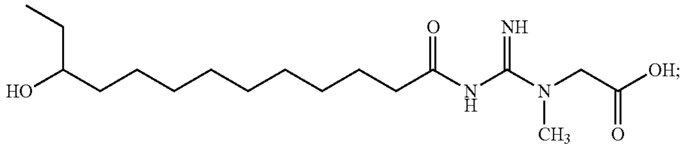 [SMILES: CCC(O)CCCCCCCCCC(=O)NC(=N)N(C)CC(=O)O]
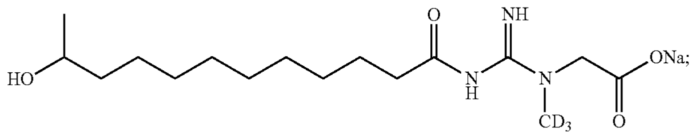
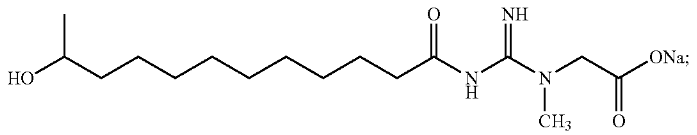
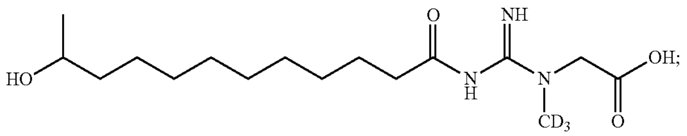
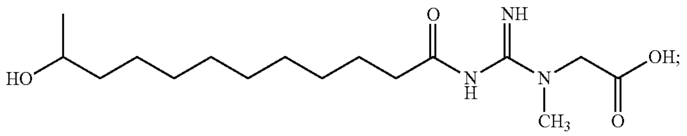 [SMILES: [2H]C([2H])([2H])N(CC(=O)O)C(=N)NC(=O)CCCCCCCCCC(C)O]
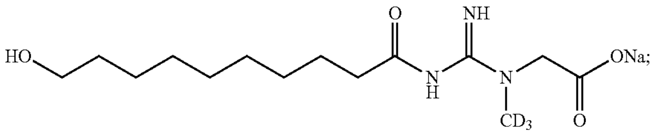

TABLE A-continued
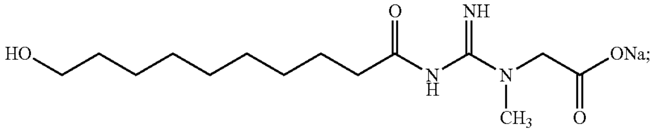
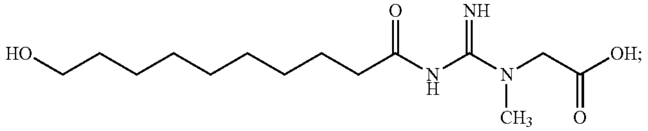
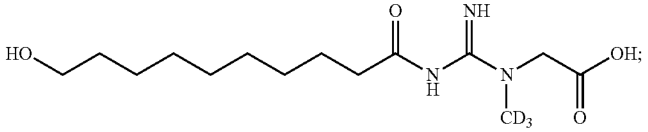 [SMILES: [2H]C([2H])([2H])N(CC(=O)O)C(=N)NC(=O)CCCCCCCCCO]
In one embodiment of Formula (I), the compound is selected from Table B, or a pharmaceutically acceptable salt thereof:
TABLE B
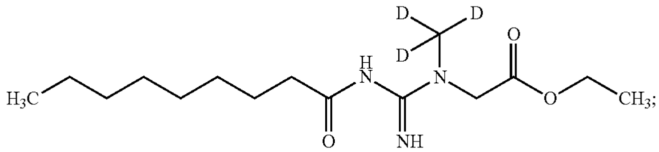 [SMILES: [2H]C([2H])([2H])N(CC(=O)OCC)C(=N)NC(=O)CCCCCCCC]
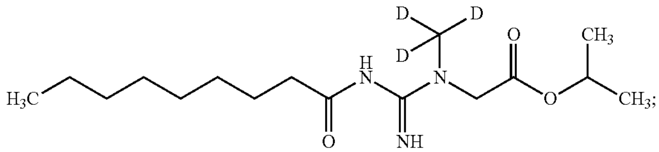 [SMILES: [2H]C([2H])([2H])N(CC(=O)OC(C)C)C(=N)NC(=O)CCCCCCCC]
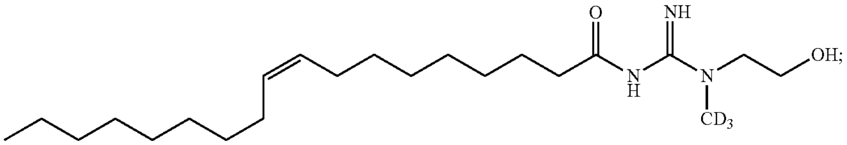 [SMILES: [2H]C([2H])([2H])N(CCO)C(=N)NC(=O)CCCCCCC/C=C\CC(C)CCCCCC]
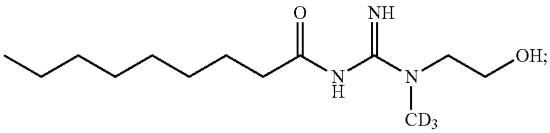 [SMILES: [2H]C([2H])([2H])N(CCO)C(=N)NC(=O)CCCCCCCC]
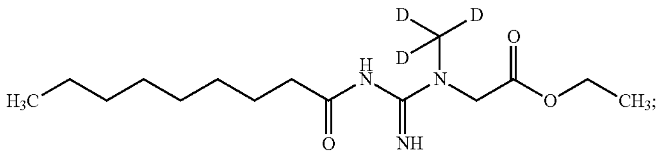 [SMILES: [2H]C([2H])([2H])N(CC(=O)OCC)C(=N)NC(=O)CCCCCCCC]
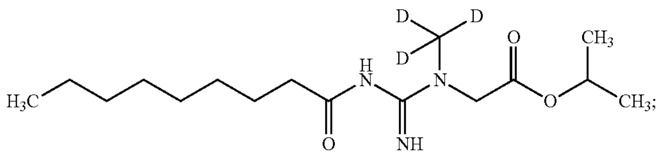 [SMILES: [2H]C([2H])([2H])N(CC(=O)OC(C)C)C(=N)NC(=O)CCCCCCCC]

TABLE B-continued
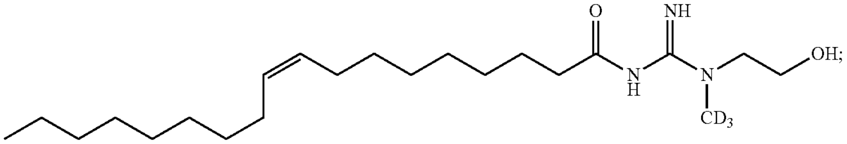 [SMILES: [2H]C([2H])([2H])N(CCO)C(=N)NC(=O)CCCCCCC/C=C\CC(C)CCCCCC]
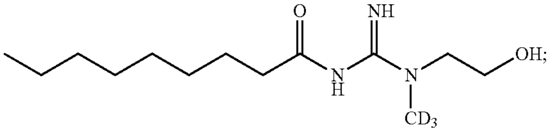 [SMILES: [2H]C([2H])([2H])N(CCO)C(=N)NC(=O)CCCCCCCC]
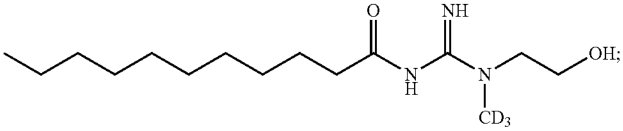 [SMILES: [2H]C([2H])([2H])N(CCO)C(=N)NC(=O)CCCCCCCCCC]
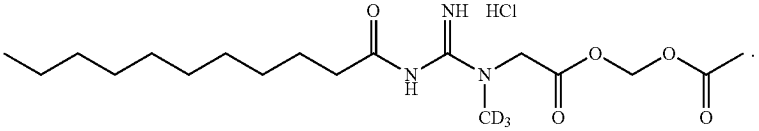 [SMILES: [2H]C([2H])([2H])N(CC(=O)OCOC(C)=O)C(=N)NC(=O)CCCCCCCCCC ; Cl]
In one embodiment of Formula (I), the compound is selected from Table C or a pharmaceutically acceptable salt thereof:
TABLE C
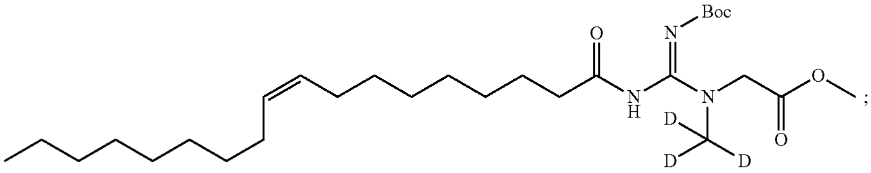 [SMILES: [2H]C([2H])([2H])N(CC(=O)OC)/C(=N\C(=O)OC(C)(C)C)NC(=O)CCCCCCC/C=C\CCCCCCCC]
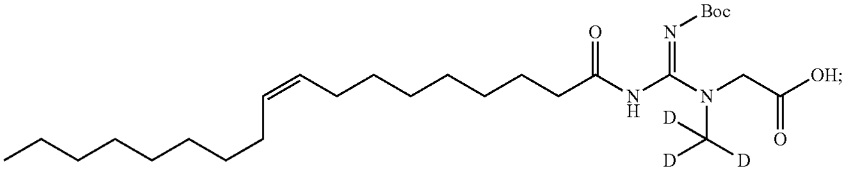 [SMILES: [2H]C([2H])([2H])N(CC(=O)O)/C(=N\C(=O)OC(C)(C)C)NC(=O)CCCCCCC/C=C\CCCCCCCC]
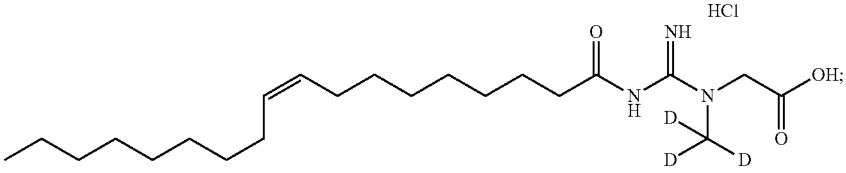 [SMILES: Cl ; [2H]C([2H])([2H])N(CC(=O)O)C(=N)NC(=O)CCCCCCC/C=C\CCCCCCCC]
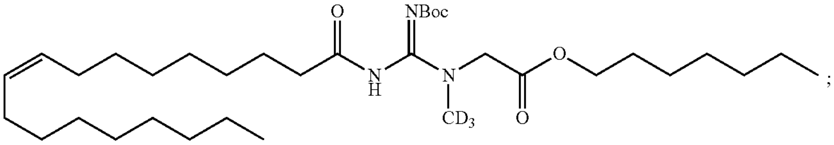
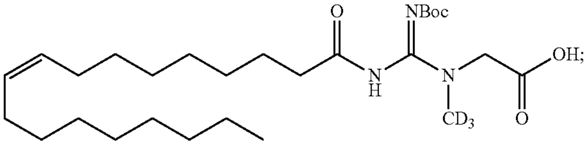

TABLE C-continued
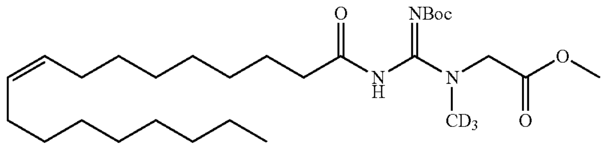
;
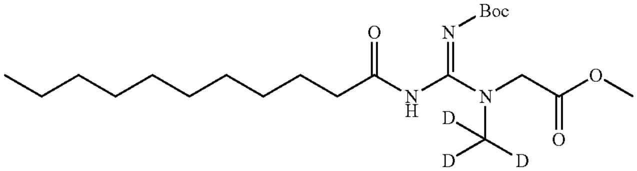
;
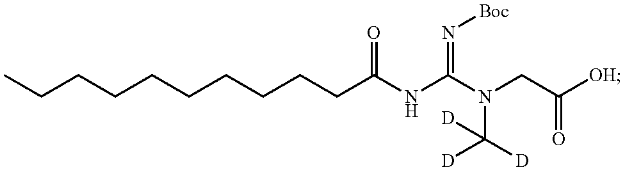 [SMILES: [2H]C([2H])([2H])N(CC(=O)O)/C(=N\C(=O)OC(C)(C)C)NC(=O)CCCCCCCCCC]
;
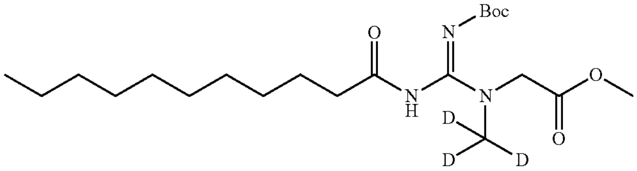
;
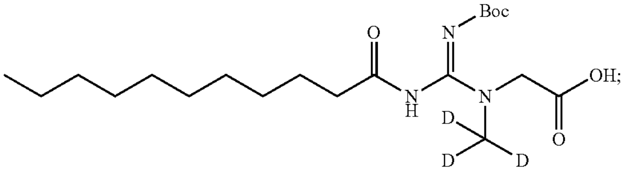 [SMILES: [2H]C([2H])([2H])N(CC(=O)O)/C(=N\C(=O)OC(C)(C)C)NC(=O)CCCCCCCCCC]
;
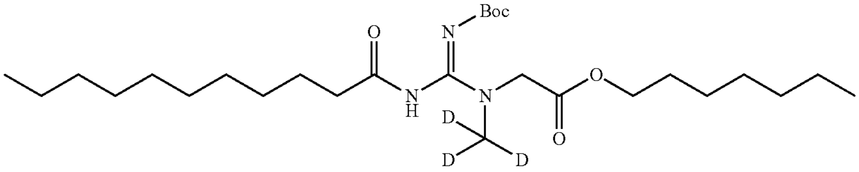
;
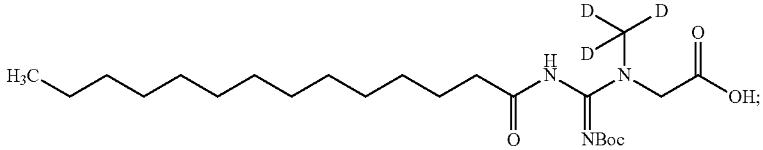
;
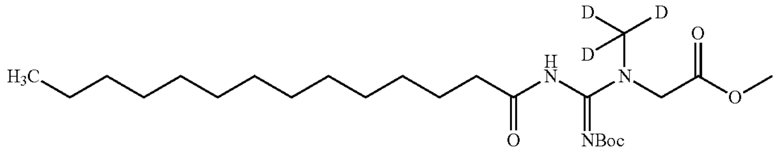
;
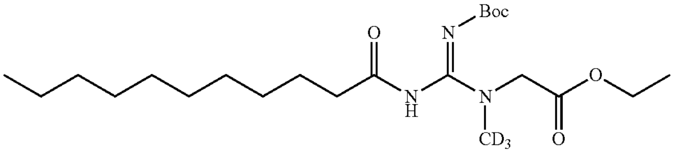
; or TABLE C-continued
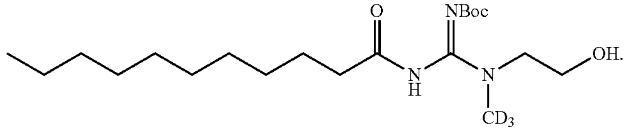
In one embodiment of Formula (I), (I-A), (II), (III), and/or (III-A), the compound is selected from Table D or a pharmaceutically acceptable salt thereof:
TABLE D
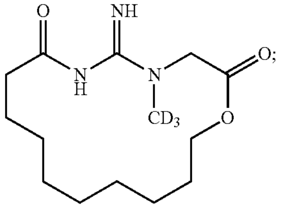 [SMILES: [2H]C([2H])([2H])N1CC(=O)OCCCCCCCCCC(=O)NC1=N]
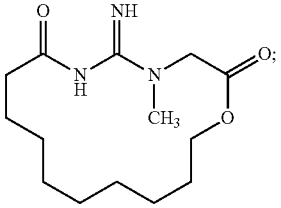 [SMILES: CN1CC(=O)OCCCCCCCCCC(=O)NC1=N]
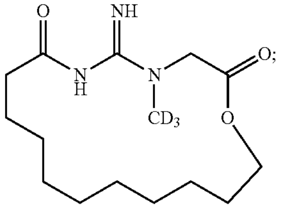 [SMILES: [2H]C([2H])([2H])N1CC(=O)OCCCCCCCCCCC(=O)NC1=N]
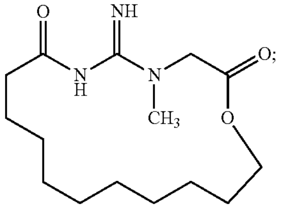 [SMILES: CN1CC(=O)OCCCCCCCCCCC(=O)NC1=N]
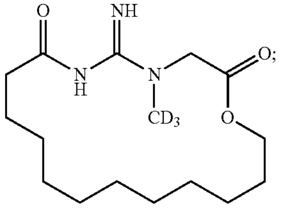 [SMILES: [2H]C([2H])([2H])N1CC(=O)OCCCCCCCCCCCC(=O)NC1=N]
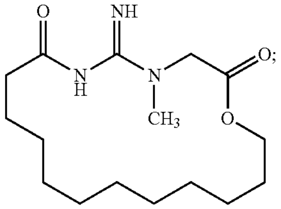 [SMILES: CN1CC(=O)OCCCCCCCCCCCC(=O)NC1=N]
TABLE D-continued
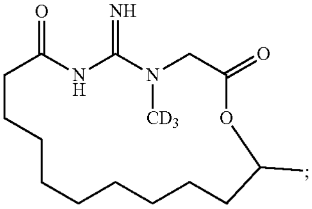
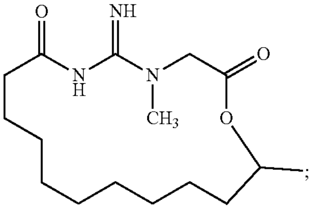 [SMILES: CC1CCCCCCCCCC(=O)NC(=N)N(C)CC(=O)O1]
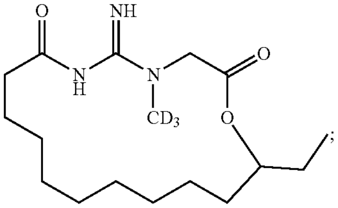 [SMILES: [2H]C([2H])([2H])N1CC(=O)OC(CC)CCCCCCCCCC(=O)NC1=N]
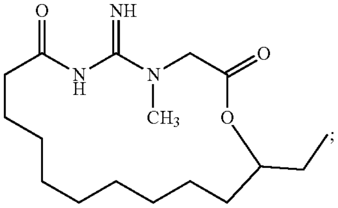 [SMILES: CCC1CCCCCCCCCC(=O)NC(=N)N(C)CC(=O)O1]
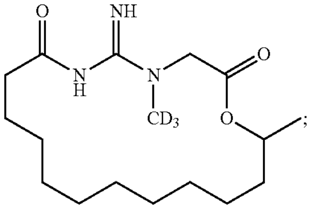 [SMILES: [2H]C([2H])([2H])N1CC(=O)OC(C)CCCCCCCCCCC(=O)NC1=N]
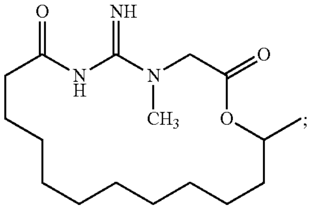 [SMILES: CC1CCCCCCCCCCC(=O)NC(=N)N(C)CC(=O)O1]

TABLE D-continued
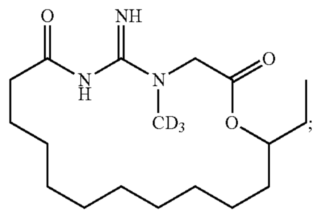 [SMILES: [2H]C([2H])([2H])N1CC(=O)OC(CC)CCCCCCCCCCC(=O)NC1=N]
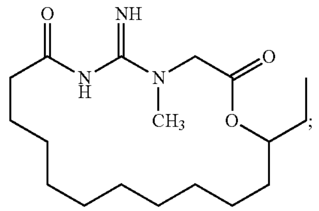 [SMILES: CCC1CCCCCCCCCCC(=O)NC(=N)N(C)CC(=O)O1]
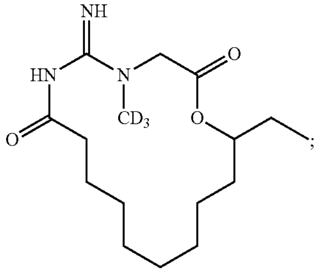 [SMILES: [2H]C([2H])([2H])N1CC(=O)OC(CC)CCCCCCCCC(=O)NC1=N]
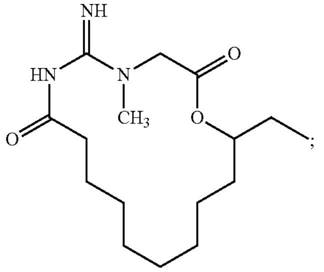 [SMILES: CCC1CCCCCCCCC(=O)NC(=N)N(C)CC(=O)O1]
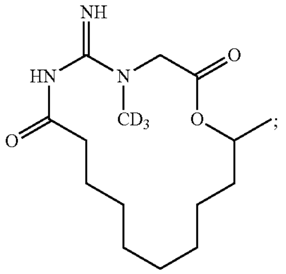 [SMILES: [2H]C([2H])([2H])N1CC(=O)OC(C)CCCCCCCCC(=O)NC1=N]
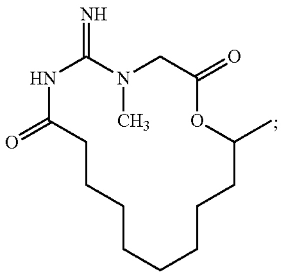
TABLE D-continued
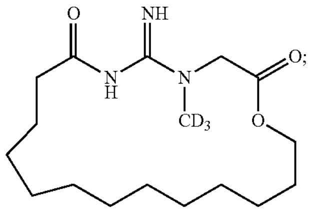
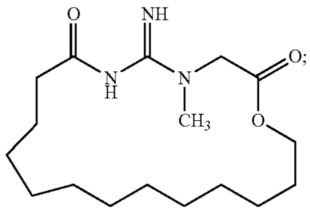 [SMILES: [2H]C([2H])([2H])N1CC(=O)OCCCCCCCCCCCCC(=O)NC1=N]
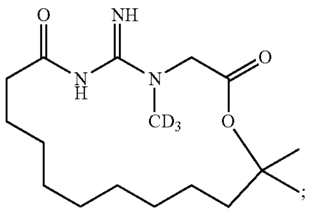 [SMILES: [2H]C([2H])([2H])N1CC(=O)OC(C)(C)CCCCCCCCCC(=O)NC1=N]
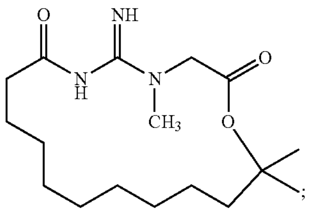 [SMILES: CN1CC(=O)OC(C)(C)CCCCCCCCCC(=O)NC1=N]
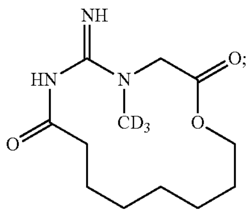 [SMILES: [2H]C([2H])([2H])N1CC(=O)OCCCCCCCC(=O)NC1=N]
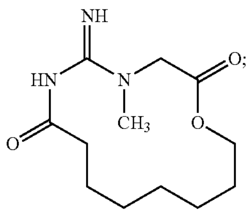 [SMILES: CN1CC(=O)OCCCCCCCC(=O)NC1=N]
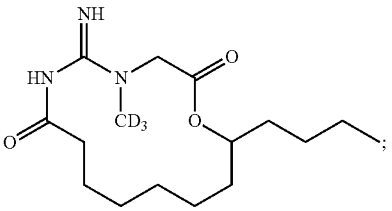 [SMILES: [2H]C([2H])([2H])N1CC(=O)OC(CCCC)CCCCCCC(=O)NC1=N]

TABLE D-continued
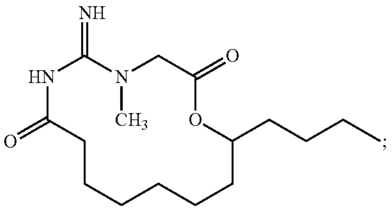 [SMILES: CCCCC1CCCCCCC(=O)NC(=N)N(C)CC(=O)O1]
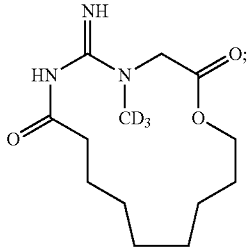 [SMILES: [2H]C([2H])([2H])N1CC(=O)OCCCCCCCCC(=O)NC1=N]
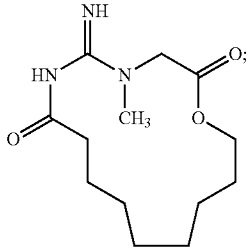 [SMILES: CN1CC(=O)OCCCCCCCCC(=O)NC1=N]
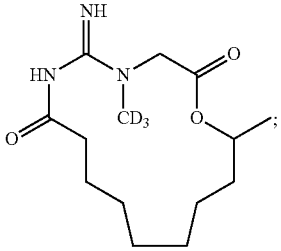
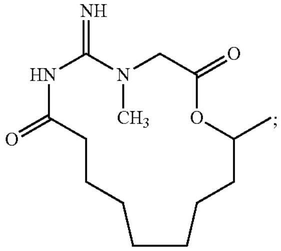 [SMILES: [2H]C([2H])([2H])N1CC(=O)OC(C)CCCCCCCC(=O)NC1=N]
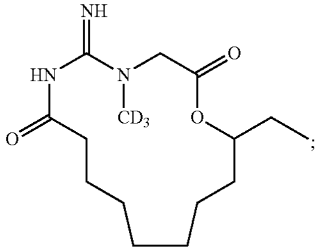 [SMILES: [2H]C([2H])([2H])N1CC(=O)OC(CC)CCCCCCCC(=O)NC1=N]
TABLE D-continued
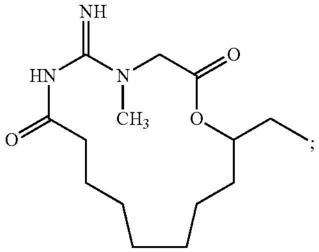 [SMILES: CCC1CCCCCCCC(=O)NC(=N)N(C)CC(=O)O1]
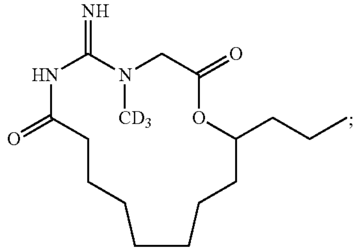 [SMILES: [2H]C([2H])([2H])N1CC(=O)OC(CCC)CCCCCCCC(=O)NC1=N]
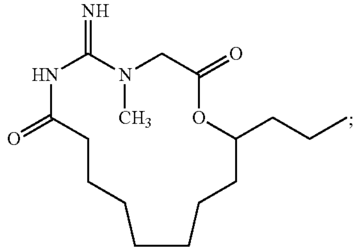 [SMILES: CCCC1CCCCCCCC(=O)NC(=N)N(C)CC(=O)O1]
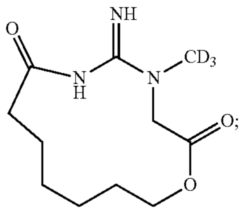 [SMILES: [2H]C([2H])([2H])N1CC(=O)OCCCCCCC(=O)NC1=N]
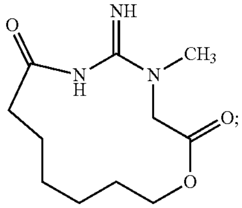 [SMILES: CN1CC(=O)OCCCCCCC(=O)NC1=N]
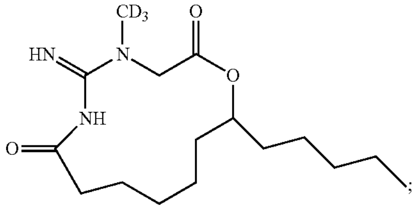 [SMILES: [2H]C([2H])([2H])N1CC(=O)OC(CCCCC)CCCCCC(=O)NC1=N]

TABLE D-continued
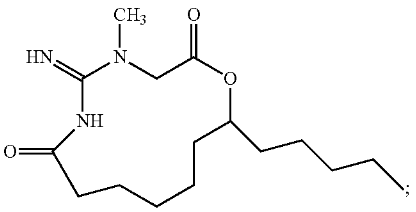 [SMILES: CCCCCC1CCCCCC(=O)NC(=N)N(C)CC(=O)O1]
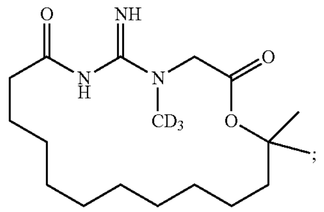 [SMILES: [2H]C([2H])([2H])N1CC(=O)OC(C)(C)CCCCCCCCCCC(=O)NC1=N]
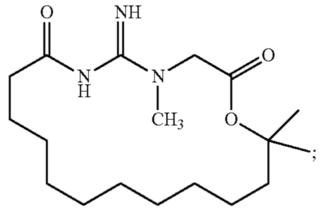 [SMILES: CN1CC(=O)OC(C)(C)CCCCCCCCCCC(=O)NC1=N]
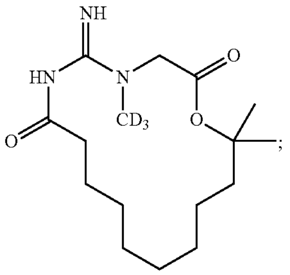
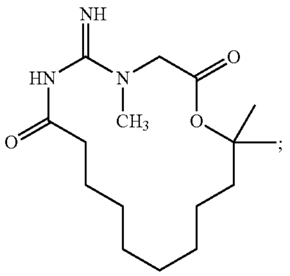 [SMILES: [2H]C([2H])([2H])N1CC(=O)OC(C)(C)CCCCCCCCC(=O)NC1=N]
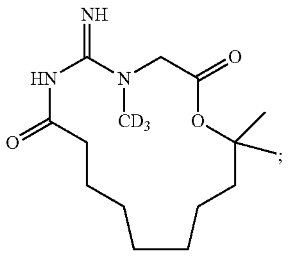 [SMILES: [2H]C([2H])([2H])N1CC(=O)OC(C)(C)CCCCCCCC(=O)NC1=N]
TABLE D-continued
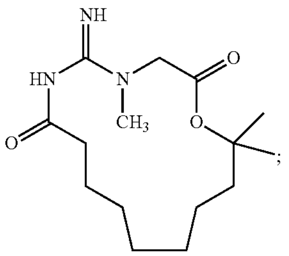 [SMILES: CN1CC(=O)OC(C)(C)CCCCCCCC(=O)NC1=N]
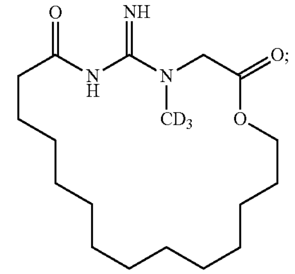 [SMILES: [2H]C([2H])([2H])N1CC(=O)OCCCCCCCCCCCCCC(=O)NC1=N]
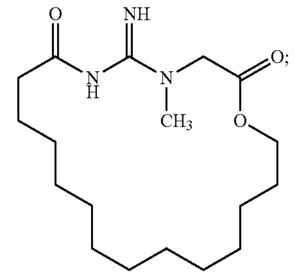 [SMILES: CN1CC(=O)OCCCCCCCCCCCCCC(=O)NC1=N]
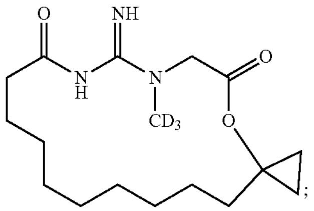 [SMILES: [2H]C([2H])([2H])N1CC(=O)OC2(CCCCCCCCCC(=O)NC1=N)CC2]
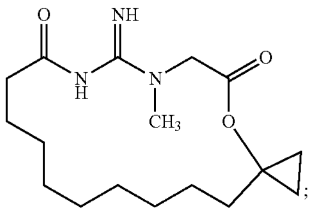 [SMILES: CN1CC(=O)OC2(CCCCCCCCCC(=O)NC1=N)CC2]
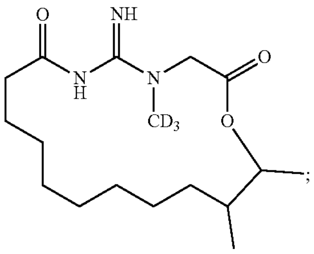

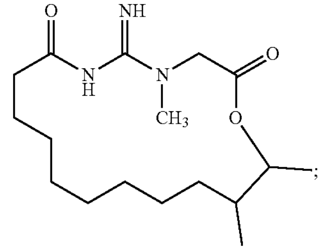 [SMILES: [2H]C([2H])([2H])N1CC(=O)OC(C)C(C)CCCCCCCCC(=O)NC1=N]
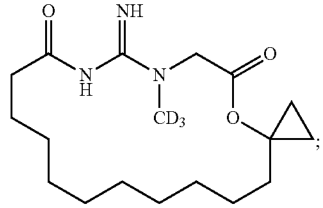 [SMILES: [2H]C([2H])([2H])N1CC(=O)OC2(CCCCCCCCCCC(=O)NC1=N)CC2]
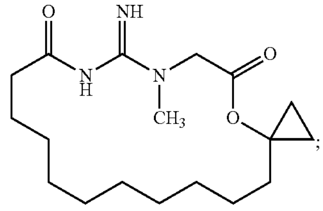 [SMILES: CN1CC(=O)OC2(CCCCCCCCCCC(=O)NC1=N)CC2]
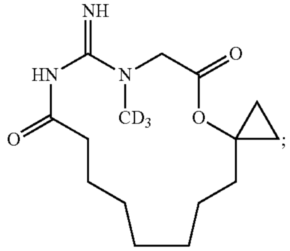
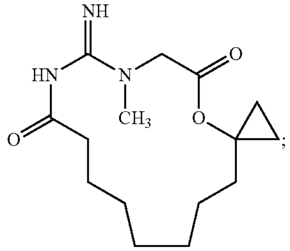 [SMILES: [2H]C([2H])([2H])N1CC(=O)OC2(CCCCCCCC(=O)NC1=N)CC2]
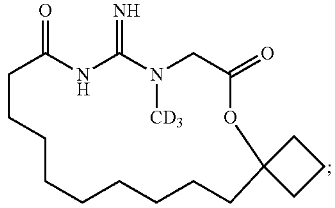 [SMILES: [2H]C([2H])([2H])N1CC(=O)OC2(CCCCCCCCCC(=O)NC1=N)CCC2]
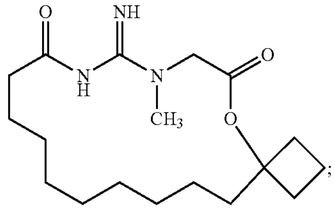 [SMILES: CN1CC(=O)OC2(CCCCCCCCCC(=O)NC1=N)CCC2]
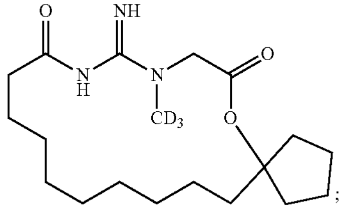 [SMILES: [2H]C([2H])([2H])N1CC(=O)OC2(CCCCCCCCCC(=O)NC1=N)CCCC2]
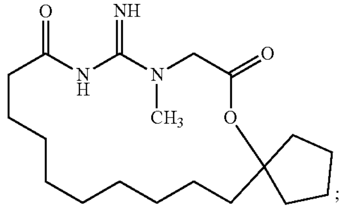 [SMILES: CN1CC(=O)OC2(CCCCCCCCCC(=O)NC1=N)CCCC2]
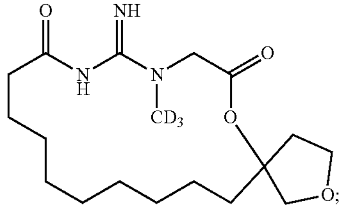 [SMILES: [2H]C([2H])([2H])N1CC(=O)OC2(CCCCCCCCCC(=O)NC1=N)CCOC2]
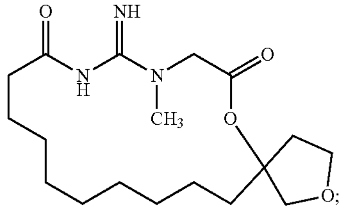 [SMILES: CN1CC(=O)OC2(CCCCCCCCCC(=O)NC1=N)CCOC2]
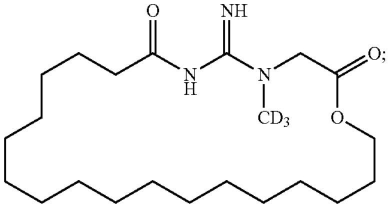 [SMILES: [2H]C([2H])([2H])N1CC(=O)OCCCCCCCCCCCCCCCCCC(=O)NC1=N]
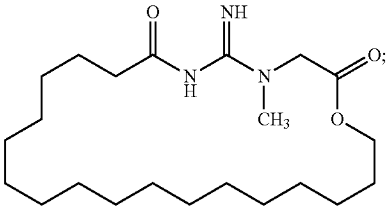 [SMILES: CN1CC(=O)OCCCCCCCCCCCCCCCCCC(=O)NC1=N]
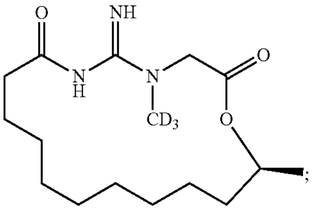 [SMILES: [2H]C([2H])([2H])N1CC(=O)O[C@@H](C)CCCCCCCCCC(=O)NC1=N]

TABLE D-continued
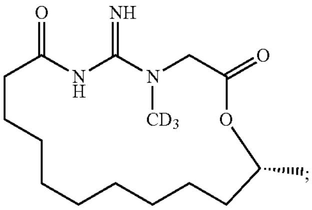 [SMILES: [2H]C([2H])([2H])N1CC(=O)O[C@H](C)CCCCCCCCCC(=O)NC1=N];
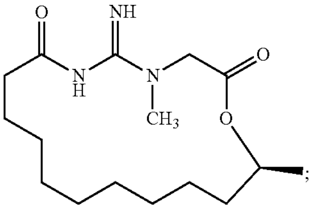 [SMILES: C[C@H]1CCCCCCCCCC(=O)NC(=N)N(C)CC(=O)O1];
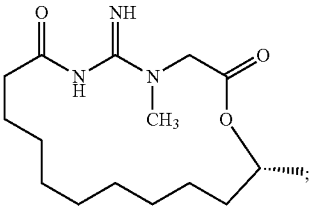;
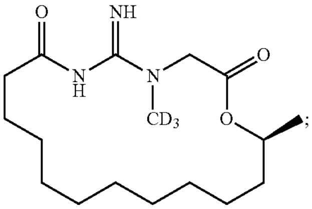 [SMILES: [2H]C([2H])([2H])N1CC(=O)O[C@@H](C)CCCCCCCCCCC(=O)NC1=N];
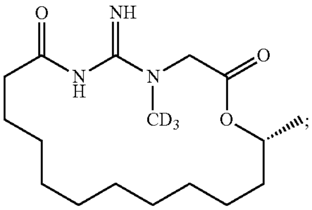 [SMILES: [2H]C([2H])([2H])N1CC(=O)O[C@H](C)CCCCCCCCCCC(=O)NC1=N];
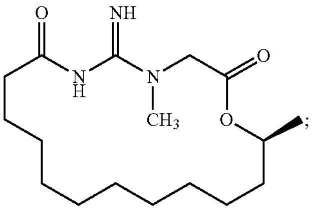 [SMILES: C[C@H]1CCCCCCCCCCC(=O)NC(=N)N(C)CC(=O)O1];
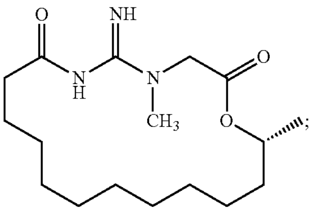 [SMILES: C[C@@H]1CCCCCCCCCCC(=O)NC(=N)N(C)CC(=O)O1];
TABLE D-continued
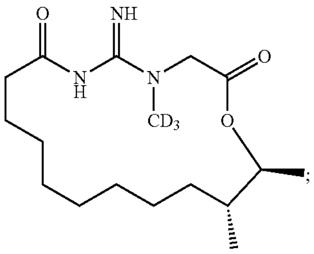 [SMILES: [2H]C([2H])([2H])N1CC(=O)O[C@@H](C)[C@H](C)CCCCCCCCC(=O)NC1=N];
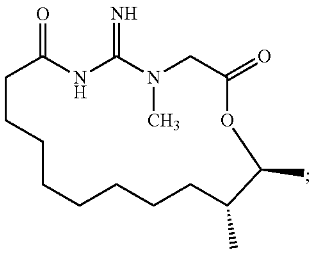;
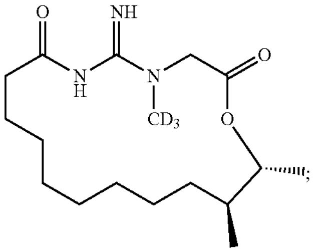 [SMILES: [2H]C([2H])([2H])N1CC(=O)O[C@H](C)[C@@H](C)CCCCCCCCC(=O)NC1=N];
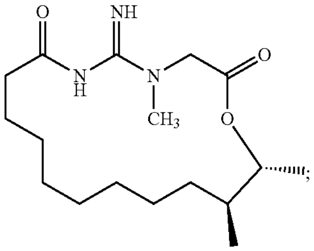 [SMILES: C[C@H]1CCCCCCCCC(=O)NC(=N)N(C)CC(=O)O[C@@H]1C];
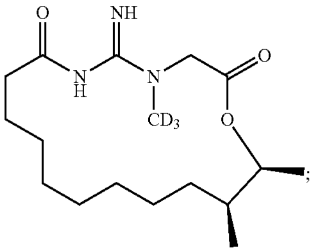 [SMILES: [2H]C([2H])([2H])N1CC(=O)O[C@@H](C)[C@@H](C)CCCCCCCCC(=O)NC1=N];
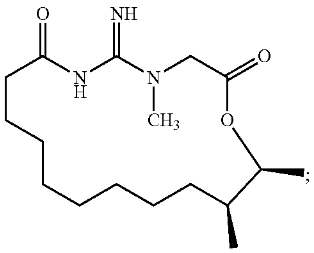 [SMILES: C[C@@H]1OC(=O)CN(C)C(=N)NC(=O)CCCCCCCC[C@@H]1C];

TABLE D-continued
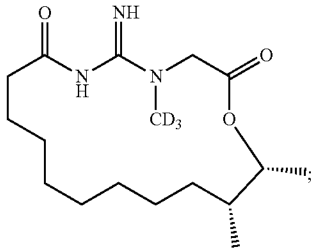
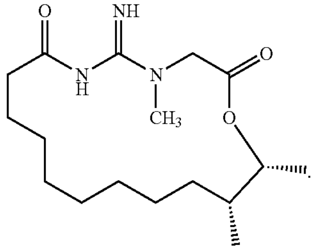 [SMILES: C[C@@H]1CCCCCCCCC(=O)NC(=N)N(C)CC(=O)O[C@@H]1C]
In one embodiment of Formula (I), (I-A), (II), (III), and/or (III-A), the compound is selected from Table E:
TABLE E
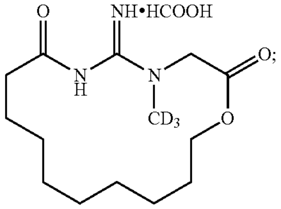
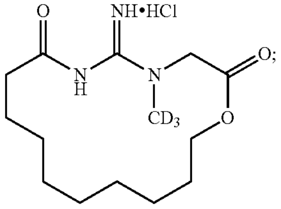
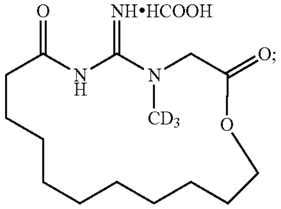
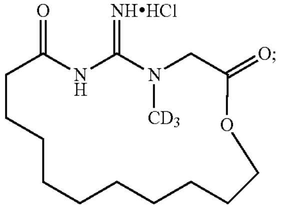
TABLE E-continued
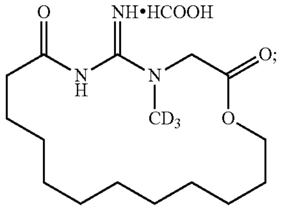
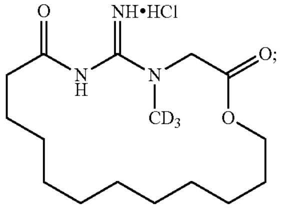
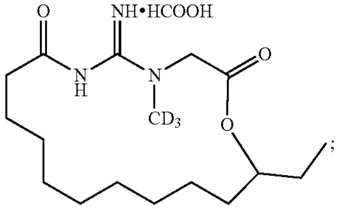
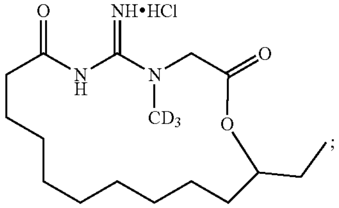
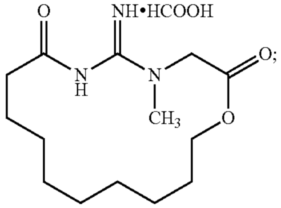
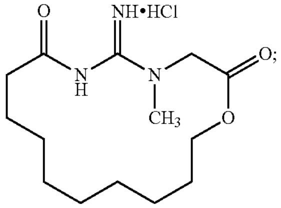
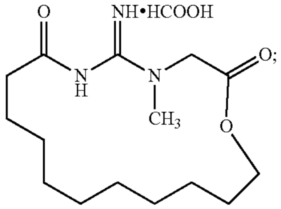

TABLE E-continued
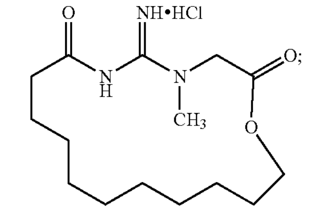
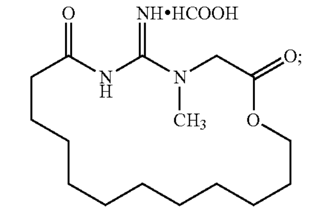
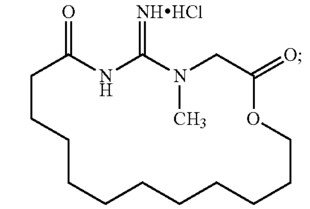
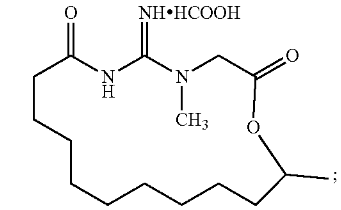
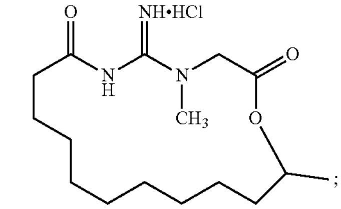
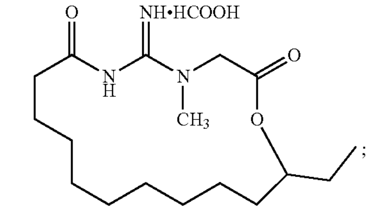
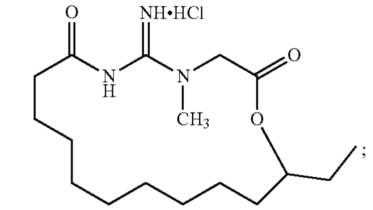
TABLE E-continued
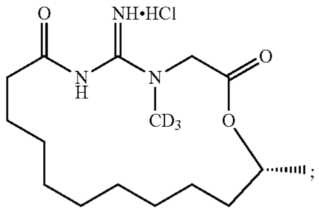
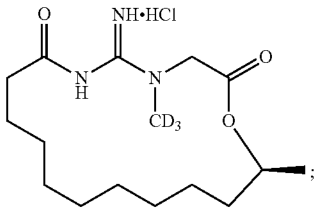
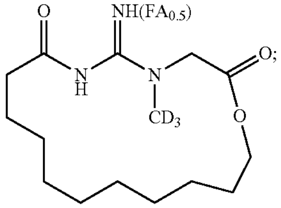
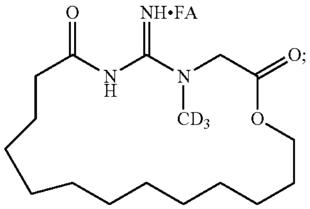
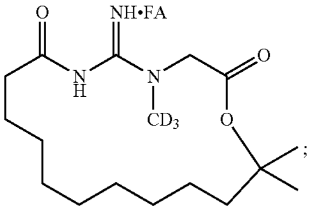
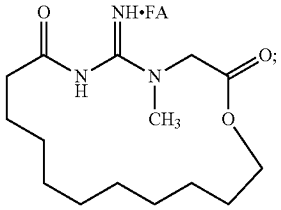
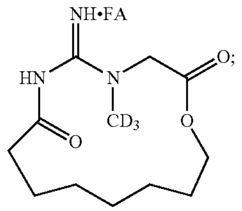

TABLE E-continued
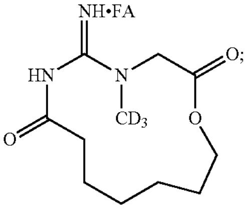
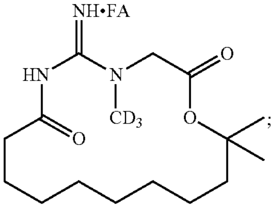
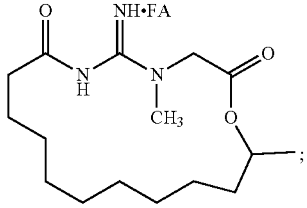
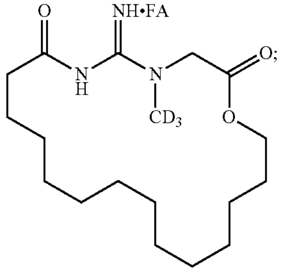
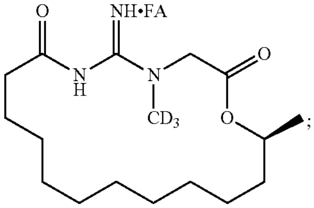
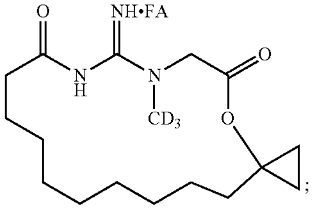
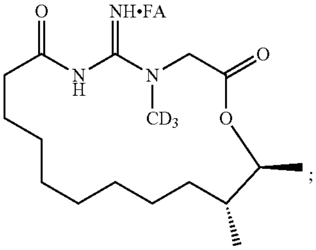
TABLE E-continued
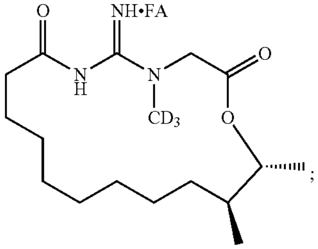
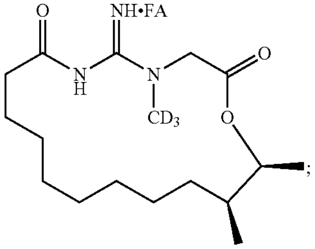
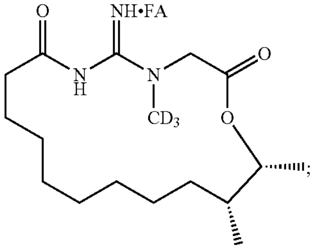
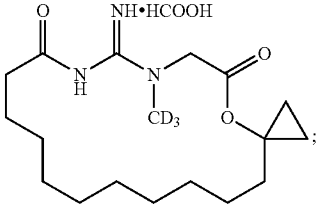
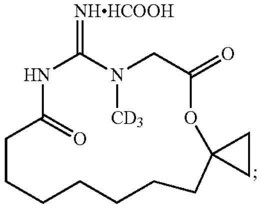
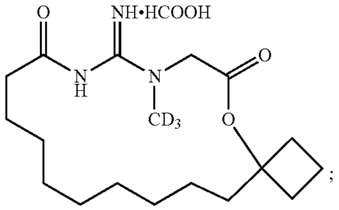
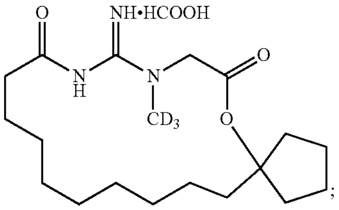

TABLE E-continued

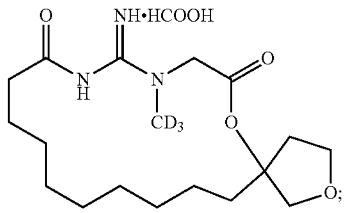

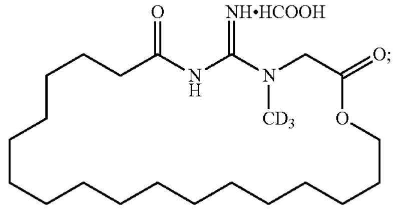

wherein FA is formic acid (HCOOH).

In one embodiment of the compound of Formula (I), the compound is selected from Table S1. In one embodiment of the compound of Formula (I), the compound is selected from Table S2. In one embodiment of the compound of Formula (I), the compound is selected from Table 2A, 2B3, or 2C. In one embodiment of the compound of Formula (I), the compound is selected from Table 2B. In one embodiment of the compound of Formula (I), the compound is selected from Table 3A or 3B. In one embodiment of the compound of Formula (I), the compound is selected from Table 3B.

In one embodiment, the compounds of the present disclosure are designed to increase creatine release during prodrug cleavage. In another embodiment, the compounds of the present disclosure are designed to minimize cyclization into creatinine, which is a dead-end metabolite.

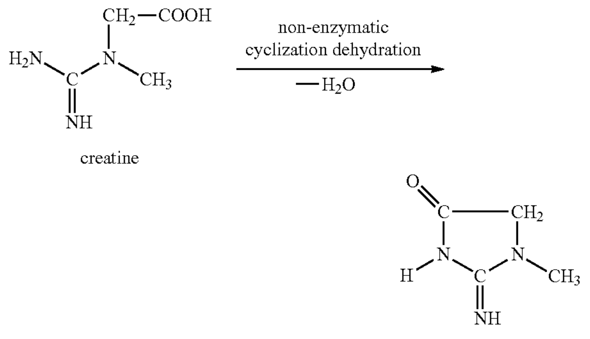

creatine creatinine

In some embodiments of the compounds of formula (I), $R^3$ is —C(O)OR$^6$, where $R^6$ is a straight or branched alkyl have enhanced BBB crossing and/or uptake by neurons/glial cells in brain by: 1) shielding the negative charge of the corresponding acid (COOH) at physiological pH, 2) increasing the hydrophobicity of the compound, and/or 3) protecting the compound from efflux across BBB and/or from neurons/glial cells in brain.

In one embodiment, without being bound to any theory, the cleavage of the compounds of the present disclosure with fatty acid amide chains ($R^1$ is alkyl or alkenyl in formula (I)) can be mediated by fatty acid amide hydrolyse (FAAH) enzymes (FAAH1/2), predominantly expressed in the brain. In other embodiments, the cleavage of the compounds of the present disclosure can be mediated by other enzymes.

The compounds of the present disclosure comprising one or more deuterium atom, in one embodiment, can be useful in facilitating detection and differentiation from endogenous creatine in tissues.

Embodiments of Compositions and Routes of Administration

A compound of the present disclosure can be formulated as a pharmaceutical composition. In one embodiment, such a composition comprises a compound of the present disclosure, or a pharmaceutically acceptable salt or solvate thereof. In one embodiment, the composition further comprises a pharmaceutically acceptable carrier or a pharmaceutically acceptable vehicle. In certain embodiments, a pharmaceutical composition can include more than one compound of the present disclosure. Pharmaceutically acceptable vehicles include diluents, adjuvants, excipients, and carriers.

Pharmaceutical compositions can be produced using standard procedures (see, e.g., "Remington's The Science and Practice of Pharmacy," 21st edition, Lippincott, Williams & Wilcox, 2005, incorporated herein by reference in its entirety). Pharmaceutical compositions may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds disclosed herein into preparations, which can be used pharmaceutically. Proper formulation can depend, in part, on the route of administration.

In one embodiment, the pharmaceutical compositions can provide therapeutic plasma concentrations of a compound of the present disclosure (a creatine prodrug), creatine, or deuterated creatine upon administration to a patient. The promoiety of a creatine prodrug can be cleaved in vivo either chemically and/or enzymatically to release creatine. One or more enzymes present in the intestinal lumen, intestinal tissue, blood, liver, brain or any other suitable tissue of a mammal can enzymatically cleave the promoiety of the administered prodrugs. For example, the promoiety can be cleaved after absorption by the gastrointestinal tract (e.g., in intestinal tissue, blood, liver or other suitable tissue of a mammal). In certain embodiments, a creatine remains conjugated to the promoiety during transit across the intestinal mucosal barrier to provide protection from presystemic metabolism. In certain embodiments, a creatine prodrug is essentially not metabolized to release the corresponding creatine within enterocytes, but is metabolized to the parent drug within the systemic circulation. Cleavage of the promoiety of a creatine prodrug after absorption by the gastrointestinal tract may allow the prodrug to be absorbed into the systemic circulation either by active transport, passive diffusion or by a combination of both active and passive processes.

Creatine prodrugs can remain intact until after passage of the prodrug through a biological barrier, such as the blood-brain barrier. In certain embodiments, prodrugs provided by the present disclosure can be partially cleaved, e.g., one or more, but not all, of the promoieties can be cleaved before passage through a biological barrier or prior to being taken up by a cell, tissue, or organ. Creatine prodrugs can remain intact in the systemic circulation and be absorbed by cells of an organ, either passively or by active transport mechanisms. In certain embodiments, a creatine prodrug will be lipophilic and can passively translocate through cellular membranes. Following cellular uptake, the creatine prodrug can be cleaved chemically and/or enzymatically to release the corresponding compound into the cellular cytoplasm, resulting in an increase in the intracellular concentration of the compound. In certain embodiments, a creatine prodrug can be permeable to intracellular membranes such as the mitochondrial membrane, and thereby facilitate delivery of a prodrug, and following cleavage of the promoiety or promoieties, and the compound of the present disclosure, to an intracellular organelle such as mitochondria.

In one embodiment, a pharmaceutical composition or the present disclosure can include one or more pharmaceutically acceptable vehicles, including excipients, adjuvants, carriers, diluents, binders, lubricants, disintegrants, colorants, stabilizers, surfactants, fillers, buffers, thickeners, emulsifiers, wetting agents, and the like. Vehicles can be selected to alter the porosity and permeability of a pharmaceutical composition, alter hydration and disintegration properties, control hydration, enhance manufacturability, etc.

In certain embodiments, a pharmaceutical composition of the present disclosure can include an adjuvant that facilitates absorption of a compound of the disclosure through the gastrointestinal epithelia. Such enhancers can, for example, open the tight-junctions in the gastrointestinal tract or modify the effect of cellular components, such as p-glycoprotein and the like. Suitable enhancers can include alkali metal salts of salicylic acid, such as sodium salicylate, caprylic or capric acid, such as sodium caprylate or sodium caprate, and the like. Enhancers can include, for example, bile salts, such as sodium deoxycholate. Various p-glycoprotein modulators are described in U.S. Pat. Nos. 5,112,817 and 5,643,909. Various absorption enhancing compounds and materials are described in U.S. Pat. No. 5,824,638, and U.S. Application No. 2006/0046962. Other adjuvants that enhance permeability of cellular membranes include resorcinol, surfactants, polyethylene glycol, and bile acids.

In certain embodiments, a pharmaceutical composition of the present disclosure can include an adjuvant that reduces enzymatic degradation of a compound of the disclosure. Microencapsulation using proteinoid microspheres, liposomes, polysaccharides or the like, can also be effective in reducing enzymatic degradation of administered compounds.

The pharmaceutical composition of the present disclosure can be administered by any suitable routes, which include, but are not limited to administering orally, parenterally, intravenously, intraarterially, intracoronarily, pericardially, perivascularly, intramuscularly, subcutaneously, intradermally, intraperitoneally, intraarticularly, intramuscularly, intraperitoneally, intranasally, epidurally, sublingually, intranasally, intracerebrally, intravaginally, transdermally, rectally, by inhalation spray, rectally, or topically in dosage unit formulations containing conventional nontoxic pharmaceutically acceptable carriers, adjuvants, and vehicles as desired.

In certain embodiments, a pharmaceutical composition of the present disclosure can be formulated for oral administration. Pharmaceutical compositions formulated for oral administration can provide for uptake of a compound of the present disclosure throughout the gastrointestinal tract, or in a particular region or regions of the gastrointestinal tract. In certain embodiments, a pharmaceutical composition can be formulated to enhance uptake a compound of the present disclosure from the upper gastrointestinal tract, and in certain embodiments, from the small intestine. Such compositions can be prepared in a manner known in the pharmaceutical art and can further comprise, in addition to a compound of the present disclosure, one or more pharmaceutically acceptable vehicles, permeability enhancers, and/or a second therapeutic agent.

In certain embodiments, a pharmaceutical composition of the present disclosure can further comprise substances to enhance, modulate and/or control release, bioavailability, therapeutic efficacy, therapeutic potency, stability, and the like. For example, to enhance therapeutic efficacy a compound of the disclosure can be co-administered with one or more active agents to increase the absorption or diffusion of a compound of the disclosure from the gastrointestinal tract or to inhibit degradation of the drug in the systemic circulation. In certain embodiments, a compound of the disclosure can be co-administered with active agents having pharmacological effects that enhance the therapeutic efficacy of a compound of the disclosure.

Pharmaceutical compositions of the present disclosure can take the form of solutions, suspensions, emulsions, tablets, pills, pellets, capsules, capsules containing liquids, powders, sustained-release formulations, suppositories, emulsions, aerosols, sprays, suspensions, or any other form suitable for use. Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles can be of pharmaceutical grade. For oral liquid preparations such as, for example, suspensions, elixirs, and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines, and the like may be added.

When a compound of the present disclosure is acidic, it may be included in any of the above-described formulations as the free acid, a pharmaceutically acceptable salt, a solvate, or a hydrate. Pharmaceutically acceptable salts substantially retain the activity of the free acid, may be prepared by reaction with bases, and tend to be more soluble in aqueous and other protic solvents than the corresponding free acid form. In some embodiments, sodium salts of a compound of the present disclosure are used in the above-described formulations.

The pharmaceutical compositions of the present disclosure can formulated for parenteral administration including administration by injection, for example, into a vein (intravenously), an artery (intraarterially), a muscle (intramuscularly), under the skin (subcutaneously or in a depot formulation), to the pericardium, to the coronary arteries, or used as a solution for delivery to a tissue or organ, for example, use in a cardiopulmonary bypass machine or to bathe transplant tissues or organs. Injectable compositions can be pharmaceutical compositions for any route of injectable administration, including, but not limited to, intravenous, intraarterial, intracoronary, pericardial, perivascular, intramuscular, subcutaneous, intradermal, intraperitoneal, and intraarticular. In certain embodiments, an injectable pharmaceutical composition can be a pharmaceutically appropriate composition for administration directly into the heart, pericardium or coronary arteries.

The pharmaceutical compositions of the present disclosure suitable for parenteral administration can comprise one or more compounds of the present disclosure in combination with one or more pharmaceutically acceptable sterile isotonic aqueous, water-miscible, or non-aqueous vehicles. Pharmaceutical compositions for parenteral use may include substances that increase and maintain drug solubility such as complexing agents and surface acting agents, compounds that make the solution isotonic or near physiological pH such as sodium chloride, dextrose, and glycerin, substances that enhance the chemical stability of a solution such as antioxidants, inert gases, chelating agents, and buffers, substances that enhance the chemical and physical stability, substances that minimize self-aggregation or interfacial induced aggregation, substances that minimize protein interaction with interfaces, preservatives including antimicrobial agents, suspending agents, emulsifying agents, and combinations of any of the foregoing. Pharmaceutical compositions for parenteral administration can be formulated as solutions, suspensions, emulsions, liposomes, microspheres, nanosystems, and powder to be reconstituted as solutions. Parenteral preparations are described in "Remington, The Science and Practice of Pharmacy," 21st edition, Lippincott, Williams & Wilkins, Chapter 41-42, pages 802-849, 2005.

In certain embodiments a pharmaceutical composition of the present disclosure can be formulated for bathing transplantation tissue or organs before, during, or after transit to an intended recipient. Such compositions can be used before or during preparation of a tissue or organ for transplant. In certain embodiments, a pharmaceutical composition can be a cardioplegic solution administered during cardiac surgery. In certain embodiments, a pharmaceutical composition can be used, for example, in conjunction with a cardiopulmonary bypass machine to provide the pharmaceutical composition to the heart. Such pharmaceutical compositions can be used during the induction, maintenance, or reperfusion stages of cardiac surgery (see e.g., Chang et al., Masui 2003, 52(4), 356-62; Ibrahim et al., *Eur. J. Cardiothorac Surg* 1999, 15(1), 75-83; von Oppell et al., *J Thorac Cardiovasc Surg.* 1991, 102(3), 405-12; and Ji et al., *J. Extra Corpor Technol* 2002, 34(2), 107-10). In certain embodiments, a pharmaceutical composition can be delivered via a mechanical device such as a pump or perfuser (see e.g., Hou and March, *J Invasive Cardiol* 2003, 15(1), 13-7; Maisch et al., *Am. J Cardiol* 2001, 88(11), 1323-6; and Macris and Igo, *Clin Cardiol* 1999, 22(1, Suppl 1), 136-9).

For prolonged delivery, a pharmaceutical composition of the present disclosure can be provided as a depot preparation, for administration by implantation, e.g., subcutaneous, intradermal, or intramuscular injection. Thus, in certain embodiments, a pharmaceutical composition can be formulated with suitable polymeric or hydrophobic materials, e.g., as an emulsion in a pharmaceutically acceptable oil, ion exchange resins, or as a sparingly soluble derivative, e.g., as a sparingly soluble salt form of a compound of the present disclosure.

The pharmaceutical compositions of the present disclosure can be formulated so as to provide immediate, sustained, or delayed release of a compound of the present disclosure after administration to the patient by employing procedures known in the art (see, e.g., Allen et al., "Ansel's Pharmaceutical Dosage Forms and Drug Delivery Systems," 8th ed., Lippincott, Williams & Wilkins, August 2004), which is incorporated by reference in its entirety.

Embodiments of Dosage Forms

The pharmaceutical compositions of the present disclosure can be formulated in a unit dosage form. Unit dosage form refers to a physically discrete unit suitable as a unitary dose for patients undergoing treatment, with each unit containing a predetermined quantity of a compound of the present disclosure calculated to produce an intended therapeutic effect. A unit dosage form can be for a single daily dose or one of multiple daily doses, e.g., 2 to 4 times per day. When multiple daily doses are used, the unit dosage can be the same or different for each dose. One or more dosage forms can comprise a dose, which may be administered to a patient at a single point in time or during a time interval.

The pharmaceutical compositions of the present disclosure can be used in dosage forms that provide immediate release and/or sustained release of a compound of the present disclosure. The appropriate type of dosage form can depend on the disease, disorder, or condition being treated, and on the method of administration. For example, for the treatment of acute ischemic conditions such as cardiac failure or stroke the use of an immediate release pharmaceutical composition or dosage form administered parenterally may be appropriate. For treatment of chronic neurodegenerative disorders, controlled release pharmaceutical composition or dosage form administered orally may be appropriate.

In certain embodiments, a dosage form can be adapted to be administered to a patient once, twice, three times, or more frequently per day. Dosing may be provided alone or in combination with other drugs and may continue as long as required for effective treatment of the disease, disorder, or condition.

Pharmaceutical compositions of the present disclosure comprising a creatine prodrug of the present disclosure can be formulated for immediate release for parenteral administration, oral administration or by any other appropriate route of administration.

Controlled drug delivery systems can be designed to deliver a drug in such a way that the drug level is maintained within the therapeutic windows and effective and safe blood levels are maintained for a period as long as the system continues to deliver the drug at a particular rate. Controlled drug delivery can produce substantially constant blood levels of a drug as compared to fluctuations observed with immediate release dosage forms. For some drugs, maintaining a constant bloodstream and tissue concentration throughout the course of therapy is the most desirable mode of treatment. Immediate release of these drugs can cause blood levels to peak above the level required to elicit the desired response, which wastes the drug and may cause or exacerbate toxic side effects. Controlled drug delivery can result in optimum therapy, and not only can reduce the frequency of dosing, and may also reduce the severity of side effects. Examples of controlled release dosage forms include dissolution controlled systems, diffusion controlled systems, ion exchange resins, osmotically controlled systems, erodible matrix systems, pH independent formulations, gastric retention systems, and the like.

In certain embodiments, an oral dosage form of the present disclosure can be a controlled release dosage form. Controlled delivery technologies can improve the absorption of a drug in a particular region or regions of the gastrointestinal tract. The appropriate oral dosage form for a particular pharmaceutical composition of this disclosure can depend, at least in part, on the gastrointestinal absorption properties of the compound of the disclosure, the stability of the compound of the present disclosure in the gastrointestinal tract, the pharmacokinetics of the compound of the disclosure, and the intended therapeutic profile. An appropriate controlled release oral dosage form can be selected for a particular the compound of the disclosure. For example, gastric retention oral dosage forms can be appropriate for compounds absorbed primarily from the upper gastrointestinal tract, and sustained release oral dosage forms can be appropriate for compounds absorbed primarily form the lower gastrointestinal tract.

Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect. Gastric retention dosage forms, i.e., dosage forms that are designed to be retained in the stomach for a prolonged period of time, can increase the bioavailability of drugs that are most readily absorbed by the upper gastrointestinal tract. The residence time of a conventional dosage form in the stomach is 1 to 3 hours. After transiting the stomach, there is approximately a 3 to 5 hour window of bioavailability before the dosage form reaches the colon. However, if the dosage form is retained in the stomach, the drug can be released before it reaches the small intestine and will enter the intestine in solution in a state in which it can be more readily absorbed. Another use of gastric retention dosage forms is to improve the bioavailability of a drug that is unstable to the basic conditions of the intestine (see, e.g., Hwang et al., Critical Reviews in Therapeutic Drug Carrier Systems, 1998, 15, 243-284). To enhance drug absorption from the upper gastrointestinal tract, several gastric retention dosage forms have been developed. Examples include, hydrogels (see, e.g., U.S. Application No. 2003/0008007), buoyant matrices (see, e.g., U.S. Application No. 2006/0013876), polymer sheets (see, e.g., U.S. Application No. 2005/0249798), microcellular foams (see, e.g., U.S. Application No. 2005/0202090), and swellable dosage forms (see, e.g., U.S. Application No. 2005/0019409; U.S. Pat. No. 6,797,283; U.S. Application No. 2006/0045865; U.S. Application No. 2004/0219186; U.S. Pat. Nos. 6,723,340; 6,476,006; 6,120,803; 6,548,083; 6,635,280; 5,780,057). Bioadhesive polymers can also provide a vehicle for controlled delivery of drugs to a number of mucosal surfaces in addition to the gastric mucosa (see, e.g., U.S. Pat. Nos. 6,235,313; 6,207,197; U.S. Application No. 2006/0045865 and U.S. Application No. 2005/0064027). Ion exchange resins have been shown to prolong gastric retention, potentially by adhesion.

In a swelling and expanding system, dosage forms that swell and change density in relation to the surrounding gastric content can be retained in the stomach for longer than a conventional dosage form. A dosage form can absorb water and swell to form a gelatinous outside surface and float on the surface of gastric content surface while maintaining integrity before releasing a drug. Fatty materials can be added to impede wetting and enhance flotation when hydration and swelling alone are insufficient. Materials that release gases may also be incorporated to reduce the density of a gastric retention dosage form. Swelling also can significantly increase the size of a dosage form and thereby impede discharge of the non-disintegrated swollen solid dosage form through the pylorus into the small intestine. Swellable dosage forms can be formed by encapsulating a core containing drug and a swelling agent or by combining a drug, swelling agent, and one or more erodible polymers.

Gastric retention dosage forms can also be in the form of a folded thin sheet containing a drug and water-insoluble diffusible polymer that opens in the stomach to its original size and shape, which is sufficiently large to prevent or inhibit passage of the expanded dosage from through the pyloric sphincter.

Floating and buoyancy gastric retention dosage forms can be designed to trap gases within sealed encapsulated cores that can float on the gastric contents, and thereby be retained in the stomach for a longer time, e.g., 9 to 12 hours. Due to the buoyancy effect, these systems can provide a protective layer preventing the reflux of gastric content into the esophageal region and can also be used for controlled release devices. A floating system can, for example, contain hollow cores containing drug coated with a protective membrane. The trapped air in the cores floats the dosage from on the gastric content until the soluble ingredients are released and the system collapses. In other floating systems, cores contain drug and chemical substances capable of generating gases when activated. For example, coated cores, containing carbonate and/or bicarbonate can generate carbon dioxide in the reaction with hydrochloric acid in the stomach or incorporated organic acid in the system. The gas generated by the reaction is retained to float the dosage form. The inflated dosage form later collapses and clears form the stomach when the generated gas permeates slowly through the protective coating.

Bioadhesive polymers can also provide a vehicle for controlled delivery of drugs to a number of mucosal surfaces in addition to the gastric mucosa (see, e.g., U.S. Pat. Nos. 6,235,313; and 6,207,197). A bioadhesive system can be designed by incorporation of a drug and other excipients within a bioadhesive polymer. On ingestion, the polymer hydrates and adheres to the mucus membrane of the gastrointestinal tract. Bioadhesive polymers can be selected that adhere to a desired region or regions of the gastrointestinal tract. Bioadhesive polymers can be selected to optimized delivery to targeted regions of the gastrointestinal tract including the stomach and small intestine. The mechanism of the adhesion is thought to be through the formation of electrostatic and hydrogen bonding at the polymer-mucus boundary. U.S. Application Nos. 2006/0045865 and 2005/0064027 disclose bioadhesive delivery systems which are useful for drug delivery to both the upper and lower gastrointestinal tract.

Ion exchange resins have been shown to prolong gastric retention, potentially by adhesion.

Gastric retention oral dosage forms can be appropriately used for delivery of drugs that are absorbed mainly from the upper gastrointestinal tract. For example, certain compounds of the present disclosure may exhibit limited colonic absorption, and be absorbed primarily from the upper gastrointestinal tract. Thus, dosage forms that release the compound of the present disclosure in the upper gastrointestinal tract and/or retard transit of the dosage form through the upper gastrointestinal tract will tend to enhance the oral bioavailability of the compound of the disclosure. Other forms of creatine prodrugs disclosed herein can be appropriately used with gastric retention dosage forms.

Polymer matrices have also been used to achieve controlled release of the drug over a prolonged period of time. Such sustained or controlled release can be achieved by limiting the rate by which the surrounding gastric fluid can diffuse through the matrix and reach the drug, dissolve the drug and diffuse out again with the dissolved drug or by using a matrix that slowly erodes, continuously exposing fresh drug to the surrounding fluid. Disclosures of polymer matrices that function by these methods are found, for example, in Skinner, U.S. Pat. Nos. 6,210,710 and 6,217,903; 5,451,409; 5,945,125; PCT International Publication No. WO 96/26718: U.S. Pat. Nos. 4,915,952; 5,328,942; 5,783,212; 6,120,803; and 6,090,411.

Other drug delivery devices that remain in the stomach for extended periods of time include, for example, hydrogel reservoirs containing particles (U.S. Pat. No. 4,871,548); swellable hydroxypropylmethylcellulose polymers (U.S. Pat. No. 4,871,548); planar bioerodible polymers (U.S. Pat. No. 4,767,627); plurality of compressible retention arms (U.S. Pat. No. 5,443,843); hydrophilic water-swellable, cross-linked polymer particles (U.S. Pat. No. 5,007,790); and albumin-cross-linked polyvinylpyrrolidone hydrogels (Park et al., J. Controlled Release 1992, 19, 131-134).

In certain embodiments, pharmaceutical compositions of the present disclosure can be practiced with a number of different dosage forms, which can be adapted to provide sustained release of the compound of the present disclosure upon oral administration. Sustained release oral dosage forms can be used to release drugs over a prolonged time period and are useful when it is desired that a drug or drug form be delivered to the lower gastrointestinal tract. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's Pharmaceutical Sciences," Lippincott, Williams & Wilkins, 21st edition, 2005, Chapters 46 and 47; Langer, Science 1990, 249, 1527-1533; and Rosoff, "Controlled Release of Drugs," 1989, Chapter 2).

Sustained release oral dosage forms include any oral dosage form that maintains therapeutic concentrations of a drug in a biological fluid such as the plasma, blood, cerebrospinal fluid or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's: The Science and Practice of Pharmacy," Lippincott, Williams & Wilkins, 21st edition, 2005, Chapters 46 and 47; Langer, Science 1990, 249, 1527-1533; and Rosoff, "Controlled Release of Drugs," 1989, Chapter 2).

In diffusion-controlled systems, a water-insoluble polymer controls the flow of fluid and the subsequent egress of dissolved drug from the dosage form. Both diffusional and dissolution processes are involved in release of drug from the dosage form. In reservoir devices, a core comprising a drug is coated with the polymer, and in matrix systems, the drug is dispersed throughout the matrix. Cellulose polymers such as ethylcellulose or cellulose acetate can be used in reservoir devices. Examples of materials useful in matrix systems include methacrylates, acrylates, polyethylene, acrylic acid copolymers, polyvinylchloride, high molecular weight polyvinyl alcohols, cellulose derivatives, and fatty compounds such as fatty acids, glycerides, and carnauba wax.

In dissolution-controlled systems, the rate of dissolution of the drug is controlled by slowly soluble polymers or by microencapsulation. Once the coating is dissolved, the drug becomes available for dissolution. By varying the thickness and/or the composition of the coating or coatings, the rate of drug release can be controlled. In some dissolution-controlled systems, a fraction of the total dose can comprise an immediate-release component. Dissolution-controlled systems include encapsulated/reservoir dissolution systems and matrix dissolution systems. Encapsulated dissolution systems can be prepared by coating particles or granules of drug with slowly soluble polymers of different thickness or by microencapsulation. Examples of coating materials useful in dissolution-controlled systems include gelatin, carnauba wax, shellac, cellulose acetate phthalate, and cellulose acetate butyrate. Matrix dissolution devices can be prepared, for example, by compressing a drug with a slowly soluble polymer carrier into a tablet form.

The rate of release of drug from osmotic pump systems is determined by the inflow of fluid across a semipermeable membrane into a reservoir, which contains an osmotic agent. The drug is either mixed with the agent or is located in a reservoir. The dosage form contains one or more small orifices from which dissolved drug is pumped at a rate determined by the rate of entrance of water due to osmotic pressure. As osmotic pressure within the dosage form increases, the drug is released through the orifice(s). The rate of release is constant and can be controlled within tight limits yielding relatively constant plasma and/or blood concentrations of the drug. Osmotic pump systems can provide a constant release of drug independent of the environment of the gastrointestinal tract. The rate of drug release can be modified by altering the osmotic agent and the sizes of the one or more orifices.

The release of drug from erosion-controlled systems is determined by the erosion rate of a carrier matrix. Drug is dispersed throughout the polymer and the rate of drug release depends on the erosion rate of the polymer. The drug-containing polymer can degrade from the bulk and/or from the surface of the dosage form.

Sustained release oral dosage forms can be in any appropriate form for oral administration, such as, for example, in the form of tablets, pills or granules. Granules can be filled into capsules, compressed into tablets or included in a liquid suspension. Sustained release oral dosage forms can additionally include an exterior coating to provide, for example, acid protection, ease of swallowing, flavor, identification, and the like.

In certain embodiments, sustained release oral dosage forms can comprise a therapeutically effective amount of a compound of the present disclosure and a pharmaceutically acceptable vehicle. In certain embodiments, a sustained release oral dosage form can comprise less than a therapeutically effective amount of a compound of the present disclosure and a pharmaceutically effective vehicle. Multiple sustained release oral dosage forms, each dosage form comprising less than a therapeutically effective amount of a compound of the disclosure, can be administered at a single time or over a period of time to provide a therapeutically effective dose or regimen for treating a disease in a patient associated with a dysfunction in energy metabolism such as, for example, ischemia, oxidative stress, a neurodegenerative disease, including amyotrophic lateral sclerosis (ALS), Huntington's disease, Parkinson's disease or Alzheimer's disease, ischemic reperfusion injury, a cardiovascular disease, multiple sclerosis (MS), a psychotic disorder, a genetic disease affecting the creatine kinase system or muscle fatigue.

Sustained release oral dosage forms of the present disclosure can release a compound of the disclosure from the dosage form to facilitate the ability of the compounds of the disclosure to be absorbed from an appropriate region of the gastrointestinal tract, for example, in the small intestine or in the colon. In certain embodiments, a sustained release oral dosage from can release a compound of the present disclosure from the dosage form over a period of at least about 4 hours, at least about 8 hours, at least about 12 hours, at least about 16 hours, at least about 20 hours, and in certain embodiments, at least about 24 hours. In certain embodiments, a sustained release oral dosage form can release a compound of the disclosure from the dosage form in a delivery pattern of from about 0 wt % to about 20 wt % in about 0 to about 4 hours, about 20 wt % to about 50 wt % in about 0 to about 8 hours, about 55 wt % to about 85 wt % in about 0 to about 14 hours, and about 80 wt % to about 100 wt % in about 0 to about 24 hours. In certain embodiments, a sustained release oral dosage form can release a compound of Formula (I) and/or Formula (II) from the dosage form in a delivery pattern of from about 0 wt % to about 20 wt % in about 0 to about 4 hours, about 20 wt % to about 50 wt % in about 0 to about 8 hours, about 55 wt % to about 85 wt % in about 0 to about 14 hours, and about 80 wt % to about 100 wt % in about 0 to about 20 hours. In certain embodiments, a sustained release oral dosage form can release a compound of the present disclosure from the dosage form in a delivery pattern of from about 0 wt % to about 20 wt % in about 0 to about 2 hours, about 20 wt % to about 50 wt % in about 0 to about 4 hours, about 55 wt % to about 85 wt % in about 0 to about 7 hours, and about 80 wt % to about 100 wt % in about 0 to about 8 hours.

Sustained release oral dosage forms comprising a compound of the present disclosure can provide a concentration of the corresponding compound of the present disclosure in the plasma, blood, or tissue of a patient over time, following oral administration to the patient. The concentration profile of a compound of the present disclosure can exhibit an AUC that is proportional to the dose of the corresponding compound of the present disclosure.

Regardless of the specific form of controlled release oral dosage form used, a compound of the present disclosure can be released from an orally administered dosage form over a sufficient period of time to provide prolonged therapeutic concentrations of the compound of the present disclosure in the plasma and/or blood of a patient. Following oral administration, a dosage form comprising a compound of the present disclosure can provide a therapeutically effective concentration of the corresponding compound of the present disclosure in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of a compound of the present disclosure is maintained can be the same or different. The continuous period of time during which a therapeutically effective plasma concentration of a compound of the present disclosure is maintained can begin shortly after oral administration or after a time interval.

In certain embodiments, an oral dosage for treating a disease, disorder, or condition in a patient can comprise a compound of the present disclosure wherein the oral dosage form is adapted to provide, after a single administration of the oral dosage form to the patient, a therapeutically effective concentration of the corresponding compound of the present disclosure in the plasma of the patient for a first continuous time period selected from at least about 4 hours, at least about 8 hours, at least about 12 hours, and at least about 16 hours, and at least about 20 hours.

Embodiments of the Utilities of the Present Compounds (Creatine Prodrugs)

The creatine kinase (creatine-creatine phosphate) system serves a number of functions in maintaining intracellular energy homeostasis (see e.g., Walsh et al., J Physiol, 2001, 537, 971-978). Phosphocreatine acts as a temporal energy buffer at intracellular sites of high energy translocation which operates when the rate of ATP utilization is greater than the rate of ATP production by mitochondrial respiration. Mitochondrial creatine kinase allows the high energy phosphate bond of newly synthesized ATP to be transferred to creatine, thus generating phosphocreatine, which is much more stable than ATP. Phosphocreatine can diffuse throughout a cell and its high energy phosphate bond can be used to regenerate ATP from ADP at heavy energy utilization sites where other creatine kinase enzymes are strategically positioned. These sites include membranes that engage in ion transport, axonal regions involved in transporting material along microtubules to and from presynaptic endings, and presynaptic endings where energy is required for neurotransmission. Neurons synthesize creatine but also rely heavily on transport of creatine into neurons via Creatine Transporter, however the amount of creatine can be severely depleted during injury. As with skeletal and heart muscle, neuronal creatine stores can to some extent be increased by oral supplementation of creatine. The creatine kinase system also serves as an intracellular spatial energy transport mechanism. In this role as an energy carrier, energy generated by the ATP-ADP system within mitochondria is coupled to the creatine-creatine phosphate system in the cytosol, which in turn is coupled to extra-mitochondrial ATP-ADP systems at sites of high intracellular energy transduction. The creatine-creatine phosphate system is also believed to act as a low threshold ADP sensor that maintains ATP-ADP concentration ratios in subcellular locations wherein creatine kinase is functionally coupled to ATP-consuming and ATP-producing pathways. For example, it has been shown that creatine can react with ATP derived from mitochondrial respiration in a reaction catalyzed by mitochondrial creatine kinase and functionally coupled to adenine nucleotide translocase, thereby resulting in an increase in local ADP concentration and the stimulation of mitochondrial respiration. The creatine kinase system is therefore particularly important in maintaining energy homeostasis, including ATP homeostasis, in cells, tissues, and organs with high-energy consumption requirements such as neurons and muscles.

Compounds of the present disclosure, in one embodiment, are designed to transport across blood-brain barrier (BBB) and into neurons and glia of brain either by passive diffusion or active transport mechanism, separate from the creatine transporter. In some embodiments, the compound of the present disclosure, upon uptake into cells will release creatine or deuterated creatine if the prodrug is deuterated. In one embodiment, the compounds of the present disclosure are useful in delivering creatine to the brain of a creatine transporter deficient (CTD) patient, who is characterized to have overall deficiency in creatine and phosphocreatine.

In one embodiment, the compounds of the present disclosure can deliver higher concentration of creatine (or deuterated creatine) to the targeted tissues because the compounds of the present disclosure have improved uptake and absorption when administered to a subject in need thereof, when compared to administration of previously known creatine analogs or unprotected creatine. In some embodiments, the improved uptake and absorption can be useful in treating or ameliorating conditions or diseases where the creatine transporter expression or activity is down-regulated. In one embodiment, the compounds of the present disclosure when administered to a patient can counter or offset the effects of down-regulated creatine transporter activity by providing creatine to the subject in need thereof, which is facilitated by the compounds of the disclosure's improved uptake and absorption properties. A non-functional or a down-regulated creatine transporter can cause inefficiency or ineffectiveness in delivery of creatine to the brain.

CTD patients lack creatine transport and therefore are unable to import creatine from exogenous sources or to exchange creatine from places of synthesis to places of consumption within the brain. Creatine converts into phosphocreatine as energy storage of ATP. During increased energy demand, ATP re-synthesized from phosphocreatine via reversible reaction. Delivery of either creatine or phosphocreatine would therefore restore or improve the energy storage system in the patients.

In one embodiment, the compounds of the present disclosure is capable of first being transported and taken up into neurons and/or glial cells or the like, then subsequently, the compounds of the present disclosure can release creatine (or deuterated creatine) directly to the brain or the targeted cells where the creatine delivery is necessary.

In one embodiment, compounds of the present disclosure and pharmaceutical compositions as described herein can be useful in treating of diseases, disorders or conditions in a patient associated with a dysfunction in energy metabolism. In certain embodiments, the dysfunction in energy metabolism comprises depletion in intracellular ATP concentration, a decreased intracellular creatine and creatine phosphate concentration, a decreased intracellular creatine phosphate to ATP concentration ratio, and/or a dysfunction in the creatine kinase system in a tissue or organ affected by the disease. In certain embodiments, a dysfunction in energy metabolism comprises a decreased intracellular ATP concentration in a tissue or organ affected by the disease. In certain embodiments, a dysfunction in energy metabolism comprises a decreased intracellular creatine and creatine phosphate concentration in a tissue or organ affected by the disease. In certain embodiments, the dysfunction in energy metabolism comprises a dysfunction in the creatine kinase system and/or other intracellular energy pathway in a tissue or organ affected by the disease. In certain embodiments, a disease associated with a dysfunction in energy metabolism is selected from ischemia, oxidative stress, a neurodegenerative disease, ischemic reperfusion injury, a cardiovascular disease, multiple sclerosis, a psychotic disease, and muscle fatigue. In certain embodiments, treating a disease comprises effecting energy homeostasis in a tissue or organ affected by the disease.

Compounds of the invention and pharmaceutical compositions thereof can be used to treat a disease in a patient associated with oxidative stress by administering to a patient in need of such treatment a therapeutically effective amount of a compound of the invention or a pharmaceutical composition thereof. In certain embodiments, the oxidative stress is associated with ischemia or a neurodegenerative disorder. Methods of the invention include treating an oxidatively stressed tissue or organ by contacting the tissue or organ with a compound of the invention or a pharmaceutical composition thereof.

Compounds and pharmaceutical compositions of the invention can be useful in treating diseases, disorders or conditions in which a rapid increase in intracellular creatine levels has a therapeutic effect.

In one embodiment of the present disclosure, the compounds described herein can be used for the treatment of creatine deficiencies by administering an effective amount of the compound of the present disclosure, or a pharmaceutically acceptable salt or solvate thereof, to a patient in need of such treatment. In another embodiment, the method comprises administering a compound of the present disclosure, or a pharmaceutically acceptable salt or solvate thereof, to a patient in need of such treatment; wherein upon administration, the compound, or a pharmaceutically acceptable salt or solvate thereof, continuously provides a therapeutically effective amount of creatine for more than about 4 hours. In some embodiments, the diseases, disorders, or conditions associated with creatine deficiency is ischemia, ischemic Reperfusion Injury, transplant Perfusion, neurodegenerative Diseases, Parkinson's Disease, Alzheimers Disease, Huntington's Disease, Amyotrophic Lateral Sclerosis, Amyotrophic lateral sclerosis (ALS), cerebral creatine deficiency syndromes (CCDS) including creatine transporter dysfunction and creatine biosynthesis disorders, Multiple Sclerosis, psychotic disorders, Schizophrenia, bipolar disorder, anxiety, epilepsy including myoclonic epilepsy, and seizure including seizures with clinical manifestations in muscle, muscular dystrophy, myopathy associated with mitochondrial diseases, such as mitochondrial myopathy, genetic diseases affecting the creatine kinase system, muscle fatigue, muscle strength, organ and cell viability, or diseases related to glucose level regulation. As used herein, "muscular dystrophy" refers to muscle diseases that are typically characterized by progressive skeletal muscle weakness, defects in muscle proteins, and the death of muscle cells and tissue. Muscular dystrophy often weakens the musculoskeletal system and hampers locomotion. Examples of muscular dystrophies include, but are not limited to, Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, oculopharyngeal muscular dystrophy, or any combinations thereof. More details can be found in patent publication, U.S. Pat. No. 8,202,852, the contents of which are incorporated by reference.

The term "cerebral creatine deficiency syndrome" includes a disorder characterized by an inborn error creatine synthesis or by an inborn error of creatine transport. In one embodiment, cerebral creatine deficiency syndrome includes creatine biosynthesis disorders (AGAT and GAMT deficiencies) and creatine transporter disorders. The aberrant creatine transport function in the brain may cause the subject to suffer from a low concentration of creatine in the brain of a subject due to creatine transporter dysfunction. In this disorder, impaired energy metabolism is believed to be associated with impaired learning dysfunction, cognitive function, and neurological syndrome, such as developmental delay, mild epilepsy and severe expressive language impairment. For example, creatine transporter dysfunction can lead to cerebral creatine deficiency syndromes (CCDS) which include a group of inborn errors of creatine biosynthesis and transport through the cellular membranes. These diseases are associated with severe neurologic features: mental retardation, expressive speech and language delay, pervasive developmental disorder, autism, autism spectrum disorder, autistic-like behavior, Asperger's syndrome, attention deficit hyperactivity disorder (ADHD), epilepsy including myoclonic epilepsy, and seizure including seizures with clinical manifestations in muscle. They are characterized by a deficiency of creatine in the brain and metabolic disturbances in the nervous system since the creatine is involved in the cellular phosphocreatine energy system. The only way to treat patients is to restore the cerebral creatine pool by bringing creatine into the brain and more specifically into the target cells. The absence of functional creatine transporters at the blood-brain barrier (BBB) may prevent the entry of creatine into the brain, thus affecting the cognitive functions. For instance, creatine amino acids and phosphocreatine-Mg complex show neuroprotective activity in in vivo animal models of cerebral stroke, ischemia or hypoxia. In addition, a 9-week treatment with cyclocreatine as a treatment in Creatine Transporter SLC6A8 knockout mice resulted in an increase in cyclocreatine and phosphocyclocreatine $^{31}$P-MRS signals as well as normalization of behavioral test findings.

As the brain cells are the ultimate target for creatine delivery, it is imperative that it has to cross the blood brain barrier (BBB), travel into the intersticial space and penetrate into the target brain cells. Creatine does not diffuse easily across biological membranes by itself but cross the BBB efficiently via the active transport process mediated by the Creatine Transporter SLC6A8. In some embodiments, the compounds of the present disclosure can pass the BBB and/or be release inside the targeted cells as free creatine.

In some embodiments, the present compounds are stable in biological fluids, to enter cells by either passive diffusion or active transport, and to release the corresponding creatine or creatine analog into the cellular cytoplasm. Such prodrug analogs can also cross important barrier tissues such as the intestinal mucosa, the blood-brain barrier, and the blood-placental barrier. Because of the ability to pass through biological membranes, these prodrugs can restore and maintain energy homeostasis in ATP depleted cells via the creatine kinase system, and restore ATP levels for normal energy homeostasis and to protect tissues from further ischemic stress.

In other embodiments, the method can continuously provide a therapeutically effective amount of creatine for a period from about 1 hour to about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 hours.

In some embodiments, the method as disclosed herein can provide creatine or d3-creatine accumulation in the brain over the same fold ratio of the number of doses, e.g., 7 daily doses will lead to a 7 fold increase of creatine or d3-creatine in the brain.

In one embodiment, the therapeutically effective amount refers to the amount administered to the patient. In yet another embodiment, the therapeutically effective amount refers to the amount delivered to muscle tissue of the individual. The compounds of the present disclosure, upon administration, are converted to creatine in vivo. That is, the present compounds, upon administration, are metabolized to one or more compounds in the creatine pathway or derivatives thereof (including creatine itself).

Compounds of the present disclosure and the present compositions can be useful in treating of diseases, disorders, or conditions in a patient associated with a dysfunction in energy metabolism. In certain embodiments, a disease associated with a dysfunction in energy metabolism is selected from ischemia, oxidative stress, a neurodegenerative disease, ischemic reperfusion injury, a cardiovascular disease, multiple sclerosis, a psychotic disease, and muscle fatigue. In certain embodiments, treating a disease comprises effecting energy homeostasis in a tissue or organ affected by the disease.

Ischemia

Compounds and pharmaceutical compositions of the invention can be used to treat acute or chronic ischemic diseases, disorders or conditions. Ischemia is an imbalance of oxygen supply and demand in a cell, tissue or organ. Ischemia is characterized by hypoxia, including anoxia, insufficiency of metabolic substrates for normal cellular bioenergetics, and accumulation of metabolic waste. Ischemia in a tissue or organ may be caused by a vascular insufficiency such as arteriosclerosis, thrombosis, embolism, torsion or compression, hypotension such as shock or hemorrhage, increased tissue mass (hypertrophy), increased workload (tachycardia, exercise), and/or by decreased tissue stress such as cardiac dilation. Ischemia can also result from trauma or surgical procedures. Depending on the severity and duration of the injury, ischemia can lead to a reversible loss of cellular function or to irreversible cell death. Different cell types have different thresholds to ischemic injury depending, at least in part, on the cellular energy requirements of the tissue(s) or organ(s) affected. Parenchymal cells such as neurons (3-4 minutes), cardiac muscles, hepatocytes, renal tubular cells, gastrointestinal epithelium (20-80 minutes) and fibroblasts, epidermis, and skeletal muscle (hours) are more susceptible to ischemic injury than are stromal cells. A number of studies suggest a correlation between the functional capacity of the creatine kinase system and ischemic tolerance of a given tissue, and indicate that strategies toward improving the functional capacity of the creatine kinase system may be effective for improving ischemic tolerance in tissue (see e.g., Wyss and Kaddurah-Daouk, Physiological Reviews, 2000, 80(3), 1107-1213, which is incorporated by reference herein in its entirety). For example oral creatine supplementation inhibits mitochondrial cytochrome C release and downstream caspase-3 activation, resulting in ischemic neuroprotection. Associated with inhibition of cytochrome C release and caspase-3 activation and with neuroprotection, creatine administration inhibits ischemia-mediated ATP depletion.

Compounds and pharmaceutical compositions of the invention can be used to treat acute or chronic ischemia. In certain embodiments, a compound or composition can be particularly useful in acute or emergency treatment of ischemia in tissue or organs characterized by high energy demand such as the brain, neurons, heart, lung, kidney or the intestine.

The high energy requirements compared to the low energy reserves render the brain particularly vulnerable to hypoxic conditions. Although the brain constitutes only a small fraction of total body weight (about 2%), it accounts for a disproportionately large percentage of 02 consumption (about 20%). Under physiological conditions, enhanced demand for 02 is rapidly and adequately compensated for by an increase in cerebral blood flow. The longer the duration of hypoxia/ischemia, the larger and more diffuse the areas of the brain that are affected. The area most vulnerable to ischemic damage are the brainstem, hippocampus, and cerebral cortex. Injury progresses and eventually becomes irreversible except if oxygenation is not restored. Acute cell death occurs mainly through necrosis but hypoxia also causes delayed apoptosis. In addition glutamate release from presynaptic neurons can further enhance $Ca^{2+}$ influx and result in catastrophic collapse in postsynaptic cells. If the ischemia is not too severe, cells can suppress some functions, i.e., protein synthesis and spontaneous electrical activity, in a process called penumbra, which can be reversed provided that $O_2$ supply is resumed. However, the process of restoring oxygen levels to ischemically stressed tissue, e.g., reperfusion, can also induce irreversible cell death, mainly through the generation of reactive oxygen species and inflammatory cell infiltration.

The neuron is limited by its availability of energy-generating substrates, being limited to using primarily glucose, ketone bodies or lactate. The neuron does not produce or store glucose or ketone bodies and cannot survive for any significant period of time without a substrate, which is absorbed and used directly or indirectly from the bloodstream. Thus, a constant supply of an energy-generating substrate must be present in the blood at all times in an amount sufficient to supply the entire brain and the rest of the body with energy-generating substrates. Brain cells require a concentration of about 5 mM glucose (or its equivalent) in order to maintain its optimal rate of oxidative phosphorylation to produce ATP. Nutrients enter cells by passing through the cell membrane. Nutrient delivery frequently relies upon mechanisms outside the cell membranes such as oral intake, absorption, circulatory transport and interstitial flux. Once localized in the vicinity of the cell, membrane-specific processes play a role in nutrient transport sequentially across the blood-brain barrier and then into the interior of the cell and into various subcellular organelles. Nutrient transport is made possible by the breakdown of ATP by ATPases. $Na^+$ gradients created by $Na^+/K^+$ ATPases can be used by cells to transport nutrient molecules across cell membranes.

Lack of oxygen or glucose prevents or limits the ability of neurons to synthesize ATP. The intracellular creatine/phosphocreatine system can to some extent compensate for the lack of oxygen or glucose. Creatine kinase catalyses the synthesis of phosphocreatine from creatine in normal brain tissue. Under conditions of ATP depletion, phosphocreatine can donate its phosphate group to ADP to resynthesize ATP. However, neuronal phosphocreatine content is limited following complete anoxia or ischemia phosphocreatine is also rapidly depleted. ATP depletion is believed to block $Na^+/K^+$ ATPases causing neurons to depolarize and lose membrane potential.

Depleted oxygen levels have several other consequences on cellular bioenergetics and function that can ultimately lead to cell death. For example, dysfunctional bioenergetics also involves impaired calcium homeostasis. The regulation of calcium plays a central role in the proper functioning and survival of neurons. Calcium pumps, located on cell membranes, use ATP to transport calcium ions out of the neuron. Proper activity of the calcium pump is essential in the maintenance of neuronal, mitochondrial, and endoplasmic reticulum homeostasis. Alterations in calcium pump function modulate enzyme activity within a cell and also play a critical role in triggering the mitochondrial permeability transition, which may lead to cell death. For example, intracellular $Ca^{2+}$ metabolism is believed to contribute to cell death in Alzheimer's disease. For example, under conditions of oxidative stress, the production of oxygen free radicals exceeds endogenous free radical protective mechanisms. This impairs neuronal metabolism and function by direct free radical damage to important cellular biomolecules including membrane lipids, nucleic acids, and functional proteins; and by modulation of critical signal transduction pathways. Neural function is dependent upon transmission of electrical impulses between cells. This activity relies upon the precise actions of multiple membrane proteins each suspended in a phospholipid bilayer. The optimal activity of this dynamic membrane microenvironment depends upon the exact status and chemical composition of the lipid constituents. Lacking the appropriate phospholipid environment, cell channel proteins, enzymes, and receptors are not able to achieve sustained levels of optimal function. In addition, oxidative stress and/or abnormal methyl metabolism can reduce the fluidity of the membranous lipid bilayer with subsequent adverse effects upon embedded functional proteins. Dysfunctional bioenergetics may also adversely affect passage of high-energy electrons along the respiratory chain.

Apoptosis refers to the energy-requiring process of programmed cell death whereupon an individual nerve cell under appropriate circumstances initiates a process leading to cell death. Certain of the mechanisms discussed above may initiate apoptotic pathways including oxidative stress, calcium overload, cellular energy deficiency, trophic factor withdrawal, and abnormal amyloid precursor protein processing. In ischemia, neurons in the brain tissue region that are most severely affected by hypoxic injury die rapidly by necrosis, whereas neurons exposed to lesser degrees of hypoxia die by apoptosis. The shift from necrotic cell death to apoptotic cell death is associated with increasing levels of intra cellular ATP. It has been shown that creatine supplementation can result in a greater ability to buffer ATP levels and reduce cell death and thereby provide protection from anoxic and ischemic damage (Balestrino et al., Amino Acids, 2002, 23, 221-229; and Zhu et al., J Neurosci 2004, 24(26), 5909-5912, each of which is incorporated by reference herein in its entirety).

In certain embodiments, compounds and pharmaceutical compositions of the invention can be used to treat a cardiovascular disease, including cerebral ischemia (stroke) and myocardial ischemia (heart infarction). Ischemic heart disease, as the underlying cause of many cases of acute myocardial infarction, congestive heart failure, arrhythmias, and sudden cardiac death, is a leading cause of morbidity and mortality in all industrialized nations. In the United States, ischemic heart disease causes nearly 20% of all deaths (about 600,000 deaths each year) with many of these deaths occurring before the patient arrives at the hospital. An estimated 1.1 million Americans will have a new or recurrent acute myocardial infarction each year, and many survivors will experience lasting morbidity, with progression to heart failure and death. As the population grows older and co-morbidities such as obesity and diabetes become more prevalent, the public health burden caused by ischemic heart disease is likely to increase.

Optimal cellular bioenergetics rely on: (1) adequate delivery of oxygen and substrates to the mitochondria; (2) the oxidative capacity of mitochondria; (3) adequate amounts of high-energy phosphate and the creatine phosphate/ATP ratio; (4) efficient energy transfer from mitochondria to sites of energy utilization; (5) adequate local regulation of ATP/ADP ratios near ATPases; and (6) efficient feedback signaling from utilization sites to maintain energetic homeostasis in the cell. Defects in these cardiac energetic pathways have been found in cardiovascular diseases such as dilated and hypertrophic cardiomyopathies of various origins, cardiac conduction defects, and ischemic heart diseases (Saks et al., J Physiol 2006, 571.2, 253-273; Ventura-Clapier et al., J Physiol 2003, 555.1, 1-13; and Ingwall and Weiss, Circ Res 2004, 95, 135-145, each of which is incorporated by reference herein in its entirety). A decrease in the creatine phosphate/ATP ratio is consistently reported in failing human heart and experimental heart failure, even at moderate workloads. Creatine, creatine transporter, creatine phosphate, and ATP are significantly reduced and the decrease in the creatine phosphate/ATP ratio is a predictor of mortality in congenital heart failures. Also, a down-regulation of creatine transporter protein expression has been shown in experimental animal models of heart disease, as well as in failing human myocardium, indicating that the generally lowered creatine phosphate and creatine levels measured in failing hearts are related to down-regulated creatine transporter capacity.

Cardiovascular disease includes hypertension, heart failure such as congestive heart failure or heart failure following myocardial infarction, arrhythmia, diastolic dysfunction such as left ventricular diastolic dysfunction, diastolic heart failure or impaired diastolic filling, systolic dysfunction, ischemia such as myocardial ischemia, cardiomyopathy such as hypertrophic cardiomyopathy and dilated cardiomyopathy, sudden cardiac death, myocardial fibrosis, vascular fibrosis, impaired arterial compliance, myocardial necrotic lesions, vascular damage in the heart, vascular inflammation in the heart, myocardial infarction including both acute post-myocardial infarction and chronic post-myocardial infarction conditions, coronary angioplasty, left ventricular hypertrophy, decreased ejection fraction, coronary thrombosis, cardiac lesions, vascular wall hypertrophy in the heart, endothelial thickening, myocarditis, and coronary artery disease such as fibrinoid necrosis or coronary arteries. Ventricular hypertrophy due to systemic hypertension in association with coronary ischemic heart disease is recognized as a major risk factor for sudden death, post infarction heart failure, and cardiac rupture. Patients with severe left ventricular hypertrophy are particularly susceptible to hypoxia or ischemia.

Neuroprotective effects of compounds of the invention can be determined using animal models of cerebral ischemia such as those described, for example, in Cimino et al., Neurotoxicol 2005, 26(5), 9929-33; Konstas et al., Neurocrit Care 2006, 4(2), 168-78; Wasterlain et al., Neurology 1993, 43(11), 2303-10; and Zhu et al., J Neuroscience 2004, 24(26), 5909-5912.

Ischemic Reperfusion Injury

Reperfusion injury is damage to tissue when blood supply returns to the tissue after a period of ischemia. The absence in a tissue or organ of oxygen and nutrients from blood creates a condition in which the restoration of circulation results in inflammation and oxidative damage from the oxygen, rather than restoration of normal function. The damage of ischemic reperfusion injury is due in part to the inflammatory response of damaged tissue. Reperfusion contributes to the ischemic cascade in the brain, which is involved in stroke and brain trauma. Repeated bouts of ischemia and reperfusion also are believed to be a factor leading to the formation and failure to heal of chronic wounds such as pressure sores and diabetic foot ulcers (Mustoe, Am J Surgery 2004, 187(5), S65-S70, which is incorporated by reference herein in its entirety). In certain embodiments, the methods and compositions of the disclosure can protect the muscle and organs such as, for example, the heart, liver, kidney, brain, lung, spleen and steroidogenic organs, e.g. thyroid, adrenal glands, and gonads, from damage as a result of ischemia reperfusion injury.

Ischemia followed by reperfusion is a major cause of skeletal and cardiac muscle damage in mammals. Ischemia is caused by a reduction in oxygen supplied to tissues or organs as a result of reduced blood flow and can lead to organ dysfunction. Reduced blood supply can result from occlusion or blood diversion due to vessel thrombosis, such as myocardial infarction, stenosis, accidental vessel injury or surgical procedures. Subsequent reestablishment of an adequate supply of oxygenated blood to the tissue or organ can result in increased damage, a process known as ischemia reperfusion injury or occlusion reperfusion injury. Complications arising from ischemia reperfusion injury include stroke, fatal or non-fatal myocardial infarction, myocardial remodeling, aneurysms, peripheral vascular disease, tissue necrosis, kidney failure, and post-surgical loss of muscle tone.

Restoration of coronary blood flow following a transient period of ischemia (reperfusion), though necessary for myocyte survival and to restore aerobic metabolism, introduces a separate series of stresses that can exacerbate cell injury. Reactive oxygen species generated during reperfusion damage proteins and membrane structures within cardiomyocytes and can activate signal transduction pathways that lead to apoptosis. Adherence of leukocytes to post ischemic endothelial cells can clog capillaries and release inflammatory mediators. Upon reperfusion, the influx of activated complement, catecholamines, and other signaling molecules contained in plasma or elaborated locally within the myocardial wall may also influence the course of events within cells of the myocardium. As with the direct consequences of ischemia, reperfusion injury is an important feature of acute coronary syndromes. Such injury occurs both spontaneously, as a result of fibrinolysis of coronary thromboses, and as a consequence of fibrinolytic drugs of acute angioplasty, treatments that are now commonly used to open occluded vessels.

In certain embodiments, compounds of the invention and compositions thereof can be used to treat a condition associated with ischemic reperfusion injury or reduce ischemic reperfusion injury. Ischemic reperfusion injury can be associated with oxygen deprivation, neutrophil activation, and/or myeloperoxidase production. Ischemic reperfusion injury can be the result of a number of disease states or can be iatrogenically induced, for example, by blood clots, stenosis or surgery.

In certain embodiments, compounds of the invention and compositions thereof can be used to treat stroke, a fatal or non-fatal myocardial infarction, peripheral vascular disease, tissue necrosis, and kidney failure, and post-surgical loss of muscle tone resulting from ischemic reperfusion injury. In certain embodiments, the methods and compositions of the invention reduce or mitigate the extent of ischemic reperfusion injury.

In certain embodiments, compounds of the invention and compositions thereof can be used to treat, reduce or prevent ischemic reperfusion injury associated with occlusion or blood diversion due to vessel stenosis, thrombosis, accidental vessel injury or surgical procedures.

In certain embodiments, compounds of the invention and compositions thereof can also be used to treat any other condition associated with ischemic reperfusion such as myocardial infarction, stroke, intermittent claudication, peripheral arterial disease, acute coronary syndrome, cardiovascular disease and muscle damage as a result of occlusion of a blood vessel.

In certain embodiments, compounds of the invention and compositions thereof can be used to treat reperfusion injury associated with myocardial infarction, stenosis, at least one blood clot, stroke, intermittent claudication, peripheral arterial disease, acute coronary syndrome, cardiovascular disease or muscle damage as a result of occlusion of a blood vessel.

In certain embodiments, compounds of the invention and compositions thereof can be used in conjunction with cardiac surgery, for example, in or with cardioplegic solutions to prevent or minimize ischemia or reperfusion injury to the myocardium. In certain embodiments, the methods and compositions can be used with a cardiopulmonary bypass machine during cardiac surgery to prevent or reduce ischemic reperfusion injury to the myocardium.

In certain embodiments, the methods and compositions of the invention can protect muscle and organs such as, for example, the heart, liver, kidney, brain, lung, spleen and steroidogenic organs, e.g. thyroid, adrenal glands, and gonads, from damage as a result of ischemia reperfusion injury.

Compounds and pharmaceutical compositions of the invention can be used to treat ischemic reperfusion injury in a tissue or organ by contacting the tissue or organ with an effective amount of the compound or the pharmaceutical composition. The tissue or organ may be in a patient or outside of a patient, i.e., extracorporeal. The tissue or organ can be a transplant tissue or organ, and the compound or the pharmaceutical composition can be contacted with the transplant tissue or organ before removal, during transit, during transplantation, and/or after the tissue or organ is transplanted in the recipient.

In certain embodiments, compounds or pharmaceutical compositions of the invention can be used to treat ischemic perfusion injury caused by surgery, such as cardiac surgery. A compound or a pharmaceutical composition can be administered before, during, and/or after surgery. In certain embodiments, a compound or a pharmaceutical composition of the invention can be used to treat ischemic reperfusion injury to muscle, including cardiac muscle, skeletal muscle or smooth muscle, and in certain embodiments, to treat ischemic reperfusion injury to an organ such as the heart, lung, kidney, spleen, liver, neuron or brain. A compound of the invention or a pharmaceutical composition thereof can be administered before, during, and/or after surgery.

In certain embodiments, compounds of the invention or pharmaceutical compositions of the invention can be used to treat ischemic perfusion injury to a muscle, including cardiac muscle, skeletal muscle, and smooth muscle.

The efficacy of a compound of the invention for treating ischemic reperfusion injury may be assessed using animal models and in clinical trials. Examples of useful methods for assessing efficacy in treating ischemic reperfusion injury are disclosed, for example, in Prass et al., J Cereb Blood Flow Metab 2007, 27(3), 452-459; Arya et al., Life Sci 2006, 79(1), 38-44; Lee et al., Eur. J. Pharmacol 2005, 523(1-3), 101-108; and U.S. Application No. 2004/0038891. Useful methods for evaluating transplant perfusion/reperfusion are described, for example, in Ross et al., Am J. Physiol-Lung Cellular Mol. Physiol. 2000, 279(3), L528-536.

Transplant Perfusion

In certain embodiments, compounds of the invention or pharmaceutical compositions thereof can be used to increase the viability of organ transplants by perfusing the organs with a compound of the invention or pharmaceutical compositions thereof. Increased creatine phosphate levels are expected to prevent or minimize ischemic damage to an organ. Perfusing with a creatine prodrug during organ removal, following removal of a donor organ, during implantation, and/or following organ transplantation, can enhance the viability of the organ, especially a metabolically active organ, such as the heart or pancreas, and thereby reduce rejection rates, and/or increase the time window for organ transplants.

In certain embodiments, compounds of the invention and compositions thereof can be used to treat, prevent or reduce ischemia reperfusion injury in extracorporeal tissue or organs. Extracorporeal tissue or organs are tissue or organs not in an individual (also termed ex vivo), such as in transplantation. For tissue and organ transplantation, donor tissue and organs removed are also susceptible to reperfusion injury during removal, while in transit, during implantation and following transplantation into a recipient. The methods and compositions can be used to increase the viability of a transplantable tissue or organ by, for example, supplementing solutions used to maintain or preserve transplantable tissues or organs. For example, the methods and compositions can be used to bathe the transplantable tissue or organ during transport or can be placed in contact with the transplantable tissue or organ prior to, during or after transplantation.

Neurodegenerative Diseases

Neurodegenerative diseases featuring cell death can be categorized as acute, e.g., stroke, traumatic brain injury, spinal cord injury, and chronic, e.g., amyotrophic lateral sclerosis, Huntington's disease, Parkinson's disease, and Alzheimer's disease. Although these diseases have different causes and affect different neuronal populations, they share similar impairment in intracellular energy metabolism. For example, the intracellular concentration of ATP is decreased, resulting in cystolic accumulation of $Ca^{2+}$ and stimulation of formation of readily oxygen species. $Ca^{2+}$ and reactive oxygen species, in turn, can trigger apoptotic cell death. For these disorders, impairment of brain creatine metabolism is also evident as reflected in decreased total creatine concentration, creatine phosphate concentration, creatine kinase activity, and/or creatine transporter content (see e.g., Wyss and Kaddurah-Daouk, Physiol Rev 2000, 80, 1107-1213; Tarnopolsky and Beal, Ann Neurol 2001, 49, 561-574; and Butterfield and Kanski, Mech Ageing Dev 2001, 122, 945-962, each of which is incorporated by reference herein in its entirety).

Acute and chronic neurodegenerative diseases are illnesses associated with high morbidity and mortality and few options are available for their treatment. A characteristic of many neurodegenerative diseases, which include stroke, brain trauma, spinal cord injury, amyotrophic lateral sclerosis, Huntington's disease, Alzheimer's disease, and Parkinson's disease, is neuronal-cell death. Cell death occurs by necrosis or apoptosis. Necrotic cell death in the central nervous system follows acute ischemia or traumatic injury to the brain or spinal cord. It occurs in areas that are most severely affected by abrupt biochemical collapse, which leads to the generation of free radicals and excitotoxins. Mitochondrial and nuclear swelling, dissolution of organelles, and condensation of chromatin around the nucleus are followed by the rupture of nuclear and cytoplasmic membranes and the degradation of DNA by random enzymatic cuts. Apoptotic cell death can be a feature of both acute and chronic neurological diseases. Apoptosis occurs in areas that are not severely affected by an injury. For example, after ischemia, there is necrotic cell death in the core of the lesion, where hypoxia is most severe, and apoptosis occurs in the penumbra, where collateral blood flow reduces the degree of hypoxia. Apoptotic cell death is also a component of the lesion that appears after brain or spinal cord injury. In chronic neurodegenerative diseases, apoptosis is the predominant form of cell death. In apoptosis, a biochemical cascade activates proteases that destroy molecules required for cell survival and others that mediate a program of cell death. Caspases directly and indirectly contribute to the morphologic changes of the cell during apoptosis (Friedlander, N Engl J Med 2003, 348(14), 1365-75). Oral creatine supplementation has been shown to inhibit mitochondrial cytochrome C release and downstream caspase-3 activation, and ATP depletion inhibition of the caspase-mediated cell death cascades in cerebral ischemia (Zhu et al., J Neurosci 2004, 24(26), 5909-5912) indicating that manipulation of the creatine kinase system may be effective in controlling apoptotic cell death in chronic neurodegenerative diseases.

Creatine administration shows neuroprotective effects, particularly in animal models of Parkinson's disease, Huntington's disease, and ALS (Wyss and Schulze, Neuroscience 2002, 112(2), 243-260, which is incorporated by reference herein in its entirety) and it is recognized that the level of oxidative stress may be a determinant of metabolic determination in a variety of neurodegenerative diseases. Current hypotheses regarding the mechanisms of creatine-mediated neuroprotection include enhanced energy storage, as well as stabilization of the mitochondrial permeability transition pore by octameric conformation of creatine kinase. It is therefore believed that higher levels of intracellular creatine improve the overall bioenergetic status of a cell, rendering the cell more resistant to injury.

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate and thereby reduce the production of dopamine and the number of connections between nerve cells in the basal ganglia. As a result, the basal ganglia are unable to smooth muscle movement and coordinate changes in posture, leading to tremor, incoordination, and slowed, reduced movement (bradykinesia) (Blandini, et al., Mol. Neurobiol. 1996, 12, 73-94).

It is believed that oxidative stress may be a factor in the metabolic deterioration seen in Parkinson's disease tissue (Ebadi et al., Prog Neurobiol 1996, 48, 1-19; Jenner and Olanow, Ann Neurol 1998, 44 Suppl 1, S72-S84; and Sun and Chen, J Biomed Sci 1998, 5, 401-414, each of which is incorporated by reference herein in its entirety) and creatine supplementation has been shown to exhibit neuroprotective effects (Matthews et al., Exp Neurol, 1999, 157, 142-149, which is incorporated by reference herein in its entirety).

The efficacy of administering a compound of the invention for treating Parkinson's disease may be assessed using animal and human models of Parkinson's disease and clinical studies. Animal and human models of Parkinson's disease are known (see, e.g., O'Neil et al., CNS Drug Rev. 2005, 11(1), 77-96; Faulkner et al., Ann. Pharmacother. 2003, 37(2), 282-6, Olson et al., Am. J. Med. 1997, 102(1), 60-6; Van Blercom et al., Clin Neuropharmacol. 2004, 27(3), 124-8; Cho et al., Biochem. Biophys. Res. Commun. 2006, 341, 6-12; Emborg, J. Neuro. Meth. 2004, 139, 121-143; Tolwani et al., Lab Anim Sci 1999, 49(4), 363-71; Hirsch et al., J Neural Transm Suppl 2003, 65, 89-100; Orth and Tabrizi, Mov Disord 2003, 18(7), 729-37; Betarbet et al., Bioessays 2002, 24(4), 308-18; and McGeer and McGeer, Neurobiol Aging 2007, 28(5), 639-647).

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

It is believed that oxidative stress may be a factor in the metabolic deterioration seen in Alzheimer's disease tissue with creatine kinase being one of the targets of oxidative damage (Pratico et al., FASEB J 1998, 12, 1777-1783: Smith et al., J Neurochem 1998, 70, 2212-2215; and Yatin et al., Neurochem Res 1999, 24, 427-435, each of which is incorporated by reference herein in its entirety) and studies have shown a correlation between intracellular levels of creatine phosphate and the progress of dementia (Pettegrew et al., Neurobiol Aging 1994, 15, 117-132, which is incorporated by reference herein in its entirety).

The efficacy of administering a compound of the invention for treating Alzheimers disease may be assessed using animal and human models of Alzheimer's disease and clinical studies. Useful animal models for assessing the efficacy of compounds for treating Alzheimer's disease are disclosed, for example, in Van Dam and De Dyn, Nature Revs Drug Disc 2006, 5, 956-970; Simpkins et al., Ann NY Acad Sci, 2005, 1052, 233-242; Higgins and Jacobsen, Behav Pharmacol 2003, 14(5-6), 419-38; Janus and Westaway, Physiol Behav 2001, 73(5), 873-86; and Conn, ed., "Handbook of Models in Human Aging," 2006, Elsevier Science & Technology.

Huntington's Disease

Huntington's disease is an autosomal dominant neurodegenerative disorder in which specific cell death occurs in the neostriatum and cortex (Martin, N Engl J Med 1999, 340, 1970-80, which is incorporated by reference herein in its entirety). Onset usually occurs during the fourth or fifth decade of life, with a mean survival at age onset of 14 to 20 years. Huntington's disease is fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin. A number of studies suggest that there is a progressive impairment of energy metabolism, possibly resulting from mitochondrial damage caused by oxidative stress as a consequence of free radical generation. Preclinical studies in animal models of Huntington's disease have documented neuroprotective effects of creatine administration. For example, neuroprotection by creatine is associated with higher levels of creatine phosphate and creatine and reduced lactate levels in the brain, consistent with improved energy production (see, Ryu et al., Pharmacology & Therapeutics 2005, 108(2), 193-207, which is incorporated by reference herein in its entirety).

The efficacy of administering a compound of the invention for treating Huntington's disease may be assessed using animal and human models of Huntington's disease and clinical studies. Animal models of Huntington's disease are disclosed, for example, in Riess and Hoersten, U.S. Application No. 2007/0044162; Rubinsztein, Trends in Genetics, 2002, 18(4), 202-209; Matthews et al., J. Neuroscience 1998, 18(1), 156-63; Tadros et al., Pharmacol Biochem Behav 2005, 82(3), 574-82, and in U.S. Pat. No. 6,706,764, and U.S. Application Nos. 2002/0161049, 2004/0106680, and 2007/0044162. A placebo-controlled clinical trial evaluating the efficacy of creatine supplementation to treat Huntington's disease is disclosed in Verbessem et al., Neurology 2003, 61, 925-230.

Amyotrophic Lateral Sclerosis (ALS)

Amyotrophic lateral sclerosis (ALS) is a progressive neurodegenerative disorder characterized by the progressive and specific loss of motor neurons in the brain, brain stem, and spinal cord (Rowland and Schneider, N Engl J Med 2001, 344, 1688-1700, which is incorporated by reference herein in its entirety). ALS begins with weakness, often in the hands and less frequently in the feet, that generally progresses up an arm or leg. Over time, weakness increases and spasticity develops characterized by muscle twitching and tightening, followed by muscle spasms and possibly tremors. The average age of onset is 55 years, and the average life expectancy after clinical onset is 4 years. The only recognized treatment for ALS is riluzole, which can extend survival by only about three months. Oral creatine has been shown to provide neuroprotective effects in a transgenic animal model of ALS (Klivenyi et al., Nat Med 1999, 5, 347-50, which is incorporated by reference herein in its entirety).

The efficacy of administering a compound of the invention for treating ALS may be assessed using animal and human models of ALS and clinical studies. Natural disease models of ALS include mouse models (motor neuron degeneration, progressive motor neuropathy, and wobbler) and the hereditary canine spinal muscular atrophy canine model (Pioro and Mitsumoto, Clin Neurosci, 19954996, 3(6), 375-85). Experimentally produced and genetically engineered animal models of ALS can also useful in assessing therapeutic efficacy (see e.g., Doble and Kennelu, Amyotroph Lateral Scler Other Motor Neuron Disord. 2000, 1(5), 301-12; Grieb, Folia Neuropathol. 2004, 42(4), 239-48; Price et al., Rev Neurol (Paris), 1997, 153(8-9), 484-95; and Klivenyi et al., Nat Med 1999, 5,347-50). Specifically, the SOD1-G93A mouse model is a recognized model for ALS. Examples of clinical trial protocols useful in assessing treatment of ALS are described, for example, in Mitsumoto, Amyotroph Lateral Scler Other Motor Neuron Disord. 2001, 2 Suppl 1, S10-S14; Meininger, Neurodegener Dis 2005, 2, 208-14; and Ludolph and Sperfeld, Neurodegener Dis. 2005, 2(3-4), 215-9.

Multiple Sclerosis

Multiple sclerosis (MS) is a multifaceted inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, Lab Invest 2001, 81, 263-281; and Virley, NeruoRx 2005, 2(4), 638-649). Although the causal events that precipitate the disease are not fully understood, most evidence implicates an autoimmune etiology together with environmental factors, as well as specific genetic predispositions. Functional impairment, disability, and handicap are expressed as paralysis, sensory and octintive disturbances spasticity, tremor, a lack of coordination, and visual impairment, which impact on the quality of life of the individual. The clinical course of MS can vary from individual to individual, but invariably the disease can be categorized in three forms: relapsing-remitting, secondary progressive, and primary progressive. Several studies implicate dysfunction of creatine phosphate metabolism with the etiology and symptoms of the disease (Minderhoud et al., Arch Neurol 1992, 49(2), 161-5: He et al., Radiology 2005, 234(1), 211-7; Tartaglia et al., Arch Neurology 2004, 61(2), 201-207; Duong et al., J Neurol 2007, Apr. 20; and Ju et al., Magnetic Res Imaging 2004, 22, 427-429), although creatine ingestion alone does not appear to be effective in improving exercise capacity in individuals with MS (Lambert et al., Arch Phys Med Rehab 2003, 84(8), 1206-1210).

Assessment of MS treatment efficacy in clinical trials can be accomplished using tools such as the Expanded Disability Status Scale (Kurtzke, Neurology 1983, 33, 1444-1452) and the MS Functional Composite (Fischer et al., Mult Scler, 1999, 5, 244-250) as well as magnetic resonance imaging lesion load, biomarkers, and self-reported quality of life (see e.g., Kapoor, Cur Opinion Neurol 2006, 19, 255-259). Animal models of MS shown to be useful to identify and validate potential therapeutics include experimental autoimmune/allergic encephalomyelitis (EAE) rodent models that simulate the clinical and pathological manifestations of MS (Werkerle and Kurschus, Drug Discovery Today: Disease Models, Nervous System Disorders, 2006, 3(4), 359-367; Gijbels et al., Neurosci Res Commun 2000, 26, 193-206; and Hofstetter et al., J Immunol 2002, 169, 117-125), and nonhuman primate EAE models ('t Hart et al., Immunol Today 2000, 21, 290-297).

Psychotic Disorders

In certain embodiments, compounds of the invention or pharmaceutical compositions thereof can be used to treat psychotic disorders such as, for example, schizophrenia, bipolar disorder, and anxiety.

Schizophrenia

Schizophrenia is a chronic, severe, and disabling brain disorder that affects about one percent of people worldwide, including 3.2 million Americans. Schizophrenia encompasses a group of neuropsychiatric disorders characterized by dysfunctions of the thinking process, such as delusions, hallucinations, and extensive withdrawal of the patient's interests from other people. Schizophrenia includes the subtypes of paranoid schizophrenia characterized by a preoccupation with delusions or auditory hallucinations, hebephrenic or disorganized schizophrenia characterized by disorganized speech, disorganized behavior, and flat or inappropriate emotions; catatonic schizophrenia dominated by physical symptoms such as immobility, excessive motor activity or the assumption of bizarre postures; undifferentiated schizophrenia characterized by a combination of symptoms characteristic of the other subtypes; and residual schizophrenia in which a person is not currently suffering from positive symptoms but manifests negative and/or cognitive symptoms of schizophrenia (see DSM-IV-TR classifications 295.30 (Paranoid Type), 295.10 (Disorganized Type), 295.20 (Catatonic Type), 295.90 (Undifferentiated Type), and 295.60 (Residual Type); Diagnostic and Statistical Manual of Mental Disorders, $4^{th}$ Edition, American Psychiatric Association, 297-319, 2005). Schizophrenia includes these and other closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and unspecified psychotic disorders (DSM-IV-TR, $4^{th}$ Edition, pp. 297-344, American Psychiatric Association, 2005).

Schizophrenia symptoms can be classified as positive, negative or cognitive. Positive symptoms of schizophrenia include delusion and hallucination, which can be measured using, for example, the Positive and Negative Syndrome Scale (PANSS) (Kay et al., Schizophrenia Bulletin 1987, 13, 261-276). Negative symptoms of schizophrenia include affect blunting, anergia, alogia and social withdrawal, which can be measured for example, using (the Scales for the Assessment of Negative Symptoms (SANS) (Andreasen, 1983, Scales for the Assessment of Negative Symptoms (SANS), Iowa City, Iowa). Cognitive symptoms of schizophrenia include impairment in obtaining organizing, and using intellectual knowledge which can be measured using the Positive and Negative Syndrome Scale-cognitive subscale (PANSS-cognitive subscale) (Lindenmayer et al., J Nerv Ment Dis 1994, 182, 631-638) or by assessing the ability to perform cognitive tasks such as, for example, using the Wisconsin Card Sorting Test (see, e.g., Green et al., Am J Psychiatry 1992, 149, 162-67; and Koren et al., Schizophr Bull 2006, 32(2), 310-26).

A number of studies support a correlation of schizophrenia with a dysfunction in brain high energy phosphate metabolism (Fukuzako, World J Biol Psychiatry 2001, 2(2), 70-82; and Gangadhar et al., Prog Neuro-Psychopharmacology & Biological Psychiatry 2006, 30, 910-913. Patients suffering from schizophrenia exhibit lower phosphocreatine levels in the left and right frontal regions of the brain, which are highly correlated with hostility-suspiciousness and anxiety-depression assessment subscales (Deicken et al., Biol Psychiatry 1994, 36(8), 503-510; Volz et al., Biol Psychiatry 1998, 44, 399-404; and Volz et al., Biol Psychiatry 2000, 47, 954-961). Creatine supplementation has accordingly been proposed for treating schizophrenia (see e.g., Lyoo et al., Psychiatry Res: Neuroimaging 2003, 123, 87-100).

The efficacy of creatine prodrugs and pharmaceutical compositions thereof for treating schizophrenia may be determined by methods known to those skilled in the art. For example, negative, positive, and/or cognitive symptom(s) of schizophrenia may be measured before and after treatment of the patient. Reduction in such symptom(s) indicates that a patient's condition has improved. Improvement in the symptoms of schizophrenia may be assessed using, for example, the Scale for Assessment of Negative Symptoms (SANS), Positive and Negative Symptoms Scale (PANSS) (see, e.g., Andreasen, 1983, Scales for the Assessment of Negative Symptoms (SANS), Iowa City, Iowa; and Kay et al., Schizophrenia Bulletin 1987, 13, 261-276), and using Cognitive Deficits tests such as the Wisconsin Card Sorting Test (WCST) and other measures of cognitive function (see, e.g., Keshavan et al., Schizophr Res 2004, 70(2-3), 187-194; Rush, Handbook of Psychiatric Measures, American Psychiatric Publishing 2000; Sajatovic and Ramirez, Rating Scales in Mental Health, 2nd ed, Lexi-Comp, 2003, Keefe, et al., Schizophr Res. 2004, 68(2-3), 283-97; and Keefe et al., Neuropsychopharmacology, 19 Apr. 2006.

The efficacy of creatine prodrugs and pharmaceutical compositions thereof may be evaluated using animal models of schizophrenic disorders (see e.g., Geyer and Moghaddam, in "Neuropsychopharmacology," Davis et al., Ed., Chapter 50, 689-701, American College of Neuropsychopharmacology, 2002). For example, conditioned avoidance response behavior (CAR) and catalepsy tests in rats are shown to be useful in predicting antipsychotic activity and EPS effect liability, respectively (Wadenberg et al., Neuropsychopharmacology, 2001, 25, 633-641).

Bipolar Disorder

Bipolar disorder is a psychiatric condition characterized by periods of extreme mood. The moods can occur on a spectrum ranging from depression (e.g., persistent feelings of sadness, anxiety, guilt, anger, isolation, and/or hopelessness, disturbances in sleep and appetite, fatigue and loss of interest in usually enjoyed activities, problems concentrating, loneliness, self-loathing, apathy or indifference, depersonalization, loss of interest in sexual activity, shyness or social anxiety, irritability, chronic pain, lack of motivation, and morbid/suicidal ideation) to mania (e.g., elation, euphoria, irritation, and/or suspiciousness). Bipolar disorder is defined and categorized in the Diagnostic and Statistical Manual of Mental Disorders, $4^{th}$ Ed., Text Revision (DSM-IV-TR), American Psychiatric Assoc., 200, pages 382-401. Bipolar disorder includes bipolar I disorder, bipolar II disorder, cyclothymia, and bipolar disorder not otherwise specified.

Patients with bipolar depression are shown to have impaired brain high energy phosphate metabolism characterized by reduced levels of phosphocreatine and creatine kinase (Kato et al., J Affect Disord 1994, 31(2), 125-33; and Segal et al., Eur Neuropsychopharmacology 2007, 17, 194-198) possibly involving mitochondrial energy metabolism (Stork and Renshaw, Molecular Psychiatry 2005, 10, 900-919).

Treatment of bipolar disorder can be assessed in clinical trials using rating scales such as the Montgomery-Asberg Depression Rating Scale, the Hamilton Depression Scale, the Raskin Depression Scale, Feighner criteria, and/or Clinical Global Impression Scale Score (Gijsman et al., Am J Psychiatry 2004, 161, 1537-1547).

Anxiety

Anxiety is defined and categorized in the Diagnostic and Statistical Manual of Mental Disorders, $4^{th}$ Ed., Text Revision (DSM-IV-TR), American Psychiatric Assoc., 200, pages 429-484. Anxiety disorders include panic attack, agoraphobia, panic disorder without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder, and anxiety disorder not otherwise specified. Recent work has documented a correlation of decreased levels of creatine/phosphocreatine in centrum semiovale (a representative region of the cerebral white matter) with the severity of anxiety (Coplan et al., Neuroimaging, 2006, 147, 27-39).

Useful animal models for assessing treatment of anxiety include fear-potentiated startle (Brown et al., J Experimental Psychol, 1951, 41, 317-327), elevated plus-maze (Pellow et al., J Neurosci. Methods 1985, 14, 149-167; and Hogg, Pharmacol Biochem Behavior 1996, 54(1), 21-20), and fear-potentiated behavior in the elevated plus-maze (Korte and De Boer, Eur J Pharmacol 2003, 463, 163-175). Genetic animal models of anxiety are known (Toh, Eur J Pharmacol 2003, 463, 177-184) as are other animal models sensitive to anti-anxiety agents (Martin, Acta Psychiatr Scand Suppl 1998, 393, 74-80).

In clinical trials, efficacy can be evaluated using psychological procedures for inducing experimental anxiety applied to healthy volunteers and patients with anxiety disorders (see e.g., Graeff, et al., Brazilian J Medical Biological Res 2003, 36, 421-32) or by selecting patients based on the Structured Clinical interview for DSM-IV Axis I Disorders as described by First et al., Structured Clinical Interview for DSM-IV Axis I Disorders, Patient Edition (SCIDIP), Version 2. Biometrics Research, New York State Psychiatric Institute, New York, 1995. Any of a number of scales can be used to evaluate anxiety and the efficacy of treatment including, for example, the Penn State Worry Questionnaire (Behar et al., J Behav Ther Exp Psychiatr 2003, 34, 25-43), the Hamilton Anxiety and Depression Scales, the Spielberger State-Trait Anxiety Inventory, and the Liebowitz Social Anxiety Scale (Hamilton, J Clin Psychiatry 1980, 41, 21-24; Spielberger and Vagg, J Personality Assess 1984, 48, 95-97; and Liebowitz, J Clin Psychiatry 1993, 51, 31-35 (Suppl.)).

Genetic Diseases Affecting the Creatine Synthesis and Transport System

The intracellular creatine pool is maintained by uptake of creatine from the diet and by endogenous creatine synthesis. Many tissues, especially the brain, liver and pancreas, contain the $Na^+$—$Cl^-$ dependent creatine transport (SLC6A8), which is responsible for active creatine transport through the plasma membrane. Creatine biosynthesis involves the action of two enzymes: L-arginine:glycine amidinotransferase (AGAT) and guanidinoacetate transferase (GAMT). AGAT catalyses the transfer of the amidino group of arginine to glycine to generate ornithine and guanidinoacetate. Guanidino acetate is methylated at the amidino group by GAMT to give creatine (see e.g., Wyss and Kaddurah-Daouk, Phys Rev 2000, 80, 1107-213).

In humans, two genetic errors in creatine biosynthesis and one in creatine transporter are known and involve deficiencies of AGAT, GAMT, and creatine transporter (Schulze, Cell Biochem, 2003, 244(1-2), 143-50; Sykut-Cegielska et al., Acta Biochimica Polonica 2004, 51(4), 875-882). Patients with disorders of creatine synthesis have systemic depletion of creatine and creatine phosphate. Patients affected with AGAT deficiency can show mental and motor retardation, severe delay in speech development, and febrile seizures (Item et al., Am J Hum Genet. 2001, 69, 1127-1133). Patients affected with GAMT deficiency can show developmental delay with absence of active speech, autism with self-injury, extra pyramidal symptoms, and epilepsy (Stromberger et al., J Inherit Metab Dis 2003, 26, 299-308). Patients with creatine transporter deficiency exhibit intracellular depletion of creatine and creatine phosphate. The gene encoding the creatine transporter is located on the X-chromosome, and affected male patients show mild to severe mental retardation with affected females having a milder presentation (Salomons et al., J. Inherit Metab Dis 2003, 26, 309-18; Rosenberg et al., Am J Hum Genet. 2004, 75, 97-105; deGrauw et al., Neuropediatrics 2002, 33(5), 232-238; Clark et al., Hum Genet, 2006, April).

Creatine supplementation in dosages from about 350 mg to 2 g/kg body weight per day have been shown effective in resolving the clinical symptoms of AGAT or GAMT deficiencies (see e.g., Schulze, Cell Biochem, 2003, 244(1-2), 143-50). However, unlike in patients with GAMT and AGAT deficiency, in patients with creatine transporter deficiency oral creatine supplementation does not result in an increase in brain creatine levels (see Stockler-Ipsiroglu et al., in Physician's Guide to the Treatment and Follow up of Metabolic Diseases, eds Blau et al., Springer Verlag, 2004).

Muscle Fatigue

During high-intensity exercise, ATP hydrolysis is initially buffered by creatine phosphate via the creatine kinase reaction (Kongas and van Beek, $2^{nd}$ Int. Conf. Systems Biol 2001, Los Angeles Calif., Omnipress, Madison, Wis., 198-207; and Walsh et al., J Physiol 2001, 537.3, 971-78, each of which is incorporated by reference herein in its entirety). During exercise, whereas creatine phosphate is available instantaneously for ATP regeneration, glycolysis is induced with a delay of a few seconds, and stimulation of mitochondrial oxidative phosphorylation is delayed even further. Because the creatine phosphate stores in muscle are limited, during high-intensity exercise, creatine phosphate is depleted within about 10 seconds. It has been proposed that muscle performance can be enhanced by increasing the muscle stores of creatine phosphate and thereby delay creatine phosphate depletion. Although creatine and/or creatine phosphate supplementation may improve muscle performance in intermittent, supramaximal exercise, there is no indication that supplementation enhances endurance performance. On the other hand, intravenous injection of creatine phosphate appears to improve exercise tolerance during prolonged submaximal exercise (Clark, J Athletic Train, 1997, 32, 45-51, which is incorporated by reference herein in its entirety).

Muscle Strength

Dietary creatine supplementation in normal healthy individuals has beneficial side effects on muscle function, and as such its use by amateur and professional athletics has increased. There is evidence to suggest that creatine supplementation can enhance overall muscle performance by increasing the muscle store of creatine phosphate, which is the most important energy source for immediate regeneration of ATP in the first few seconds of intense exercise, by accelerating restoration of the creatine phosphate pool during recovery periods, and by depressing the degradation of adenosine nucleotides and possibly also accumulation of lactate during exercise (see e.g., Wyss and Kaddurah-Daouk, Physiol Rev 2000, 80(3), 1107-1213).

However, in normal healthy individuals, the continuous and prolonged use of creatine fails to maintain elevated creatine and creatine phosphate in muscle (see e.g., Juhn et al., Clin J Sport Med 1998, 8, 286-297; Terjung et al., Med Sci Sports Exerc 2000, 32, 706-717; and Vandenberghe et al., J Appl Physiol 1997, 83, 2055-2063, each of which is incorporated by reference herein in its entirety), possibly as a result of the down regulation of the creatine transporter activity and the transporter protein content (Snow and Murphy, Mol Cell Biochem 2001, 224(1-2), 169-181, which is incorporated by reference herein in its entirety). Thus, creatine prodrugs of the invention independent of creatine transporter may be used to maintain, restore, and/or enhance muscle strength in a mammal, and in particular a human.

The efficacy of administering a compound of the invention for maintaining, restoring, and/or enhancing muscle strength may be assessed using animal and human models and clinical studies. Animal models that can be used for evaluation of muscle strength are disclosed, for example, in Wirth et al., J Applied Physiol 2003, 95, 402-412 and Timson, J. Appl Physiol 1990, 69(6), 1935-1945. Muscle strength can be assessed in humans using methods disclosed, for example, in Oster, U.S. Application No. 2007/0032750, U.S. Application No. 2007/0012105, and/or using other methods known to those skilled in the art.

Organ and Cell Viability

In certain embodiments, the isolation of viable brain, muscle, pancreatic or other cell types for research or cellular transplant can be enhanced by perfusing cells and/or contacting cells with an isolation or growth media containing a creatine or creatine phosphate analog prodrug. In certain embodiments, the viability of a tissue organ or cell can be improved by contacting the tissue organ or, cell with an effective amount of a compound of the invention or a pharmaceutical composition thereof.

Diseases Related to Glucose Level Regulation

Administration of creatine phosphate reduces plasma glucose levels, and therefore can be useful in treating diseases related to glucose level regulation such as hyperglycemia, insulin dependent or independent diabetes, and related diseases secondary to diabetes (U.S. Application No 2005/0256134).

The efficacy of administering a compound of the invention for treating diseases related to glucose level regulation may be assessed using animal and human models and clinical studies. Compounds can be administered to animals such as rats, rabbits or monkeys, and plasma glucose concentrations determined at various times (see e.g., U.S. Application No. 2003/0232793). The efficacy of compounds for treating insulin dependent or independent diabetes and related diseases secondary to diabetes can be evaluated using animal models of diabetes such as disclosed, for example, in Shafrir, "Animal Models of Diabetes," Ed., 2007, CRC Press; Mordes et al., "Animal Models of Diabetes," 2001, Harwood Academic Press; Mathe, Diabete Metab 1995, 21(2), 106-111; and Rees and Alcolado, Diabetic Med. 2005, 22, 359-370.

Embodiments of the Dosing and Administration of the Present Compounds

Compounds of the present disclosure or pharmaceutically acceptable salts or pharmaceutically acceptable solvates of any of the foregoing can be administered to treat diseases or disorders as described herein.

The amount of a compound of the invention that will be effective in the treatment of a particular disease, disorder or condition disclosed herein will depend on the nature of the disease, disorder or condition, and can be determined by standard clinical techniques known in the art. In addition, in vitro or in vivo assays may optionally be employed to help identify optimal dosage ranges. The amount of a compound administered can depend on, among other factors, the patient being treated, the weight of the patient, the health of the patient, the disease being treated, the severity of the affliction, the route of administration, the potency of the compound, and the judgment of the prescribing physician.

For systemic administration, a therapeutically effective dose can be estimated initially from in vitro assays. For example, a dose can be formulated in animal models to achieve a beneficial circulating composition concentration range. Initial doses can also be estimated from in vivo data, e.g., animal models, using techniques that are known in the art. Such information can be used to more accurately determine useful doses in humans. One having ordinary skill in the art can optimize administration to humans based on animal data.

Creatine occurs naturally in the human body and is partly synthesized by the kidney, pancreas, and liver (approximately 1-2 grams per day), and partly ingested with food (approximately 1-5 grams per day). Cells actively take up creatine via the creatine transporter. Within a cell, creatine kinase phosphorylates creatine to form a pool of creatine phosphate that can act as a temporal and spatial energy buffer.

Creatine, creatine phosphate, and analogs thereof can be administered in a high dose without adverse side effects. For example, creatine monohydrate has been administered to athletes and body builders in amounts ranging from 2-3 gm/day, and creatine phosphate has been administered to patients with cardiac diseases by intravenous injection up to 8 gm/day, without adverse side effects. Animals fed a diet containing up to 1% cyclocreatine also do not exhibit adverse effects (see, e.g., Griffiths and Walker, J. Biol. Chem. 1976, 251(7), 2049-2054; Annesley et al., J Biol Chem 1978, 253(22), 8120-25; Lillie et al., Cancer Res 1993, 53, 3172-78; and Griffiths, J Biol Chem 1976, 251(7), 2049-54).

In certain embodiments, a therapeutically effective dose of a compound of the invention can comprise from about 1 mg-equivalents to about 20,000 mg-equivalents of a creatine phosphate analog per day, from about 100 mg-equivalents to about 12,000 mg-equivalents of creatine phosphate analog per day, from about 1,000 mg-equivalents to about 10,000 mg-equivalents of creatine phosphate analog per day, and in certain embodiments, from about 4,000 mg-equivalents to about 8,000 mg-equivalents of creatine phosphate analog per day.

A dose can be administered in a single dosage form or in multiple dosage forms. When multiple dosage forms are used the amount of compound contained within each dosage form can be the same or different. The amount of a compound of the invention contained in a dose can depend on the route of administration and whether the disease, disorder or condition in a patient is effectively treated by acute, chronic or a combination of acute and chronic administration.

In certain embodiments an administered dose is less than a toxic dose. Toxicity of the compositions described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a pharmaceutical composition can exhibit a high therapeutic index. The data obtained from these cell culture assays and animal studies can be used in formulating a dosage range that is not toxic for use in humans. A dose of a pharmaceutical composition of the invention can be within a range of circulating concentrations in for example the blood, plasma or central nervous system, that include the effective dose and that exhibits little or no toxicity. A dose may vary within this range depending upon the dosage form employed and the route of administration utilized.

During treatment, a dose and dosing schedule can provide sufficient or steady state levels of an effective amount of creatine and creatine phosphate to treat a disease. In certain embodiments, an escalating dose can be administered.

In one embodiment, the present disclosure provides a sustained release pharmaceutical composition comprising a compound of the present disclosure, or a pharmaceutically acceptable salt or solvate thereof, wherein the release of the compound of the present disclosure, creatine, or deuterated creatine, is over a period of about 4 hours or more. In other embodiments, the release of the compound is over a period of about 5, about 6, about 7, about 8, about 9, about 10, about 11, about 12, about 13, about 14, about 15, about 16, about 17, about 18, about 19, about 20, about 21, about 22, about 23, or about 24 hours.

In another embodiment, the present disclosure provides a sustained release pharmaceutical composition comprising a compound of the present disclosure, or a pharmaceutically acceptable salt or solvate thereof, wherein the pharmacological effect from the compounds of the present disclosure, creatine, or deuterated creatine lasts about 4 hours or more upon administration of the composition. In other embodiments, the pharmacological effect from the compound lasts about 5, about 6, about 7, about 8, about 9, about 10, about 11, about 12, about 13, about 14, about 15, about 16, about 17, about 18, about 19, about 20, about 21, about 22, about 23, or about 24 hours.

In another embodiment, the present disclosure provides a sustained release pharmaceutical composition comprising a compound of the present disclosure, or a pharmaceutically acceptable salt or solvate thereof, wherein the composition, upon administration, provides a therapeutically effective amount of the compound for about 4 hours or more. In other embodiments, the composition provides a therapeutically effective amount of the compound for about 5, about 6, about 7, about 8, about 9, about 10, about 11, about 12, about 13, about 14, about 15, about 16, about 17, about 18, about 19, about 20, about 21, about 22, about 23, or about 24 hours.

In certain embodiments, a compound of the present disclosure or a pharmaceutical composition thereof can be administered as a single, one time dose or chronically. By chronic it is meant that the methods and compositions of the disclosure are practiced more than once to a given individual. For example, chronic administration can be multiple doses of a pharmaceutical composition administered to an animal, including an individual, on a daily basis, twice daily basis, or more or less frequently, as will be apparent to those of skill in the art. In another embodiment, the methods and compositions are practiced acutely. By acute it is meant that the methods and compositions of the disclosure are practiced in a time period close to or contemporaneous with the ischemic or occlusive event. For example, acute administration can be a single dose or multiple doses of a pharmaceutical composition administered at the onset of an ischemic or occlusive event such as acute myocardial infarction, upon the early manifestation of an ischemic or occlusive event such as, for example, a stroke, or before, during or after a surgical procedure. A time period close to or contemporaneous with an ischemic or occlusive event will vary according to the ischemic event but can be, for example, within about 30 minutes of experiencing the symptoms of a myocardial infarction, stroke, or intermittent claudication. In certain embodiments, acute administration is administration within about an hour of the ischemic event. In certain embodiments, acute administration is administration within about 2 hours, about 6 hours, about 10 hours, about 12 hours, about 15 hours or about 24 hours after an ischemic event.

In certain embodiments, a compound of the present disclosure or a pharmaceutical composition thereof can be administered chronically. In certain embodiments, chronic administration can include several intravenous injections administered periodically during a single day. In certain embodiments, chronic administration can include one intravenous injection administered as a bolus or as a continuous infusion daily, about every other day, about every 3 to 15 days, about every 5 to 10 days, and in certain embodiments, about every 10 days.

In certain embodiments, a compound of the present disclosure, a pharmaceutically acceptable salt thereof, or a pharmaceutically acceptable solvate of any of the foregoing, can be used in combination therapy with at least one other therapeutic agent. A compound of the present disclosure and other therapeutic agent(s) can act additively or, and in certain embodiments, synergistically. In some embodiments, a compound of the present disclosure can be administered concurrently with the administration of another therapeutic agent, such as for example, a compound for treating a disease associated with a dysfunction in energy metabolism; treating muscle fatigue; enhancing muscle strength and endurance; increasing the viability of organ transplants; and improving the viability of isolated cells. In some embodiments, a compound of the present disclosure, a pharmaceutically acceptable salt, or a pharmaceutically acceptable solvate of any of the foregoing can be administered prior to or subsequent to administration of another therapeutic agent, such as for example, a compound for treating a disease associated with a dysfunction in energy metabolism such as CCDS/CTD, ischemia, ventricular hypertrophy, a neurodegenerative disease such as ALS, Huntington's disease, Parkinson's disease, or Alzheimer's disease, surgery related ischemic tissue damage, and reperfusion tissue damage; treating multiple sclerosis (MS), treating a psychotic disorder such as schizophrenia, bipolar disorder, or anxiety; treating muscle fatigue; enhancing muscle strength and endurance; increasing the viability of organ transplants; and improving the viability of isolated cells.

Embodiments of a Combinational Use

In certain embodiments, a compound of the invention, a pharmaceutically acceptable salt, solvate, tautomer or stereoisomer thereof or a pharmaceutically acceptable solvate of any of the foregoing, can be used in combination therapy with at least one other therapeutic agent. A compound of the invention and other therapeutic agent(s) can act additively or, and in certain embodiments, synergistically. In some embodiments, a compound of the invention can be administered concurrently with the administration of another therapeutic agent, such as for example, a compound for treating a disease associated with a dysfunction in energy metabolism; treating muscle fatigue; enhancing muscle strength and endurance; increasing the viability of organ transplants; and improving the viability of isolated cells. In some embodiments, a compound of the invention, a pharmaceutically acceptable salt or a pharmaceutically acceptable solvate of any of the foregoing can be administered prior to or subsequent to administration of another therapeutic agent, such as for example, a compound for treating a disease associated with a dysfunction in energy metabolism such as CCDS/CTD, ischemia, ventricular hypertrophy, a neurodegenerative disease such as ALS, Huntington's disease, Parkinson's disease or Alzheimer's disease, surgery related ischemic tissue damage, and reperfusion tissue damage; treating multiple sclerosis (MS), treating a psychotic disorder such as schizophrenia, bipolar disorder or anxiety; treating muscle fatigue; enhancing muscle strength and endurance; increasing the viability of organ transplants; and improving the viability of isolated cells.

Pharmaceutical compositions of the invention can include, in addition to one or more compounds of the invention, one or more therapeutic agents effective for treating the same or different disease, disorder or condition.

Methods of the invention include administration of one or more compounds or pharmaceutical compositions of the invention and one or more other therapeutic agents provided that the combined administration does not inhibit the therapeutic efficacy of the one or more compounds of the invention and/or does not produce adverse combination effects.

In certain embodiments, compositions of the invention can be administered concurrently with the administration of another therapeutic agent, which can be part of the same pharmaceutical composition or dosage form as or in a different composition or dosage form from, that containing the compounds of the invention. In certain embodiments, compounds of the invention can be administered prior or subsequent to administration of another therapeutic agent. In certain embodiments of combination therapy, the combination therapy comprises alternating between administering a composition of the invention and a composition comprising another therapeutic agent, e.g., to minimize adverse side effects associated with a particular drug. When a compound of the invention is administered concurrently with another therapeutic agent that potentially can produce adverse side effects including, but not limited to, toxicity, the therapeutic agent can advantageously be administered at a dose that falls below the threshold at which the adverse side effect is elicited.

In certain embodiments, compounds or pharmaceutical compositions of the invention include or can be administered to a patient together with, another compound for treating Parkinson's disease such as amantadine, benztropine, bromocriptine, levodopa, pergolide, pramipexole, ropinirole, selegiline, trihexyphenidyl or a combination of any of the foregoing.

In certain embodiments, compounds or pharmaceutical compositions of the invention include or can be administered to a patient together with, another compound for treating Alzheimer's disease such as donepezil, galantamine, memantine, rivastigmine, tacrine or a combination of any of the foregoing.

In certain embodiments, compounds or pharmaceutical compositions of the invention include or can be administered to a patient together with, another compound for treating ALS such as riluzole.

In certain embodiments, compounds or pharmaceutical compositions of the invention include or can be administered to a patient together with, another compound for treating ischemic stroke such as aspirin, nimodipine, clopidogrel, pravastatin, unfractionated heparin, eptifibatide, a β-blocker, an angiotensin-converting enzyme (ACE) inhibitor, enoxaparin or a combination of any of the foregoing.

In certain embodiments, compounds or pharmaceutical compositions of the invention include or can be administered to a patient together with, another compound for treating ischemic cardiomyopathy or ischemic heart disease such as ACE inhibitors such as ramipril, captopril, and lisinopril; n-blockers such as acebutolol, atenolol, betaxolol, bisoprolol, carteolol, nadolol, penbutolol, propranolol, timolol, metoprolol, carvedilol, and aldosterone; diuretics; digitoxin or a combination of any of the foregoing.

In certain embodiments, compounds or pharmaceutical compositions of the invention include or can be administered to a patient together with, another compound for treating a cardiovascular disease such as, blood-thinners, cholesterol lowering agents, anti-platelet agents, vasodilators, β-blockers, angiotensin blockers, digitalis and is derivatives or combinations of any of the foregoing.

In certain embodiments, compounds or pharmaceutical compositions of the invention include or can be administered to a patient together with, another compound for treating MS. Examples of drugs useful for treating MS include corticosteroids such as methylprednisolone; IFN-β such as IFN-β1a and IFN-β1b; glatiramer acetate (Copaxone®); monoclonal antibodies that bind to the very late antigen-4 (VLA-4) integrin (Tysabri®) such as natalizumab; immunomodulatory agents such as FTY 720 sphingosine-1 phosphate modulator and COX-2 inhibitors such as BW755c, piroxicam, and phenadone; and neuroprotective treatments including inhibitors of glutamate excitotoxicity and iNOS, free-radical scavengers, and cationic channel blockers; memantine; AMPA antagonists such as topiramate; and glycine-site NMDA antagonists (Virley, NeruoRx 2005, 2(4), 638-649, and references therein; and U.S. Application No. 2004/0102525).

In certain embodiments, compounds or pharmaceutical compositions of the invention include or can be administered to a patient together with, another compound for treating schizophrenia. Examples of antipsychotic agents useful in treating schizophrenia include, but are not limited to, acetophenazine, alseroxylon, amitriptyline, aripiprazole, astemizole, benzquinamide, carphenazine, chlormezanone, chlorpromazine, chlorprothixene, clozapine, desipramine, droperidol, aloperidol, fluphenazine, flupenthixol, glycine, oxapine, mesoridazine, molindone, olanzapine, ondansetron, perphenazine, pimozide, prochlorperazine, procyclidine, promazine, propiomazine, quetiapine, remoxipride, reserpine, risperidone, sertindole, sulpiride, terfenadine, thiethylperzaine, thioridazine, thiothixene, trifluoperazine, triflupromazine, trimeprazine, and ziprasidone. Other antipsychotic agents useful for treating symptoms of schizophrenia include amisulpride, balaperidone, blonanserin, butaperazine, carphenazine, eplavanserin, iloperidone, lamictal, onsanetant, paliperidone, perospirone, piperacetazine, raclopride, remoxipride, sarizotan, sonepiprazole, sulpiride, ziprasidone, and zotepine; serotonin and dopamine (5HT/D2) agonists such as asenapine and bifeprunox; neurokinin 3 antagonists such as talnetant and osanetant; AMPAkines such as CX-516, galantamine, memantine, modafinil, ocaperidone, and tolcapone; and α-amino acids such as D-serine, D-alanine, D-cycloserine, and N-methylglycine.

In certain embodiments, compounds or pharmaceutical compositions of the invention include or can be administered to a patient together with, another compound for treating bipolar disorder such as aripiprazole, carbamazepine, clonazepam, clonidine, lamotrigine, quetiapine, verapamil, and ziprasidone.

In certain embodiments, compounds or pharmaceutical compositions of the invention include or can be administered to a patient together with, another compound for treating anxiety such as alprazolam, atenolol, busipirone, chlordiazepoxide, clonidine, clorazepate, diazepam, doxepin, escitalopram, halazepam, hydroxyzine, lorazepam, prochlorperazine, nadolol, oxazepam, paroxetine, prochlorperazine, trifluoperazine, and venlafaxine.

EXAMPLES

The following examples describe in detail assays for the characterization of compounds of the invention and uses of compounds of the invention. It will be apparent to those skilled in the art that many modifications, both to materials and methods, may be practiced without departing from the scope of the disclosure.

General Experimental

The NMR spectra of compounds were acquired at 400 MHz (1H) at 25° C. 1H NMR spectra were processed with 0.3 Hz line broadening unless otherwise specified. For LC-MS analysis, a Waters XBridge C18 4.6×50 mm, 3.5 mm, was used at a temperature of 45° C. and at a flow rate of 1.8 mL/min, 10 mL injection, mobile phase: A=water with 0.05% $NH_4HCO_3$, B=acetonitrile; retention time given in minutes. Method details: (I) runs on a Binary Pump G1312A™ with UV/Vis diode array detector G1315D and Agilent 6110™ mass spectrometer in positive and negative ion electrospray mode with UV-detection at 214 and 254 nm with a gradient of 5-95% B in a 1.3 min linear gradient (II) hold for 1.4 min at 95% B (III) decrease from 95-5% B in a 0.1 min linear gradient (IV) hold for 0.3 min at 5% B.

Reaction progress was monitored by thin layer chromatography on silica gel coated glass plates using UV light and/or treatment with iodine to visualize. Normal phase flash chromatographic purification was carried out on a Biotage with a variable flow rate from 5-100 mL/min. Peaks were detected by variable wavelength UV absorption (200-360 nm). Preparative reverse phase chromatography was accomplished using a Waters 2767 Liquid Handler equipped with Waters 2545 Binary pumps operated using MassLynx 4.1 software. Detection was achieved using Waters 2489 UV-Vis and Waters 3100 Mass. (I) gradient of 5-95% B in a 5 min linear gradient (II) hold for 4 min at 95% B (III) decrease from 95-5% B in a 0.2 min linear gradient (IV) hold for 3 min at 5% B. For Prep-HPLC, an Agela Durasher Prep C18 10 μm 21.5×250 mm, was used at a temperature of 25° C. and at a flow rate of 30 mL/min, 1000 mL injection, mobile phase: A=water with 0.05% $NH_4HCO_3$, mobile phase B=acetonitrile.

TABLE S1

Structure information of Synthesized Compounds (Examples 1-7)

| Compound | $R^{1*}$ | R1 Metabolite | R | Salt | Double Bond |
|---|---|---|---|---|---|
| 1 | C18 | oleic acid | H | Na | cis-9 |
| 2 | C18 | oleic acid | ester, C7 | HCl | cis-9 |
| 3 | C11 | undecylic acid | H | free | 0 |
| 4 | C11 | undecylic acid | H | Na | 0 |
| 5 | C11 | undecylic acid | ester, C7 | HCl | 0 |
| 6 | C14 | myristic acid | H | free | 0 |
| 7 | C14 | myristic acid | H | Li | 0 |
| 8 | C11 | undecylic acid | ester, C2 | HCl | 0 |
| 9 | C11 | undecylic acid | ethanol | HCl | 0 |

*$R^1$ carbon count includes the carbonyl carbon to which $R^1$ is attached to.

Example 1: Synthesis of Sodium N-(methyl-d3)-N-(N-oleoylcarbamimidoyl)glycinate (Compound 1)

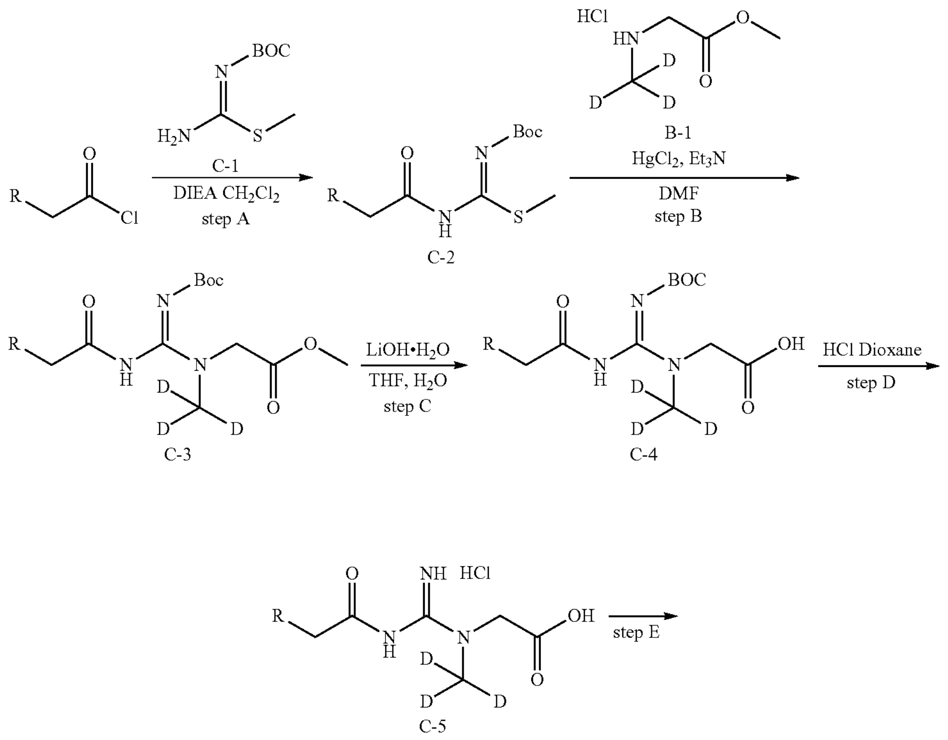

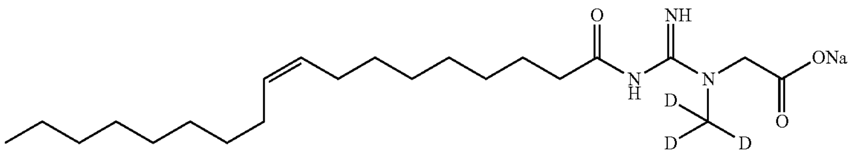

Compound 1

R =

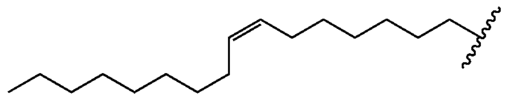

Synthesis of B-1

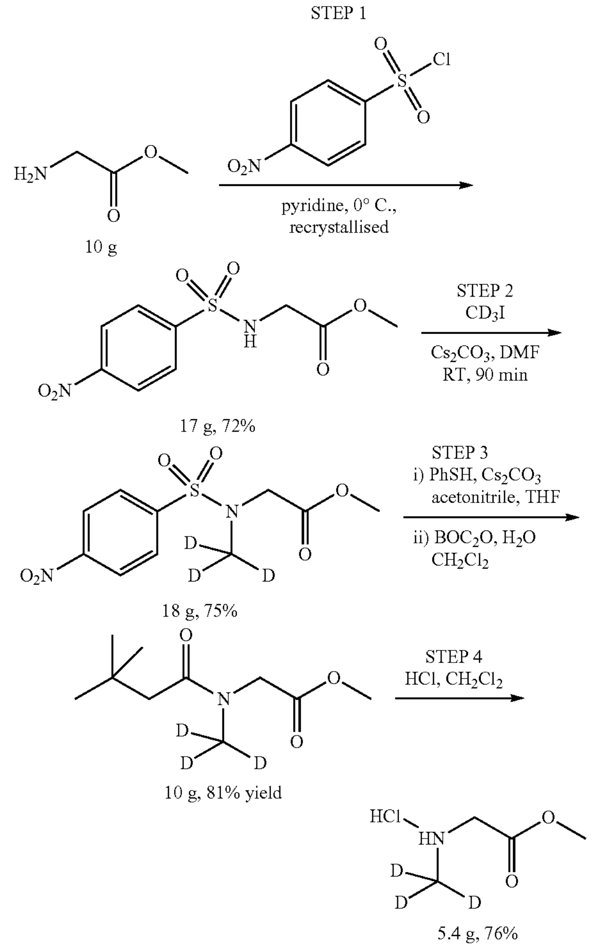

Step 1: Synthesis of methyl 2-[(4-nitrophenyl)sulfonylamino]acetate

A round bottom flask equipped with a stir bar and nitrogen inlet was charged with glycine methyl ester hydrochloride (10.5 g, 84 mmol) and pyridine (80 mL). The mixture was cooled to 0° C. and 4-nitrobenzenesulfonyl chloride (18.6 g, 84 mmol) was added portion-wise keeping the mixture below 10° C. The reaction was then allowed to warm to rt with stirring overnight. After 18 h, the reaction mixture was poured into water (500 mL). A precipitate formed which was filtered and dried under vacuum. The material was used as is in the next step. Amount obtained: 16.6 g, 61 mmol, 72% yield. $^{1}$H NMR (CHLOROFORM-d) δ: 8.33-8.41 (m, J=8.9 Hz, 2H), 8.03-8.11 (m, J=8.9 Hz, 2H), 5.21 (br. s., 1H), 3.89 (s, 2H), 3.68 (s, 3H).

Step 2: Synthesis of methyl 2-[(4-nitrophenylsulfonyl-(trideuteriomethyl)amino]acetate A round bottom flask equipped with a stir bar and nitrogen inlet was charged with methyl 2-[(4-nitrophenyl)sulfonylamino]acetate (16.4 g, 60 mmol), DMF (240 mL) and $CD_3I$ (3.7 mL, 60 mmol). To this mixture at rt was added $Cs_2CO_3$ (19.5 g, 60 mmol) and the reaction was allowed 45 min. LCMS showed consumption of starting material. The reaction mixture was poured into water (1000 mL), extracted with EtOAc (3×500 mL), the combined organic phases were washed with LiCl (500 mL), dried ($Na_2SO_4$) and the solvent was evaporated under reduced pressure. The material was used as is in the next step. Amount obtained: 18.0 g, 60 mmol, ~100% yield. $^{1}$H NMR (CHLOROFORM-d) δ: 8.38 (d, J=9.0 Hz, 2H), 8.02 (d, J=9.0 Hz, 2H), 4.11 (s, 2H), 3.67 (s, 3H). (NMR showed some DMF).

Step 3: Synthesis of methyl 2-[tert-butoxycarbonyl(trideuteriomethyl)amino]acetate A round bottom flask equipped with a stir bar and nitrogen inlet was charged methyl 2-[(4-nitrophenyl)sulfonyl-(trideuteriomethyl)amino]acetate (17.5 g, 60 mmol), $Cs_2CO_3$ (39.0 g, 120 mmol) acetonitrile (100 mL) and THF (10 mL). To this solution was added thiophenol (25 mL, 240 mmol) and the reaction was heated at 45° C. for 90 min. LCMS and TLC showed consumption of starting material. The reaction mixture was diluted with MTBE (500 mL) and extracted with water (5×100 mL). The combined water extracts were then washed with MTBE (500 mL). Then, to the water mixture was added DCM (500 mL) followed by $BOC_2O$ (26.2 g, 120 mmol). The biphasic reaction mixture was stirred vigorously overnight. The phases were separated, the aqueous was extracted with DCM (250 mL×5), the combined organic phases dried ($Na_2SO_4$) and the solvent was evaporated under reduced pressure. The material was purified by chromatography using a 120 g silica cartridge eluting with heptane-EtOAc, gradient 0 to 30% EtOAc. Amount obtained: 10 g, 48.5 mmol, 81% yield. $^{1}$H NMR (CHLOROFORM-d) &: 3.99 (s, 1H), 3.91 (s, 1H), 3.75 (d, J=2.9 Hz, 3H), 1.44 (s, 4H), 1.48 (s, 5H).

Step 4: Synthesis of methyl 2-(trideuteriomethylamino)acetate·HCl (B-1)

A round bottom flask equipped with a stir bar was charged with methyl 2-[tert-butoxycarbonyl(trideuteriomethyl)amino]acetate (10.3 g, 50 mmol) and dry DCM (50 mL). To this mixture was added 50 mL of HCl (4.0 M in dioxane). After 1 h, TLC showed consumption of SM. The mixture was poured into MTBE (500 mL) and the resulting precipitate was filtered and dried under vacuum. The material was used as is in the next step. Amount obtained: 5.4 g, 38 mmol, 76% yield. $^{1}$H NMR (METHANOL-$d_4$) δ: 3.97 (s, 2H), 3.85 (s, 3H).

Step A: Synthesis of C-2

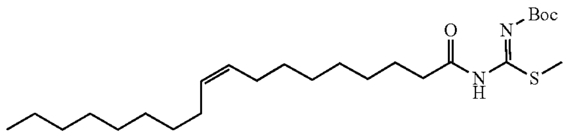 [SMILES: CCCCCCCC/C=C\CCCCCCCC(=O)N/C(=N/C(=O)OC(C)(C)C)SC]

To a round bottom flask equipped with a stir bar and nitrogen inlet was added C-1 (1.1 g, 5.5 mmol), oleoyl chloride (1.5 g, 5 mmol), and DIPEA (1.3 g, 10 mmol) in dichloromethane (30 mL). The mixture was stirred at room temperature for 2 h. The mixture was then washed with brine (80 mL), dried ($Na_2SO_4$) and the solvent was evaporated under reduced pressure. The material was purified by chromatography using a 20 g silica cartridge eluting with PE-EA, gradient of 0/6 to 15% ethyl acetate. To give C-2 as a colorless oil: 2.1 g, 4.6 mmol, 90% yield. ES LC-MS m/z=455.7 (M+H$^{+}$).

Step B: Synthesis of C-3

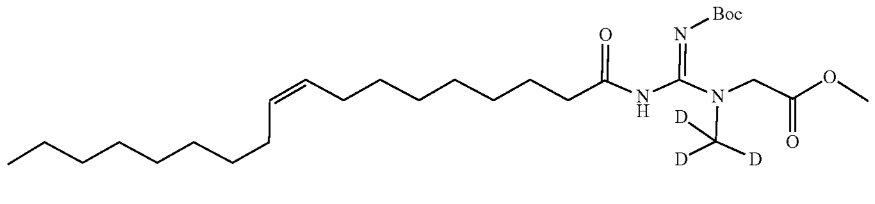 [SMILES: [2H]C([2H])([2H])N(CC(=O)OC)/C(=N\C(=O)OC(C)(C)C)NC(=O)CCCCCCC/C=C\CCCCCCCC]

To a round bottom flask equipped with a stir bar and nitrogen inlet was added C-2 (2.1 g, 4.6 mmol), B-1 (723 mg, 5.1 mmol), $HgCl_2$ (1.4 g, 5.1 mmol) and $Et_3N$ (1.4 g, 13.8 mmol) in DMF (15 mL). The mixture was stirred at room temperature for 2 h. After adding 50 ml of EA, the mixture was washed with brine (80 ml×3), dried ($Na_2SO_4$) and the solvent was evaporated under reduced pressure. The material was purified by chromatography using a 20 g silica cartridge eluting with PE-EA, gradient 0% to 15% ethyl acetate to give C-3 as an yellow oil: 2 g, 3.90 mmol, 85% yield. ES LC-MS m/z=513.7 ($M+H^+$).

Step C: Synthesis of C-4

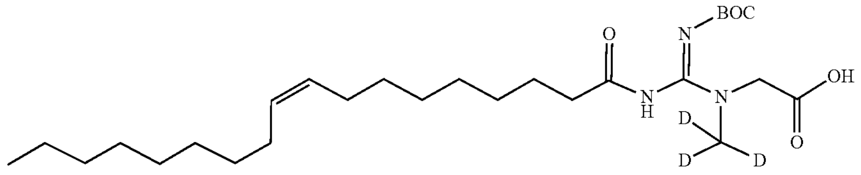 [SMILES: [2H]C([2H])([2H])N(CC(=O)O)/C(=N\C(=O)OC(C)(C)C)NC(=O)CCCCCCC/C=C\CCCCCCCC]

To a round bottom flask equipped with a stir bar and nitrogen inlet was charged with C-3 (2.0 g, 3.9 mmol) and $LiOH{\cdot}H_2O$ (195 mg, 4.4 mmol) in 20 ml of ($THF{:}H_2O$=6:1). The mixture was stirred at room temperature for 1 h and then concentrated under reduced pressure. After adding 20 ml of water, the mixture, HCl (1N) was added until pH=5. Then 50 ml of EA was added and the mixture was washed with brine (50 mL), dried ($Na_2SO_4$) and the solvent was evaporated under reduced pressure. The material was purified by chromatography using a 20 g silica cartridge eluting with PE-EA, gradient 0% to 30% ethyl acetate. This gave C-4 as an yellow oil: 1.7 g, 3.4 mmol, 75% yield. ES LC-MS m/z=499.6 ($M+H^+$).

Step D: Synthesis of C-5

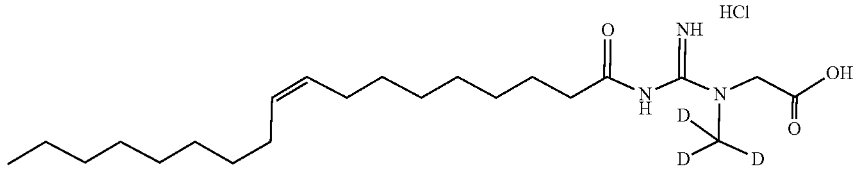 [SMILES: Cl ; [2H]C([2H])([2H])N(CC(=O)O)C(=N)NC(=O)CCCCCCC/C=C\CCCCCCCC]

To a vial equipped with a stir bar was added C-4 (700 mg, 1.4 mmol) in 15 ml of HCl 1,4-Dioxane (4N). The mixture was stirred at room temperature for 3 h and concentrated under reduced pressure. To the residue was then added 5 ml THE and purified by HPLC to give compound C-5 as a white solid: 150 mg, 0.37 mmol, 33% yield. ES LC-MS m/z=399.7 ($M+H^+$).

Step E: Synthesis of Sodium N-(methyl-d3)-N-(N-oleoylcarbamimidoyl)glycinate (Compound 1)

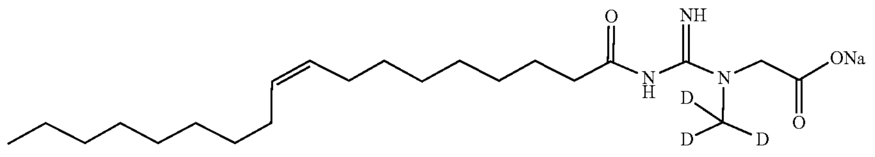

To a vial equipped with a stir bar was added C-5 (150 mg, 0.37 mmol) and NaOH (20 mg, 0.41 mmol) in 15 ml of water. The mixture was stirred at room temperature for 0.5 h. The solvent was removed on a lyophilizer to give sodium N-(methyl-d3)-N-(N-oleoylcarbamimidoyl)glycinate (Compound 1) as a white solid: 70 mg, 0.16 mmol, 50% yield. ES LC-MS m/z=399.7 (M+H$^+$). NMR (400 MHz, d6-DMSO): 5.27-5.35 (2H, m), 3.70-4.00 (1H, br), 3.42-3.58 (1H, br), 2.02-2.14 (2H, m), 1.90-2.02 (4H, m), 1.40-1.55 (2H, m), 1.15-1.35 (20H, m), 0.85 (3H, t, J=6.2 Hz).

Example 2: Synthesis of (Z)-heptyl 2-(1-trideuteriomethyl-3-oleoylguanidino)acetate hydrochloride (Compound 2)

Step 1: Synthesis of D-2

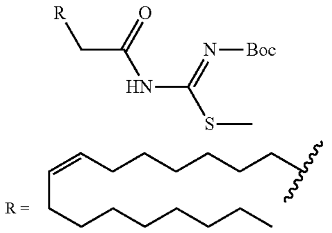

To a round bottom flask equipped with a stir bar and nitrogen inlet was added D-1 (846 mg, 2.82 mmol), (Z)-tert-butyl amino(methylthio)methylenecarbamate (447 mg, 2.35 mmol, C-1), and DIPEA (909 mg, 7.05 mmol) in dichloromethane (20 mL). The mixture was stirred at room temperature for 2 h. The mixture was then washed with brine (80 mL), dried ($Na_2SO_4$) and the solvent was evaporated

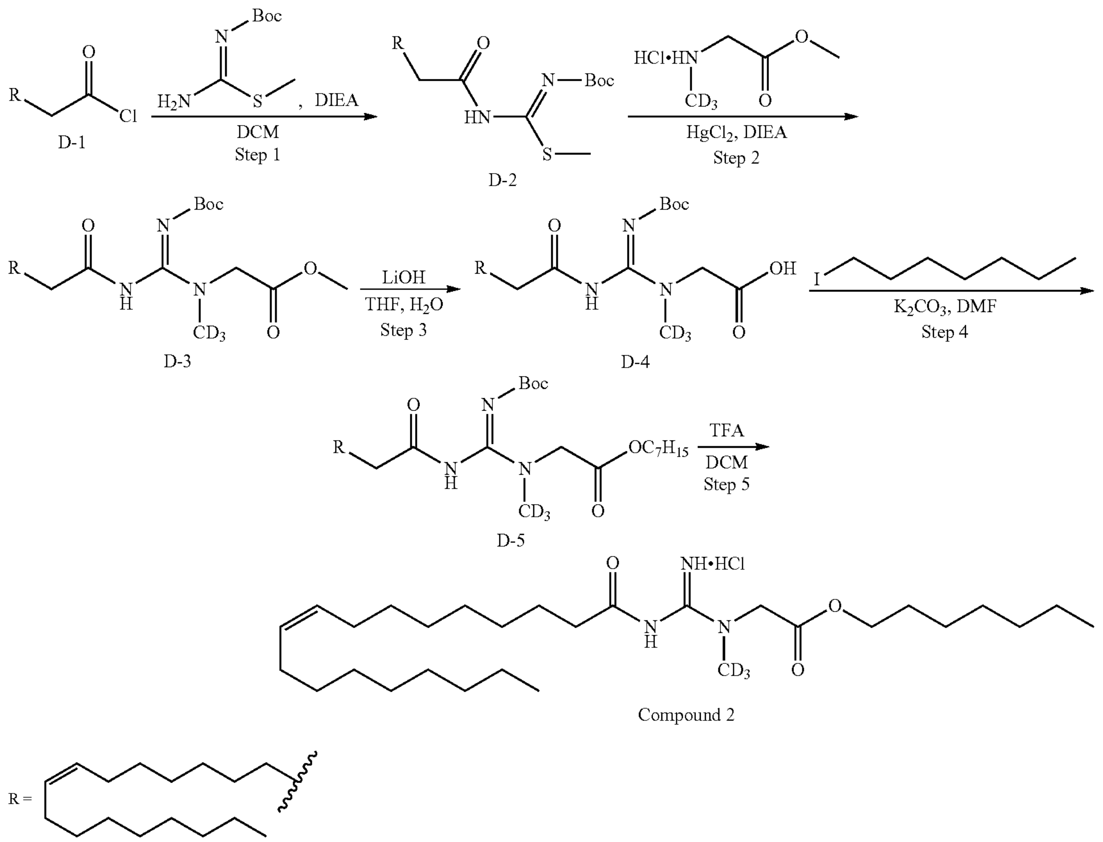

D-1 D-2 D-3 D-4 D-5

Compound 2 under reduced pressure. The crude material was purified by chromatography using a 20 g silica cartridge eluting with PE-EA, gradient 0% to 15% ethyl acetate, to give D-2 as a colorless oil: 846 mg, 1.86 mmol, 79% yield. ES LC-MS m/z=455.4 ($M+H^+$).

Step 2: Synthesis of D-3

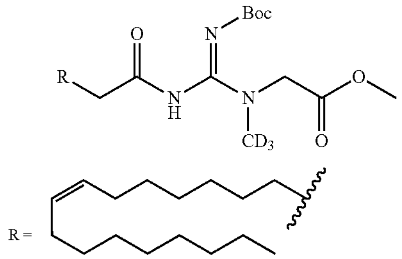

To a round bottom flask equipped with a stir bar and nitrogen inlet was added D-2 (846 mg, 1.86 mmol), methyl 2-(trideuteriomethylamino)acetate hydrochloride (265 mg, 1.86 mmol), $HgCl_2$ (505 mg, 1.86 mmol) and DIPEA (720 mg, 5.58 mmol) in DMF (15 mL). The mixture was stirred at room temperature for 2 h at which time 50 ml of $H_2O$ was added and the mixture was extracted with Ethyl acetate (30 ml×3), washed with brine (80 ml×3), dried ($Na_2SO_4$) and the solvent was evaporated under reduced pressure. The crude material was purified by chromatography using a 20 g silica cartridge eluting with PE-EA, gradient 0% to 15% ethyl acetate to give D-3 as a colorless oil: 850 mg, 1.66 mmol, 89% yield. ES LC-MS m/z=513.4 ($M+H^+$).

Step 3: Synthesis of D-4

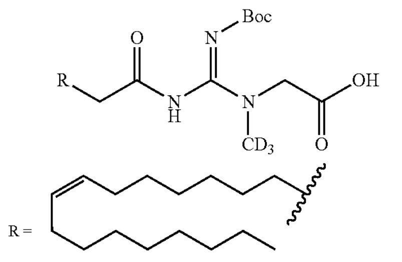

To a round bottom flask equipped with a stir bar and nitrogen inlet was added D-3 (850 mg, 1.66 mmol) and $LiOH{\cdot}H_2O$ (350 mg, 8.30 mmol) in 20 ml of ($THF:H_2O$=6:1). The mixture was stirred at room temperature for 1 h and then concentrated under reduced pressure. After adding 20 ml of water, the mixture was acidified with HCl (1N) until pH=5 and was extracted with ethyl acetate, washed with brine (50 mL), dried ($Na_2SO_4$) and the solvent was evaporated under reduced pressure to give crude D-4 as a yellow oil: 800 mg. ES LC-MS m/z=499.4 ($M+H^+$).

Step 4: Synthesis of D-5

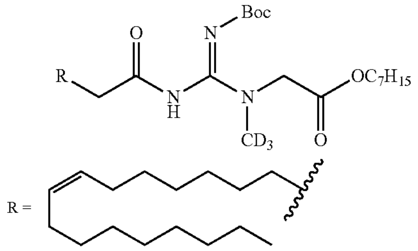

To a round bottom flask equipped with a stir bar and containing D-4 (800 mg crude from step 3) in DMF (15 ml) were added 1-1-iodoheptane (375 mg, 1.66 mmol) and $K_2CO_3$ (343 mg, 2.49 mmol). The mixture was stirred at 50° C. for 3 hours. The resulting mixture was poured into water (60 ml) and extracted with EA (3×30 ml). The combined organic extract was washed with brine (2×20 ml), dried over $MgSO_4$ and concentrated. The crude residue was purified by flash chromatography (PE:EA from 1:0 to 1:1) to give D-5 as a colorless oil: 620 mg, 1.04 mmol, 63% yield. ES LC-MS m/z=597.4 $(M+H)^+$.

Step 5: Synthesis of D-5

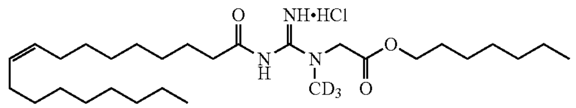

To a round bottom flask equipped with a stir bar was added D-5 (500 mg, 0.84 mmol), 6 ml DCM and TFA (3 ml). The mixture was stirred at room temperature for 2 h. After the reaction was completed, the solvent and extra TFA were removed and the crude residue was purified by Prep-HPLC using standard TFA additive conditions. The fractions obtained by Prep-HPLC were combined and HCl (aq. 1 M, 6 ml) was added. The solution was stirred at room temperature for 30 minutes and freeze dried to give (Z)-heptyl 2-(1-trideuteriomethyl-3-oleoylguanidino)acetate hydrochloride (Compound 2) as a white solid: 105 mg, 0.20 mmol, 23% yield. ES LC-MS m/z=497.4 $(M-HCl+H)^+$. NMR (400 MHz, d6-DMSO): 11.08-11.02 (1H, m), 9.33-9.19 (2H, s), 5.37-5.32 (2H, m), 4.62-4.41 (2H, m), 4.11-4.09 (2H, t, J=6.2 Hz), 1.98 (4H, m), 1.59-1.57 (4H, m), 1.26-1.24 (30H, m), 0.86-0.84 (3H, t, J=4.6 Hz).

Example 3: Synthesis of N-(trideuteriomethyl)-N-(N-undecanoylcarbamimidoyl)glycine (Compound 3) and Sodium 2-(1-trideuteriomethyl)-3-undecanoylguanidino)acetate salt (Compound 4)

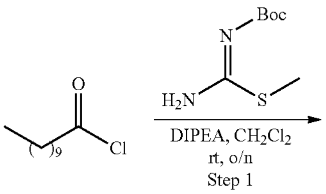

-continued

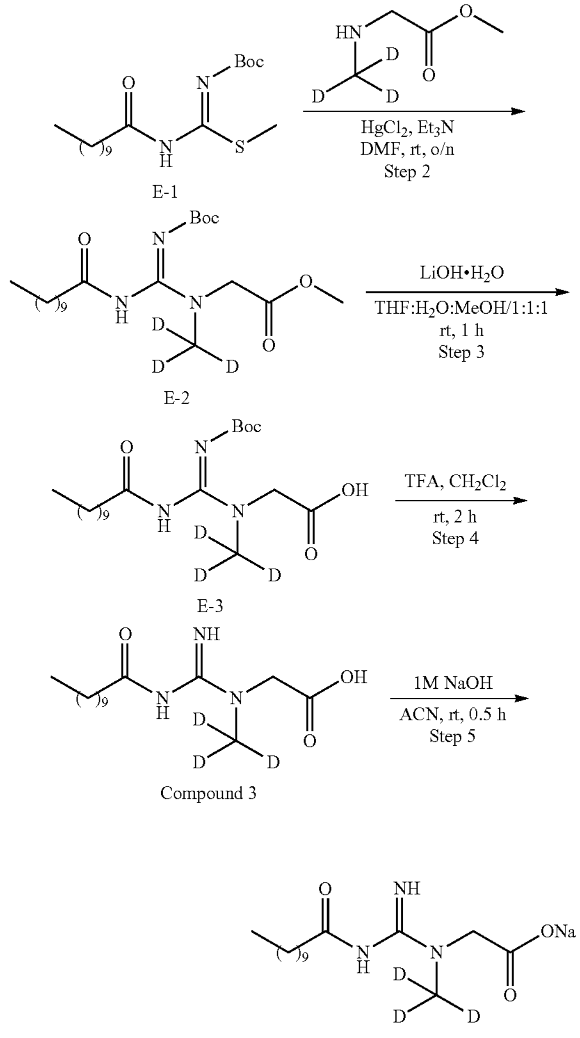

E-1

E-2

E-3

Compound 3

Compound 4

Step 1: Synthesis of E-1

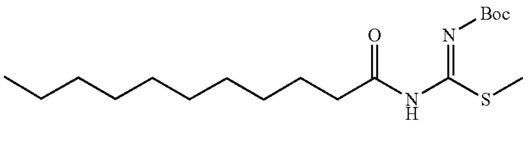 [SMILES: CCCCCCCCCCC(=O)N/C(=N/C(=O)OC(C)(C)C)SC]

To a round bottom flask equipped with a stir bar was added (Z)-tert-butyl amino(methylthio)methylenecarbamate (2.5 g, 13.15 mmol) and N,N-Diisopropylethylamine (4.24 g, 32.89 mmol) in dichloromethane (100 mL). To the mixture was then added dropwise undecanoyl chloride (4.03 g, 19.73 mmol) in DCM (2 mL) at room temperature and overnight. Once the reaction was completed DCM (200 mL) was added and washed with water (60 mL×3), brine (60 mL), dried and evaporated. The crude was purified by SGC (PE:EA/20:1) to give (Z)-tert-butyl methylthio(undecanamido)methylenecarbamate (E-1) (4.56 g, 12.74 mmol, 96% yield) as a white solid. ES LC-MS m/z=359.2 (M+H$^+$).

Step 2: Synthesis of E-2

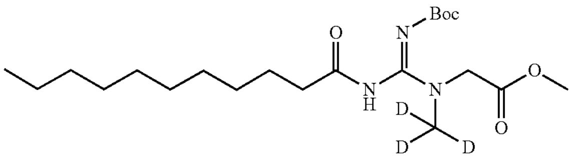 [SMILES: [2H]C([2H])([2H])N(CC(=O)OC)/C(=N\C(=O)OC(C)(C)C)NC(=O)CCCCCCCCCC]

To a round bottom flask equipped with a stir bar was added (Z)-tert-butyl methylthio(undecanamido)methylenecarbamate (1.7 g, 4.75 mmol), methyl 2-[tert-butoxycarbonyl(trideuteriomethyl)amino]acetate hydrochloride (B-1, see Example 1) (810 mg, 5.70 mmol) and triethylamine (1.44 g, 14.25 mmol) in DMF (50 mL). To the reaction was then added mercury(II) chloride (1.41 g, 5.22 mmol). The mixture was stirred at RT overnight, at which time was added ethyl acetate (200 mL), washed with water (3×60 mL), brine (60 mL), dried and evaporated to give (Z)-methyl 2-(2-(tert-butoxycarbonyl)-1-trideuteriomethyl-3-undecanoylguanidino)acetate (E-2) (1.9 g, 4.56 mmol, 101% yield) as a pale yellowish solid which was used directly in the next step without further purification. ES LC-MS m/z=417.0 (M+H$^+$).

Step 3: Synthesis of E-3

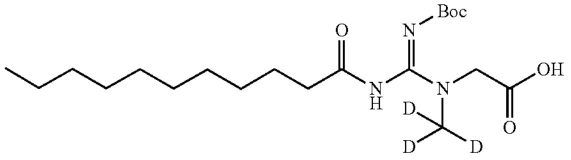 [SMILES: [2H]C([2H])([2H])N(CC(=O)O)/C(=N\C(=O)OC(C)(C)C)NC(=O)CCCCCCCCCC]

To a round bottom flask equipped with a stir bar was added (Z)-methyl 2-(2-(tert-butoxycarbonyl)-1-trideuteriomethyl-3-undecanoylguanidino) acetate (1.9 g, 4.56 mmol) and lithium hydroxide hydrate (798 mg, 19 mmol) in THF:MeOH:$H_2O$ (1:1:1, 209 mL) and was stirred at RT for 2 h. The mixture was then evaporated, water (20 mL) was added, extracted with dichloromethane (2×10 mL), adjusted to pH=6 with 1N of HCl, extracted with ethyl acetate (3×50 mL), dried and evaporated to give (Z)-2-(2-(tert-butoxycarbonyl)-1-trideuteriomethyl-3-undecanoylguanidino) acetate acid (E-3) (1.12 g, 2.78 mmol, 58% yield) as a colorless oil which was used directly in the next step without further purification. ES LC-MS m/z=403.3 (M+H$^+$).

Step 4: Synthesis of N-(trideuteriomethyl)-N-(N-undecanoylcarbamimidoyl)glycine (Compound 3)

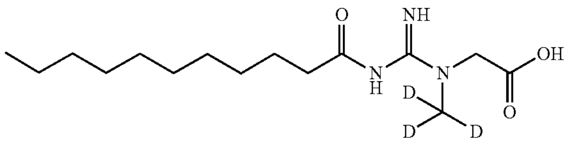 [SMILES: [2H]C([2H])([2H])N(CC(=O)O)C(=N)NC(=O)CCCCCCCCCC]

To a round bottom flask equipped with a stir bar and charged with (Z)-methyl 2-(2-(tert-butoxycarbonyl)-1-trideuteriomethyl-3-undecanoylguanidino) acetate acid (880 mg, 2.18 mmol) in dichloromethane (5 mL) was added trifluoroacetic acid (3 mL). The mixture was stirred at RT for 2 h. The reaction was then evaporated, dissolved in AcCN (8 mL), adjusted to pH=7 with aqueous of $K_2CO_3$, DMF (10 mL) was added, filtered and purified by flash chromatography (SNAP C18, 40 G) eluting with water-AcCN (gradient 0% to 69% AcCN) to give 2-(1-trideuteriomethyl-3-undecanoylguanidino)acetic acid (Compound 3) as a white solid (286 mg, 0.94 mmol, 43% yield).

Step 5: Synthesis of Sodium 2-(1-trideuteriomethyl)-3-undecanoylguanidino)acetate salt (Compound 4)

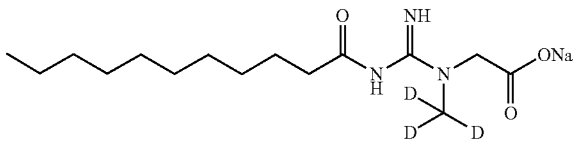

To a round bottom flask equipped with a stir bar and charged with 2-(1-trideuteriomethyl-3-undecanoylguanidino)acetic acid (130 mg, 0.43 mmol) in AcCN (10 mL) was added dropwise 0.43 mL of 1M NaOH. The mixture formed a suspension after 5 minutes and the reaction was stirred at RT for 30 minutes. To the reaction was then added water (30 mL) and lyophilized to give 2-(1-trideuteriomethyl-3-undecanoylguanidino)acetic acid sodium salt (Compound 4) as a white solid (133.8 mg, 0.41 mmol, 91% yield). ES LC-MS m/z=303.2 (M+H$^+$). $^1$H NMR (DIMETHYL SULFOXIDE-d) δ: 3.85 (s, 1H), 3.47 (s, 1H), 2.06 (s, 2H), 1.48 (s, 2H), 1.23 (s, 14H), 0.87 (t, J=13.6 Hz, 3H).

Example 4: Synthesis of Heptyl N-(methyl-d3)-N-(N-undecanoylcarbamimidoyl)glycinate hydrochloride (Compound 5)

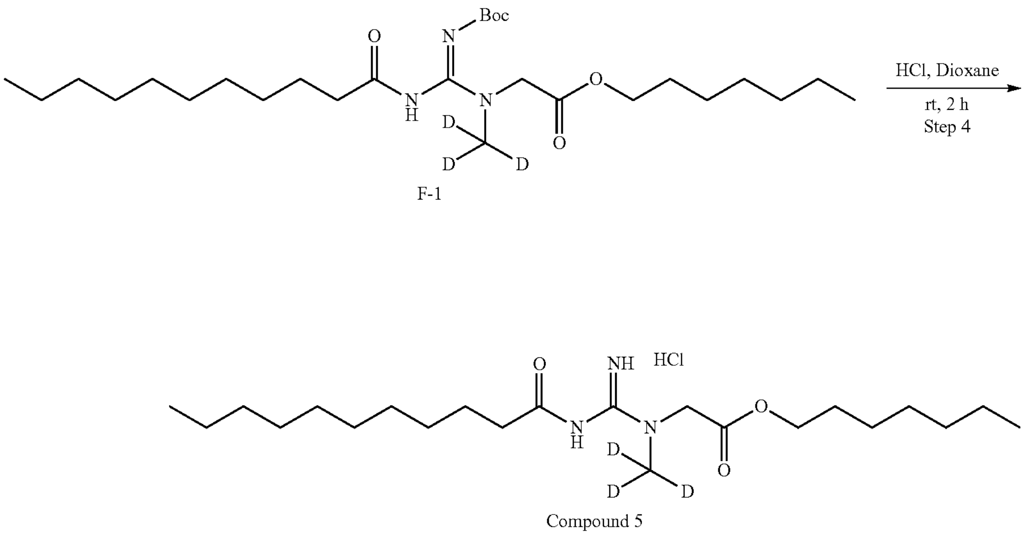

F-1

Compound 5

To a vial equipped with a stir bar was added F-1 (425 mg, 0.85 mmol), synthesized according to Example 2, in 25 ml of HCl 1,4-Dioxane (4N). The mixture was stirred at room temperature for 3 h and concentrated under reduced pressure. To the residue was added 5 ml THF and purified by HPLC. Top the purified fractions were added 0.1 ml HCl (1N) and freeze-dried to give the title compound (Compound 5) as a white solid: 150 mg, 0.38 mmol, 44% yield. ES LC-MS m: =401.7 (M+H$^+$). NMR (400 MHz, d6-DMSO): 10.8-11.4 (1H, br), 9.10-9.40 (2H, m), 4.30-4.75 (2H, m), 4.10 (2H, t, J=6.2 Hz), 1.42-1.66 (4H, m), 1.10-1.40 (24H, m), 0.82-0.92 (6H, m).

Example 5: Synthesis of N-(trideuteriomethyl)-N-(N-tetradecanoylcarbamimidoyl)glycine (Compound 6) and lithium 2-(1-trideuteriomethyl-3-tetradecanoyluanidino) acetate (Compound 7)

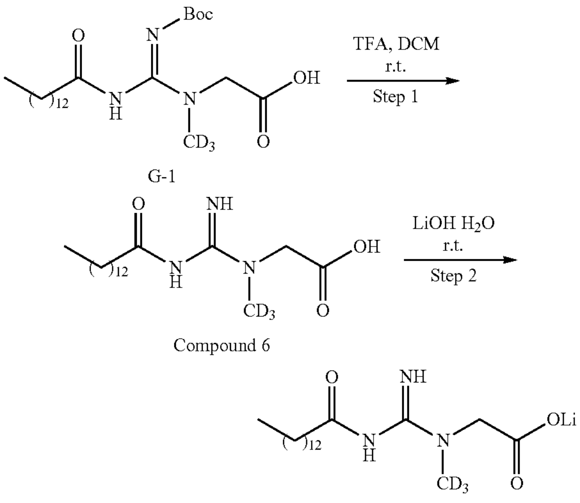

G-1

Compound 6

Compound 7

Step 1: Synthesis of N-(trideuteriomethyl)-N-(N-tetradecanoylcarbamimidoyl)glycine (Compound 6)

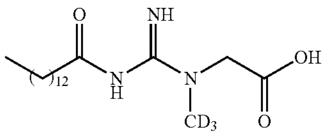

To a round bottom flask equipped with a stir bar and charged with (Z)-methyl 2-(2-(tert-butoxycarbonyl)-1-trideuteriomethyl-3-tetradecanoylguanidino)acetate (1.0 g, 2.2 mmol, G-1), synthesized according to Example 3, in tetrahydrofuran (20 ml) was added a solution of $LiOH{\cdot}H_2O$ (275 mg, 6.6 mmol) in $H_2O$ (10 ml). The mixture was stirred for 1.0 h at RT. After reaction, solvent was removed in vacuo and the residual aqueous solution was acidified to pH=4 with 1N HCl solution at 0° C., extracted with ethyl acetate (3×30 ml) then. The combined organic extract was washed with brine, dried over $MgSO_4$ and concentrated. The residue was purified by flash chromatography (petroleum ether:ethyl acetate from 50 to 100%) to afford (Z)-2-(2-(tert-butoxycarbonyl)-1-trideuteriomethyl-3-tetradecanoylguanidino)acetic acid (460 mg, 1.04 mmol, Compound 6, 47% yield) as a colorless oil. ES LC-MS m/z=445.3 $(M+H^+)$.

Step 2: Synthesis of lithium 2-(1-trideuteriomethyl-3-tetradecanoylguanidino) acetate (Compound 7)

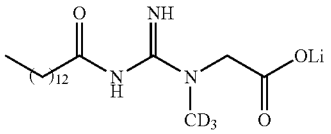

To a round bottom flask equipped with a stir bar was charged with 2-(1-trideuteriomethyl-3-tetradecanoylguanidino)acetic acid (80.0 mg, 0.23 mmol; Compound 6) and $H_2O$ (20 ml). To this solution was added $LiOH{\cdot}H_2O$ (8.4 mg, 0.20 mmol). The mixture was stirred at room temperature for 30 minutes and then extracted with dichloromethane (10 ml×2). The aqueous phase was separated and lyophilized to give lithium 2-(1-trideuteriomethyl-3-tetradecanoylguanidino) acetate (52 mg, 0.148 mmol, Compound 7, 64.3% yield) as a white solid. ES LC-MS m/z=345.3 (M−Li+2H)~. $^1H$ NMR (400 MHz, $d^6$-DMSO): δ: 3.80-4.10 (br, 1H), 3.45-3.60 (br, 1H), 2.07 (t, J=7.3 Hz, 2H), 1.42-1.53 (m, 2H), 1.15-1.30 (m, 20H), 0.85 (t, J=6.8 Hz, 3H).

Example 6: Synthesis of ethyl 2-(1-trideuteriomethyl)-3-undecanoylguanidino)acetate hydrogen chloride salt (Compound 8)

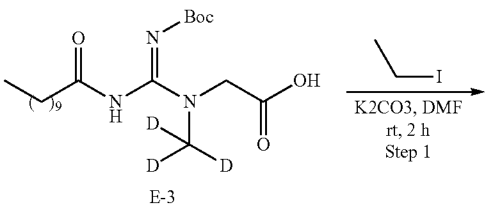

E-3

-continued

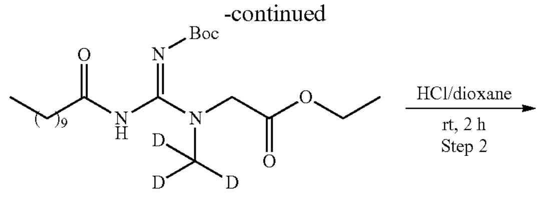

H-1

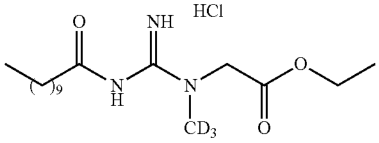

Compound 8

Step 1: Synthesis of H-1

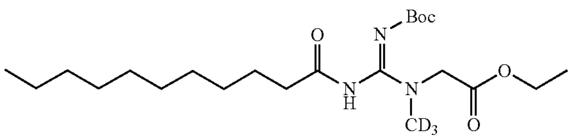 [SMILES: [2H]C([2H])([2H])N(CC(=O)OCC)/C(=N\C(=O)OC(C)(C)C)NC(=O)CCCCCCCCCC]

A round bottom flask equipped with a stir bar was charged with 2-(1-trideuteriomethyl-3-undecanoylguanidino)acetic acid (400 mg, 0.995 mmol), Compound E-3 synthesized according to Example 3, and potassium carbonate (275 mg, 1.99 mmol) in N,N-dimethylformamide (4 mL) was added dropwise iodoethane (233 mg, 1.493 mmol). The reaction was stirred at RT for 1.5 h. The reaction was added Ethyl acetate (60 mL), washed with water (20 mL×3) and brine (20 mL), dried and evaporated, purified by Prep-TLC (PE: EA/4:1) to give (Z)-ethyl 2-(2-(tert-butoxycarbonyl)-1-trideuteriomethyl-3-undecanoylguanidino)acetate (270 mg, 0.628 mmol, 62% yield) as a white solid. ES LC-MS m/z=431.0 $(M+H^+)$.

Step 2: Synthesis of ethyl 2-(1-trideuteriomethyl)-3-undecanoylguanidino)acetate hydrogen chloride salt (Compound 8)

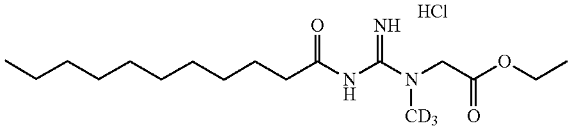 [SMILES: Cl ; [2H]C([2H])([2H])N(CC(=O)OCC)C(=N)NC(=O)CCCCCCCCCC]

To round bottom flask equipped with a stir bar was added (Z)-ethyl 2-(2-(tert-butoxycarbonyl)-1-trideuteriomethyl-3-undecanoylguanidino) acetate (270 mg, 0.628 mmol; Compound H-1) in HCl/dioxane (5 mL). The reaction was stirred at 35° C. for 1 h. The reaction was then evaporated, dissolved in acetonitrile (1 mL) and water (2.5 mL), purified by Prep-HPLC (formic acid), aqueous of hydrogen chloride (2 mL, 1 N) was added and lyophilized to obtain Ethyl 2-(1-trideuteriomethyl)-3-undecanoylguanidino)acetate hydrogen chloride salt (62.8 mg, 0.171 mmol, Compound 8, 30% yield) as a white solid. ES LC-MS m/z=331.3 $(M+H^+)$. $^1H$ NMR (DIMETHYL SULFOXIDE-d) δ: 11.20-11.12 (m, 1H), 9.21 (br s, 2H), 4.59-4.37 (m, 2H), 4.18-4.13 (m, 2H), 2.50 (m, 2H), 1.53 (m, 2H), 1.24-1.20 (m, 17H), 0.87-0.84 (m, 3H).

Example 7: Synthesis of (N-(N-(2-hydroxyethyl)-N-trideuteriomethyl carbamimidoyl)undecanamide (Compound 9)

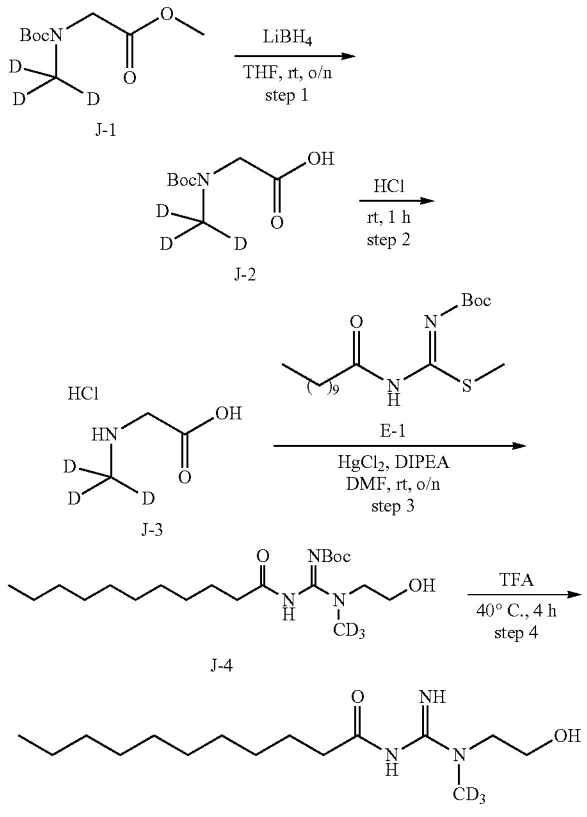

Compound 9

Step 1: Synthesis of J-2

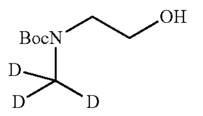

To a solution of methyl 2-(tert-butoxycarbonyl(trideuteriomethyl)amino)acetate (5.0 g, 24.3 mmol, see Example 1, synthesis of B-1 as reference) in 30 mL of THF was added LiBH4 (18 mL, 1M in THF) at 0° C. and the mixture was stirred at rt overnight. The reaction mixture was quenched with HCOOH to pH=6. The solvent was removed and the residual aqueous solution was extracted with EtOAc (3×30 ml). Then the combined organic phase was dried over $Na_2SO_4$ and concentrated to afford tert-butyl 2-hydroxyethyl (trideuteriomethyl)carbamate (3.76 g, 87% yield; Compound J-2) as a colorless oil. ES LC-MS m/z=201 $(M+Na^+)$.

Step 2: Synthesis of J-3

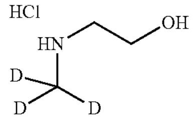

A mixture of tert-butyl 2-hydroxyethyl(trideuteriomethyl) carbamate (3.76 g, 21.1 mmol) in HCl (10 ml, 4 M in dioxane) was stirred at rt for 1 h. The resulting mixture was concentrated to 2-(trideuteriomethyl amino)ethanol (2.45 g, 100% yield; Compound J-3) as a colorless oil used for next step directly.

Step 3: Synthesis of J-4

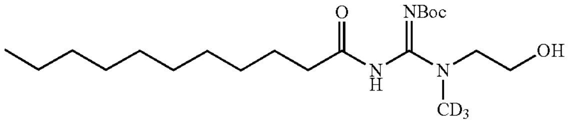

To a solution of tert-butyl methylthio(undecanamido) methylenecarbamate (700 mg, 1.96 mmol), Compound E-1 synthesized according to Example 3, and 2-(trideuteriomethyl amino)ethanol (313 mg, 2.74 mmol; Compound J-3) in 15 mL of DMF was added $HgCl_2$ (533 mg, 1.96 mmol) and DIPEA (759 mg, 5.88 mmol) and the mixture was stirred at 25° C. for 3 hours. 50 mL of EA was added and the mixture was washed with water (3×50 ml). Then the organic phase was dried over $Na_2SO_4$ and concentrated to give tert-butyl ((2-hydroxyethyl)(trideuteriomethyl)amino)(undecanamido)methylenecarbamate (758 mg, crude, dissolved in 2 mL of EA) as a solid (Compound J-4). ES LC-MS m/z=389 $(M+H)^+$.

Step 4: Synthesis of (N-(N-(2-hydroxyethyl)-N-trideuteriomethyl carbamimidoyl)undecanamide (Compound 9)

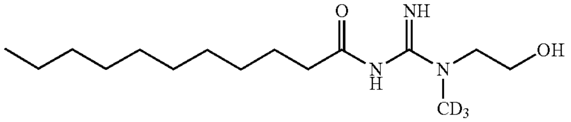 [SMILES: [2H]C([2H])([2H])N(CCO)C(=N)NC(=O)CCCCCCCCCC]

A mixture of tert-butyl ((2-hydroxyethyl)(trideuteriomethyl)amino)(undecanamido)methylenecarbamate (758 mg, crude, dissolved in 2 mL of EA; Compound J-4) in TFA (15 ml) was stirred at 40° C. for 4 h. The resulting mixture was concentrated and the residue was purified by Prep-HPLC (TFA condition). The product was converted to an HCL salt by adding 1 N HCl to give HCl salt (N-(N-(2-hydroxyethyl)-N-trideuteriomethyl carbamimidoyl)undecanamide) (39.5 mg, 7% yield, Compound 9) as a white solid. ES LC-MS m/z=289 $(M+H)^+$. $^1$H NMR (MeOD) δ: $^1$H NMR (400 MHz, MeOD): δ 3.82-3.84 (m, 2H), 3.68 (brs, 2H), 2.53 (brs, 2H), 1.69 (d, J=7.2 Hz, 2H), 1.32-1.36 (m, 14H), 0.92 (t, J=6.4 Hz, 3H).

General Procedures for Macrocyclic Compounds

Example PDT could be prepared using standard chemistry techniques in the appropriate solvents (Scheme 1). For example intermediate 3 could be prepared by first forming the acid chloride of 1 using standard conditions followed by addition of intermediate 2. Removal of the 4-Nitrophenylsulfonyl group using cesium carbonate with phenyl sulfide gave intermediate 4. Coupling of the appropriately protected SM-1 (Boc or Cbz) to SM-2 with a standard coupling reagent such as HATU with an amine base such as DIPEA gave 5 which then could be coupled to 4 using mercury chloride and the amine base such as TEA to give intermediate 6. A ring closing metathesis reaction using an appropriate catalyst such as Grubb II ruthenium catalyst and intermediate 6 under dilute conditions gave intermediate 7. Subjecting intermediate 7 to the appropriate catalyst such as Pd/C or PtO2 under an atmosphere of hydrogen gas gave Example PDT when a Cbz group was used or Intermediate 7 when a Boc protecting group was employed. Intermediate 7 containing a Boc protecting group could easily be converted to Example PDT by treatment with TFA or 1N HCl in Dioxane.

Scheme 1. General Synthesis

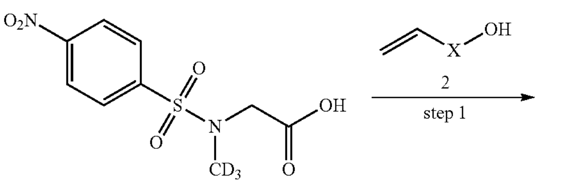

1

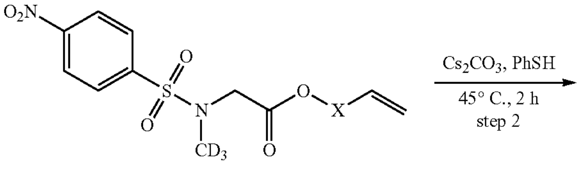

3

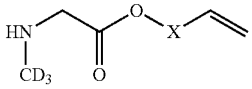

4

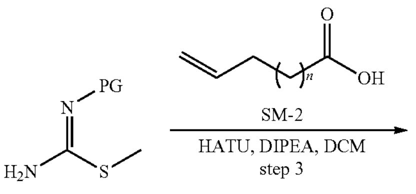

SM-1

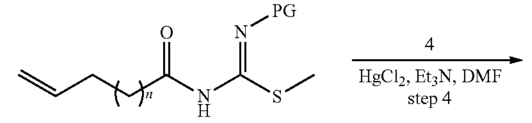

5

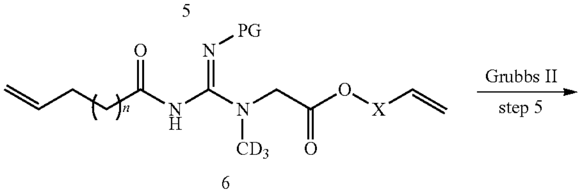

6

-continued

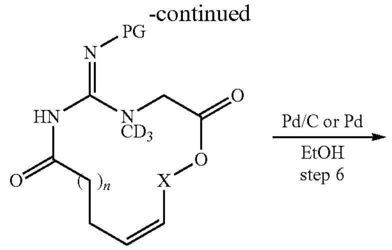

7

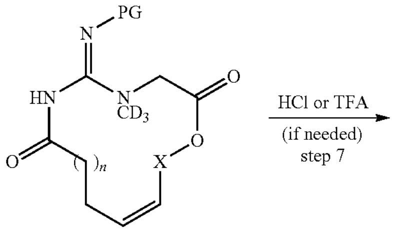

8

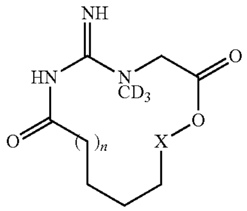

Example PDT

General Procedure for Intermediate 2 (Scheme 1)

Intermediate 2 can be prepared (if not commercially available) using several standard chemistry techniques depending on X. Below are examples of synthesizing variety of Intermediate 2.

General Procedure for Intermediate 2-1

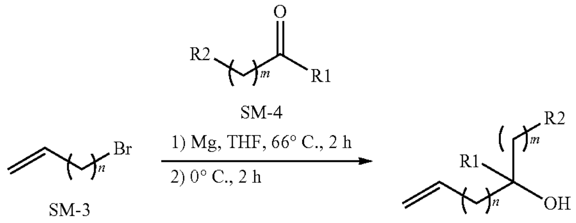

2-1

Intermediate 2-1 can be prepared using standard chemistry techniques in the appropriate solvents. For example SM-3 could be converted to the corresponding Grignard reagent by treatment with Magnesium metal at elevated temperature which then could be reacted with either the appropriate ketone or aldehyde to give 2-1.

General Procedure for Intermediate 2-2

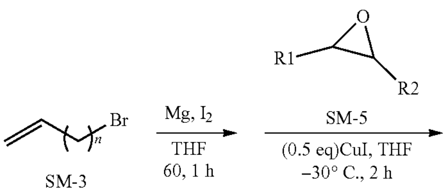

SM-3

-continued

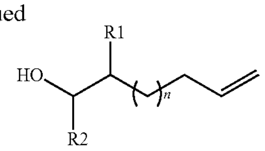

2-2

Intermediate 2-2 can be prepared using standard chemistry techniques in the appropriate solvents. For example SM-3 could be converted to the Grignard reagent by treatment with Magnesium metal and Iodine at elevated temperature which then could be reacted with either the appropriate epoxide in the presence of Copper Iodide at the appropriate temperature to give 2-2.

General Procedure for Intermediate 2-3

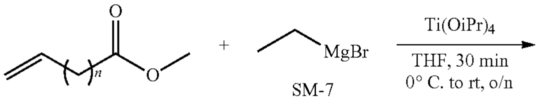

SM-6 SM-7

-continued

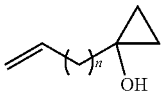

2-3

Intermediate 2-3 can be prepared using standard chemistry techniques in the appropriate solvents. For example intermediate 2-3 could be prepared using a Kulinkovich reaction by reacted SM-6 with Ethyl Grignard (SM-7) in the presence of Titanium (IV) at low temperature Example 7: Synthesis of 5-imino-4-trideuteriomethylguanidino-17-dimethyl-1-oxa-4,6-diazacycloheptadecane-2,7-dione dihydrochloride (Compound K)

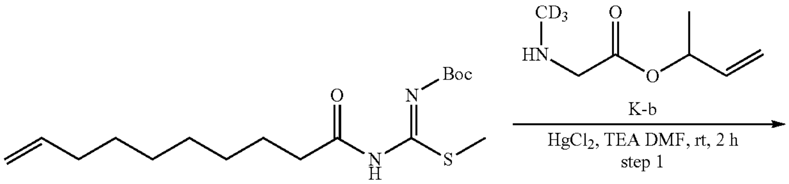

K-a

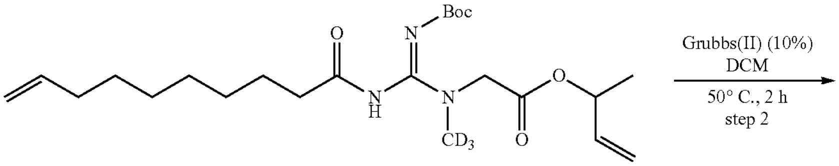

K-1

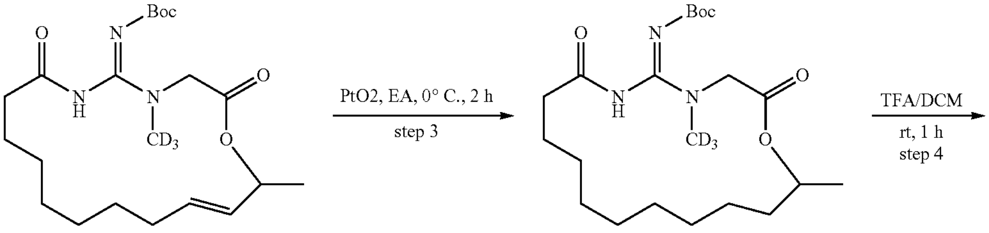

K-2 K-3

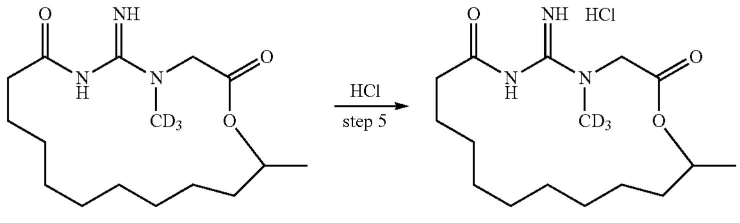

K-4 Compound K

Step a: Synthesis of Compound K-a

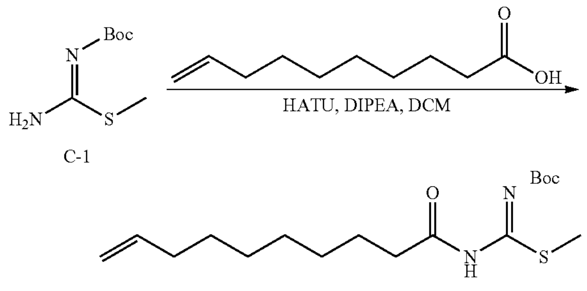

C-1

K-a

Compound K-a was synthesized according to Example 10, step 3, starting from (Z)-tert-butyl amino(methylthio) methylenecarbamate and dec-9-enoic acid. See also, Example 29, step 1, starting from tert-butyl (Z)-(amino (methylthio)methylene)carbamate instead of benzyl (Z)-(amino(methylthio)methylene)carbamate.

Step b: Synthesis of Compound K-b

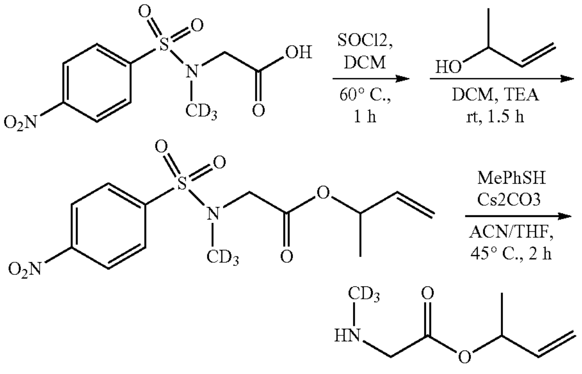

K-b

A mixture of 2-(N-trideuteriomethylguanidino-4-nitrophenylsulfonamido)acetic acid (3.78 g, 13.6 mmoL) in thionyl chloride (20 mL) and dichloromethane (20 mL) was stirred at 60° C. for 1 h. The combined organic was concentrated. Then, the resulting compound was dissolved in dichloromethane (40 mL) and but-3-en-2-ol (980 mg, 13.6 mmoL), triethylamine (4.12 g, 40.8 mmoL) was added and the resulting mixture was stirred at rt for 1 h. Water (50 mL) was added and the combined organic phase was washed with brine, dried over sodium sulfate and concentrated. The residue was purified by flash (Petroleum ether:Ethyl acetate/5:1) to afford but-3-en-2-yl 2-(N-trideuteriomethylguanidino-4-nitrophenylsulfonamido)acetate (3.6 g, 80% yield) as a white solid. ES LC-MS m/z=332.1 (M+H$^+$).

A mixture of but-3-en-2-yl 2-(N-trideuteriomethylguanidino-4-nitrophenylsulfonamido)acetate (3.6 g, 10.87 mmoL), p-Thiocresol (1.61 g, 13 mmoL), caesium carbonate (5.31 g, 16.3 mmoL) in acetonitrile (50 mL) and tetrahydrofuran (5 mL) was stirred at 45° C. for 1.5 h. The reaction mixture was filtrated, the filtrates were concentrated, the residue was purify by chromatography (Methanol:Dichloromethane/5:1) to afford but-3-en-2-yl 2-(trideuteriomethylguanidino)acetate (K-b, 1 g, 63% yield) as a yellow liquid. $^1$H NMR (DMSO-d) δ: 5.91-5.83 (m, 1H), 5.32-5.10 (m, 2H), 3.25 (s, 2H), 1.26-1.25 (m, 3H).

Step 1: Synthesis of Compound K-1

A mixture of (Z)-tert-butyl-dec-9-enamido(methylthio) methylenecarbamate (2.3 g, 6.7 mmoL), Compound K-b (982 mg, 6.7 mmoL) and a solution of triethylamine (2.03 g, 20.1 mmoL) in N,N-dimethylformamide (35 mL) was stirred at rt. A mixture of mercury dichloride (2.18 g, 8.04 mmoL) was added, the mixture was stirred at rt overnight. Water (40 mL) was added and the mixture was extracted with ethyl acetate (40 mL×3), the combined organic phase was washed with brine, dried over sodium sulfate and concentrated. The residue was purified by flash (petroleum ether:ethyl acetate 5:1) to afford (Z)-but-3-en-2-yl-2-(2-(tert-butoxycarbonyl)-3-dec-9-enoyl-1-trideuteriomethyl-guanidino)acetate (Compound K-1; 2.7 g, 91% yield) as a white solid. ES LC-MS m/z=441.3 (M+H$^+$).

Step 2: Synthesis of Compound K-2

A mixture of Compound K-1 (953 mg, 2.17 mmoL) and Grubbs(II) (183 mg, 0.217 mmoL) in dichloromethane (950 mL) was stirred at 50° C. for 2 h. The combined organic was concentrated. The residue was purified by flash (petroleum ether:ethyl acetate 5:1) to afford (Z)-tert-butyl-((E)-4-trideuteriomethylguanidino-17-methyl-2,7-dioxo-1-oxa-4,6-diazacycloheptadec-15-en-5-ylidene)carbamate (Compound K-2; 693 mg, 77% yield) as a pale yellow oil. ES LC-MS m/z=413.2 (M+H$^+$).

Step 3: Synthesis of Compound K-3

A mixture of Compound K-2 (310 mg, 0.75 mmoL) and platinum(IV) oxide (31 mg, 10%) in ethyl acetate (10 mL) was stirred under $H_2$ balloon for 2 h. The reaction mixture was filtrated and the filtrates were concentrated. The residue was purified by flash (petroleum ether:ethyl acetate 3:1) to afford (Z)-tert-butyl-4-trideuteriomethylguanidino-17-methyl-2,7-dioxo-1-oxa-4,6-diazacycloheptadecan-5-ylidenecarbamate (Compound K-3; 93 mg, 30% yield) as a yellow oil. ES LC-MS m/z=415.2 (M+H$^+$).

Step 4: Synthesis of Compound K-4

A mixture of Compound K-3 (100 mg, 0.24 mmoL) in dichloromethane (4 mL) and trifluoroacetic acid (1 mL) was stirred at rt for 1 h. The combined organic concentrated. The residue was dissolved with methanol purified by Pre-HPLC (FA) to afford 5-imino-4-trideuteriomethylguanidino-17-dimethyl-1-oxa-4,6-diazacycloheptadecane-2,7-dione (Compound K-4; 48 mg, 63% yield) as a white oil. ES LC-MS m/z=314.2 (M+H$^+$).

Step 5: Synthesis of Compound K

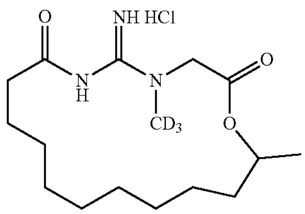

A mixture of Compound K-4 (120 mg, 0.38 mmoL) in water (50 mL) and acetonitrile (4 mL). The pH of the solution was adjusted to 4-5 with hydrochloric acid (1N). The solution was vacuum freeze drying to afford 5-imino-4-trideuteriomethylguanidino-17-dimethyl-1-oxa-4,6-diaza-cycloheptadecane-2,7-dione dihydrochloride (Compound K; 90 mg, 75% yield) as a white oil. ES LC-MS m: =314.2 (M+H$^+$). $^1$H NMR (DMSO-d) δ: 11.46 (s, 1H), 9.38 (s, 1H), 9.25 (s, 1H), 5.27 (1H, AB, J=18.1 Hz), 4.90-5.03 (m, 1H), 4.35 (1H, AB, J=19.0 Hz), 2.66-2.81 (m, 1H), 2.25-2.40 (m, 1H), 1.43-1.45 (m, 4H), 1.21 (3H, d, J=6.3 Hz), 1.20-1.35 (m, 12H).

Example 8: Synthesis of 17-ethyl-5-imino-4-trideuteriomethyl-1-oxa-4,6-diazacycloheptadecane-2,7-dione hydrochloric acid salt (Compound L)

Synthesis of Compound 1

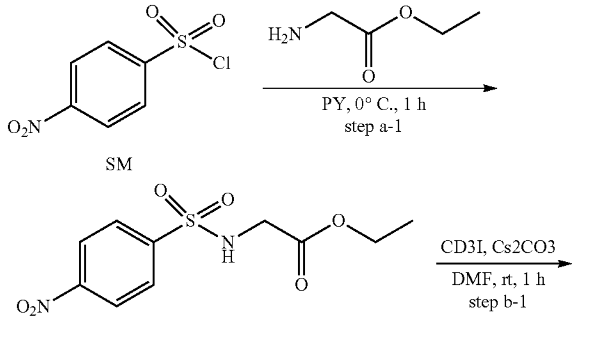

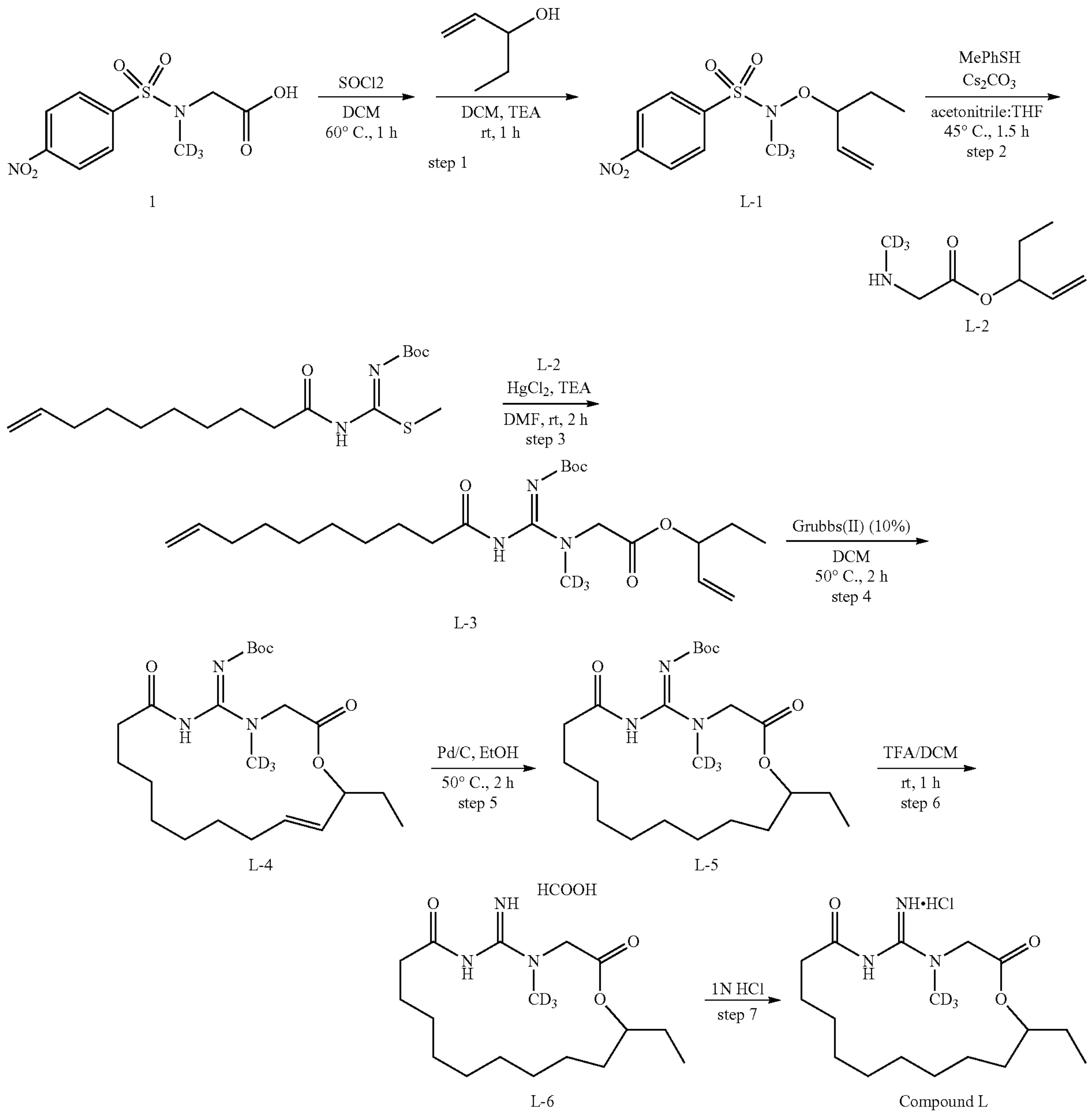

-continued

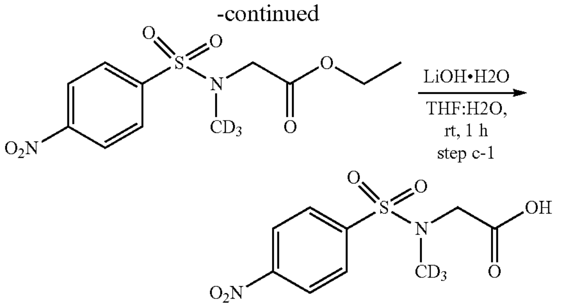

Step a-1

A mixture of ethyl 2-aminoacetate (64 g, 288 mmoL) in pyridine (140 mL) was stirred at 0° C., a mixture of 4-nitrobenzene-1-sulfonyl chloride (40 g, 288 mmoL) in pyridine (60 mL) was added drop wise, the resulting mixture was stirred at 0° C. for 1 h. The residue was purified by recrystallization to afford ethyl 2-(4-nitrophenylsulfonamido) acetate (70 g, 63% yield) as a yellow solid. ES LC-MS m/z=289.2 ($M+H^+$).

Step a-2

A mixture of ethyl 2-(4-nitrophenylsulfonamido)acetate (30 g, 104.1 mmoL), Caesium carbonate (51 g, 156.2 mmoL) and a solution of Iodomethane-d3 (16.6 g, 114.6 mmoL) in N,N-Dimethylformamide (75 mL) was stirred at rt for 1 h. Poured the reaction solution into ice water (500 mL) and filtered to afford ethyl 2-(N-trideuteriomethylguanidino-4-nitrophenylsulfonamido)acetate (30 g, 94% yield). ES LC-MS m/z=328.3 ($M+Na^+$).

Step a-3

A mixture of ethyl 2-(N-trideuteriomethylguanidino-4-nitrophenylsulfonamido) acetate (40 g, 131.1 mmoL) in tetrahydrofuran (80 mL) was stirred at rt, a solution of lithium hydroxide monohydrate (10.5 g, 262.2 mmoL) in water (40 mL) was added, the resulting mixture was stirred at rt for 1 h. The combined organic was concentrated, the pH of the solution was adjusted to 4-5 with hydrochloric acid (1N). The mixture was extracted with dichloromethane (150 mL×3), the combined organic was dried over sodium sulfate anhydrous and concentrated to afford 2-(N-trideuteriomethylguanidino-4-nitrophenylsulfonamido)acetic acid (33 g, 91% yield, 1). $^1H$ NMR (DMSO-d) δ: 12.9 (s, 1H), 8.38-8.42 (m, 2H), 8.04-8.08 (m, 2H), 3.99 (s, 1H).

Step 1: Synthesis of Compound L-1

A round bottom flask equipped with a stir bar was charged with 2-[(4-nitrophenyl)sulfonyl-(trideuteriomethyl)amino] acetic acid (2 g, 7.22 mmol) in DCM (18 mL) was added $SOCl_2$ (18 mL) at ice-bath, and refluxed at 60° C. for 1 hour. The reaction was evaporated, dissolved in DCM (30 mL). To a solution of pent-1-en-3-ol (652 mg, 7.58 mmol) and triethylamine (2.19 g, 21.66 mmol) in DCM (15 mL) was added dropwise at ice-bath, then stirred at room temperature for 1 hour. The reaction was added DCM (100 mL), washed with water (40 mL×3) and brine (40 mL), dried and evaporated, purified by flash chromatography (40 G) eluting with (PE:EA/0%-18%), to obtain pent-1-en-3-yl-2-(N-trideuteriomethyl-4-nitrophenylsulfonamido)acetate (Compound L-1; 2.78 g, 7.55 mmol, 108% yield) as a pale yellow solid. ES LC-MS m/z=368.0 ($M+Na^+$). $^1H$ NMR (DMSO-$d_6$) δ: 8.36-8.33 (m, 2H), 8.01-7.98 (m, 2H), 5.31-5.30 (m, 1H), 5.21-5.17 (m, 2H), 5.09-5.07 (m, 1H), 4.10 (s, 2H), 1.42-1.34 (m, 2H), 0.89-0.84 (m, 3H).

Step 2: Synthesis of Compound L-2

A round bottom flask equipped with a stir bar was charged with Compound L-1 (2.78 g, 7.55 mmol) and $Cs_2CO_3$ (5.2 g, 16.12 mmol) in ACN:THF (10:1, 80 mL) was added 4-methylbenzenethiol (2 g, 16.12 mmol) at rt. The reaction was stirred at 45° C. for 1.5 h. The mixture was filtered, evaporated, purified by SGC (PE:EA/10:1 to DCM:MeOH/10:1) to obtain to give pent-1-en-3-yl-2-(trideuteriomethylamino) acetate (Compound L-2; 910 mg, 5.68 mmol, 71% yield) as a pale yellow oil. The crude was directly used next step further without purification.

Step 3: Synthesis of Compound L-3

A round bottom flask equipped with a stir bar was charged with (Z)-tert-butyl dec-9-enamido(methylthio)methylenecarbamate (1.69 g, 4.74 mmol, K-a, see Example 7), Compound L-2 (910 mg, 5.68 mmol) and TEA (958 mg, 9.48 mmol) in DMF (35 mL) was added $HgCl_2$ (1420 mg, 5.21 mmol) at rt. The reaction was stirred at rt for 2 hours. The reaction was added EA (100 mL), washed with water (30 mL×3) and brine (30 mL), dried and evaporated, purified by flash chromatography (40 G) eluting with (PE:EA/0%-20%) to give (Z)-pent-1-en-3-yl-2-(2-(tert-butoxycarbonyl)-3-dec-9-enoyl-1-trideuteriomethylguanidino) acetate (Compound L-3; 1.54 g, 3.38 mmol, 71% yield) as a colorless oil. ES LC-MS m/z=455.1 ($M+H^+$). $^1H$ NMR (DMSO-$d_6$) δ: 9.95 (br s, 1H), 5.8-5.7 (m, 2H), 5.27-5.13 (m, 2H), 5.01-4.91 (m, 2H), 4.16 (s, 2H), 2.21 (br s, 2H), 2.02-1.97 (m, 2H), 1.63-1.52 (m, 2H), 1.49 (s, 2H), 1.33 (s, 10H), 1.25 (s, 8H), 0.87-0.83 (t, J=7.2 Hz, 3H).

Step 4: Synthesis of Compound L4

A round bottom flask equipped with a stir bar was charged with Compound L-3 (1.54 g, 3.38 mmol) in DCM (1200 mL) was added Grubbs(II) (575 mg, 0.67 mmol) at rt. The reaction was stirred at 50° C. with argon for 2 hours. The reaction was cooled to room temperature, quenched with ethoxyethene (10 mL), evaporated, purified by flash chromatography (20 G) eluting with (PE:EA/0%-25%) to give (Z)-tert-butyl-((E)-17-ethyl-4-trideuteriomethyl-2,7-dioxo-1-oxa-4,6-diazacycloheptadec-15-en-5-ylidene) carbamate (Compound L-4; 1220 mg, 2.86 mmol, 86% yield) as a pale brown oil. ES LC-MS m/z=427.2 ($M+H^+$).

Step 5: Synthesis of Compound L-5

A round bottom flask equipped with a stir bar was charged with Compound L4 (500 mg, 1.17 mmol) in ethyl acetate (10 mL) was added platinic oxide (51 mg) at rt. The reaction was stirred at rt with hydrogen for 3 h. The reaction was filtered, evaporated, purified by Pre-HPLC (FA) to give (Z)-benzyl-((E)-14-butyl-4-trideuteriomethyl-2,7-dioxo-1-oxa-4,6-diazacyclotetradec-11-en-5-ylidene) carbamate (Compound L-5; 400 mg, 0.93 mmol, 36% yield) as a pale white solid. ES LC-MS m/z=429.2 ($M+H^+$). $^1H$ NMR (DMSO-$d_6$) δ: 9.87 (s, 1H), 4.824.81 (d, J=4.8 Hz, 1H), 4.204.02 (m, 2H), 2.24-2.13 (m, 2H), 1.54-1.49 (m, 5H), 1.40-1.35 (m, 9H), 1.23 (s, 2H), 0.85-0.81 (t, J=7.2 Hz, 3H).

Step 6: Synthesis of Compound L-6

A round bottom flask equipped with a stir bar was charged with Compound L-5 (250 mg, 0.58 mmol) in DCM (6 mL) was added trifluoroacetic acid (2 mL), stirred at rt for 1 hour. The reaction was evaporated, dissolved in ACN (3 mL), purified by Pre-HPLC (FA), lyophilized to give 18-ethyl-5-imino-4-trideuteriomethyl-1-oxa-4,6-diazacyclooctadecane-2,7-dione (Compound L-6; 90 mg, 0.27 mmol, 47% yield) as a white solid. ES LC-MS m/z=329.2 (M+H$^+$). $^1$H NMR (DMSO-d$_6$) δ: 10.75 (br s, 11H), 9.43-9.21 (br s, 1H), 4.82 (s, 2H), 4.39 (br s, 1H), 2.41 (s, 1H), 1.57-1.51 (m, 6H), 1.25 (s, 12H), 0.86-0.82 (t, J=7.6 Hz, 3H).

Step 7: Synthesis of Compound L

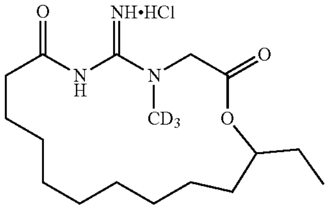

A round bottom flask equipped with a stir bar was charged with Compound L-6 (90 mg, 0.27 mmol) in ACN (5 mL) and water (5 mL) was added to 1N of HCl (0.5 mL), stirred at it for 0.5 hour. The reaction was lyophilized to obtain 17-ethyl-5-imino-4-trideuteriomethyl-1-oxa-4,6-diazacycloheptadecane-2,7-dione hydrochloric acid salt (Compound L; 84.5 mg, 0.25 mmol, 97%) as a white solid. ES LC-MS m/z=329.2 (M+H$^+$). $^1$H NMR (DMSO-d$_6$) δ: 11.30 (s, 1H), 9.40-9.23 (m, 2H), 5.24-5.20 (m, 1H), 4.85-4.84 (m, 1H), 4.43-4.38 (m, 1H), 2.69 (m, 1H), 2.31 (s, 1H), 1.58-1.51 (m, 6H), 1.26 (s, 12H), 0.87-0.83 (t, J=7.2 Hz, 3H).

Example 9: Synthesis of 5-imino-4-trideuteriomethylguanidino-18-methyl-1-oxa-4,6-diazacyclooctadecane-2,7-dione (Compound M)

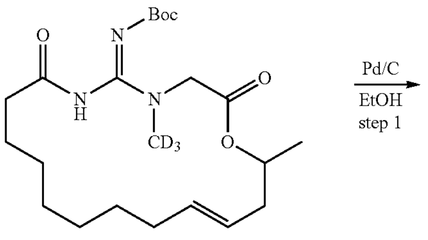

M-1

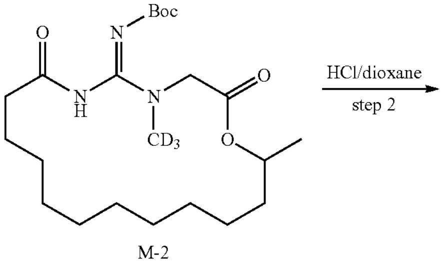

M-2

-continued

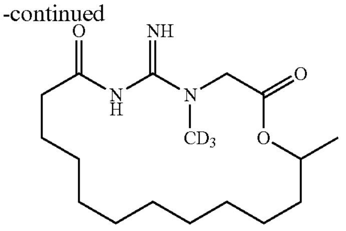

Compound M

Synthesis of M-a

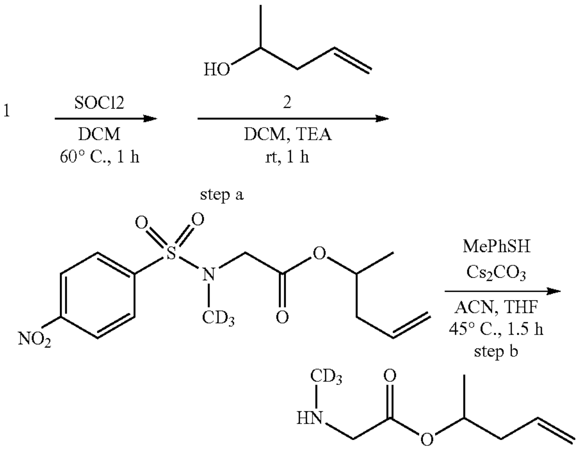

M-a

Step a: pent-4-en-2-yl 2-(N-trideuteriomethyl-4-nitrophenylsulfonamido)acetate

A mixture of 2-(N-trideuteriomethyl-4-nitrophenylsulfonamido)acetic acid (2.2 g, 7.94 mmol) and sulfurous dichloride (20 ml) in dichloromethane (20 ml) was heated to 60° C. and stirred for 2 hs. The mixture was concentrated, the residue was dissolved with dichloromethane (20 ml) which was added in a mixture of pent-4-en-2-ol (750 mg, 8.72 mmol) and triethylamine (2 g, 19.85 mmol) in dichloromethane (20 ml) at ice-water and then stirred at rt for 1 h. water (40 ml) was added and the mixture was extracted with dichloromethane (40 ml×3), the combined organic phase was washed with brine, dried over sodium sulfate and concentrated. The residue was purified by chromatography (Petroleumether:ethylacetate=5:1) to afford pent-4-en-2-yl 2-(N-trideuteriomethyl-4-nitrophenylsulfonamido)acetate (1.983 g, 72%) as a white solid. ES LC-MS m/z=368.1 (M+Na).

Step b: Synthesis of M-a

A mixture of pent-4-en-2-yl 2-(N-trideuteriomethyl-4-nitrophenylsulfonamido)acetate (1.983 g, 5.75 mmol), 4-methylbenzenethiol (1.43 g, 11.5 mmol) and Cesium carbonate (3.75 g, 11.5 mmol) in acetonitrile (30 ml) and tetrahydrofuran (3 ml) was stirred at 45° C. for 2 hs. The reaction mixture was filtrated and the filtrates were concentrated. The residue was purified by chromatography (dichloromethane:methanol=10:1 with 0.1% Ammonium hydroxide) to afford pent-4-en-2-yl 2-(trideuteriomethylamino) acetate (713 mg, 78%) as a yellow liquid. ES LC-MS m/z=161.3 ($M+H^+$).

Synthesis of M: Compound M-1 was synthesized according to Example 7, steps 1 and 2, starting with (Z)-tert-butyl-dec-9-enamido(methylthio)methylenecarbamate (K-a, see Example 7) and pent-4-en-2-yl-2-(trideuteriomethylguanidino) (M-a). Compound M-1 was obtained as a pale yellow oil (743 mg, 53% yield). ES LC-MS m/z=427.2 ($M+H^+$).

Step 1: Synthesis of Compound M-2

A mixture of Compound M-1 (500 mg, 1.17 mmoL) and palladium 10/6 on carbon (80 mg, 20%) in ethanol (5 mL) was stirred under $H_2$ balloon for 2 h. The reaction mixture was filtrated and the filtrates were concentrated to afford (Z)-tert-butyl-4-trideuteriomethylguanidino-18-methyl-2,7-dioxo-1-oxa-4,6-diazacyclooctadecan-5-ylidenecarbamate (Compound M-2; 454 mg, 90% yield) as a white solid. ES LC-MS m/z=429.3 ($M+H^+$).

Step 2: Synthesis of Compound M

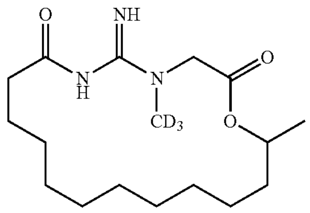 [SMILES: [2H]C([2H])([2H])N1CC(=O)OC(C)CCCCCCCCCCC(=O)NC1=N]

A mixture of afford Compound M-2 (716 mg, 1.67 mmoL) in HCl/dioxane (15 mL) was stirred at rt for overnight. The combined organic concentrated. The residue was dissolved with methanol purified by Pre-HPLC(FA) to afford 5-imino-4-trideuteriomethylguanidino-18-methyl-1-oxa-4,6-diazacyclooctadecane-2,7-dione (Compound M; 280 mg, 51% yield) as a white solid. ES LC-MS m/z=329.2 ($M+H^+$). $^1$H NMR (DMSO-d) δ: 9.4-10.2 (br, 1H), 7.0-7.8 (br, 1H), 4.80-4.92 (m, 2H), 3.85 (1H, AB, J=17.5 Hz), 1.95-2.15 (m, 2H), 1.40-1.60 (m, 4H), 1.18 (3H, dr, J=6.3 Hz), 1.15-1.35 (m, 14H).

Example 10: Synthesis of 18-ethyl-5-imino-4-trideuteriomethyl-1-oxa-4,6-diazacyclooctadecane-2,7-dione (Compound N)

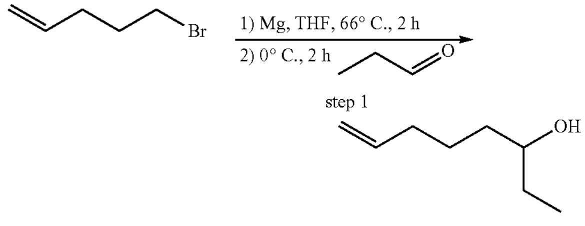

N-1

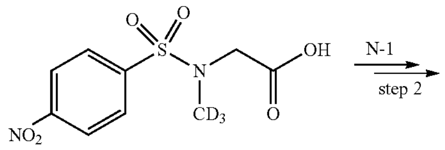

-continued

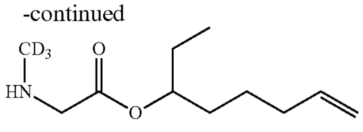

N-2

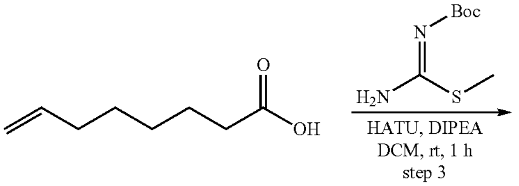

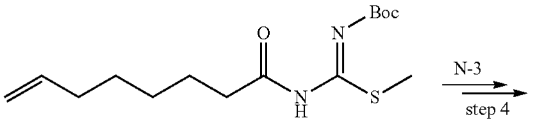

N-3

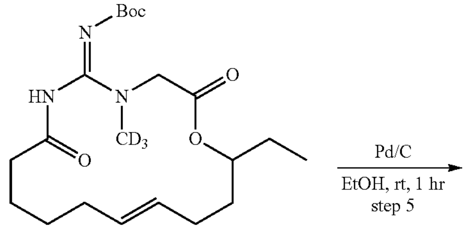

N-4

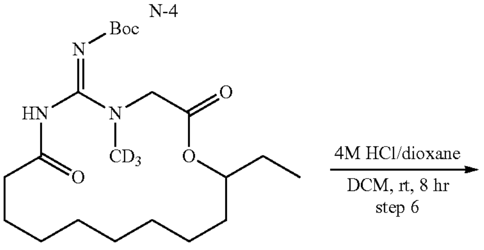

N-5

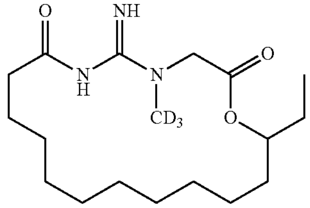

Compound N

Step 1. Synthesis of Compound N-1

A round bottom flask equipped with a stir bar and nitrogen inlet was charged with 5-bromopent-1-ene (10 g, 67.11 mmol), magnesium (2.42 g, 100.67 mmol) and iodine (5 granules) in tetrahydrofuran (dry, 100 mL). The mixture was stirred at 60° C. for two hours. The reaction was cooled to rt ("B solution"). To a solution of propionaldehyde (3.89 g, 67.11 mmol) in THF (dry, 50 mL) was added dropwise B solution at −30° C. Then the reaction was stirred at −30° C. for 30 minute. The reaction was warmed to rt for 2 hour, and quenched with sat. aqueous ammonium chloride (60 mL), extracted with ethyl acetate (80 mL×3), washed with water (60 mL×1) and brine (60 mL), dried and evaporated, distilled with vacuum at 124° C. (oil-bath) to give oct-7-en-3-ol (Compound N-1; 1.77 g, 14.04 mmol, 26% yield) as a colorless oil. $^1$H NMR (DMSO-$d_6$) δ: 5.83-5.76 (m, 1H), 5.02-4.91 (m, 2H), 4.26 (d, J=5.2 Hz, 1H), 3.31-3.28 (m, 1H), 2.06-1.97 (m, 2H), 1.47-1.22 (m, 6H), 0.88-0.81 (m, 3H).

Step 2. Synthesis of Compound N-2

Compound N-2 was synthesized according to Example 8, steps 1 and 2, starting from 2-[(4-nitrophenyl)sulfonyl-(trideuteriomethyl)amino]acetic acid and Compound N-1. Compound N-2 (oct-7-en-3-yl-2-(trideuteriomethylamino) acetate) was obtained as a pale brown oil (1.7 g, 8.42 mmol, 51% yield). $^1$H NMR (DMSO-d6) δ: 5.80-5.74 (m, 1H), 5.02-4.92 (m, 2H), 4.79-4.76 (m, 1H), 3.26 (br s, 2H), 2.04-1.97 (m, 3H), 1.57-1.44 (m, 4H), 1.38-1.29 (m, 2H), 0.85-0.80 (m, 3H).

Step 3. Synthesis of Compound N-3

A round bottom flask equipped with a stir bar was charged with oct-7-enoic acid (1 g, 7.04 mmol) and HUTU (4.01 g, 10.56 mmol) in dichloromethane (15 mL) was added drop-wise (Z)-benzyl-amino(methylthio)methylenecarbamate (1.40 g, 7.39 mmol) and DIPEA (1.82 g, 14.08 mmol) in DCM (10 mL) at room temperature. The mixture was stirred at rt for 1 h. The reaction was added DCM (100 mL), washed with water (30 mL×3) and brine (40 mL), dried and evaporated, purified by flash chromatography (40 G) eluting with (PE:EA/0%-18%), to give (Z)-tert-butyl-methylthio(oct-7-enamido)methylenecarbamate (Compound N-3; 1.72 g, 8.04 mmol, 77% yield) as a white solid. ES LC-MS m/z=215.1 (M-99$^+$). $^1$H NMR (DMSO-$d_6$) δ: 11.15 (s, 1H), 5.79-5.75 (m, 1H), 5.02-4.92 (m, 2H), 2.34-2.31 (t, J=7.2 Hz, 2H), 2.27 (s, 3H), 2.01-1.97 (m, 2H), 1.52-1.49 (m, 2H), 1.42 (S, 9H), 1.36-1.26 (m, 4H).

Step 4. Synthesis of Compound N-4

Compound N-4 was synthesized according to Example 8, steps 3 and 4, starting from Compound N-2 and Compound N-3. (Z)-benzyl-((f)-14-butyl-4-tri deuteriomethyl-2,7-dioxo-1-oxa-4,6-diazacyclotetradec-11-en-5-ylidene) carbamate (Compound N4; 900 mg, 2.45 mmol, 78% yield) as a colorless oil. ES LC-MS m/z=441.4 (M+H$^+$). $^1$H NMR (DMSO-$d_6$) δ: 9.85 (br s, 1H), 5.29-5.27 (m, 2H), 4.73 (br s, 1H), 4.19-4.09 (m, 2H), 2.18 (s, 2H), 2.00-1.96 (m, 4H), 1.48-1.15 (m, 21H), 0.85-0.81 (t, J=7.6 Hz, 3H).

Step 5. Synthesis of Compound N-5

Compound N-5 was synthesized according to Example 9, step 1 from Compound N-4. (Z)-Benzyl-((E)-14-butyl-4-trideuteriomethyl-2,7-dioxo-1-oxa-4,6-diazacyclotetradec-11-en-5-ylidene) carbamate (280 mg, 0.63 mmol, 69% yield) as a colorless oil. ES LC-MS m/z=443.4 (M+H$^+$). $^1$H NMR (DMSO-$d_6$) δ: 9.93-9.92 (d, J=6 Hz, 1H), 4.77-4.75 (t, J=5.6 Hz, 1H), 4.24-4.00 (m, 2H), 2.24-2.17 (m, 2H), 1.57-1.10 (m, 29H), 0.85-0.81 (t, J=7.6 Hz, 3H).

Step 6. Synthesis of Compound N

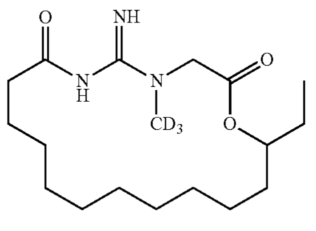 [SMILES: [2H]C([2H])([2H])N1CC(=O)OC(CC)CCCCCCCCCCC(=O)NC1=N]

Compound N was synthesized according to Example 9, step 2, starting from Compound N-5. 18-Ethyl-5-imino-4-trideuteriomethyl-1-oxa-4,6-diazacyclooctadecane-2,7-dione (Compound N; 140.2 mg, 0.408 mmol, 59% yield) as a white solid. ES LC-MS m/z=343.2 (M+H$^+$). $^1$H NMR (DMSO-d6) δ: 9.80 (br s, 1H), 7.39 (br s, 1H), 4.90-4.86 (d, J=18 Hz, 1H), 4.77-4.74 (t, J=6 Hz, 1H), 3.94-3.90 (d, J=17.2 Hz, 1H), 2.10-2.05 (q, J=6.4 Hz, 2H), 1.58-1.50 (m, 6H), 1.25 (s, 14H), 0.86-0.81 (t, J=7.6 Hz, 3H).

Example 11: Synthesis of 16-ethyl-5-imino-4-trideuteriomethyl-1-oxa-4,6-diazacyclohexadecane-2,7-dione (Compound O)

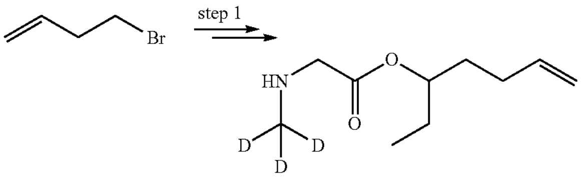

O-1

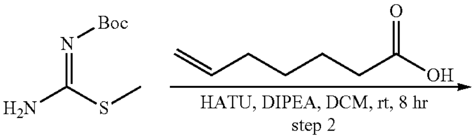

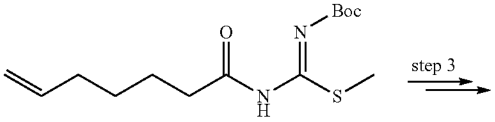

O-2

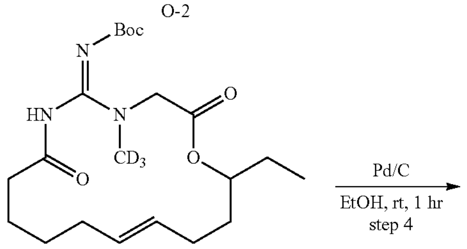

O-3

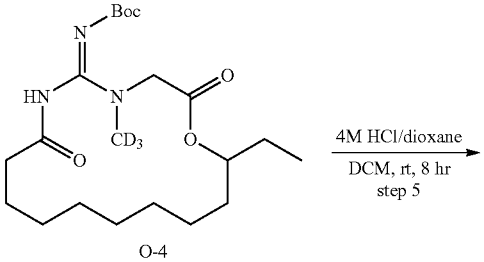

O-4

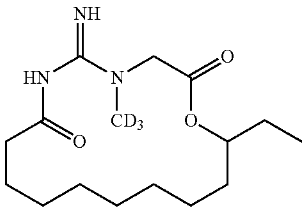

Compound O

Step 1. Synthesis of Compound O-1

Compound O-1 was synthesized according to Example 10, steps 1 and 2, starting from 4-bromobut-1-ene. Hept-6-en-3-yl-2-(trideuteriomethylamino)acetate (Compound O-1; 0.9 g, 4.79 mmol, 85% yield) was obtained as a pale yellow oil.

Step 2. Synthesis of Compound O-2

Compound O-2 was synthesized according to Example 10, step 3, starting from (Z)-tert-butyl amino(methylthio)methylenecarbamate and hept-6-enoic acid. (Z)-tert-Butyl hept-6-enamido(methylthio)methylenecarbamate (Compound 0-2; 4.4 g, 94% yield) was obtained as a white solid. ES LC-MS m/z=201.1 (M-Boc+$H^+$).

Step 3. Synthesis of Compound O-3

Compound O-3 was synthesized according to Example 8, steps 3 and 4, starting from Compound O-1 and Compound O-2. (Z)-tert-Butyl-((E)-16-ethyl-4-trideuteriomethyl-2,7-dioxo-1-oxa-4,6-diazacyclohexadec-12-en-5-ylidene)carbamate (Compound O-3; 380 mg, 81% yield) was obtained as a yellow oil. ES LC-MS m/z=413 (M+1).

Step 4. Synthesis of Compound O-4

Compound O-4 as synthesized according to Example 9, step 1 from Compound O-3. (Z)-tert-Butyl-16-ethyl-4-trideuteriomethyl-2,7-dioxo-1-oxa-4,6-diazacyclohexadecan-5-ylidenecarbamate (Compound O-4; 320 mg, 98% yield) was obtained as a brown oil. ES LC-MS m/z=415 (M+1).

Step 5. Synthesis of Compound O

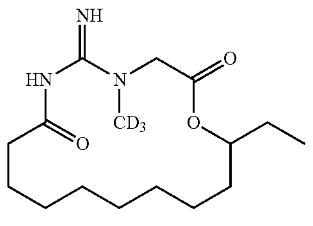 [SMILES: [2H]C([2H])([2H])N1CC(=O)OC(CC)CCCCCCCCC(=O)NC1=N]

Compound O was synthesized according to Example 9, step 2, starting from Compound O-4. 16-Ethyl-5-imino-4-trideuteriomethyl-1-oxa-4,6-diazacyclohexadecane-2,7-dione (Compound O; 80 mg, 33% yield) was obtained as a white solid. ES LC-MS m/z=315 (M+1).

Example 12: Synthesis of 5-imino-4-trideuteromethyl, 16-methyl-1-oxa-4,6-diazacyclohexadecane-2,7-dione (Compound P)

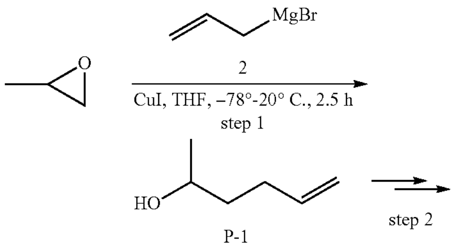

P-1

-continued

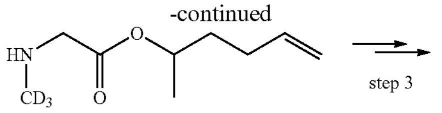

P-2

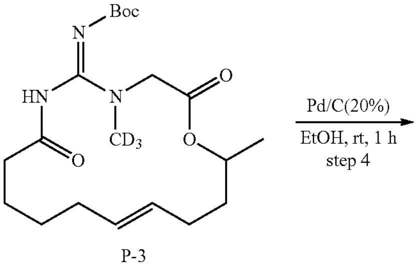

P-3

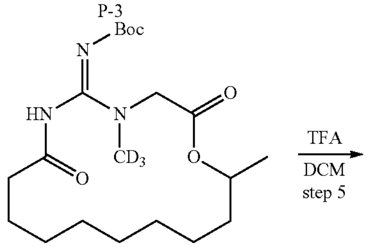

P-4

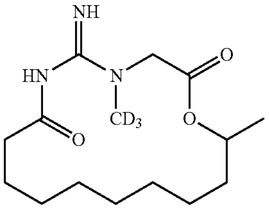

Compound P

Step 1. Synthesis of P-1

2-Methyloxirane (3.5 g, 60 mmol) was added dropwise to allylmagnesium bromide (I M in $Et_2O$, 90 mL, 90 mmol), followed by CuI (1.14 g, 6 mmol) at −78° C. and stirred for 2.5 h at this temperature. The reaction mixture was warmed to room temperature and sat. aq. $NH_4Cl$ (100 mL) was added and the organic phase separated. The organics were combined, dried ($MgSO_4$) and concentrated in vacuo to afford hex-5-en-2-ol (Compound P-1) as an oil: 3.5 g, 58% yield, ES LCMS m/z=115.3 (M+$H^+$). 1H NMR (400 MHz, DMSO) δ 5.93-5.69 (m, 1H), 5.11-4.84 (m, 2H), 4.37 (t, J=4.2 Hz, 1H), 3.58 (dt, J=11.6, 5.7 Hz, 1H), 2.18-1.86 (m, 2H), 1.48-1.24 (m, 2H), 1.18-1.10 (m, 2H), 1.03 (dd, J=8.7, 6.2 Hz, 3H).

Step 2. Synthesis of P-2

Compound P-2 was synthesized according to Example 8, steps 1 and 2, starting from 2-[(4-nitrophenyl)sulfonyl-(trideuteriomethyl)amino]acetic acid and Compound P-1. Crude hex-5-en-2-yl 2-(methylmethylamino)acetate (Compound P-2; 1.0 g, 100% yield) was obtained as a yellow oil. ES LC-MS m/z=175.1 (M+$H^+$).

Step 3. Synthesis of P-3

Compound P-3 was synthesized according to Example 8, steps 3 and 4, starting from Compound P-2 and Compound O-2. (Z)-tert-butyl-((E)-4-trideuteromethyl, 16-methyl-2,7-dioxo-1-oxa-4,6-diazacyclohexadec-12-en-5-ylidene)carbamate (Compound P-3; 400 mg, 36% yield) was obtained as an yellow oil. ES LC-MS m/z=399.2 (M+H+).

Step 4. Synthesis of P-4

Compound P4 was synthesized according to Example 9, step 1 from Compound P-3 using Pd/C (20%). (Z)-tert-Butyl-4-trideuteromethyl, 16-methyl-2,7-dioxo-1-oxa-4,6-diazacyclohexadecan-5-ylidenecarbamate (Compound P-4; 300 mg, 75% yield) was obtained as a yellow solid. ES LC-MS m/z=401.3 (M+H+).

Step 5. Synthesis of Compound P

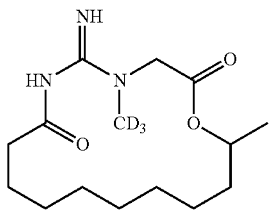 [SMILES: [2H]C([2H])([2H])N1CC(=O)OC(C)CCCCCCCCC(=O)NC1=N]

Compound P was synthesized according to Example 9, step 2, starting from Compound P4. 5-Imino-4-trideuteromethyl, 16-methyl-1-oxa-4,6-diazacyclohexadecane-2,7-dione (Compound P, 100 mg, 44% yield) was obtained as a white solid. ES LC-MS m/z=301.2 (M+H+). $^1$H NMR (400 MHz, DMSO) δ 9.82 (s, 1H), 7.38 (s, 1H), 5.17-4.89 (m, 1H), 4.68 (d, J=17.3 Hz, 1H), 4.03 (d, J=17.2 Hz, 1H), 2.24-1.91 (m, 2H), 1.50 (d, J=36.5 Hz, 4H), 1.28-0.99 (m, 13H).

Example 13: Synthesis of (R)-5-imino-4,17-dimethyl-1-oxa-4,6-diazacycloheptadecane-2,7-dione hydrochloride (Compound Q)

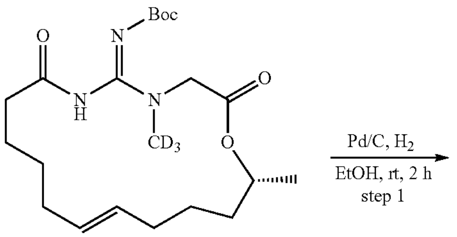

Q-1

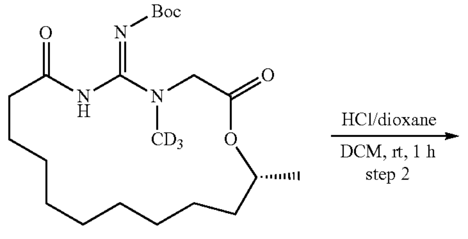

Q-2

-continued

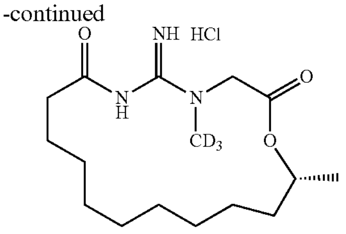

Compound Q

In general, Compound Q was synthesized according to Example 12 starting from (S)-2-methyloxirane instead of 2-methyloxirane and 4-bromobut-1-ene instead of allylmagnesium bromide. Compound Q-1, (Z)-tert-butyl-((R,E)-4-trideuteromethyl, 17-methyl-2,7-dioxo-1-oxa-4,6-diazacycloheptadec-12-en-5-ylidene)carbamate, was obtained as an yellow oil (800 mg, 88% yield). ES LC-MS m/z=413.2 (M+H+).

Step 1. Synthesis of Compound Q-2

Compound Q-2 was synthesized according to Example 9, step 1 from Compound Q-1 using Pd/C (20%). (R,Z)-tert-Butyl-4-trideuteromethyl, 17-methyl-2,7-dioxo-1-oxa-4,6-diazacycloheptadecan-5-ylidenecarbamate (Compound Q-2; 750 mg, 94% yield) was obtained as an yellow solid. ES LC-MS m/z=415.3 (M+H+).

Step 2. Synthesis of Compound Q

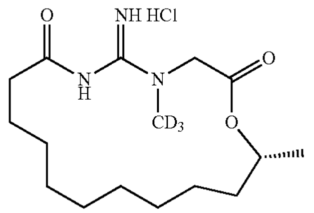

Compound Q was synthesized according to Example 9, step 2, starting from Compound Q-2. (R)-5-imino-4,17-dimethyl-1-oxa-4,6-diazacycloheptadecane-2,7-dione hydrochloride (Compound Q; 340 mg, 60% yield) was obtained as a white solid. ES LC-MS m/z=315.2 (M+H+). 1H NMR (400 MHz, DMSO) δ 11.43 (s, 1H), 9.31 (d, J=55.0 Hz, 2H), 5.25 (d, J=19.1 Hz, 1H), 4.96 (s, 1H), 4.35 (d, J=18.8 Hz, 1H), 2.72 (s, 1H), 2.33 (s, 1H), 1.51 (s, 4H), 1.37-1.04 (m, 15H).

Example 14: Synthesis of 5-imino-4-methyl-1-oxa-4,6-diazacycloheptadecane-2,7-dione formate (Compound R)

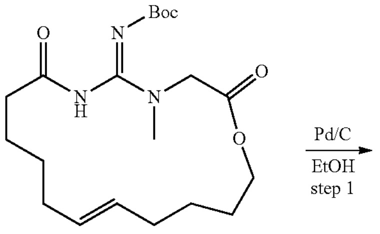

R-1

-continued

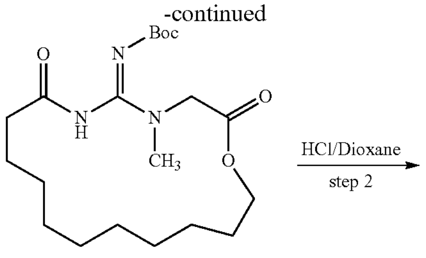

R-2

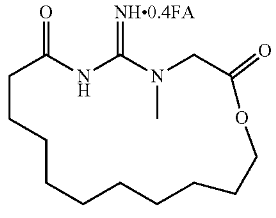

Compound R

In general, Compound R was synthesized according to Example 8 starting from N-methyl-N-((4-nitrophenyl)sulfonyl)glycine instead of 2-[(4-nitrophenyl)sulfonyl-(trideuteriomethyl)amino]acetic acid and hex-5-en-1-ol instead of pent-1-en-3-ol and then O-2 instead of (Z)-tert-butyl dec-9-enamido(methylthio)methylenecarbamate in step 3. Compound R-1, (Z)-tert-butyl-((E)-4-methyl-2,7-dioxo-1-oxa-4,6-diazacycloheptadec-12-en-5-ylidene)carbamate, was obtained as a black oil (878 mg, 81%). ES LC-MS m/z=396.3 (M+H$^+$).

Step 1. Synthesis of Compound R-2

Compound R-2 was synthesized according to Example 9, step 1 from Compound R-1 using Pd/C (20%). (Z)-tert-Butyl 4-methyl-2,7-dioxo-1-oxa-4,6-diazacycloheptadecan-5-ylidenecarbamate (Compound R-2; 660 mg, 75%) was obtained as an yellow solid. ES LC-MS m/z=398.3 (M+H$^+$).

Step 2. Synthesis of Compound R

Compound R was synthesized according to Example 9, step 2, starting from Compound R-2. 5-Imino-4-methyl-1-oxa-4,6-diazacycloheptadecane-2,7-dione formate (Compound R; 102 mg, 45%) as a white solid. ES LC-MS m/z=298.2 (M+H$^+$). $^1$H NMR (DMSO-d) δ: 8.16 (s, 0.4H), 4.32 (s, 2H), 4.15-4.12 (t, 2H), 2.92 (s, 3H), 2.04-2.00 (t, 2H), 1.55-1.51 (t, 4H), 1.30-1.24 (m, 12H).

Example 15: Synthesis of 5-imino-4-trideuteriomethyl-15-methyl-1-oxa-4,6-diazacyclopentadecane-2,7-dione (Compound S)

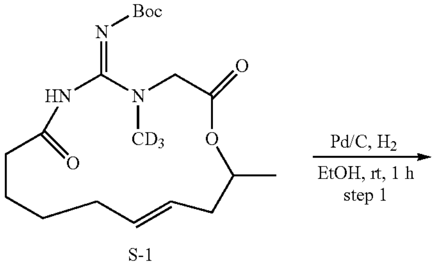

S-1

-continued

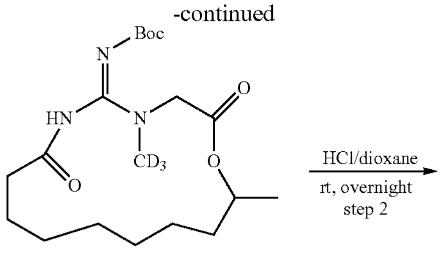

S-2

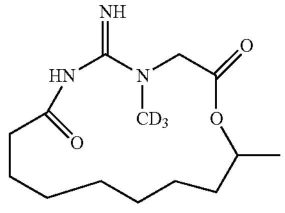

Compound S

In general, Compound S was synthesized according to Example 8 using pent-4-en-2-ol instead of pent-1-en-3-ol in step 1 and O-2 instead of (Z)-tert-butyl dec-9-enamido (methylthio)methylenecarbamate in step 3. Compound S-1, (Z)-tert-butyl-((E)-4-trideuteriomethyl-15-methyl-2,7-dioxo-1-oxa-4,6-diazacyclopentadec-12-en-5-ylidene)carbamate, was obtained as an yellow solid (1.112 g, 75%). ES LC-MS m/z=385.3 (M+H$^+$).

Step 1. Synthesis of Compound S-2

Compound S-2 was synthesized according to Example 9, step 1 from Compound S-1 using Pd/C (20%). (Z)-tert-Butyl-4-trideuteriomethyl-15-methyl-2,7-dioxo-1-oxa-4,6-diazacyclopentadecan-5-ylidenecarbamate (Compound S-2; 1.047 g, 94%) was obtained as an yellow solid. ES LC-MS m/z=387.3 (M+H$^+$).

Step 2. Synthesis of Compound S

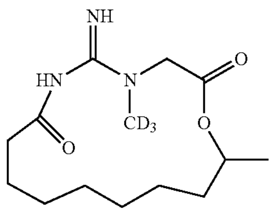 [SMILES: [2H]C([2H])([2H])N1CC(=O)OC(C)CCCCCCCC(=O)NC1=N]

Compound S was synthesized according to Example 9, step 2, starting from Compound S-2. 5-Imino-4-trideuteriomethyl-15-methyl-1-oxa-4,6-diazacyclopentadecane-2,7-dione (Compound S; 148 mg, 59%) was obtained as a white solid. ES LC-MS m/z=287.2 (M+H$^+$). $^1$H NMR (DMSO-d) δ: 5.00-4.95 (t, 1H), 4.54-4.50 (m, 1H), 3.95-3.91 (m, 1H), 2.06-1.94 (t, 2H), 1.58-1.47 (t, 4H), 1.30-1.16 (t, 11H).

Example 16: Synthesis of 5-imino-4-trideuteriomethylguanidino-1-oxa-4,6-diazacyclononadecane-2,7-dione formate (Compound T)

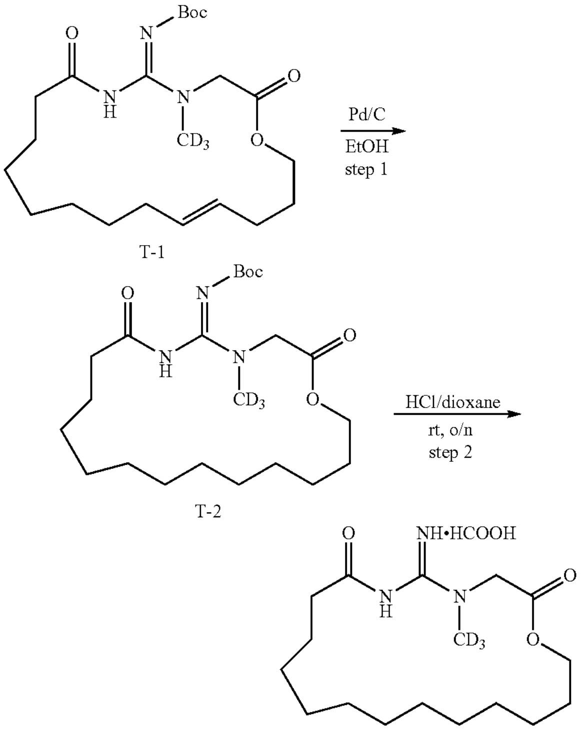

T-1

T-2

Compound T

Synthesis of T-a

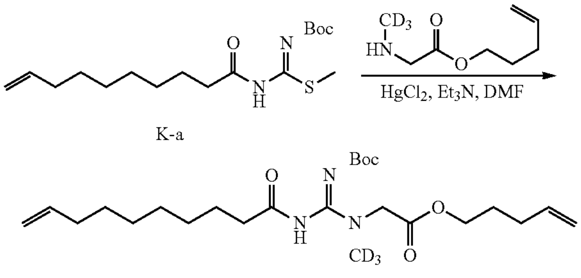

K-a

T-a

A mixture of (Z)-tert-butyl dec-9-enamido(methylthio)methylenecarbamate (1.96 g, 5.37 mmoL; K-a) pent-4-enyl 2-(trideuteriomethylguanidino)acetate (1.1 g, 6.87 mmoL) and a solution of triethylamine (1.74 g, 17.2 mmoL) in N,N-Dimethylformamide (30 mL) was stirred at rt. A mixture of mercury dichloride (1.7 g, 6.3 mmoL) was added, the mixture was stirred at rt for overnight. Water (40 mL) was added and the mixture was extracted with ethyl acetate (40 mL×3), the combined organic phase was washed with brine, dried over sodium sulfate and concentrated. The residue was purified by flash (Petroleum ether:Ethyl acetate/5.1) to afford (E)-pent-4-enyl 2-(2-(tert-butoxycarbonyl)-3-dec-9-enoyl-1-trideuteriomethylguanidino)acetate (2.39 g, 92% yield, T-a) as a white solid. ES LC-MS m/z=455.3 ($M+H^+$).

Synthesis of T

In general, Compound T was synthesized according to procedure as described in Example 8. Compound T-1, (E)-tert-butyl ((E)-4-trideuteriomethylguanidino-2,7-dioxo-1-oxa-4,6-diazacyclononadec-15-en-5-ylidene)carbamate, was synthesized from Compound T-a according to Example 8, step 4 and obtained as a pale yellow oil (892 mg, 40% yield). ES LC-MS m/z=426.3 ($M+H^+$).

Step 1. Synthesis of Compound T-2

Compound T-2 was synthesized according to Example 9, step 1 from Compound T-1 using Pd/C (20%). (E)-tert-Butyl-4-trideuteriomethylguanidino-2,7-dioxo-1-oxa-4,6-diazacyclononadecan-5-ylidenecarbamate (Compound T-2; 300 mg, 34% yield) was obtained as a white solid. ES LC-MS m/z=428.3 ($M+H^+$).

Step 2. Synthesis of Compound T

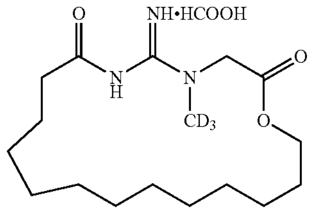

Compound T was synthesized according to Example 9, step 2, starting from Compound T-2. 5-Imino-4-trideuteriomethylguanidino-1-oxa-4,6-diazacyclononadecane-2,7-dione formate (Compound T; 65 mg, 28% yield) was obtained as a white solid. ES LC-MS m/z=329.2 ($M+H^+$). $^1H$ NMR (DMSO-d) δ: 9.3-10.0 (br, 1H), 7.1-7.7 (br, 1H), 4.25 (s, 2H), 4.08 (2H, t, J=6.3 Hz), 2.06 (2H, t, J=7.7 Hz), 1.53-1.62 (m, 2H), 1.44-1.53 (m, 2H), 1.20-1.36 (m, 16H).

Example 17: Synthesis of 5-imino-4-trideuteriomethyl-17,17-dimethyl-1-oxa-4,6-diazacycloheptadecane-2,7-dione (Compound U)

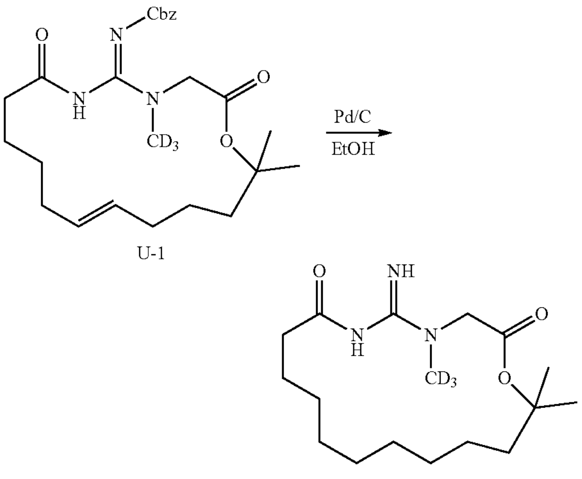

U-1

Compound U

In general, Compound U-1 was synthesized according to Example 8 using 2-methylhept-6-en-2-ol instead of pent-1-en-3-ol and using (Z)-benzyl hept-6-enamido(methylthio) methylenecarbamate instead of (Z)-tert-butyl dec-9-enamido(methylthio)methylenecarbamate.

2-Methylhept-6-en-2-ol: A mixture of 5-bromopent-1-ene (10.0 g, 67.5 mmol), magnesium (3.24 g, 135 mmol) and trace iodine in dry tetrahydrofuran (200 ml) was stirred at 60 degrees under nitrogen for 2 hs. Cooling to rt, acetone (7.83 g, 135 mmol) was added and the mixture was stirred at rt for overnight. A saturated solution of ammonium chloride and the mixture was extracted with ethyl acetate (200 ml*3), the combined organic phase was washed with brine, dried over sodium sulfate and concentrated. The residue was purified by reduced pressure distillation to afford 2-methylhept-6-en-2-ol (4.0 g, 46%) as a colorless oil. $^1$H NMR (DMSO-$d_6$) δ: 5.75-5.83 (m, 1H), 4.92-5.03 (m, 2H), 1.97-2.0 (m, 2H), 1.35-1.41 (m, 4H), 1.19 (s, 6H).

(Z)-benzyl hept-6-enamido(methylthio)methylenecarbamate can be prepared according to Example 29 using a procedure similar to that for Compound GG-1 by replacing dec-9-enoic acid with hep-6-enoic acid.

Compound U-1, (Z)-benzyl ((E)-4-trideuteriomethyl-17,17-dimethyl-2,7-dioxo-1-oxa-4,6-diazacycloheptadec-12-en-5-ylidene)carbamate, was obtained as an yellow oil (600 mg, 79%). ES LC-MS m/z=461.3 (M+H$^+$).

Compound U was synthesized according to Example 9, step 1, starting from Compound U-1 using Pd/C (20%). 5-Imino-4-trideuteriomethyl-17,17-dimethyl-1-oxa-4,6-diazacycloheptadecane-2,7-dione (Compound U; 75 mg, 35%) was obtained as a white solid. ES LC-MS m/z=329.3 (M+H$^+$). $^1$H NMR (DMSO-$d_6$) δ: 9.89 (ds, 1H), 7.45 (ds, 1H), 4.27 (s, 2H), 2.05-2.08 (m, 2H), 1.75-1.80 (m, 2H), 1.50-1.55 (m, 2H), 1.47 (s, 6H), 1.25-1.38 (m, 12H).

Example 18: Synthesis of 15-ethyl-5-imino-4-(methyl-d3)-1-oxa-4,6-diazacyclopentadecane-2,7-dione (Compound V)

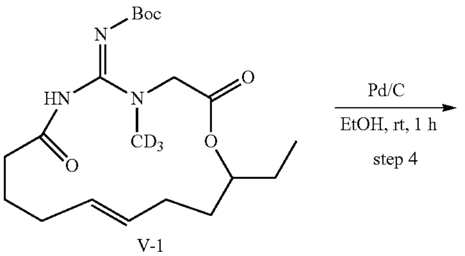

V-1

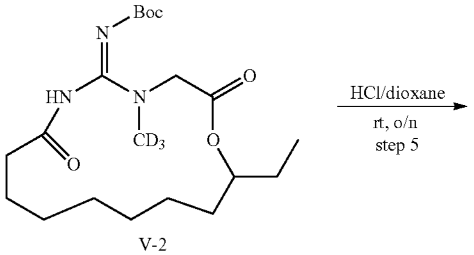

V-2

-continued

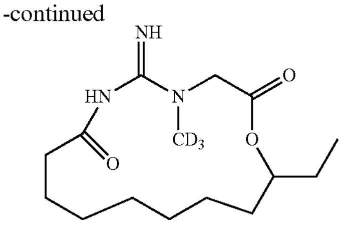

V

In general, Compound V was synthesized according to Example 11 using hex-5-enoic acid instead of hept-6-enoic acid in step 2. Compound V-1 was obtained as a brown oil (0.9 g, 2.26 mmol, yield: 74.0%). ES LC-MS m/z=399.3 (M+H)$^+$.

Step 1. Synthesis of Compound V-2

Compound V-2 was synthesized according to Example 9, step 1 from Compound V-1. Compound V-2 was obtained as a pale yellow oil (0.82 g, 2.05 mmol, yield: 96.1%). ES LC-MS m/z=401.3 (M+H)$^+$.

Step 2. Synthesis of Compound V

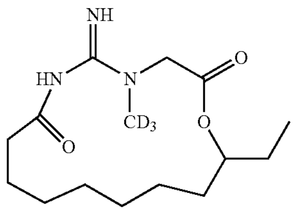 [SMILES: [2H]C([2H])([2H])N1CC(=O)OC(CC)CCCCCCCC(=O)NC1=N]

Compound V was synthesized according to Example 9, step 2, starting from Compound V-2 (375 mg, 1.25 mmol, yield: 62.5%). ES LC-MS m/z=301.2 (M+H)$^+$.

Example 19: Synthesis of 5-imino-4-trideuteriomethyl-15-propyl-1-oxa-4,6-diazacyclopentadecane-2,7-dione (Compound W)

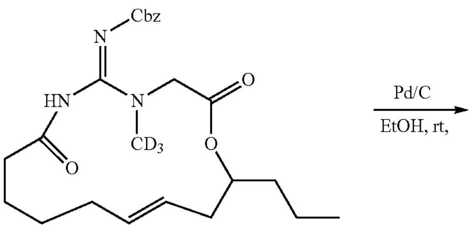

W-1

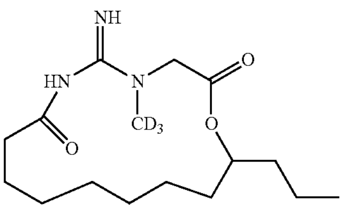

Compound W

In general, Compound W-1 was synthesized according to Example 8 using hept-1-en-4-ol instead of pent-1-en-3-ol and using benzyl (Z)-(hept-6-enamido(methylthio)methylene)carbamate (see Example 17) instead of (Z)-tert-butyl dec-9-enamido(methylthio)methylenecarbamate. Compound W-1, (Z)-benzyl ((E)-4-trideuteriomethyl-2,7-dioxo-15-propyl-1-oxa-4,6-diazacyclopentadec-12-en-5-ylidene) carbamate, was obtained as an yellow oil (880 mg, 93%). ES LC-MS m/z=447.3 ($M+H^+$).

Compound W was synthesized according to Example 9, step 1, starting from Compound W-1 using Pd/C (20%). 5-Imino-4-trideuteriomethyl-15-propyl-1-oxa-4,6-diazacyclopentadecane-2,7-dione (Compound W; 130 mg, 46%) was obtained as a white solid. ES LC-MS m/z=315.3 ($M+H^+$). $^1H$ NMR (DMSO-$d_6$) δ: 9.77 (ds, 1H), 7.39 (ds, 1H), 4.92 (s, 1H), 4.57-4.60 (m, 1H), 3.95-3.99 (m, 1H), 1.98-2.06 (m, 2H), 1.44-1.57 (m, 6H), 1.19-1.30 (m, 10H), 0.87 (t, J=7.2 Hz, 3H).

Example 20: Synthesis of 5-imino-15,15-dimethyl-4-(methyl-$d_3$)-1-oxa-4,6-diazacyclopentadecane-2,7-dione (Compound X)

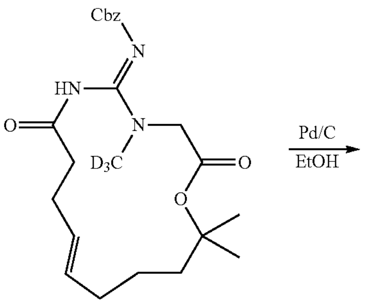

X-1

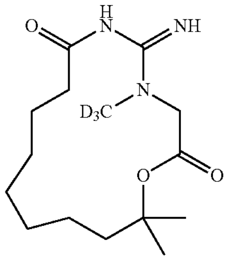

Compound X

In general, Compound X-1 was synthesized according to Example 8 using 2-methylhept-6-en-2-ol (see Example 17) instead of pent-1-en-3-ol and using benzyl (Z)-((methylthio)(pent-4-enamido)methylene)carbamate instead of (Z)-tert-butyl dec-9-enamido(methylthio)methylenecarbamate. Compound X-1 was obtained as an yellow oil (2.2 g, 50%). ES LC-MS m/z=433 [$M+H^+$].

Benzyl (Z)-((methylthio)(pent-4-enamido)methylene)carbamate: A mixture of benzyl (Z)-(amino(methylthio)methylene)carbamate (3.5 g, 15.6 mmol), pent-4-enoic acid (1.6 g, 15.6 mmol), HATU (7.11 g, 18.72 mmol) and N,N-diisopropyl-ethylamin (4.0 g, 31.2 mmol) in dichloromethane (60 ml) was stirred at rt for overnight. Water (50 ml) was added and the mixture was extracted with dichloromethane (60 ml*3), the combined organic phase was washed with brine, dried over sodium sulfate and concentrated. The residuum was purified by chromatography (Petroleumether: ethylacetate=20:1) to afford benzyl (Z)-((methylthio)(pent-4-enamido)methylene)carbamate (4.6 g, 94%) as a white solid. ES LC-MS m/z=307 [$M+H^+$].

Compound X was synthesized according to Example 9, step 1, starting from Compound X-1 using Pd/C (20%). Compound X was obtained as an yellow solid (0.2 g, 13%). ES LC-MS m/z=301.3 [$M+H^+$]. $^1HNMR$ (DMSO-d6, 400 MHz) δ: 9.84 (br s, 1H), 7.34 (bs, 1H), 4.24 (m, 2H), 2.50 (m, 2H), 2.02 (m, 2H), 1.78 (br s, 2H) 1.47 (s, 6H) 1.34 (br s, 1H) 1.29-1.22 (m, 8H).

Example 21: Synthesis of 5-imino-4-trideuteriomethyl-1-oxa-4,6-diazacycloeicosane-2,7-dione formate (Compound Y)

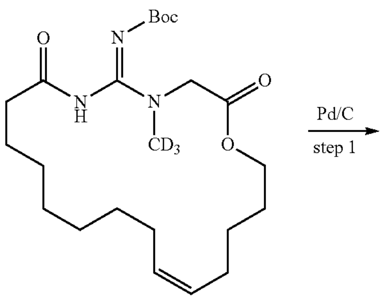

Y-1

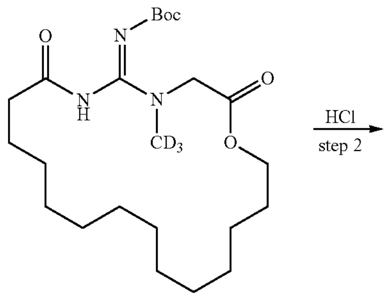

Y-2

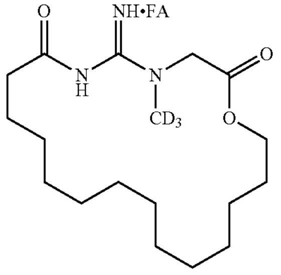

Compound Y

In general, Compound Y was synthesized according to Example 8 using hex-5-enyl 2-(trideuteriomethylamino)acetate instead of L-2 and using (Z)-tert-butyl dec-9-enamido(methylthio)methylenecarbamate (see Example 7) instead of (Z)-tert-butyl dec-9-enamido(methylthio)methylenecarbamate. Compound Y-1, (Z)-tert-butyl ((Z)-4-trideuteriomethyl-2,7-dioxo-1-oxa-4,6-diazacycloicos-15-en-5-ylidene)carbamate, was obtained as a yellow oil (1.29 g, 90%). ES LC-MS m/z=441.3 ($M+H^+$).

Hex-5-enyl 2-(trideuteriomethylamino)acetate: A mixture of hex-5-enyl 2-(N-trideuteriomethyl-4-nitrophenylsulfonamido)acetate (2.4 g, 6.69 mmol), 4-methylbenzenethiol (1.66 g, 13.38 mmol) and cesium carbonate (4.36 g, 13.38 mmol) in acetonitrile (30 ml) and tetrahydrofuran (3 ml) was stirred at 45° C. for 2 hs. The reaction mixture was filtrated and the filtrates were concentrated. The residue was purified by chromatography (dichloromethane:methanol=10:1 with 0.1% ammonium hydroxide) to afford hex-5-enyl 2-(trideuteriomethylamino)acetate (900 mg, 77%) as a yellow oil. ES LC-MS m/z=175.2 (M+H$^+$). $^1$H NMR (DMSO-d6) δ: 5.75-5.85 (m, 1H), 4.94-5.95 (m, 2H), 4.06 (t, J=6.4 Hz, 2 H), 2.01-2.07 (m, 2H), 1.55-1.62 (m, 2H), 1.36-1.49 (m, 2H).

Step 1. Synthesis of Compound Y-2

Compound Y-2 was synthesized according to Example 9, step 1 from Compound Y-1 using Pd/C (20%). (Z)-tert-Butyl 4-4-trideuteriomethyl-2,7-dioxo-1-oxa-4,6-diazacycloicosan-5-ylidenecarbamate (Compound Y-2; 1.1 g, 85%) was obtained as a yellow oil. ES LC-MS m/z=443.4 (M+H$^+$).

Step 2. Synthesis of Compound Y

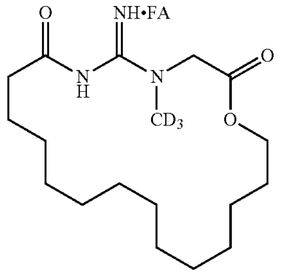

Compound Y was synthesized according to Example 9, step 2, starting from Compound Y-2. 5-Imino-4-trideuteriomethyl-1-oxa-4,6-diazacycloeicosane-2,7-dione formate (Compound Y: 100 mg, 30%) was obtained as a white solid. ES LC-MS m/z=343.3 (M+H$^+$). $^1$H NMR (DMSO-d$_6$) δ: 9.5 (bs, 1H), 8.15 (bs, 1H), 4.28 (s, 2H), 4.06 (t, J=6.0 Hz, 2H), 2.04-2.08 (m, 2H), 1.55-1.59 (m, 2H), 1.47-1.51 (m, 2H), 1.26-1.35 (m, 18H).

Example 22: Synthesis of (S)-5-imino-4-trideuteriomethyl-18-methyl-1-oxa-4,6-diazacyclooctadecane-2,7-dione (Compound Za) and (R)-5-imino-4-trideuteriomethyl-18-methyl-1-oxa-4,6-diazacyclooctadecane-2,7-dione (Compound Zb)

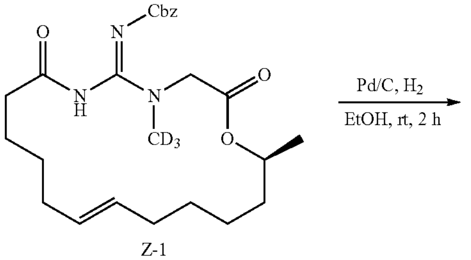

Z-1

-continued

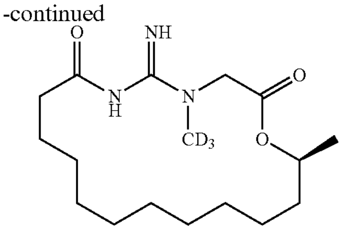

Compound Za

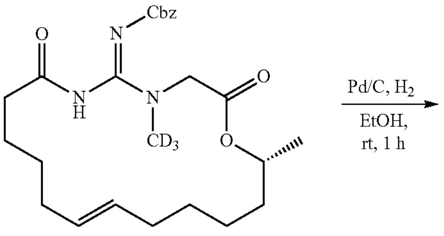

Z-2

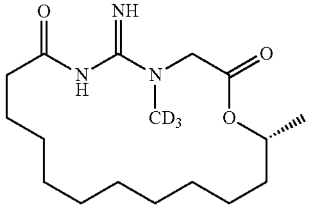

Compound Zb

In general, Compound Z-1 and Z-2 was synthesized according to Example 8 using (S)-oct-7-en-2-ol or (R)-oct-7-en-2-ol, respectively, instead of pent-1-en-3-ol and using (Z)-benzyl hept-6-enamido(methylthio)methylenecarbamate (see Example 17) instead of (Z)-tert-butyl dec-9-enamido(methylthio)methylenecarbamate. Compound Z-1, (Z)-benzyl ((S,E)-4-trideuteriomethyl-18-methyl-2,7-dioxo-1-oxa-4,6-diazacyclooctadec-12-en-5-ylidene)carbamate, was obtained as an yellow solid (490 mg, 65%). ES LC-MS m/z=461.5 (M+H$^+$). Compound Z-2, (Z)-benzyl ((R,E)-4-trideuteriomethyl-18-methyl-2,7-dioxo-1-oxa-4,6-diazacyclooctadec-12-en-5-ylidene) carbamate, was obtained as a pale brown solid (830 mg, 1.8 mmol, 94% yield). ES LC-MS m/z=461.2 (M+H$^+$).

(S)-oct-7-en-2-ol: A mixture of 5-bromopent-1-ene (14.9 g, 100 mmol), magnesium (4.8 g, 200 mmol) and 20 drops in dry tetrahydrofuran (300 ml) was stirred at 60 degrees for 2 hs. Cooling to −30° C., Copper iodide (950 mg, 5 mmol) was added and (S)-2-methyloxirane (5.8 g, 100 mmol) was added dropwise, then the mixture was stirred for 2 hs. A saturated solution of ammonia chloride (500 ml) was added and the mixture was extracted with ethyl acetate (300 ml*3), the combined organic phase was washed with brine, dried over sodium sulfate and concentrated to afford (S)-oct-7-en-2-ol (10 g, 78%) as a yellow oil for the next step. $^1$H NMR (DMSO-d) δ: 5.79-5.9 (m, 1H), 4.92-5.07 (m, 2H), 3.56-3.60 (m, 1H), 2.00-2.03 (m, 2H), 1.15-1.35 (m, 6H), 1.03 (d, J=6.4 Hz, 3H).

(R)-oct-7-en-2-ol: A round bottom flask equipped with a stir bar and nitrogen inlet was charged with 5-bromopent-1-ene (15 g, 100.67 mmol), magnesium (3.62 g, 151.01 mmol) and iodine (5 granule) in tetrahydrofuran (dry, 100 mL). The mixture was stirred at 60° C. for two hours. The reaction was cooled to room temperature and obtained B solution. To a solution of (S)-2-methyloxirane (5.84 g, 100.67 mmol) and Copper Iodide (3.22 g, 50.34 mmol) in THF (dry, 50 mL) was added dropwise B solution at −30° C. Then the reaction was stirred at −30° C. for 30 minute. The reaction was warmed to room temperature for 2 hour, and quenched with Sat. aqueous ammonium chloride (60 mL), extracted with ethyl acetate (80 mL×3), washed with water (60 mL×1) and brine (60 mL), dried and evaporated, distilled with vacuum at 124° C. (oil-bath) to give (R)-oct-7-en-2-ol (9 g, 70/6 yield) as a pale yellowish oil. $^1$H NMR (DMSO-d6) δ: 5.85-5.74 (m, 1H), 5.09-4.92 (m, 2H), 4.32 (d, J=4.8 Hz, 2H), 3.57-3.53 (m, 1H), 2.04-1.99 (m, 2H), 1.37-1.24 (m, 6H), 1.24 (s, 3H).

Compound Za was synthesized according to Example 9, step 1, starting from Compound Z-1 using Pd/C (20%). (S)-5-Imino-4-trideuteriomethyl-18-methyl-1-oxa-4,6-diazacyclooctadecane-2,7-dione (Compound Za; 137 mg, 40%) was obtained as a white solid. ES LC-MS m/z=329.5 (M+H)$^+$. $^1$H NMR (DMSO-d) δ: 4.854.91 (m, 2H), 3.83-3.84 (d, J=17.6 Hz, 1H), 2.00-2.14 (m, 2H), 1.50-1.58 (m, 2H), 1.22-1.34 (m, 14H), 1.19 (d, J=6.4 Hz, 3H).

Compound Zb was synthesized according to Example 9, step 1, starting from Compound Z-2. (R)-5-imino-4-trideuteriomethyl-18-methyl-1-oxa-4,6-diazacyclooctadecane-2,7-dione (Compound Zb; 261.9 mg, 0.796 mmol, 44% yield) as a white solid. ES LC-MS m/z=329.2 (M+H$^+$). $^1$H NMR (DMSO-d) δ: 9.80 (br s, 1H), 7.38 (br s, 1H), 4.85 (t, J=7.6 Hz, 2H) 3.85 (d, J=17.6 Hz, 1H), 2.10-2.01 (m, 2H), 1.54-1.48 (m, 4H), 1.27-1.16 (m, 17H).

Example 23: Synthesis of 8-imino-7-trideuteriomethyl-4-oxa-7,9-diazaspiro[2.16]nonadecane-5,10-dione formate (Compound AA)

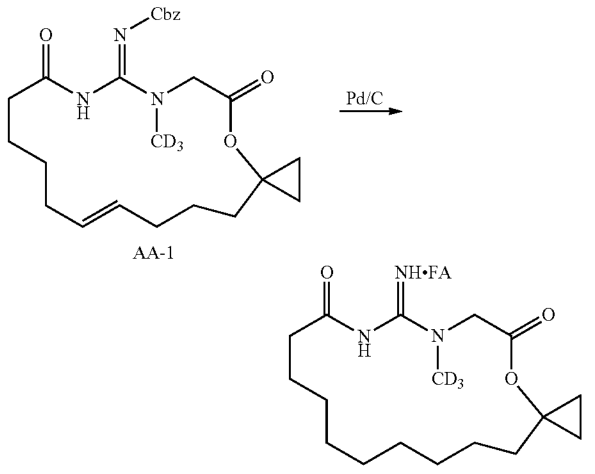

AA-1

Compound AA

In general, Compound AA-1 was synthesized according to Example 8 using 1-(pent-4-enyl)cyclopropanol instead of pent-1-en-3-ol and using (Z)-benzyl hept-6-enamido(methylthio)methylenecarbamate (see Example 17) instead of (Z)-tert-butyl dec-9-enamido(methylthio)methylenecarbamate. Compound AA-1, (Z)-benzyl ((E)-7-trideuteriomethyl-5,10-dioxo-4-oxa-7,9-diazaspiro[2.16]nonadec-15-en-8-ylidene)carbamate, was obtained as an yellow solid (800 mg, 90%). ES LC-MS m/z=459.3 (M+H$^+$).

1-(Pent-4-enyl)cyclopropanol: A mixture of methyl hex-5-enoate (2.56 g, 20 mmol) and Titannium(IV) isopropoxide (7.95 g, 28 mmol) in dry Tetrahydrofuran (60 ml) was stirred at 0 degrees, a solution of Ethylmagnesium bromide (56 ml, 56 mmol, 1.0 M in tetrahydrofuran) was added dropwise over 30 min. after adding, the mixture was stirred at rt for overnight. 1 N hydrochloric acid was added and the mixture was extracted with ethyl acetate (50 ml*3), the combined organic phase was washed with brine, dried over sodium sulfate and concentrated to afford 1-(pent-4-enyl)cyclopropanol (2.3 g, 91%) as a yellow oil. $^1$H NMR (DMSO-d) δ: 5.76-5.84 (m, 1H), 4.92-5.03 (m, 2H), 2.02-2.07 (m, 2H), 1.49-1.57 (m, 2H), 1.41-1.45 (m, 2H), 0.50-0.53 (m, 2H), 0.28-031 (m, 2H).

Compound AA was synthesized according to Example 9, step 1, starting from Compound AA-1 using Pd/C (20%). 8-Imino-7-trideuteriomethyl-4-oxa-7,9-diazaspiro[2.16]nonadecane-5,10-dione formate (Compound AA; 200 mg, 35%) was obtained as a white solid. ES LC-MS m/z=327.3 (M+H)$^+$. $^1$H NMR (DMSO-d) δ: 4.28 (s, 2H), 2.03-2.07 (m, 2H), 1.63-1.67 (m, 2H), 1.51-1.56 (m, 2H), 1.39-1.44 (m, 2H), 1.20-1.35 (m, 10H), 0.80-0.84 (m, 2H), 0.63-0.66 (m, 2H).

Example 24: Synthesis of 5-imino-4-trideuteriomethylguanidino-1-oxa-4,6-diazacyclotetradecane-2,7-dione formate (Compound BB)

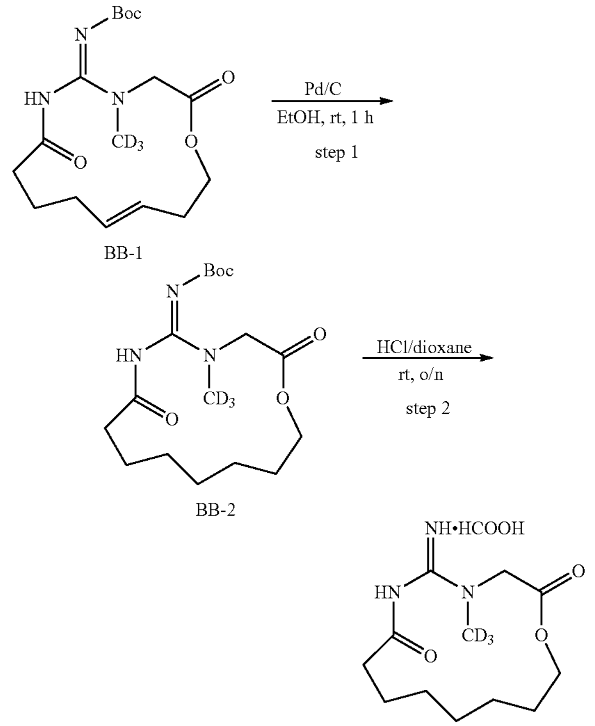

BB-1

BB-2

Compound BB

In general, Compound BB was synthesized according to Example 8 using but-3-enyl 2-(trideuteriomethylguanidino) acetate (see Example 26) instead of L-2 and using (Z)-tert-butyl hex-5-enamido(methylthio)methylenecarbamate instead of (Z)-tert-butyl dec-9-enamido(methylthio)methylenecarbamate. Compound BB-1, (Z)-tert-butyl ((E)-4-trideuteriomethylguanidino-2,7-dioxo-1-oxa-4,6-diazacyclotetradec-11-en-5-ylidene)carbamate, was obtained as a pale yellow oil (604 mg, 97% yield). ES LC-MS m/z=356.2 (M+H$^+$).

(Z)-tert-butyl dec-9-enamido(methylthio)methylenecarbamate: A mixture of (Z)-benzyl amino(methylthio)methylenecarbamate (1.8 g, 9.65 mmoL), 1-[Bis(dimethylamino)methylene]-1H-1,2,3-triazolo[4,5-b]pyridinium 3-oxid hexafluorophosphate (4 g, 10.5 mmoL) and a solution of hex-5-enoic acid (1 g, 8.77 mmol), N,N-Diisopropylethylamine (2.25 g, 17.54 mmoL) in dichloromethane (50 mL) was stirred at rt for 2 h. Water (50 mL) was added and the mixture was extracted with dichloromethane (50 mL*3), the combined organic phase was washed with brine, dried over sodium sulfate and concentrated. The residue was purified by flash (Petroleum ether:ethyl acetate/10:1) to afford (Z)-tert-butyl hex-5-enamido(methylthio)methylenecarbamate (1.54 g, 61% yield) as a white solid. ES LC-MS m/z=287.1 (M+H$^+$).

Step 1. Synthesis of Compound BB-2

Compound BB-2 was synthesized according to Example 9, step 1 from Compound BB-1 using Pd/C (20%). tert-Butyl 4-trideuteriomethylguanidino-2,7-dioxo-1-oxa-4,6-diazacyclotetradecan-5-ylidenecarbamate (Compound BB-2; 260 mg, 47% yield) was obtained as a white oil. ES LC-MS m: =359.2 (M+H$^+$).

Step 2. Synthesis of Compound BB

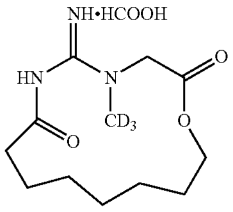

Compound BB was synthesized according to Example 9, step 2, starting from Compound BB-2. 5-Imino-4-trideuteriomethylguanidino-1-oxa-4,6-diazacyclotetradecane-2,7-dione formate (Compound BB; 90 mg, 50% yield) was obtained as a white oil. ES LC-MS m/z=259.1 (M+H$^+$). $^1$H NMR (DMSO-d) δ: 9.5-10.2 (br, 1H), 7.2-7.8 (br, 1H), 4.22 (s, 2H), 4.15 (2H, t, J=4.7 Hz), 2.06 (2H, t, J=5.9 Hz), 1.28-1.62 (m, 8H), 1.10-1.20 (m, 2H).

Example 25: Synthesis of 14-butyl-5-imino-4-trideuteriomethyl-1-oxa-4,6-diazacyclotetradecane-2,7-dione (Compound CC)

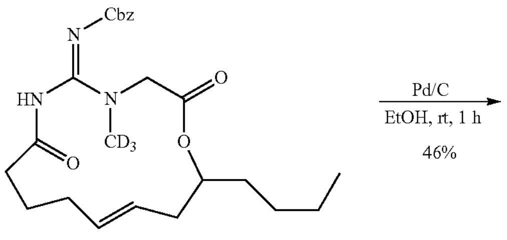

CC-1

-continued

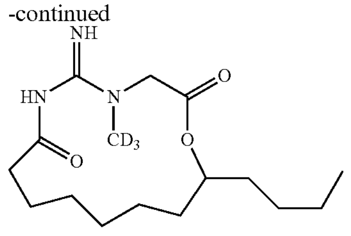

Compound CC

In general, Compound CC-1 was synthesized according to Example 8 using oct-1-en-4-ol instead of pent-1-en-3-ol and using (Z)-benzyl hex-5-enamido (methylthio) methylenecarbamate instead of (Z)-tert-butyl dec-9-enamido(methylthio)methylenecarbamate. Compound CC-1, (Z)-benzyl ((E)-14-butyl-4-trideuteriomethyl-2,7-dioxo-1-oxa-4,6-diazacyclotetradec-11-en-5-ylidene) carbamate, was obtained as a colorless oil (930 mg, 2.09 mmol, 79% yield). ES LC-M S m/z=447.1 (M+H$^+$). $^1$H NMR (DIMETHYL SULFOXIDE-d6) δ: 9.81 (s, 1H), 7.39-7.30 (m, 5H), 5.21-5.20 (m, 2H), 4.95-4.85 (m, 3H), 4.44 (br s, 1H), 4.18 (br s, 1H), 4.054.00 (m, 2H), 2.36 (br s, 1H), 2.16-1.98 (m, 8H), 1.69-1.51 (m, 4H), 1.29-1.15 (m, 8H), 0.87-0.84 (m, 3H).

Oct-1-en-4-ol: A round bottom flask equipped with a stir bar and nitrogen inlet was charged with pentanal (10 g, 116.28 mmol) in tetrahydrofuran (dry, 100 mL). The mixture was added dropwise allylmagnesium bromide (116.28 mmol) in tetrahydrofuran (120 mL) at −30° C. The reaction was warmed to room temperature for 2 hour, and quenched with Sat. aqueous ammonium chloride (60 mL), extracted with ethyl acetate (80 mL×3), washed with water (60 mL×1) and brine (60 mL), dried and evaporated, distilled with vacuum at 124° C. (oil-bath) to give oct-1-en-4-ol (5.1 g, 34% yield) as a colorless oil. $^1$H NMR (DMSO-d6) δ: 5.85-5.78 (m, 1H), 5.04-4.96 (m, 2H), 4.40-4.39 (m, 1H), 3.44-3.43 (m, 1H), 2. 11-2.07 (m, 2H), 1.37-1.20 (m, 6H), 0.88-0.81 (m, 3H).

(Z)-Benzyl hex-5-enamido (methylthio) methylenecarbamate: A round bottom flask equipped with a stir bar was charged with hex-5-enoic acid (800 mg, 7.02 mmol) and HUTU (4 g, 10.53 mmol) in dichloromethane (15 mL) was added dropwise (Z)-benzyl amino(methylthio)methylenecarbamate (1.65 g, 7.37 mmol) and DIPEA (1.81 g, 14.04 mmol) in DCM (5 mL) at room temperature. The mixture was stirred at RT for 1 h. The reaction was added DCM (100 mL), washed with water (30 mL×3) and brine (40 mL), dried and evaporated, purified by flash chromatography (40 G) eluting with (PE:EA/0%-18%), to give (Z)-benzyl hex-5-enamido (methylthio) methylenecarbamate (1.8 g, 5.63 mmol, 80% yield) as a white solid. ES LC-MS m/z=321.0 (M+H$^+$). $^1$H NMR (DIMETHYL SULFOXIDE-d6) δ: 11.20 (s, 11H), 7.40-7.32 (m, 5H), 5.80-5.74 (m, 1H), 5.084.96 (m, 4H), 2.36-2.33 (t, J=14.8 Hz, 2H), 2.27 (s, 3H), 2.04-1.98 (m, 2H), 1.62-1.55 (m, 2H).

Compound CC was synthesized according to Example 9, step 1, starting from Compound CC-1. 14-Butyl-5-imino-4-trideuteriomethyl-1-oxa-4,6-diazacyclotetradecane-2,7-dione (Compound CC; 319.1 mg, 1.02 mmol, 46% yield) was obtained as a white solid. ES LC-MS m/z=315.1 (M+H$^+$). $^1$H NMR (DMSO-d6) δ: 9.74 (br s, 11H), 7.39 (br s, 1H), 4.80-4.78 (t, J=5.6 Hz, 1H), 4.53-4.90 (m, 1H), 3.93-3.89 (m, 1H), 2.18-2.13 (m, 11H), 1.96-1.90 (m, 1H), 1.70-1.64 (m, 2H), 1.54-1.44 (m, 2H), 1.33-1.05 (m, 12H), 0.87-0.84 (t, J1=13.6 Hz, 3H).

Example 26: Synthesis of 5-imino-4-trideuteriomethyl-1-oxa-4,6-diazacyclopentadecane-2,7-dione (Compound DD)

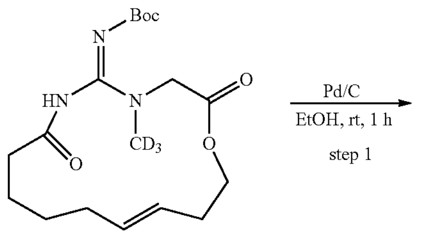

DD-1

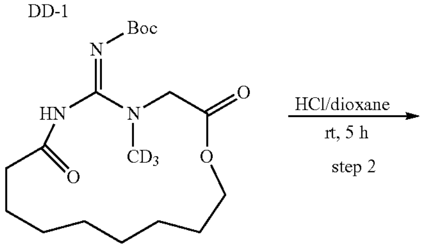

DD-2

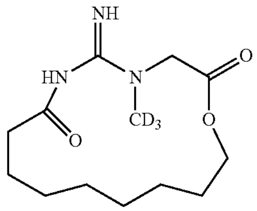

Compound DD

In general, Compound DD was synthesized according to Example 8 using but-3-enyl 2-(trideuteriomethylamino)acetate instead of L-2 and using (Z)-tert-butyl hept-6-enamido (methylthio)methylenecarbamate (see Example 17) instead of (Z)-tert-butyl dec-9-enamido(methylthio)methylenecarbamate. Compound DD-1, (Z)-tert-butyl ((E)-4-trideuteriomethyl-2,7-dioxo-1-oxa-4,6-diazacyclopentadec-12-en-5-ylidene) carbamate, was obtained as a pale yellow oil (600 mg, 1.62 mmol), 75% yield). ES LC-MS m/z=371.1 ($M+H^+$). $^1H$ NMR (DMSO-d) δ: 9.78 (br s, 1H), 5.36-5.34 (m, 2H), 4.17-4.03 (m, 4H), 2.29-2.28 (m, 2H), 2.26-2.09 (m, 2H), 1.98-1.95 (m, 2H), 1.50-1.32 (m, 13H).

But-3-enyl 2-(trideuteriomethylamino)acetate was synthesized according to Example 9 described for synthesis of Compound M-a using but-3-en-1-ol instead of pent-4-en-2-ol, to provide but-3-enyl 2-(N-trideuteriomethyl-4-nitrophenylsulfonamido) acetate, which was converted to But-3-enyl 2-(trideuteriomethylamino)acetate. But-3-enyl 2-(N-trideuteriomethyl-4-nitrophenylsulfonamido) acetate was obtained as a pale yellowish solid (1.6 g, 4.83 mmol, 67% yield). ES LC-MS m/z=332.0 ($M+H^+$), 349.0 ($M+H2O^+$). $^1H$ NMR (DMSO-d6) δ: 8.43-8.40 (m, 2H), 8.09-8.06 (m, 2H), 5.76-5.69 (m, 1H), 5.11-5.03 (m, 2H), 4.12 (s, 2H), 4.06-4.03 (t, J=6.4 Hz, 2H), 2.29-2.24 (q, J=6.8 Hz 2H). A round bottom flask equipped with a stir bar was charged with but-3-enyl 2-(N-trideuteriomethyl-4-nitrophenylsulfonamido) acetate (2.1 g, 6.34 mmol) and $Cs_2CO_3$ (4.12 g, 12.69 mmol) in ACN:THF (10.1, 80 mL) was added 4-methylbenzenethiol (1.57 g, 12.69 mmol) at room temperature. The reaction was stirred at 45° C. for 1.5 h. The mixture was filtered, evaporated, purified by SGC (PE:EA/10:1-DCM: MeOH/10:1) to obtain to give but-3-enyl 2-(trideuteriomethylamino) acetate (930 mg, 6.37 mmol) 46% yield) as a pale yellowish oil. $^1H$ NMR (DMSO-d6) δ: 5.83-5.73 (m, 1H), 5.13-5.03 (m, 2H), 4.11-4.06 (m, 2H), 3.02 (s, 2H), 2.36-2.31 (m, 2H), 1.92 (s, 1H).

Step 1. Synthesis of Compound DD-2

Compound DD-2 was synthesized according to Example 9, step 1 from Compound DD-1. (Z)-tert-Butyl 4-trideuteriomethyl-2,7-dioxo-1-oxa-4,6-diazacyclopentadecan-5-ylidenecarbamate was obtained as a colorless oil (Compound DD-2; 210 mg, 0.78 mmol, 34% yield). ES LC-MS m/z=373.2 ($M+H^+$). $^1H$ NMR (DMSO-d) δ: 9.88 (s, 1H), 4.19 (s, 4H), 2.19-2.17 (m, 2H), 1.52-1.50 (m, 4H), 1.36-1.31 (m, 17H).

Step 2. Synthesis of Compound DD

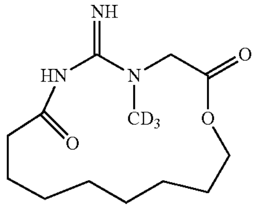 [SMILES: [2H]C([2H])([2H])N1CC(=O)OCCCCCCCCC(=O)NC1=N]

Compound DD was synthesized according to Example 9, step 2, starting from Compound DD-2. 5-Imino-4-trideuteriomethyl-1-oxa-4,6-diazacyclopentadecane-2,7-dione as a white solid (Compound DD; 80.2 mg, 0.29 mmol, 37% yield). ES LC-MS m/z=273.1 ($M+H^+$). $^1H$ NMR (DMSO-d) δ: 9.67 (br s, 1H), 7.37 (br s, 1H), 4.23-4.14 (m, 4H), 2.01-1.98 (t, J=6.4 Hz 2H), 1.59 (s, 2H), 1.50-1.46 (m, 2H), 1.29-1.25 (m, 8H).

Example 27: Synthesis of 5-imino-4-trideuteriomethyl-1-oxa-4,6-diazacyclotridecane-2,7-dione (Compound EE)

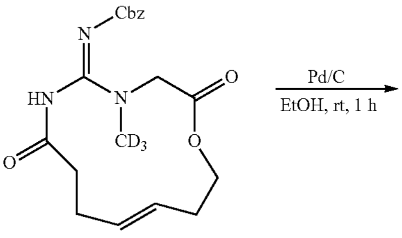

EE-1

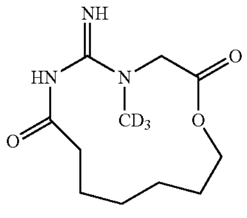

Compound EE

In general, Compound EE-1 was synthesized according to Example 8 using but-3-en-1-ol instead of pent-1-en-3-ol and using (Z)-benzyl methylthio(pent-4-enamido)methylenecarbamate (see Example 20) instead of (Z)-tert-butyl dec-9-enamido(methylthio)methylenecarbamate. Compound EE-1, (Z)-benzyl ((E)-14-butyl-4-trideuteriomethyl-2,7-dioxo-1-oxa-4,6-diazacyclotetradec-11-en-5-ylidene) carbamate, was obtained as a colorless oil (270 mg, 0.72 mmol, 53% yield). ES LC-MS m/z=377.1 (M+H$^+$). $^1$H NMR (DMSO-d6) δ: 9.89 (s, 1H), 7.39-7.29 (m, 5H), 5.32-5.16 (m, 2H), 4.92 (s, 2H), 4.26 (br s, 4H), 2.23-2.15 (m, 6H).

Compound EE was synthesized according to Example 9, step 1, starting from Compound EE-1. 5-Imino-4-trideuteriomethyl-1-oxa-4,6-diazacyclotridecane-2,7-dione (Compound EE; 69.7 mg, 0.28 mmol, 41% yield) was obtained as a white solid. ES LC-MS m/z=245.1 (M+H$^+$). $^1$H NMR (DMSO-d6) δ: 9.64 (br s, 1H), 7.40 (br s, 1H), 4.22-4.05 (m, 2H), 4.05 (s, 2H), 2.07-2.04 (m, 2H), 1.70-1.64 (m, 2H), 1.53-1.40 (m, 4H), 1.25-1.20 (m, 2H).

Example 28: Synthesis of 5-imino-4-trideuteriomethyl-1-oxa-4,6-diazacyclotridecane-2,7-dione (Compound FF)

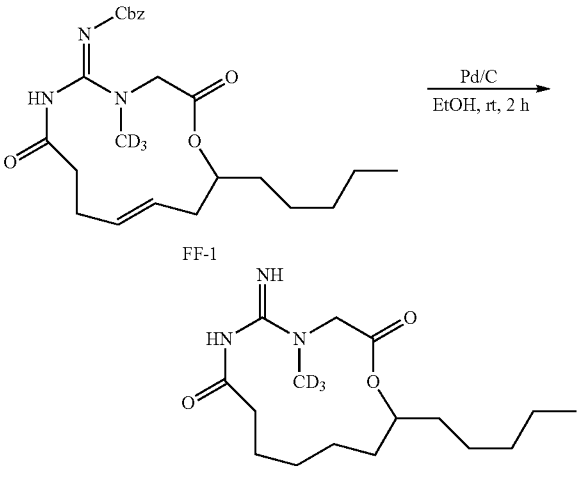

FF-1

Compound FF

In general, Compound FF-1 was synthesized according to Example 8 using non-1-en-4-ol instead of pent-1-en-3-ol and using (Z)-benzyl methylthio(pent-4-enamido)methylenecarbamate (see Example 20) instead of (Z)-tert-butyl dec-9-enamido(methylthio)methylenecarbamate. Compound FF-1, (Z)-benzyl ((E)-4-trideuteriomethyl-2,7-dioxo-13-pentyl-1-oxa-4,6-diazacyclotridec-10-en-5-ylidene) carbamate, was obtained as a pale yellow solid (600 mg, 1.34 mmol, 67% yield). ES LC-MS m/z=447.1 (M+H$^+$). $^1$H NMR (DMSO-d6) δ: 9.90 (s, 1H), 7.36-7.29 (m, 5H), 5.28-5.21 (m, 2H), 4.97-4.86 (m, 3H), 4.45-4.06 (m, 2H), 2.29-1.96 (m, 6H), 1.48-1.47 (d, J=4.4 Hz, 2H), 1.23 (s, 7H), 0.86-0.83 (t, J=6.8 Hz, 3H).

Non-1-en-4-ol: To a round bottom flask equipped with a stir bar was charged with hexanal (10 g, 100 mmol) in tetrahydrofuran (100 mL) was added dropwise allylmagnesium bromide (100 mL, 100 mmol) at −20° C. Then the mixture was warmed to room temperature for 2 hours. The reaction was quenched with aqueous ammonium chloride (60 mL), extracted with Ethyl acetate (100 mL×3), washed with water (60 mL×3) and brine (60 mL), dried and evaporated to the crude. The crude was distilled with oil-bath (110~120° C.) to obtain non-1-en-4-ol (5 g, 35.21 mmol, 35% yield) as a colorless oil. $^1$H NMR (CDCl3) δ: 5.85-5.79 (m, 1H), 5.02-4.96 (m, 2H), 4.42-4.40 (m, 1H), 3.46-3.42 (m, 1H), 2.11-2.08 (q, J=6 Hz, 2H), 1.40-1.25 (m, 8H), 0.87-0.80 (m, 3H).

Compound FF was synthesized according to Example 9, step 1, starting from Compound FF-1. 5-Imino-4-trideuteriomethyl-13-pentyl-1-oxa-4,6-diazacyclotridecane-2,7-dione (Compound FF; 239.7 mg, 0.763 mmol, 56% yield) was obtained as a white solid. ES LC-MS m/z=315.2 (M+H$^+$). $^1$H NMR (DMSO-d6) δ: 9.61 (br s, 1H), 7.40 (br s, 1H), 4.94-4.90 (m, 1H), 4.37 (d, J=16.4 Hz, 1H), 3.78 (m, J=16.8 Hz 1H), 2.49-2.18 (m, 1H), 1.91-1.85 (m, 1H), 1.71-1.04 (m, 16H), 0.86-0.83 (t, J=13.6 Hz, 3H).

Example 29: Synthesis of 5-imino-4-trideuteriomethylguanidino-18-dimethyl-1-oxa-4,6-diazacyclooctadecane-2,7-dione (Compound GG)

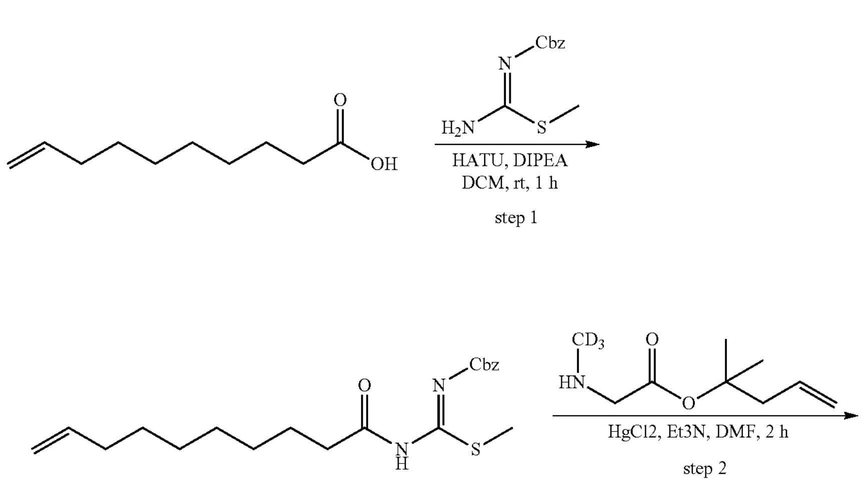

GG-1

-continued

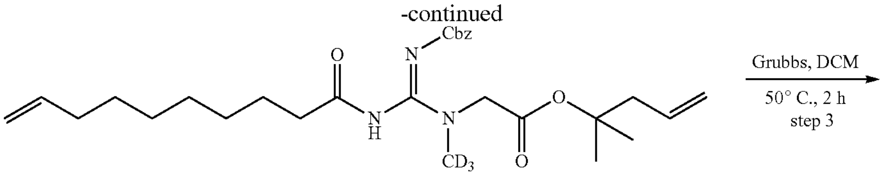

GG-2

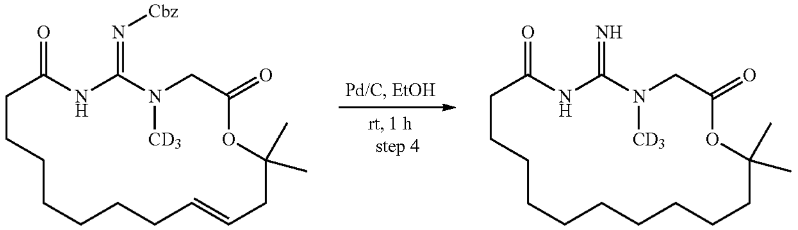

GG-3

GG

Step 1

A mixture of (Z)-benzyl amino(methylthio)methylenecarbamate (1 g, 5.88 mmoL), 1-[Bis(dimethylamino)methylene]-1H-1,2,3-triazolo[4,5-b]pyridinium 3-oxid hexafluorophosphate (2.68 g, 7.05 mmoL) and a solution of dec-9-enoic acid (1.45 g, 6.47 mmol), N,N-Diisopropylethylamine (1.52 g, 11.76 mmoL) in dichloromethane (35 mL) was stirred at rt for 2 h. Water (40 mL) was added and the mixture was extracted with dichloromethane (40 mL*3), the combined organic phase was washed with brine, dried over sodium sulfate and concentrated. The residue was purified by flash (Petroleum ether:ethyl acetate/10:1) to afford (Z)-benzyl dec-9-enamido(methylthio)methylenecarbamate (GG-1, 1.88 g, 86% yield) as a white solid. ES LC-MS m/z=377.1 (M+H$^+$).

Step 2

A mixture of Compound GG-1 (1.88 g, 5 mmoL), 2-methylpent-4-en-2-yl 2-(trideuteriomethylguanidino)acetate (820 mg, 4.7 mmoL) and a solution of triethylamine (1.42 g, 14.1 mmoL) in N,N-Dimethylformamide (40 mL) was stirred at rt. A mixture of mercury dichloride (1.4 g, 5.2 mmoL) was added, the mixture was stirred at rt for overnight. Water (40 mL) was added and the mixture was extracted with ethyl acetate (40 mL×3), the combined organic phase was washed with brine, dried over sodium sulfate and concentrated. The residue was purified by flash (Petroleum ether:Ethyl acetate/5:1) to afford (Z)-2-methylpent-4-en-2-yl 2-(2-(benzyloxycarbonyl)-3-dec-9-enoyl-1-trideuteriomethylguanidino)acetate (GG-2, 1.8 g, 72% yield) as a white solid. ES LC-MS m/z=503.3 (M+H$^+$).

Step 3

A mixture of Compound GG-2 (1 g, 2 mmoL) and Grubbs(II) (170 mg, 0.2 mmoL) in dichloromethane (1L) was stirred at 50° C. for 2 h. The combined organic was concentrated. The residue was purified by flash (Petroleum ether:Ethyl acetate/5:1) to afford (Z)-benzyl ((E)-4-trideuteriomethylguanidino-18-dimethyl-2,7-dioxo-1-oxa-4,6-diazacyclooctadec-14-en-5-ylidene)carbamate (750 mg, 79% yield) as a pale yellow oil. ES LC-MS m/z=475.2 (M+H$^+$).

Step 4. Synthesis of Compound GG

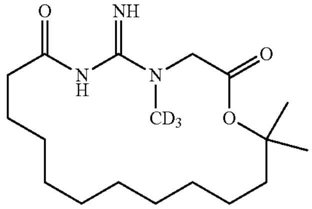

Compound GG

Compound GG was synthesized according to Example 9, step 1, starting from Compound GG-1. 5-imino-4-trideuteriomethylguanidino-18-dimethyl-1-oxa-4,6-diazacyclooctadecane-2,7-dione (Compound GG; 40 mg, 25% yield) was obtained as a white solid. ES LC-MS m/z=343.2 (M+H$^+$). $^1$H NMR (DMSO-d) δ: 9.4-10.1 (br, 1H), 7.0-7.7 (br, 1H), 4.28 (s, 2H), 2.06 (2H, t, J=7.0 Hz), 1.70-1.82 (m, 2H), 1.46-1.55 (m, 2H), 1.38 (s, 6H), 1.20-1.35 (m, 16H).

Example 30: Synthesis of 5-imino-4-trideuteriomethyl-16,16-Dimethyl-1-oxa-4,6-diazacyclohexadecane-2,7-dione (Compound HH)

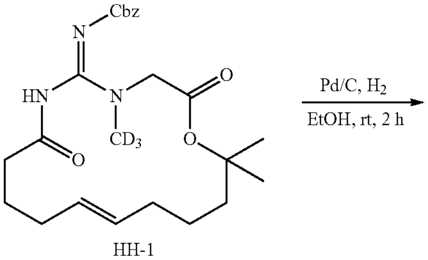

HH-1

-continued

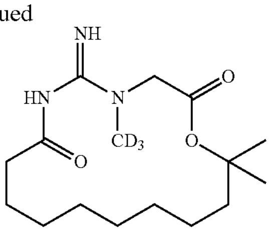

Compound HH

In general, Compound HH-1 was synthesized according to Example 8 using 2-methylhept-6-en-2-ol (see Example 17) instead of pent-1-en-3-ol and using (Z)-benzyl hex-5-enamido(methylthio)methylenecarbamate (see Example 25) instead of (Z)-tert-butyl dec-9-enamido(methylthio)methylenecarbamate. Compound HH-1, (Z)-benzyl ((E)-4-trideuteriomethyl-16,16-Dimethyl-2,7-dioxo-1-oxa-4,6-diazacyclohexadec-11-en-5-ylidene)carbamate, was obtained as an yellow oil (600 mg, 71% yield). ES LC-MS m/z=447 (M+1).

Compound HH was synthesized according to Example 9, step 1, starting from Compound HH-1. 5-Imino-4-trideuteriomethyl-16,16-Dimethyl-1-oxa-4,6-diazacyclohexadecane-2,7-dione (155 mg, 37% yield) was obtained as a white solid. ES LC-MS m/z=315 (M+1). $^1$H NMR (400 MHz, DMSO) δ 9.94 (s, 1H), 7.38 (s, 1H)), 4.30 (s, 2H), 2.15-2.03 (m, 2H), 1.81 (s, 2H), 1.53 (d, J=5.8 Hz, 2H), 1.36 (s, 6H), 1.20 (t, J=24.5 Hz, 10H).

Example 31: Synthesis of 5-imino-4-trideuteriomethylguanidino-17-methyl-1-oxa-4,6-diazacycloheptadecane-2,7-dione formate (Compound JJ)

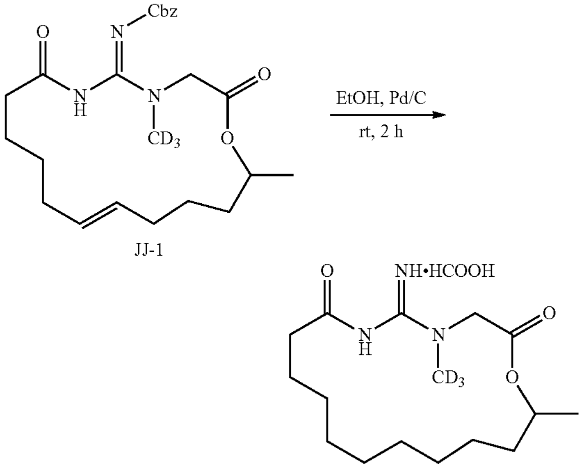

JJ-1

Compound JJ

In general, Compound JJ-1 was synthesized according to Example 8 using hept-6-en-2-yl 2-(trideuteriomethylguanidino)acetate instead of Compound L-2 and using (Z)-benzyl-hept-6-enamido-(methylthio)-methylenecarbamate (see Example 17) instead of (Z)-tert-butyl dec-9-enamido(methylthio)methylenecarbamate. Compound JJ-1, (Z)-benzyl ((E)-4-trideuteriomethylguanidino-17-methyl-2,7-dioxo-1-oxa-4,6-diazacycloheptadec-12-en-5-ylidene)carbamate, was obtained as a pale yellow oil (500 mg, 53% yield). ES LC-MS m/z=447.2 (M+H$^+$).

Hept-6-en-2-yl 2-(trideuteriomethylguanidino)acetate: A mixture of hept-6-en-2-yl 2-(N-trideuteriomethylguanidino-4-nitrophenylsulfonamido)acetate (2.04 g, 5.47 mmoL), p-thiocresol (814 mg, 6.56 mmoL), caesium carbonate (2.67 g, 8.2 mmoL) in acetonitrile (20 mL) and tetrahydrofuran (2 mL) was stirred at 45° C. for 1.5 h. The reaction mixture was filtrated, the filtrates were concentrated, the residue was purify by chromatography (Methanol:Dichloromethane/5:1) to afford hept-6-en-2-yl 2-(trideuteriomethylguanidino)acetate (1 g, 97% yield) as a yellow liquid. $^1$H NMR (DMSO-d) δ: 5.79-5.74 (m, 1H), 5.02-4.84 (m, 2H), 3.21 (s, 2H), 2.38 (s, 1H), 2.03-1.98 (m, 2H), 1.52-1.33 (m, 4H), 1.15 (s, 3H).

Compound JJ was synthesized according to Example 9, step 1, starting from Compound JJ-1 using Pd/C (20%). 5-Imino-4-trideuteriomethylguanidino-17-methyl-1-oxa-4,6-diazacycloheptadecane-2,7-dione formate (Compound JJ; 310 mg, 44% yield) as a white solid. ES LC-MS m/z=315.2 (M+H$^+$). $^1$H NMR (DMSO-d) δ: 9.3-10.2 (br, 1H), 7.0-7.8 (br, 1H), 4.92-5.00 (m, 1H), 4.88 (1H, AB, J=17.6 Hz), 3.26 (1H, AB, J=17.7 Hz), 1.92-2.12 (m, 2H), 1.40-1.58 (m, 4H), 1.20-1.35 (m, 12H), 1.17 (3H, d, J=6.4 Hz).

Example 32: Synthesis of 5-imino-4-trideuteriomethylguanidino-17-methyl-1-oxa-4,6-diazacycloheptadecane-2,7-dione formate (Compound KK)

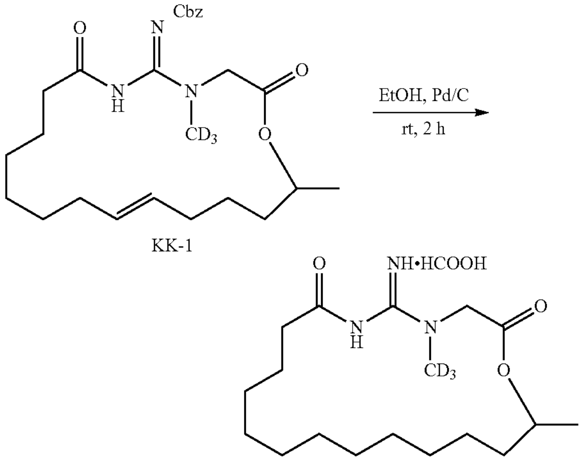

KK-1

Compound KK

In general, Compound KK-1 was synthesized according to Example 8 using hept-6-en-2-yl 2-(trideuteriomethylguanidino)acetate (see Example 31) instead of Compound L-2 and using (Z)-benzyl methylthio(non-8-enamido)methylenecarbamate instead of (Z)-tert-butyl dec-9-enamido(methylthio)methylenecarbamate. Compound KK-1, (E)-benzyl ((E)-4-trideuteriomethylguanidino-19-methyl-2,7-dioxo-1-oxa-4,6-diazacyclononadec-14-en-5-ylidene)carbamate, was obtained as a pale yellow liquid (557 mg, 59% yield). ES LC-MS m/z=475.3 (M+H$^+$).

Synthesis of (Z)-Benzyl methylthio(non-8-enamido) methylenecarbamate: A mixture of (Z)-benzyl amino(methylthio)methylenecarbamate (1.44 g, 6.4 mmoL), 1-[Bis(dimethylamino)methylene]-1H-1,2,3-triazolo[4,5-b] pyridinium 3-oxid hexafluorophosphate (1.65 g, 7.68 mmoL) and a solution non-8-enoic acid (1 g, 6.4 mmol), N,N-diisopropylethylamine (2.92 g, 7.68 mmoL) in dichloromethane (30 mL) was stirred at rt for 2 h. Water (60 mL)

was added and the mixture was extracted with dichloromethane (60 mL*3), the combined organic phase was washed with brine, dried over sodium sulfate and concentrated. The residue was purified by flash (Petroleumether:ethylacetate/10:1) to afford (Z)-benzyl methylthio(non-8-enamido)methylenecarbamate (1.82 g, 78% yield) as a white solid. ES LC-MS m/z=385.1 (M+Na$^+$).

Compound KK was synthesized according to Example 9, step 1, starting from Compound KK-1 using Pd/C (20%). 5-Imino-4-trideuteriomethylguanidino-19-dimethyl-1-oxa-4,6-diazacyclononadecane-2,7-dioneformate (Compound KK; 180 mg, 57% yield) was obtained as a white solid. ES LC-MS m/z: =343.2 (M+H$^+$). $^1$H NMR (DMSO-d) δ9.3-10.1 (br, 1H), 7.1-7.8 (br, 1H), 4.81-4.91 (m, 1H), 4.75 (1H, AB, J=17.1 Hz), 3.78 (1H, AB, J=17.4 Hz), 1.98-2.15 (m, 2H), 1.40-1.60 (m, 4H), 1.17 (3H, d, J=6.3 Hz), 1.19-1.35 (m, 16H).

Example 33: Synthesis of (16S,17S)-5-imino-4-trideuterio methyl-16, 17-dimethyl-2,7-dione formate (Compound LL)

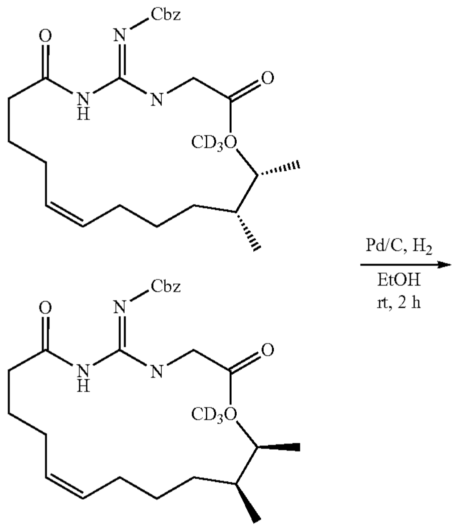

LL-1 (mixture)

-continued

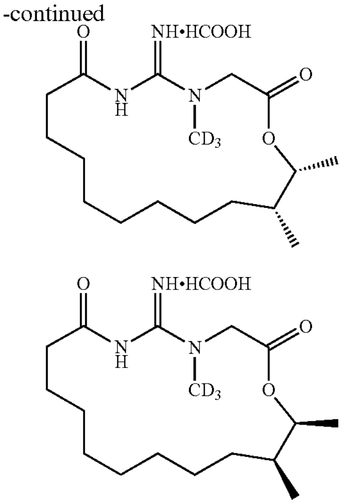

Compound LL (mixture)

In general, Compound LL-1 was synthesized according to Example 8 using (2R,3S)-2,3-dimethylhept-6-enyl-2-(trideuteriomethylguanidino)acetate instead of Compound L-2 and using (Z)-benzyl hex-5-enamido(methylthio)methylenecarbamate (see Example 25) instead of (Z)-tert-butyl dec-9-enamido(methylthio)methylenecarbamate. Compound LL-1, (Z)-benzyl ((16S, 17S, Z)-4-trideuterio methyl-16, 17-dimethyl-2,7-dioxo-1-oxa-4, 6-diazacycloheptadec-11-en-5-ylidene) carbamate, was obtained as a colorless liquid (1.16 g, 99% yield). ES LC-MS m/z=461.2 (M+H$^+$).

Synthesis of (2R,3S)-2,3-dimethylhept-6-enyl-2-(trideuteriomethylguanidino)acetate

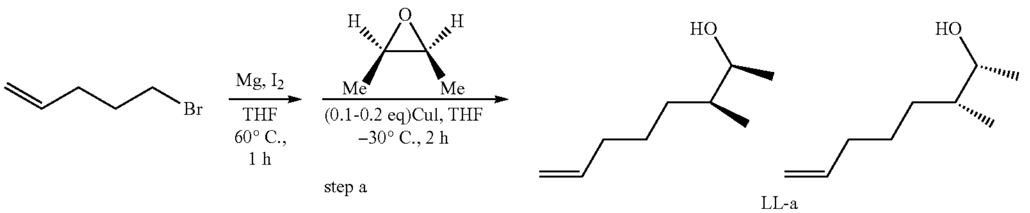

LL-a

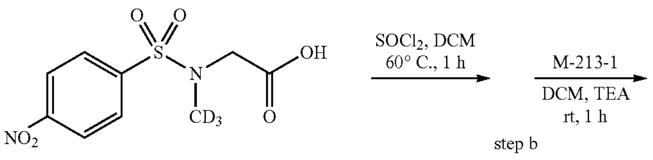

-continued

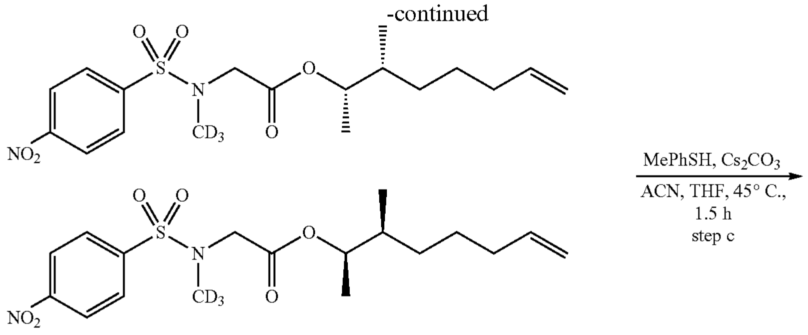

LL-b

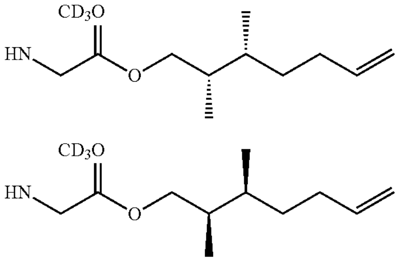

LL-c

Step a. To a stirred suspension of Mg turnings (1.94 g, 81.1 mmoL) in tetrahydrofuran (200 mL), 5-bromopent-1-ene (10 g, 67.57 mmoL), iodine (a little) was added and the reaction was started by occasional heating with a heat gun, and after 10 min of stirring at this temp. A solution of (2R,3S)-2,3-dimethyloxirane (4.86 g, 67.57 mmoL) in tetrahydrofuran (50 mL) was added dropwise. The resulting mixture was stirred at −30° C. for 2 h. Saturated ammonium chloride was added and the mixture with ethyl acetate (200 mL×3). The combined organic was washed with brine dried over anhydrous sodium sulfate, concentrated and distill to afford (2S,3S)-3-methyloct-7-en-2-ol (LL-a, 4.15 g, 43% yield) as a yellow liquid. $^1$H NMR (DMSO-d) δ: 5.80-5.78 (m, 1H), 5.01-4.91 (m, 2H), 4.25 (s, 1H), 3.5 (s, 1H), 2.01-1.98 (m, 2H), 1.41-1.29 (m, 4H), 0.99-0.98 (m, 3H), 0.80-0.78 (m, 3H).

Step b. A mixture of 2-(N-trideuteriomethylguanidino-4-nitrophenylsulfonamido)acetic acid (3 g, 10.8 mmoL) in thionyl chloride (25 mL) and dichloromethane (25 mL) was stirred at 60° C. for 1 h. The combined organic was concentrated. Then, the resulting compound was dissolved in dichloromethane (50 mL) and (2S,3S)-3-methyloct-7-en-2-ol (1.85 g, 13 mmoL), triethylamine (3.28 g, 32.5 mmoL) was added and the resulting mixture was stirred at rt for 1 h. Water (50 mL) was added and the combined organic phase was washed with brine, dried over sodium sulfate and concentrated. The residue was purified by flash (Petroleum ether:Ethyl acetate/5:1) to afford (2R,3S)-3-methyloct-7-en-2-yl 2-(N-trideuteriomethylguanidino-4-nitrophenylsulfonamido)acetate (LL-b, 2.89 g, 66% yield) as a white solid. ES LC-MS m: =424.1 (M+Na$^+$).

Step c. A mixture of (2R,3S)-3-methyloct-7-en-2-yl 2-(N-trideuteriomethylguanidino-4-nitrophenylsulfonamido)acetate (2.89 g, 7.2 mmoL), p-thiocresol (1.07 mg, 8.65 mmoL), caesium carbonate (3.52 g, 10.8 mmoL) in acetonitrile (40 mL) and tetrahydrofuran (4 mL) was stirred at 45° C. for 1.5 h. The reaction mixture was filtrated, the filtrates were concentrated, the residue was purify by chromatography (Methanol:Dichloromethane/5:1) to afford (2S,3R)-2,3-dimethylhept-6-enyl 2-(trideuteriomethylguanidino)acetate (LL-c, 1.2 g, 80/6 yield) as a yellow liquid. $^1$H NMR (DMSO-d) δ: 5.79-5.75 (m, 1H), 5.02-4.92 (m, 2H), 4.81-3.21 (m, 1H), 2.00-1.99 (m, 2H), 1.98 (s, 1H), 1.72-1.50 (m, 1H), 1.37-1.31 (m, 3H), 1.31-1.30 (m, 3H), 0.86-0.84 (m, 3H).

Synthesis of Compound LL. Compound LL was synthesized according to Example 9, step 1, starting from Compound LL-1 (mixture). (16S,17S)-5-Imino-4-trideuterio methyl-16, 17-dimethyl-2,7-dione formate (Compound LL mixture; 188 mg, 46% yield) was obtained as a white solid. ES LC-MS m/z=329.2 (M+H$^+$). $^1$H NMR (DMSO-d) δ: 9.4-10.1 (br, 1H), 7.1-7.7 (br, 1H), 4.92-5.01 (m, 1H), 4.80 (1H, AB, J=17.5 Hz), 3.86 (1H, AB, J=17.6 Hz), 1.94-2.12 (m, 2H), 1.12 (3H, d, J=6.6 Hz), 0.86 (3H, d, J=6.9 Hz), 1.04-1.64 (m, 5H).

Example 34: Synthesis of 8-imino-7-trideuteriomethyl-4-oxa-7,9-diazaspiro[2.17]icosane-5,10-dione (Compound MM)

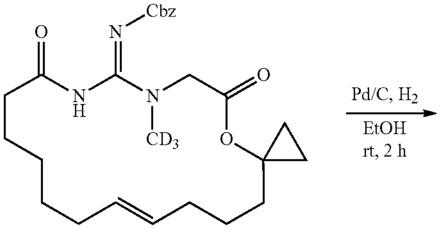

MM-1

-continued

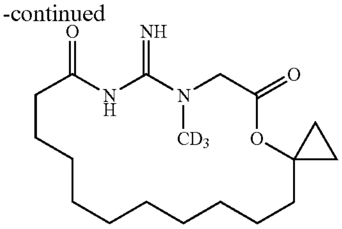

Compound MM

In general, Compound MM-1 was synthesized according to Example 8 using 1-(pent-4-enyl)cyclopropyl 2-(trideuteriomethylamino)acetate (see Example 23) instead of Compound L-2 and using (Z)-benzyl methylthio(oct-7-enamido) methylenecarbamate instead of (Z)-tert-butyl dec-9-enamido(methylthio)methylenecarbamate. Compound MM-1, (Z)-benzyl ((E)-7-trideuteriomethyl-5,10-dioxo-4-oxa-7,9-diazaspiro[2.17]icos-16-en-8-ylidene)carbamate, was obtained as an yellow oil (900 mg, 81% yield). ES LC-MS m/z=473 (M+1).

(Z)-Benzyl methylthio(oct-7-enamido)methylenecarbamate: A mixture of (Z)-benzyl amino(methylthio)methylenecarbamate (1.7 g, 7.74 mmol), oct-7-enoic acid (1.0 g, 7.04 mmol), HATU (3.2 g, 8.45 mmol) and TEA (2.9 ml, 21.12 mmol) in dichloromethane (20 ml) was stirred at rt for overnight. Water (50 ml) was added and the mixture was extracted with dichloromethane (50 ml×3), the combined organic phase was washed with brine, dried over sodium sulfate and concentrated. The residum was purified by chromatography (Petroleumether:ethylacetate=10:1) to afford (Z)-benzyl methylthio(oct-7-enamido)methylenecarbamate (1.9 g, 77% yield) as a white solid. ES LC-MS m/z=349 (M+1).

Compound MM was synthesized according to Example 9, step 1, starting from Compound MM-1 using Pd/C (20%). 8-Imino-7-trideuteriomethyl-4-oxa-7,9-diazaspiro[2.17] icosane-5,10-dione (Compound MM: 101.7 mg, 31% yield) was obtained as a white solid. ES LC-MS m/z=341 (M+1). $^1$H NMR (400 MHz, DMSO) δ 9.79 (s, 1H), 7.74-6.95 (m, 1H), 4.33 (s, 2H), 2.14-1.95 (m, 2H), 1.74-1.61 (m, 2H), 1.57-1.47 (m, 2H), 1.30 (t, J=19.8 Hz, 14H), 0.80 (t, J=6.3 Hz, 2H), 0.64 (q, J=5.9 Hz, 2H).

Example 35: Synthesis of 5-imino-4-trideuteriomethyl-16-cyclopropyl-1-oxa-4,6-diazacyclohexadecane-2,7-dione (Compound NN)

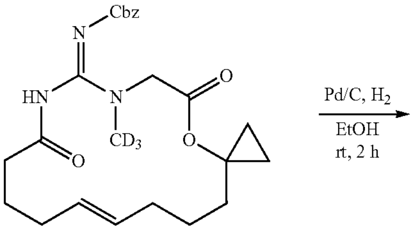

NN-1

-continued

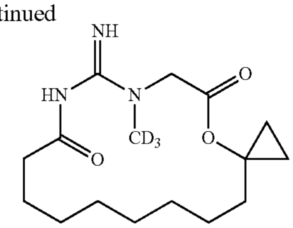

Compound NN

In general, Compound NN-1 was synthesized according to Example 8 using 1-(pent-4-enyl)cyclopropyl-2-(trideuteriomethylamino)acetate (see Example 23) instead of Compound L-2 and using (Z)-benzyl-hex-5-enamido-(methylthio)-methylenecarbamate (see Example 25) instead of (Z)-tert-butyl dec-9-enamido(methylthio)methylenecarbamate. Compound NN-1, (Z)-benzyl ((E)-4-trideuteriomethyl-16-cyclopropyl-1-2,7-dioxo-1-oxa-4,6-diazacyclohexadec-11-en-5-ylidene)carbamate, was obtained as a colorless oil (370 mg, 0.83 mmol, 91% yield). ES LC-MS m/z=445.3 (M+H$^+$).

Compound NN was synthesized according to Example 9, step 1, starting from Compound NN-1. 5-Imino-4-trideuteriomethyl-16-cyclopropyl-1-oxa-4,6-diazacyclohexadecane-2,7-dione (Compound NN; 145 mg, 0.46 mmol, 57% yield) was obtained as a white solid. ES LC-MS m/z=313.2 (M+H$^+$). $^1$H NMR (DMSO-d6) δ: 9.83 (br s, 1H), 7.40 (br s, 1H), 4.25 (br s, 1H), 2.12-2.09 (t, 0.1=6.0 Hz, 2H), 1.70-1.62 (m, 4H), 1.43-1.41 (m, 2H), 1.26 (s, 6H), 1.18-1.17 (m, 2H), 0.80-0.78 (d, J=6.4 Hz, 3H), 0.64-0.60 (t, J=6.0 Hz, 2H).

Example 36: Synthesis of 5-imino-4-trideuteriomethyl-16-cyclopropyl-1-oxa-4,6-diazacyclohexadecane-2,7-dione (Compound OO)

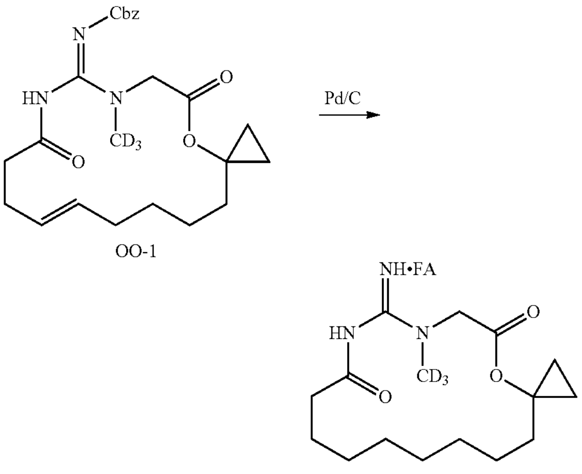

Compound OO

In general, Compound OO-1 was synthesized according to Example 8 using 1-(pent-4-enyl)cyclopropyl 2-(trideuteriomethylamino)acetate (see Example 23) instead of Compound L-2 and using (Z)-benzyl methylthio(pent-4-enamido)methylenecarbamate (see Example 20) instead of (Z)-tert-butyl dec-9-enamido(methylthio)methylenecarbamate. Compound OO-1, (Z)-benzyl ((E)-4-trideuteriomethyl-15-cyclopropyl-2,7-dioxo-1-oxa-4,6-diazacyclopentadec-10-en-5-ylidene)carbamate, was obtained as a colorless oil (644 mg, 1.49 mmol, 80% yield). ES LC-MS m/z: =431 (M+H$^+$). $^1$H NMR (DIMETHYL SULFOXIDE-d6) δ: 9.99 (s, 1H), 7.38-7.31 (m, 5H), 5.37-5.36 (m, 2H), 4.95 (m, 2H), 4.16 (s, 2H), 2.22 (m, 4H), 2.00-1.98 (s, 2H), 1.49 (s, 2H), 1.23 (s, 2H), 0.81 (m, 2H), 0.66 (m, 2H).

Compound OO was synthesized according to Example 9, step 1, starting from Compound OO-1. 5-Imino-4-trideuteriomethy-15-cyclopropyl-1-oxa-4,6-diazacyclopentadecane-2,7-dione formate (268 mg, 0.90 mmol, 60% yield) as a white solid. ES LC-MS m/z=299.2 (M+H$^+$). $^1$H NMR (DMSO-d6) δ: 4.20 (s, 2H), 2.07-2.04 (m, 2H), 1.67-1.63 (m, 2H), 1.51-1.48 (m, 2H), 1.41-1.40 (m, 2H), 1.29-1.24 (m, 6H), 0.81-0.78 (m, 2H), 0.64-0.60 (m, 2H).

Example 37: Synthesis of (S)-5-imino-17-methyl-4-(methyl-d3)-1-oxa-4,6-diazacycloheptadecane-2,7-dione hydrochloride (Compound PP)

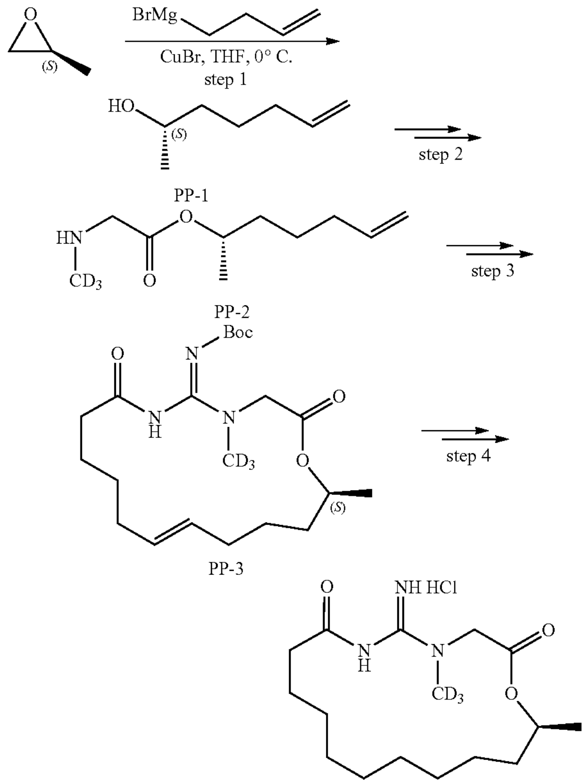

PP-1
PP-2
PP-3
PP

Step 1. Synthesis of PP-1

(S)-2-methyloxirane (2.1 mL, 30 mmol) was dissolved in 70 mL of anhydrous THF under an argon atmosphere. To the solution was added CuBr (214 mg, 1.5 mmol) and it was cooled to 0° C. 3-Butenylmagnesium bromide (0.5 M in THF, 70 mL, 35 mmol) was added dropwise over 15 minutes to the stirring reaction mixture. After the addition was completed, the reaction mixture was allowed to warm to room temperature over 30 min. Once the reaction judged completed by LCMS, sat. aq. $NH_4Cl$ (100 mL) was added and the organic phase separated. The organics were combined, dried ($MgSO_4$) and concentrated under vacuum to afford crude (S)-hept-6-en-2-ol. The crude product was purified by silica gel flash chromatography with a gradient of 5% to 40% ethyl acetate in hexanes to yield pure (S)-hept-6-en-2-ol (Compound PP-1) as an colorless oil: 2.42 g, 70% yield, ES LCMS m/z=115.3 (M+H$^+$). 1H NMR (400 MHz, CHLOROFORM-d) δ ppm 5.82 (ddt, J=17.03, 10.26, 6.68, 6.68 Hz, 1H) 5.02 (dq, J=17.16, 1.73 Hz, 1H) 4.96 (ddt, J=10.20, 2.16, 1.10, 1.10 Hz, 1H) 3.76-3.87 (m, 1H) 2.02-2.16 (m, 2H) 1.36-1.57 (m, 6H) 1.20 (d, J=6.02 Hz, 3H).

Step 2. Synthesis of PP-2

Compound PP-2 was synthesized according to Example 8, steps 1 and 2, starting from 2-[(4-nitrophenyl)sulfonyl-(trideuteriomethyl)amino]acetic acid and Compound PP-1. (S)-hept-6-en-2-yl (methyl-d3)glycinate (Compound PP-2; 0.87 g, 42% yield) was obtained as an oil. ES LC-MS m/z=189.1 (M+H$^+$).

Step 3. Synthesis of PP-3

Compound PP-3 was synthesized according to Example 8, steps 3 and 4, starting from Compound PP-2 and Compound O-2. tert-Butyl ((S,5Z,12E)-17-methyl-4-(methyl-d3)-2,7-dioxo-1-oxa-4,6-diazacycloheptadec-12-en-5-ylidene)carbamate (Compound PP-3; 675 mg, 64%/o yield) was obtained as an oil. ES LC-MS m/z=413.3 (M+H$^+$).

Step 4. Synthesis of Compound PP

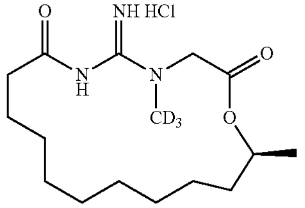

Compound PP was synthesized according to Example 13, step 1 and step 2 from Compound PP-3 using Pd/C (10%) in step 1. (S)-5-imino-17-methyl-4-(methyl-d3)-1-oxa-4,6-diazacycloheptadecane-2,7-dione hydrochloride (Compound PP; 193 mg, 88% yield) was obtained as a white solid. ES LC-MS m/z=315.2 (M+H$^+$). 1H NMR (400 MHz, DMSO) δ 11.43 (s, 11H), 9.31 (d, J=55.0 Hz, 2H), 5.25 (d, J=19.1 Hz, 1H), 4.96 (s, 1H), 4.35 (d, J=18.8 Hz, 1H), 2.72 (s, 1H), 2.33 (s, 1H), 1.51 (s, 4H), 1.37-1.04 (m, 15H).

Example 38: Synthesis of 5-imino-4-trideuteriomethyl-1-oxa-4,6-diazacyclooctadecane-2,7-dione (Compound QQ)

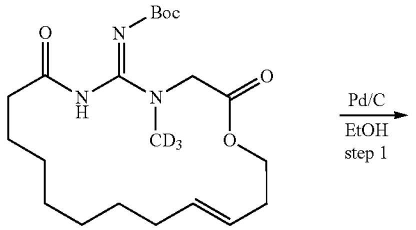

QQ-1

-continued

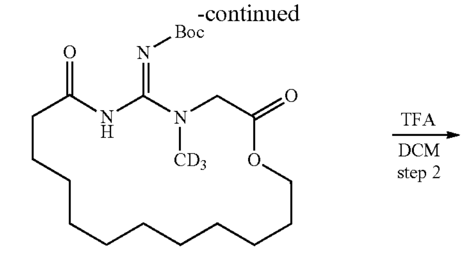

QQ-2

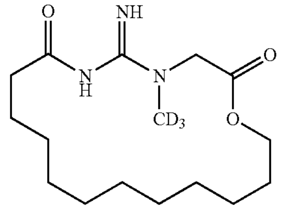

QQ

In general, Compound QQ-1 was synthesized according to Example 8 using but-3-enyl 2-(trideuteriomethylamino) acetate (see Example 26) instead of L-2 and using tert-butyl (Z)-(dec-9-enamido(methylthio)methylene)carbamate (see Example 7) instead of (Z)-tert-butyl dec-9-enamido(methylthio)methylenecarbamate. Compound QQ-1, (Z)-tert-butyl ((E)-4-trideuteriomethyl-2,7-dioxo-1-oxa-4,6-diazacyclooctadec-15-en-5-ylidene)carbamate, was obtained as a black oil (2.165 g, 80%). ES LC-MS m/z=413.4 (M+H$^+$).

Step 1. Synthesis of Compound QQ-2

Compound QQ-2 was synthesized according to Example 9, step 1 from Compound QQ-1 using Pd/C (20%). (Z)-tert-Butyl 4-trideuteriomethyl-2,7-dioxo-1-oxa-4,6-diazacyclooctadecan-5-ylidenecarbamate was obtained as an yellow oil (Compound QQ-2; 1.3 g, 60%). ES LC-MS m/z=415.4 (M+H$^+$).

Step 2. Synthesis of Compound QQ

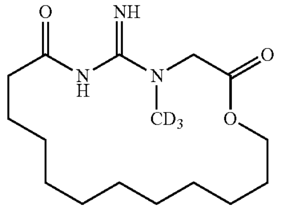 [SMILES: [2H]C([2H])([2H])N1CC(=O)OCCCCCCCCCCCC(=O)NC1=N]

Compound QQ was synthesized according to Example 9, step 2, starting from Compound QQ-2. 5-Imino-4-trideuteriomethyl-1-oxa-4,6-diazacyclooctadecane-2,7-dione was obtained as a white solid (Compound QQ; 510 mg, 52%). ES LC-MS m % z=315.4 (M+H$^+$). $^1$H NMR (DMSO-d) δ: 4.35 (s, 2H), 4.10-4.07 (t, 2H), 2.07-2.03 (t, 2H), 1.60-1.59 (m, 2H), 1.52-1.49 (t, 2H), 1.30-1.26 (t, 14H).

Example 39: Synthesis of 5-imino-4-trideuteriomethyl-1-oxa-4,6-diazacyclohexadecane-2,7-dione (Compound RR) and 5-imino-4-trideuteriomethyl-1-oxa-4,6-diazacyclohexadecane-2,7-dione formic acid salt (Compound SS)

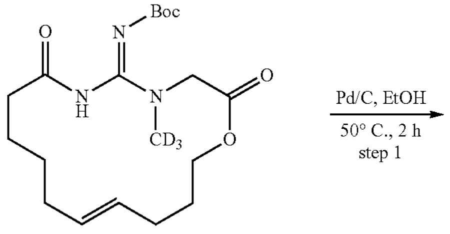

RR-1

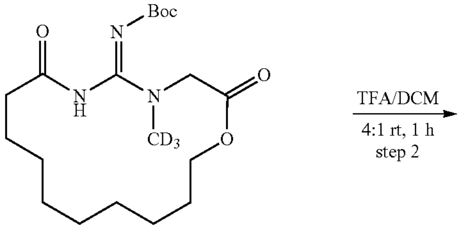

RR-2

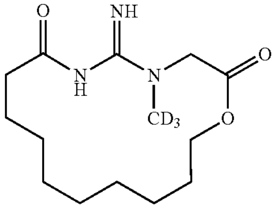

OR

RR

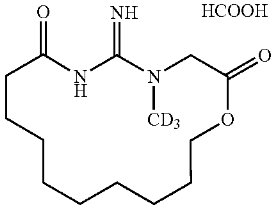

SS

In general, Compound RR-1 was synthesized according to Example 8 using pent-4-enyl 2-(trideuteriomethylamino) acetate instead of L-2 and using (Z)-tert-butyl hept-6-enamido (methylthio) methylenecarbamate (see Example 10) instead of (Z)-tert-butyl dec-9-enamido(methylthio)methylenecarbamate. Compound RR-1, (Z)-tert-butyl ((E)-4-trideuteriomethyl-2,7-dioxo-1-oxa-4, 6-diazacyclohexadec-12-en-5-ylidene) carbamate, was obtained as a colorless oil (290 mg, 0.75 mmol, 59% yield). ES LC-MS m/z=385.3 (M+H$^+$).

Synthesis of pent-4-enyl 2-(trideuteriomethylamino) acetate

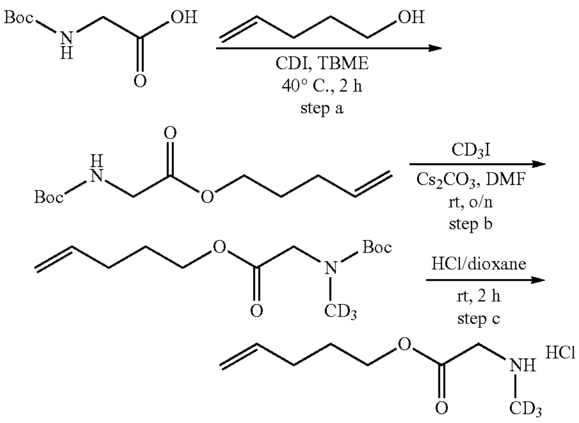

Step a. A round bottom flask equipped with a stir bar and nitrogen inlet was charged with CDI (4.4 g, 27.14 mmol) in TBME (15 mL) was heated to ~40° C. A solution of 2-(tert-butoxycarbonylamino) acetic acid (5 g, 28.57 mmol) in TBME (20 mL) was prepared and added to the slurry. After 0.5 hour pent-4-en-1-ol (2.33 g, 27.14 mmol) was added drop wise over 20 minutes. The reaction was stirred at 40° C. for 2 hours. The reaction was cooled to RT, added 1 N HCl of solution (12 mL), separated and the organic layer was washed with 1 N HCl of solution (12 mL×1) and water (12 mL×1), dried and evaporated to give pent-4-enyl 2-(tert-butoxycarbonylamino) acetate (4.3 g, 17.7 mmol, 60%) as a colorless oil. ES LC-MS m/z=144.2 ($M-99^+$). $^1H$ NMR (DMSO-d6) δ: 5.8505.74 (m, 1H), 5.05-4.99 (m, 3H), 4.16-4.12 (t, J=6.8 Hz, 2H), 3.88 (s, 2H), 2.13-2.08 (m, 2H), 1.76-1.71 (q, J=6.8 Hz, 2H), 1.43 (s, 9H).

Step b. A round bottom flask equipped with a stir bar was charged with Sodium hydrogen (1.5 g, 39.51 mmol) in THF:DMF (10:1, 45 mL) was stirred at ice-bath for 20 minutes. Then the reaction was added drop wise pent-4-enyl 2-(tert-butoxycarbonylamino) acetate (4.8 g, 19.75 mmol) in THF:DMF (10:1, 2 mL) at ice-bath for 15 minutes. Then Deuterium iodide (8.6 g, 59.26 mmol) was added dropwise at ice-bath. The reaction was warmed to RT, and stirred for 2 hours. The reaction was added drop wise water (20 mL) at ice-bath and added ethyl acetate (150 mL), separated and washed with water (30 mL×2) and brine (30 mL), dried and evaporated, purified by SGC (PE:EA/90:1) to give pent-4-enyl 2-(tert-butoxycarbonyl (trideuteriomethyl) amino) acetate (1.6 g, 6.15 mmol, 31%) as a pale yellowish oil. $^1H$ NMR (DMSO-d6) δ: 5.84-5.77 (m, 1H), 5.05-4.97 (m, 2H), 4.10-4.04 (m, 2H), 3.95-3.92 (t, J=4.8 Hz, 2H), 2.10-2.05 (m, 2H), 1.69-1.64 (m, 2H), 1.39-1.33 (m, 9H).

Step c. A round bottom flask equipped with a stir bar was charged with pent-4-enyl 2-(tert-butoxycarbonyl (trideuteriomethyl) amino) acetate (1.6 g, 6.15 mmol) in HCl/dioxane (20 mL) was stirred at room temperature for 2 h. The mixture was evaporated to give pent-4-enyl 2-(trideuteriomethylamino) acetate (1.5 g, 7.65 mmol, 125% yield) as a white solid. $^1H$ NMR (DMSO-d6) δ: 9.57 (br s, 2H), 5.85-5.75 (m, 1H), 5.07-4.96 (m, 2H), 4.18-4.13 (t, J=7.2 Hz, 2H), 3.92 (s, 2H), 2.12-2.07 (q, 0.1=6.8 Hz, 2H), 1.72-1.65 (m, 3H).

Step 1. Synthesis of Compound RR-2

Compound RR-2 was synthesized according to Example 9, step 1 from Compound RR-1. (Z)-tert-Butyl 4-trideuteriomethyl-2,7-dioxo-1-oxa-4, 6-diazacyclohexadecan-5-ylidenecarbamate was obtained as a white solid (Compound RR-2; 380 mg, 0.75 mmol, 131% yield). The crude was directly used next step further without purification. ES LC-MS m/z=387.3 ($M+H^+$).

Step 2. Synthesis of Compound RR and Compound SS

RR

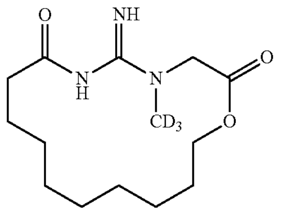

OR

SS

HCOOH

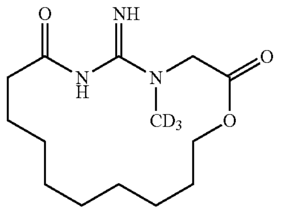

A round bottom flask equipped with a stir bar was charged with Compound RR-2 (380 mg, 0.75 mmol) in DCM (4 mL) was added trifluoroacetic acid (1 mL), stirred at room temperature for 1 hour. The reaction was evaporated, dissolved in THF (3 mL), purified by Pre-HPLC (FA), lyophilized to give 5-imino-4-trideuteriomethyl-1-oxa-4, 6-diazacyclohexadecane-2,7-dione formic acid salt (Compound SS; 151.6 mg, 0.53 mmol, 51% yield) as a white solid ES LC-MS m/z=287.3 ($M+H^+$). $^1H$ NMR (DMSO-d6) δ: 10.58 (br s, 1H), 9.42-9.24 (m, 2H), 4.54 (s, 2H), 4.19 (s, 2H), 1.59 (s, 4H), 1.25-1.19 (m, 12H) and 5-imino-4-trideuteriomethyl-1-oxa-4, 6-diazacyclohexadecane-2,7-dione (free base) (Compound RR; 55.4 mg, 0.19 mmol, 18% yield) as a white solid. ES LC-MS m/z=287.3 ($M+H^+$). $^1H$ NMR (DMSO-d6) δ: 9.82 (br s, 1H), 7.41 (br s, 1H), 4.35 (s, 2H), 4.16-4.13 (t, J=4.8 Hz, 2H), 2.10-2.07 (t, J=6.0 Hz, 2H), 1.56-1.51 (q, J=6.0 Hz, 4H), 1.26-1.18 (m, 10H).

Example 40; Synthesis of 5-imino-4-trideuteriomethy-17-cyclobutane-1-oxà-4,6-diazacycloheptadecane-2,7-dione formate (Compound TT)

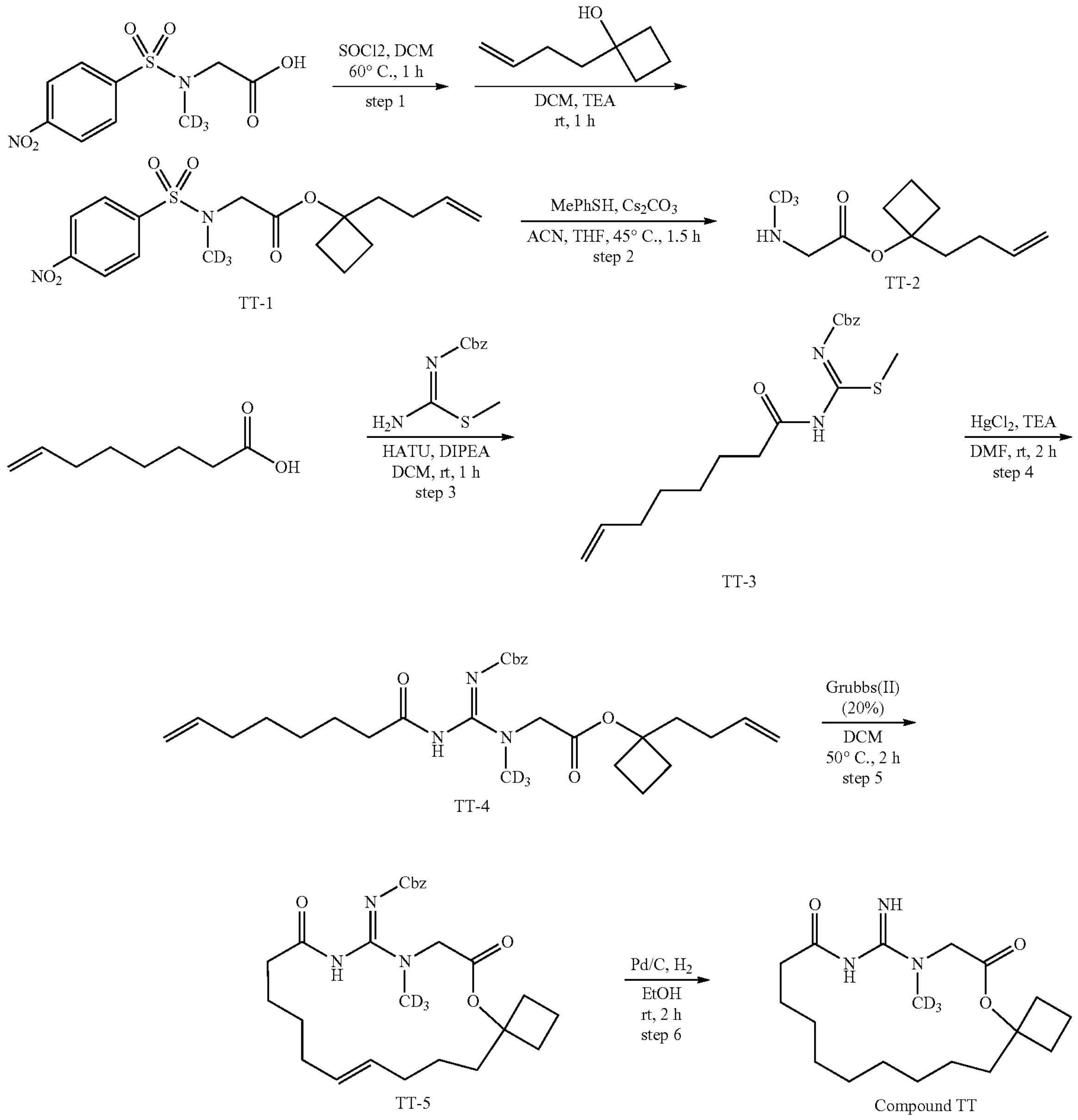

Step 1

A mixture of 2-(N-trideuteriomethyl-4-nitrophenylsulfonamido)acetic acid (2.8 g, 10 mmol) and sulfurous dichloride (50 ml) in dichloromethane (50 ml) was heated to 60 degree and stirred for 2 hs. The mixture was concentrated, the residue was dissolved with dichloromethane (50 ml) which was added in a mixture of 1-(but-3-enyl)cyclobutanol (1.27 g, 10 mmol) and triethylamine (2.02 g, 20 mmol) in dichloromethane (50 ml) at ice-water and then stirred at rt for 1 h. water (50 ml) was added and the mixture was extracted with dichloromethane (50 ml×3), the combined organic phase was washed with brine, dried over sodium sulfate and concentrated. The residue was purified by chromatography (Petroleumether:ethylacetate=10:1) to afford 1-(but-3-enyl)cyclobutyl 2-(N-trideuteriomethyl-4-nitrophenylsulfonamido)acetate (TT-1; 2.43 g, 63%) as a yellow oil. ES LC-MS m/z=407.7 (M+Na$^+$).

Step 2

A mixture of Compound TT-1 (2.43 g, 6.3 mmol), 4-methylbenzenethiol (1.56 g, 12.6 mmol) and Cesium carbonate (4.11 g, 12.6 mmol) in acetonitrile (30 ml) and tetrahydrofuran (3 ml) was stirred at 45 degree for 2 hs. The reaction mixture was filtrated and the filtrates were concentrated. The residue was purified by chromatography (dichloromethane: methanol=10:1 with 0.1% Ammonium hydroxide) to afford 1-(but-3-enyl)cyclobutyl 2-(trideuteriomethylamino)acetate (TT-2; 1.06 g, 84%) as a yellow oil. $^1$H NMR (DMSO-d) δ: 5.03-4.93 (m, 2H), 3.37 (s, 2H), 2.32-2.29 (m, 2H), 2.27-2.22 (m, 2H), 2.21-2.17 (m, 4H), 2.038-2.031 (m, 1H), 1.83 (m, 1H), 1.65 (m, 1H).

Step 3

A mixture of (Z)-benzyl amino(methylthio)methylenecarbamate (3.15 g, 14.1 mmol), oct-7-enoic acid (2 g, 14.1 mmol), O-(7-Azabenzotriazol-1-yl)-N,N,N'N'-tetramethyluronium hexafluorophosphate (6.43 g, 16.9 mmol) and N,N-Diisopropyl-ethylamine (3.64 g, 28.2 mmol) in dichloromethane (50 ml) was stirred at rt for overnight. Water (50 ml) was added and the mixture was extracted with dichloromethane (60 ml*3), the combined organic phase was washed with brine, dried over sodium sulfate and concentrated. The residum was purified by chromatography (Petroleumether:ethylacetate=10:1) to afford (Z)-benzyl methylthio(oct-7-enamido)methylenecarbamate (TT-3; 4.43 g, 90%) as a White solid. ES LC-MS m/z=370.8 (M+Na$^+$).

Step 4

A mixture of Compound TT-3 (1.4 g, 4 mmol), Compound TT-2 (805 mg, 4 mmol) and triethylamine (808 mg, 8 mmol) in N,N-Dimethylformamide (20 ml) was stirred at rt, Mercury(II) chloride (1.08 g, 4 mmol) was added and the mixture was stirred for overnight. Water (100 ml) was added and the mixture was extracted with ethyl acetate (50 ml×3), the combined organic phase was washed with brine, dried over sodium sulfate and concentrated. The residue was purified by chromatography (Petroleumether:ethylacetate=5:1) to afford (Z)-1-(pent-4-enyl)cyclobutane 2-(2-(benzyloxycarbonyl)-1-trideuteriomethylguanidino-3-oct-7-enoylguanidino)acetate (TT-4; 1.5 g, 75%) as a colorless oil. ES LC-MS m/z=522.8 (M+Na$^+$).

Step 5

A mixture of Compound TT-4 (1.7 g, 3.6 mmol) and Grubbs II (305 mg, 0.36 mmol) in dichloromethane (1500 ml) was stirred at 50 degree for 2 hs under N2, Cooling to rt, ethoxyethene (5 ml) was added and the mixture was stirred for 30 min. the mixture was concentrated and the residue was purified by chromatography (Petroleumether: ethylacetate=5:1) to afford (Z)-benzyl ((E)-4-trideuteriomethyl-17-cyclobutane-2,7-dioxo-1-oxa-4,6-diazacycloheptadec-12-en-5-ylidene)carbamate (TT-5; 533 mg, 33%) as a yellow oil. ES LC-MS m/z=473.7 (M+H$^+$).

Step 6. Synthesis of Compound TT

Compound TT

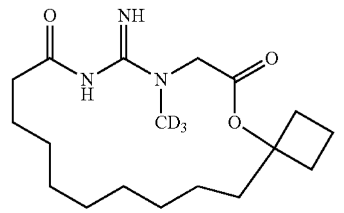

A mixture of afford Compound TT-5 (533 mg, 1.13 mmol) and Pd/C (106 mg, 20%) in ethanol (10 ml) was stirred at rt under $H_2$ balloon for overnight. The reaction mixture was filtrated and the filtrates were concentrated. The residue was purified by Pre-HPLC (40% acetonitrile in water with 0.2% formic acid) to afford 5-imino-4-trideuteriomethy-17-cyclobutane-1-oxa-4,6-diazacycloheptadecane-2,7-dione formate (54 mg, 11%) as a white solid. ES LC-MS m/z=341.4 (M+H)$^+$. $^1$H NMR (DMSO-d) δ: 4.31 (s, 2H), 2.22-2.17 (m, 2 H), 2.13-2.08 (m, 2H), 2.05-2.02 (m, 2H), 1.87-1.83 (m, 2H), 1.78-1.75 (m, 1H), 1.64-1.61 (m, 1H), 1.53-1.49 (m, 2H), 1.28-1.22 (m, 12H).

Example 41: Synthesis of 10-imino-9-trideuteriomethyl-2,6-dioxa-9,11-diazaspiro[4.16]henicosane-7,12-dione (Compound UU)

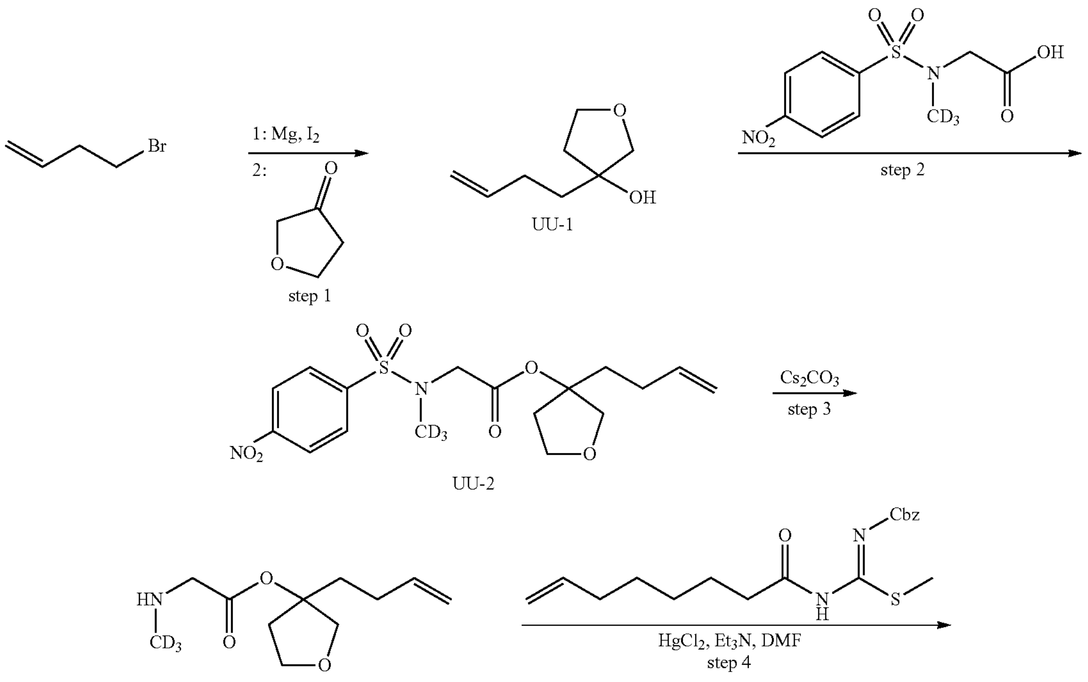

UU-1
UU-2
UU-3

-continued

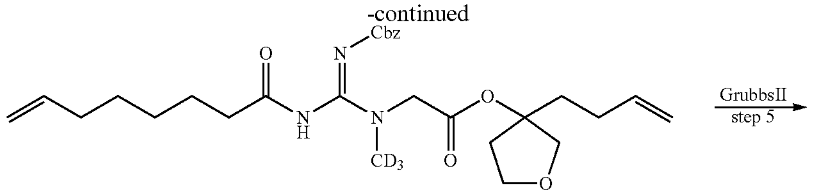

UU-4

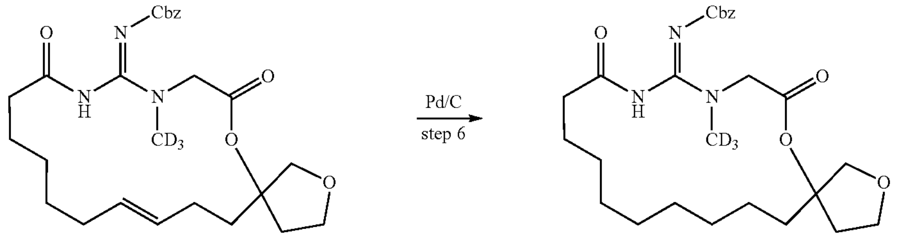

UU-5 Compound UU

Step 1

To a stirred suspension of magnesium (6.1 g, 251 mmol) in tetrahydrofuran (30 ml), 4-bromobut-1-ene (3.0 g, 22.2 mmol) was added and the reaction was started by occasional heating with a heat gun. The remained of 4-bromobut-1-ene (30.0 g, 222 mmol) was added dropwise at efflux temp after 1 h of stirring at this temp. cooling to 0 degrees, a solution of dihydrofuran-3(2H)-one (17.2 g, 200 mmol) in tetrahydrofuran (140 ml) was added dropwise. After heating to reflux for 1 h, the mixture was poured into sat·aq. ammonia chloride/ice 1:1. The mixture was extracted with ethyl acetate (300 ml*3), the combined organic phase was washed with brine, dried over sodium sulfate and concentrated. The residue was purified by a short vigreux column to afford 3-(but-3-enyl)tetrahydrofuran-3-ol (UU-1; 9.4 g, 33%) as a yellow oil. $^1H$ NMR (DMSO-$d_6$) δ: 5.81-5.87 (m, 1H), 4.92-5.04 (m, 2H), 4.61 (ds, 1H), 3.71-3.84 (m, 2H), 3.42-3.52 (m, 2H), 2.09-2.16 (m, 2H), 1.72-1.79 (m, 2H), 1.58-1.62 (m, 2H).

Step 2

A mixture of 2-(N-trideuteriomethyl-4-nitrophenylsulfonamido)acetic acid (2.77 g, 10 mmol) and sulfurous dichloride (15 ml) in dichloromethane (15 ml) was heated to 60 degree and stirred for 2 hs. The mixture was concentrated, the residue was dissolved with dichloromethane (50 ml) which was added in a mixture of Compound UU-1 (1.7 g, 12 mmol) and triethylamine (3.03 g, 30 mmol) in dichloromethane (20 ml) at ice-water and then stirred at rt for 1 h. water (50 ml) was added and the mixture was extracted with dichloromethane (50 ml*3), the combined organic phase was washed with brine, dried over sodium sulfate and concentrated. The residue was purified by chromatography (Petroleumether:ethylacetate=5:1) to afford 3-(but-3-enyl) tetrahydrofuran-3-yl 2-(N-trideuteriomethyl-4-nitrophenylsulfonamido)acetate (UU-2; 3.2 g, 80%) as a colorless oil. ES LC-MS m/z=423.7 (M+Na).

Step 3

A mixture of Compound UU-2 (3.12 g, 7.78 mmol), 4-methylbenzenethiol (1.93 g, 15.56 mmol) and Cesium carbonate (5.07 g, 5.56 mmol) in acetonitrile (40 ml) and tetrahydrofuran (4 ml) was stirred at 45 degree for 2 hs. The reaction mixture was filtrated and the filtrates were concentrated. The residue was purified by chromatography (dichloromethane:methanol=10:1 with 0.1% Ammonium hydroxide) to afford 3-(but-3-enyl)tetrahydrofuran-3-yl 2-(trideuteriomethylamino)acetate (UU-3; 1.3 g, 77%) as a red oil. $^1H$ NMR (DMSO-$d_6$) δ: 5.81-5.87 (m, 1H), 4.92-5.04 (m, 2H), 4.61 (s, 1 H), 3.72-3.84 (m, 2H), 3.42-3.52 (m, 2H), 2.09-2.16 (m, 2H), 1.72-1.79 (m, 2H), 1.60 (t, J=8.0 Hz, 2H).

Step 4

A mixture of (Z)-benzyl methylthio(oct-7-enamido)methylenecarbamate (2.09 g, 6.0 mmol), Compound UU-3 (1.3 g, 6.0 mmol) and triethylamine (1.21 g, 12 mmol) in N,N-Dimethylfornamide (30 ml) was stirred at rt, Mercury(II) chloride (1.82 g, 6.6 mmol) was added and the mixture was stirred for 2 hs. Water (150 ml) was added and the mixture was extracted with ethyl acetate (50 ml*3), the combined organic phase was washed with brine, dried over sodium sulfate and concentrated. The residue was purified by chromatography (Petroleumether:ethylacetate=5:1) to afford (Z)-3-(but-3-enyl)tetrahydrofuran-3-yl 2-(2-(benzyloxycarbonyl)-1-trideuteriomethyl-3-oct-7-enoylguanidino)acetate (UU-4; 2.7 g, 90%) as a yellow oil. ES LC-MS m/z=516.8 (M+H$^+$).

Step 5

A mixture of Compound UU-4 (2.0 g, 3.9 mmol) and Grubbs II (330 mg, 0.39 mmol) in dichloromethane (2 L) was stirred at 50 degree for 2 hs under $N_2$. Cooling to rt, ethoxyethene (5 ml) was added and the mixture was stirred for 0.5 h. the mixture was concentrated and the residue was purified by Pre-TLC (Petroleumether:ethylacetate=1:1) to afford (Z)-benzyl ((E)-9-trideuteriomethyl-7,12-dioxo-2,6-dioxa-9,11-diazaspiro[4.16]henicos-18-en-10-ylidene)carbamate (UU-5; 1.5 g, 78%) as a yellow oil. ES LC-MS m/z=488.8 (M+H$^+$).

Step 6. Synthesis of Compound UU

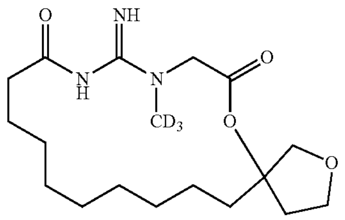

Compound UU

A mixture of afford (Z)-benzyl ((E)-9-trideuteriomethyl-7,12-dioxo-2,6-dioxa-9,11-diazaspiro[4.16]henicos-18-en-10-ylidene)carbamate (740 mg, 1.51 mmol) and Pd/C (150 mg, 20%) in ethanol (10 ml) was stirred at rt under $H_2$ balloon for overnight. The reaction mixture was filtrated and the filtrates were concentrated. The residue was purified by Pre-HPLC (20-50% acetonitrile in water with 0.2% formic acid) to afford 10-imino-9-trideuteriomethyl-2,6-dioxa-9,11-diazaspiro[4.16]henicosane-7,12-dione (Compound UU; 350 mg, 65%) as a white solid. ES LC-MS m/z=356.9 $(M+H)^+$. $^1H$ NMR (DMSO-d) δ: 4.44 (d, J=17.6 Hz, 1H), 4.30 (d, J=17.6 Hz, 1H), 3.97 (d, J=10.0 Hz, 2H), 3.76-3.79 (m, 2H), 3.62 (d, J=10.0 Hz, 1H), 2.23-2.30 (m, 1H), 1.85-2.09 (m, 5H), 1.50-1.55 (m, 2H), 1.23-127 (m, 12H).

Example 41: Synthesis of 5-imino-4-trideuteriomethyl-1-oxa-4,6-dioxacyclotetracosane-2,7-dione formate (Compound VV)

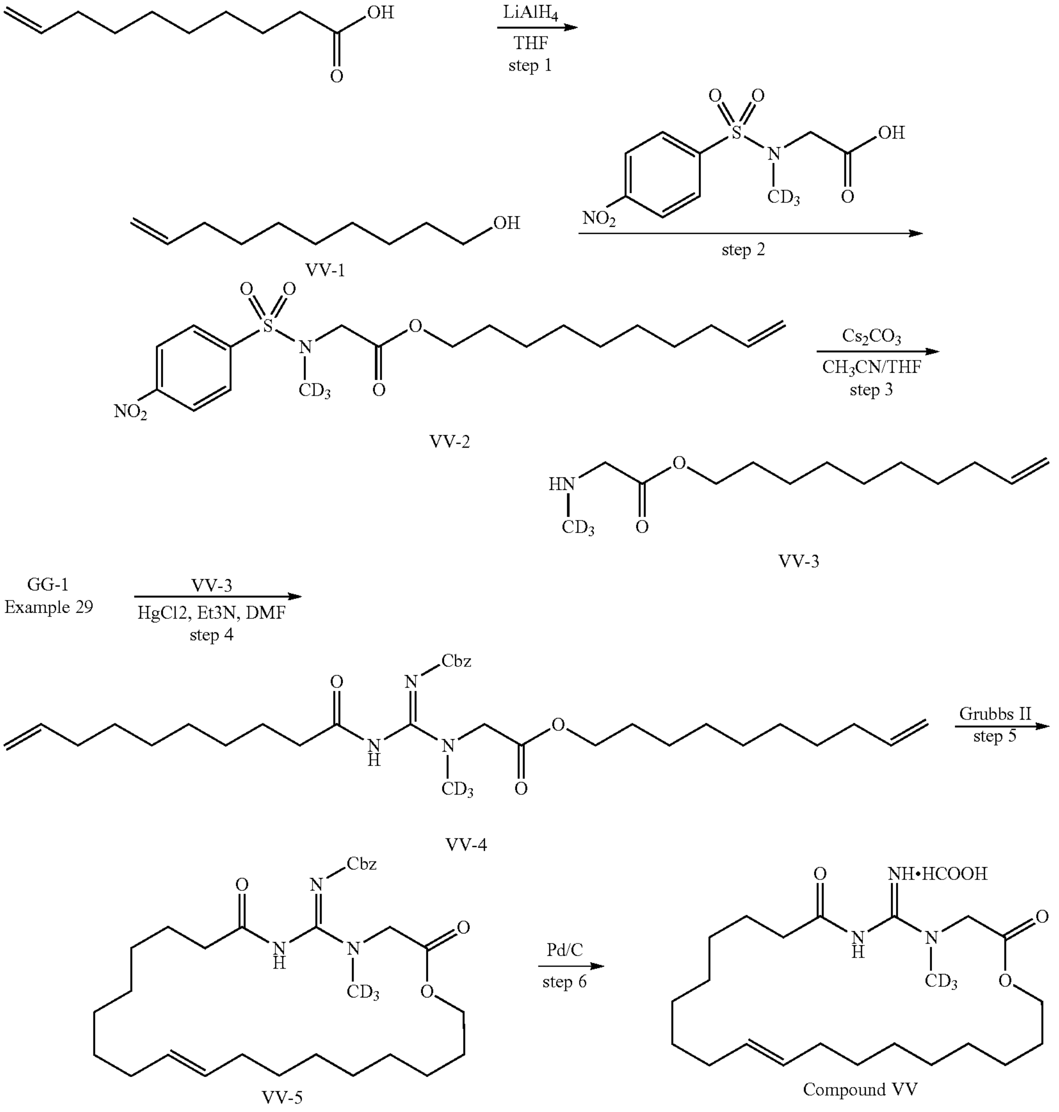

Step 1

A mixture of dec-9-enoic acid (1.7 g, 10 mmol) in tetrahydrofuran (40 ml) was stirred at 0° C., Lithium aluminium hydride (760 mg, 20 mmol) was added slowly. The mixture was stirred at rt for overnight. Water was added and the mixture was filtrated, the filtrates were extracted with ethyl acetate (50 ml×3), the combined organic phase was washed with brine, dried over sodium sulfate and concentrated to afford dec-9-en-1-ol (VV-1; 1.0 g, 64%) as a colorless oil. $^1$H NMR ($CDCl_3$) δ: 5.77-5.86 (s, 1H), 4.93-5.03 (m, 2H), 3.65 (t, J=6.4 Hz, 2H), 2.03-2.08 (m, 2H), 1.54-1.64 (m 2H), 1.26-1.45 (m, 10H).

Step 2

A mixture of 2-(N-trideuteriomethyl-4-nitrophenylsulfonamido)acetic acid (1.77 g, 6.4 mmol) and sulfurous dichloride (20 ml) in dichloromethane (20 ml) was heated to 60 degree and stirred for 2 hs. The mixture was concentrated, the residue was dissolved with dichloromethane (20 ml) which was added in a mixture of dec-9-en-1-ol (1 g, 6.4 mmol) and triethylamine (1.29 g, 12.8 mmol) in dichloromethane (30 ml) at ice-water and then stirred at rt for 1 h. water (50 ml) was added and the mixture was extracted with dichloromethane (50 ml*3), the combined organic phase was washed with brine, dried over sodium sulfate and concentrated. The residue was purified by chromatography (Petroleumether:ethylacetate=10:1) to afford dec-9-enyl 2-(N-trideuteriomethyl-4-nitrophenylsulfonamido)acetate (VV-2; 1.4 g, 53%) as a yellow oil. ES LC-MS m/z=438.1 (M+Na$^+$).

Step 3

A mixture of Compound VV-2 (1.4 g, 3.37 mmol), 4-methylbenzenethiol (837 mg, 6.75 mmol) and Cesium carbonate (2.19 g, 6.75 mmol) in acetonitrile (20 ml) and tetrahydrofuran (2 ml) was stirred at 45 degree for 2 hs. The reaction mixture was filtrated and the filtrates were concentrated. The residue was purified by chromatography (dichloromethane:methanol=10:1 with 0.1% Ammonium hydroxide) to afford dec-9-enyl 2-(trideuteriomethylamino)acetate (VV-3; 660 mg, 85%) as a yellow oil. $^1$H NMR (DMSO-d) δ: 4.92-5.01 (m, 2H), 4.01-4.05 (m, 2H), 1.99-2.01 (m, 2H), 1.54-1.56 (m, 2H), 1.26-1.33 (m, 11H).

Step 4

A mixture of Compound GG-1 (1.08 g, 2.87 mmol, see Example 29), Compound VV-3 (660 mg, 2.87 mmol) and triethylamine (580 mg, 5.74 mmol) in N,N-Dimethylformamide (15 ml) was stirred at rt, Mercury(II) chloride (932 mg, 3.4 mmol) was added and the mixture was stirred for overnight. Water (100 ml) was added and the mixture was extracted with ethyl acetate (50 ml*3), the combined organic phase was washed with brine, dried over sodium sulfate and concentrated. The residue was purified by chromatography (Petroleumether:ethylacetate=8:1) to afford (Z)-dec-9-enyl 2-(2-(benzyloxycarbonyl)-3-dec-9-enoyl-1-trideuteriomethylguanidino)acetate (VV-4; 1.35 g, 84%) as a colorless oil. ES LC-MS m/z=559.4 (M+H$^+$).

Step 5

A mixture of Compound VV-4 (1.35 g, 2.42 mmol) and Grubbs II (205 mg, 0.242 mmol) in dichloromethane (1350 ml) was stirred at 50 degree for 2 hs under N2, Cooling to rt, ethoxyethene (5 ml) was added and the mixture was stirred for 30 min. the mixture was concentrated and the residue was purified by chromatography (Petroleumether: ethylacetate=5:1) to afford (Z)-benzyl ((E)-4-trideuteriomethyl-2,7-dioxo-1-oxa-4,6-diazacyclotetracos-15-en-5-ylidene)carbamate (VV-5; 1.0 g, 78%) as a yellow solid. ES LC-MS m/z=531.4 (M+H$^+$).

Step 6. Synthesis of Compound VV

Compound VV

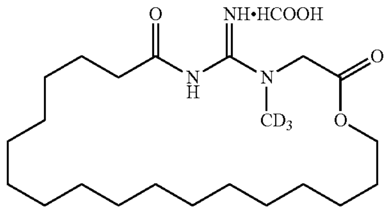

A mixture of afford Compound VV-5 (500 mg, 0.94 mmol) and Pd/C (100 mg, 20%) in ethanol (10 ml) was stirred at rt under $H_2$ balloon for overnight. The reaction mixture was filtrated and the filtrates were concentrated. The residue was purified by Pre-HPLC (40% acetonitrile in water with 0.2% formic acid) to afford 5-imino-4-trideuteriomethyl-1-oxa-4,6-dioxacyclotetracosane-2,7-dione formate (130 mg, 35%) as a white solid. ES LC-MS m/z=399.4 (M+H)$^+$. $^1$H NMR (DMSO-d) δ: 4.19 (s, 2H), 4.02-4.05 (m, 2H), 1.99-2.06 (m, 2H), 1.53-1.57 (m, 2H), 1.45-1.48 (m, 2H), 1.18-1.27 (m, 26H).

Example 42: Synthesis of 10-imino-9-trideuteriomethylguanidino-6-oxa-9,11-diazaspiro[4.16]henicosane-7,12-dione formate (Compound WW)

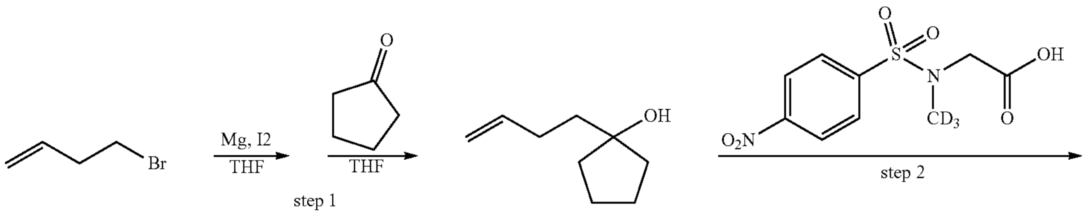

WW-1

-continued

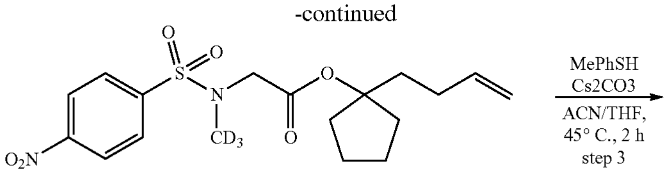

WW-2

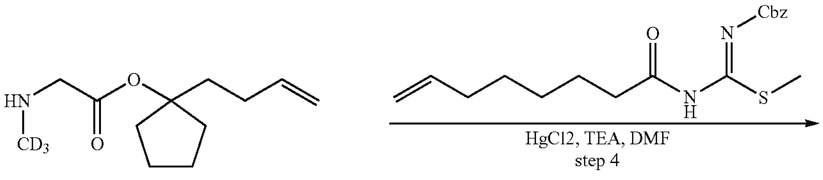

WW-3

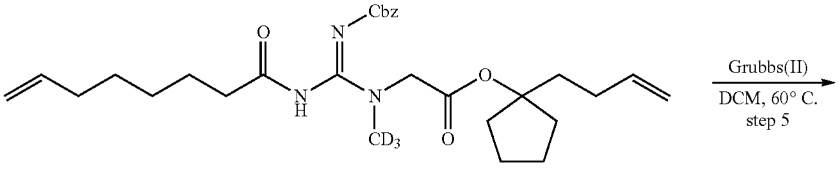

WW-4

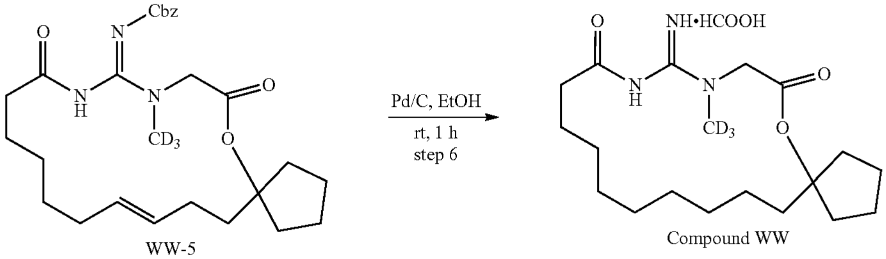

WW-5

Compound WW

Step 1

To a stirred suspension of Mg turnings (7.14 g, 297.6 mmoL) in Tetrahydrofuran (20 mL), 4-bromobut-1-ene (3 g, 22.5 mmoL) was added and the reaction was started by occasional heating with a heat gun. The remainder of the 4-bromobut-1-ene (30 g, 225.5 mmoL) was added dropwise at reflux temp, and after 10 min of stirring at this temp. A solution of cyclopentanone (20.8 g, 248 mmoL) in Tetrahydrofuran (140 mL) was added dropwise. After heating to reflux for 1 h. Saturated ammonium chloride was added and the mixture with Ethyl acetate (200 Ml×3). The combined organic was washed with brine dried over anhydrous sodium sulfate and concentrated to afford 1-(but-3-enyl)cyclopentanol (WW-1; 4.7 g, 13% yield) as a yellow liquid. $^1$H NMR (DMSO-d) δ: 5.87-5.80 (m, 1H), 5.01-4.88 (m, 2H), 4.00 (s, 1H), 2.14-2.08 (m, 2H), 1.69-1.66 (m, 2H), 1.54-1.46 (m, 6H), 1.43-1.38 (m, 2H).

Step 2

A mixture of 2-(N-trideuteriomethylguanidino-4-nitrophenylsulfonamido)acetic acid (2.77 g, 10 mmoL) in thionyl chloride (15 mL) and dichloromethane (15 mL) was stirred at 60° C. for 1 h. The combined organic was concentrated. Then, the resulting compound was dissolved in dichloromethane (30 mL) and Compound WW-1 (1.54 g, 11 mmoL), triethylamine (3.03 g, 30 mmoL) was added and the resulting mixture was stirred at rt for 1 h. Water (50 mL) was added and the combined organic phase was washed with brine, dried over sodium sulfate and concentrated. The residue was purified by flash (Petroleum ether:Ethyl acetate/5:1) to afford 1-(but-3-enyl)cyclopentyl 2-(N-trideuteriomethylguanidino-4-nitrophenylsulfonamido)acetate (WW-2; 2.83 g, 71% yield) as a white solid. ES LC-MS m/z=422.4 ($M+Na^+$).

Step 3

A mixture of Compound WW-2 (5.7 g, 14.32 mmoL), p-Thiocresol (2.1 g, 17.18 mmoL), caesium carbonate (7 g, 21.5 mmoL) in acetonitrile (70 mL) and tetrahydrofuran (7 mL) was stirred at 45° C. for 1.5 h. The reaction mixture was filtrated, the filtrates were concentrated, the residue was purify by chromatography (Methanol:Dichloromethane/5:1) to afford 1-(but-3-enyl)cyclopentyl 2-(trideuteriomethylguanidino)acetate (WW-3; 2.6 g, 87% yield) as a yellow liquid. $^1$H NMR (DMSO-d) δ: 5.82-5.75 (m, 1H), 5.02-4.91 (m, 2H), 3.15 (s, 2H), 2.05-1.99 (m, 6H), 1.67-1.54 (m, 6H).

Step 4

A mixture of (Z)-benzyl methylthio(oct-7-enamido)methylenecarbamate (3 g, 8.62 mmoL), Compound WW-3 (1.84 g, 8.62 mmoL) and a solution of triethylamine (1.74 g, 17.24 mmoL) in N,N-Dimethylformamide (40 mL) was stirred at rt. A mixture of mercury dichloride (2.8 g, 10.34 mmoL) was added, the mixture was stirred at rt for 2 h. Water (200 mL) was added and the mixture was extracted with ethylacetate (200 mL×3), the combined organic phase was washed with brine, dried over sodium sulfate and concentrated. the residue was purified by chromatography (Petroleumether:Ethylacetate/5:1) to afford (Z)-1-(but-3-enyl)cyclopentyl 2-(2-

(benzyloxycarbonyl)-1-trideuteriomethylguanidino-3-oct-7-enoylguanidino)acetate (WW-4; 4.14 g, 93% yield) as a white liquid. ES LC-MS m/z=515.6 (M+H$^+$).

Step 5

A mixture of Compound WW-4 (1 g, 1.95 mmoL) and Grubbs(II) (165 mg, 0.195 mmoL) in dichloromethane (1 L) was stirred at 50° C. for 2 h. The combined organic was concentrated. The residue was purified by flash to afford (Petroleum ether:Ethyl acetate/10:1) to afford (Z)-benzyl ((E)-9-trideuteriomethylguanidino-7,12-dioxo-6-oxa-9,11-diazaspiro[4.16]henicos-18-en-10-ylidene)carbamate (WW-5; 800 g, 84% yield) as a yellow oil. ES LC-MS m/z=487.2 (M+H$^+$).

Step. 6. Synthesis of Compound WW

Compound WW

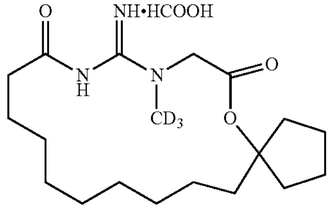

A mixture of Compound WW-5 (745 mg, 1.5 mmoL) and Palladium 10% on Carbon (150 mg, 20%) in ethanol (10 mL) was stirred under $H_2$ balloon for 2 h. The reaction mixture was filtrated and the filtrates were concentrated. The residue was purified by Pre-HPLC(FA) to afford 10-imino-9-trideuteriomethylguanidino-6-oxa-9,11-diazaspiro[4.16]henicosane-7,12-dione formate (Compound WW; 210 mg, 40% yield) as a white solid. ES LC-MS m/z=355.2 (M+H$^+$). $^1$H NMR (DMSO-d) δ: 10.0-9.5 (s, 1H), 7.75-7.25 (s, 1H), 4.30 (s, 1H), 2.08-2.04 (m, 4H), 1.86 (s, 1H), 1.65-1.49 (m, 8H), 1.24-1.22 (m, 12H).

Example 43: Synthesis of 5-imino-4-trideuteriomethyl-1-oxa-4,6-diazacycloheptadecane-2,7-dione hydrochloride (Compound 15)

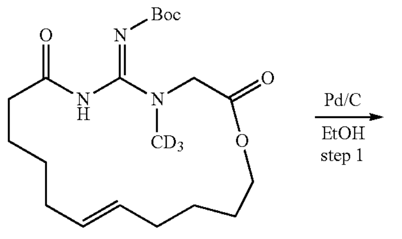

15-1

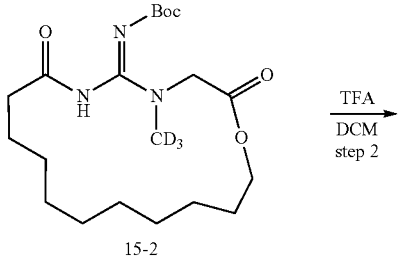

15-2

-continued

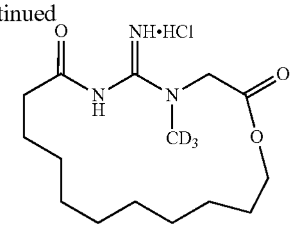

Compound 15

In general, Compound 15 was synthesized according to Example 8 using hex-5-enyl 2-(trideuteriomethylamino)acetate (see Example 21) instead of L-2 and using tert-butyl (Z)-(hept-6-enamido(methylthio)methylene)carbamate (see Example 11) instead of (Z)-tert-butyl dec-9-enamido(methylthio)methylenecarbamate. Compound 15-1, (Z)-tert-butyl ((E)-4-trideuteriomethyl-2,7-dioxo-1-oxa-4,6-diazacycloheptadec-12-en-5-ylidene)carbamate, was obtained as an yellow oil (5.2 g, 93%). ES LC-MS m/z=399.3 (M+H$^+$). $^1$H NMR (CD3Cl-$d_4$) δ: 5.32-5.36 (m, 2H), 4.19-4.23 (m, 2H), 4.11-4.15 (m, 2H), 2.28 (s, 2H), 2.0-2.05 (m, 4H), 1.59-1.68 (m, 4H), 1.50 (s, 9H), 1.29-1.47 (m, 4H).

Step 1. Synthesis of Compound 15-2

Compound 15-2 was synthesized according to Example 9, step 1 from Compound 15-1 using Pd/C (20%). (Z)-tert-Butyl 4-trideuteriomethyl-2,7-dioxo-1-oxa-4,6-diazacycloheptadecan-5-ylidenecarbamate was obtained as an yellow oil (Compound 15-2; 4.0 g, 76%). ES LC-MS m/z=401.3 (M+H$^+$). $^1$H NMR (CD3Cl-$d_4$) δ: 4.13-4.24 (m, 4H), 2.32-2.36 (m, 2H), 1.55-1.75 (m, 4H), 1.50 (s, 9H), 1.26-1.47 (m, 12H).

Step 2. Synthesis of Compound 15

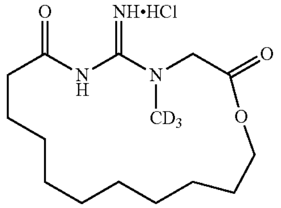

Compound 15 was synthesized according to Example 9, step 2, starting from Compound 15-2. 5-Imino-4-trideuteriomethyl-1-oxa-4,6-diazacycloheptadecane-2,7-dione hydrochloride was obtained as a white solid (Compound 15: 60 mg, 42%). ES LC-MS m/z=301.1 (M+H$^+$). $^1$H NMR (DMSO-d6) δ: 11.57 (ds, 1H), 9.37 (ds, 1H), 9.29 (ds, 1H), 4.82 (s, 2H), 4.14-4.18 (m, 2H), 1.52-1.58 (m, 4H), 1.26-1.40 (m, 14H).

Standard procedures and chemical transformation and related methods are well known to one skilled in the art, and such methods and procedures have been described, for example, in standard references such as Fiesers' Reagents for Organic Synthesis, John Wiley and Sons, New York, NY, 2002; Organic Reactions, vols. 1-83, John Wiley and Sons, New York, NY, 2006; March J. and Smith M., Advanced Organic Chemistry, 6th ed., John Wiley and Sons, New York, NY; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. For example, guanidine functional groups may be unstable under certain conditions and thereby need to be protected. A "protected" compound or derivatives means derivatives of a compound where one or more reactive site or sites or functional groups are blocked with protecting groups. Protected derivatives are useful in the preparation of the compounds of the present disclosure or in themselves; the protected derivatives may be the biologically active agent. An example of a comprehensive text listing suitable protecting groups may be found in T. W. Greene, Protecting Groups in Organic Synthesis, 3rd edition, John Wiley & Sons, Inc. 1999.

Other creatine prodrugs can be synthesized using the procedure described above by the selection of the appropriate starting material.

Example 44: Determination of Enzymatic Cleavage of Prodrugs In Vitro

For creatine prodrugs, it is generally desirable that the prodrug remains intact (i.e., uncleaved) while in the systemic circulation and be cleaved (i.e., to release the parent drug) in the target tissue. A useful level of stability can at least in part be determined by the mechanism and pharmacokinetics of the prodrug. A useful level of lability can at least in part also be determined by the pharmacokinetics of the prodrug and parent drug (e.g., creatine) in the systemic circulation and/or in the gastrointestinal tract, if orally administered. In general, prodrugs that are more stable in the gastrointestinal tract (as may be assessed by stability in simulated gastric fluid, simulated intestinal fluid, intestinal S9 fractions, pancreatin or colonic wash assays) and are more labile in mouse plasma, rat plasma, human plasma, mouse, rat and/or human liver S9, liver microsomes, and/or hepatocyte preparations can be useful as an orally administered prodrug. In general, prodrugs that are more stable in mouse plasma, rat plasma, human plasma, mouse, rat and/or human liver S9, liver microsomes, and/or hepatocyte preparations and which are more labile in target tissue cell homogenates or target tissue cell isolate preparations, such as brain, muscle, and S9 fractions, can be useful as systemically administered prodrugs and/or can be more effective in delivering a prodrug to a target tissue. In general, prodrugs that are more stable in different pH physiological buffers can be more useful as prodrugs. In general, prodrugs that are more labile in target tissue cell homogenates and/or target tissue cell isolate preparations, such brain, muscle and S9 fractions, can be intra-cellularly cleaved to release the parent drug to a target tissue. The results of tests, such as those described in this example, for determining the enzymatic or chemical cleavage of prodrugs in vitro can be used to select prodrugs for in vivo testing.

The stabilities of creatine prodrugs can be evaluated in one or more in vitro systems using a variety of preparations following methods known in the art. Experimental conditions useful for the in vitro studies are described in Table 1. Prodrug is added to each preparation in triplicate.

TABLE 1

Standard[a] Conditions for Prodrug In Vitro Stability and Metabolism Studies

| Assay | Enzyme/Protein Concentration | Substrate Concentration (μM) | Cofactors |
|---|---|---|---|
| SGF | +/−0.1 mg/mL pepsin | 1-50 | NA |
| SIF | +/−1% w/v pancreatin | 1-50 | NA |
| Plasma | NA | 1-10 | NA |
| Blood | NA | 1-10 | NA |
| Liver microsomes | 0.5 mg/mL | 1-10 | +/−NADPH[b] |
| Liver or Intestinal S9 | 1 mg/mL | 1-10 | +/−NADPH[b] |
| Hepatocytes | NA | 1-10 | NA |
| Tissue homogenate[c] | NA | 1-10 | NA |

[a]Typical test range provided, range may be exceeded dependent upon intended clinical use of prodrug;
[b]NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4;
[c]Examples: brain tissue homogenate, muscle tissue homogenate;
[d]Assay can be performed with and without addition of diisopropyl fluorophosphonate (DIFP, serine protease inhibitor) to determine if degradation is mediated by a serine protease, e.g., carboxylesterase (CES)

Chemical stability of creatine prodrugs in phosphate buffered saline (PBS), simulated intestinal fluid (SIF) without pancreatin, simulated gastric fluid (SGF) without pepsin were determined by LC-UV, LC-CAD, LC-UV-CAD or LC-MS/MS as appropriate. Creatine prodrugs of the present disclosure (50 μM) were incubated at 37° C. according to described protocols and prodrug levels were compared between t=0, t=15, t=60, and t=120 mins by peak area ratio to determine the percentage remained at t=120 mins (2 h). Metabolic stability of prodrugs were assayed in standard plasma and liver microsome assays of different species (human and mouse shown), including rat, dog and cynomolgus monkey. See Tables 2A-2C.

Most creatine prodrugs tested showed good chemical and metabolic stability (Tables 2A-2C). Creatine prodrugs with ester linkage at COOH showed tendency for being less stable than creatine prodrugs with free COOH in plasma and microsome stability, PBS and SIF assays.

Protocol for PBS, SIF and SGF Stability for Screening:

Prodrugs (50 μM) were incubated in PBS, FaSSIF (Biorelevant) or FaSSGF (Biorelevant) at 37° C. At selected time points (e.g., 0, 15, 60 and 120 min), samples were transferred into vials and immediately analyzed for prodrug peak area using LC-UV-CAD.

Protocol for Plasma Stability for Early Screen Macrocycles (Method A):

Frozen plasma was thawed by placing at 37° C. quickly and centrifuged at 3,000 rpm for 8 minutes to remove clots. Then the supernatant was pipetted and pooled as the plasma to be used in the experiment. The plasma was placed on ice until used. The test compounds and reference compounds spiking solution was prepared as a 2.5 mM test compounds spiking solution A: Add 20 μL of 10 mM test compounds stock solution to 60 μL DMSO. 0.1 mM Spiking solution B was prepared: Add 40 μL of spiking solution A to 960 μL of 0.05 mM Sodium phosphate buffer with 0.5% BSA. Then 10 μL of pre-warmed spiking solution B was added into the wells designated for all the time points (0, 5, 15, 30, 60, 120 min). For 0-min, 400 μL of ACN containing IS was added to the wells of 0-min plate and then 90 μL of plasma was added. 90 μL of pre-warmed plasma was added into the wells designated for the time points (0, 5, 15, 30, 60, 120 min) and the timing was started. At 5, 15, 30, 60, 120 min, 400 μL of ACN containing IS was added to the wells of corresponding plates, respectively, to stop the reaction. After quenching, the plates were shaken using the vibrator (IKA, MTS 2/4) for 10 min (600 rpm/min) and then centrifuged at 5594 g for 15 min (Thermo Multifuge×3R). 50 μL of the supernatant was transferred from each well into a 96-well sample plate containing 120 μL of ultra pure water (Millipore, ZMQS50F01) and analyzed by LC/MS.

Protocol for Plasma Stability (Method B):

The frozen plasma was thawed in a 37° C. water bath and then, if needed, adjusted to pH=7.4 then preheated in a 37° C. incubator. The test article was dissolved in 10% DMSO/water and spiked into plasma pre-plated into 96 well plates at a final concentration of 1 μM. Discrete incubations were performed at 37° C. and included 5 time points: t=0, 2, 5, 15, and 30 min. Samples were then crashed with 4× volume, ice cold 20% water/80% acetonitrile and spun at 4000 g for 10 mins. The supernatant was dried down and reconstituted with water and analyzed by LC-MS/MS. The half life in minute was calculated.

Protocol for Microsomal Stability:

For reference compound, a 500 μM spiking solution was prepared: add 10 μL of 10 mM DMSO stock solution into 190 μL ACN. A 1.5 μM spiking solution in microsomes (0.75 mg/mL) was prepared: add 1.5 μL of 500 μM spiking solution and 18.75 μL of 20 mg/mL liver microsomes into 479.75 μL of Buffer 0.1 M Potassium Phosphate buffer, 1.0 mM EDTA, pH 7.4 on ice. For test compound, a 5 mM spiking solution was prepared: add 10 μL of 10 mM DMSO stock solution into 10 μL ACN. And then a 15 μM spiking solution in microsomes (0.75 mg/mL) was prepared: add 1.5 μL of 5 mM spiking solution and 18.75 μL of 20 mg/mL liver microsomes into 479.75 μL of Buffer 0.1 M Potassium Phosphate buffer, 1.0 mM EDTA, pH 7.4 on ice. NADPH stock solution (6 mM) was prepared by dissolving NADPH into buffer 0.1 M Potassium Phosphate buffer, 1.0 mM EDTA, pH 7.4. 30 μL of 1.5 μM spiking solution containing 0.75 mg/mL microsomes solution was dispensed to the assay plates designated for different time points (0-, 5-, 10-, 20-, 30-min, 60-min, 60-min without NADPH) on ice. For 0-min, 135 μL of ACN containing IS was added to the wells of 0-min plate and then 15 μL of NADPH stock solution (6 mM) was added. 15 μL of NADPH stock solution (6 mM) was added to the samples designated as 0-, 5-, 10-, 20-, 30-min, 60-min; 15 μL of buffer 0.1 M Potassium Phosphate buffer, 1.0 mM EDTA, pH 7.4, was added to the samples designated as 60-min without NADPH. At 5-min, 10-min, 20-min, and 30-min, 60-min 135 μL of ACN containing IS was added to the wells of corresponding plates, respectively, to stop the reaction. After quenching, the plates were shaken using the vibrator (IKA, MTS 2/4) for 10 min (600 rpm/min) and then centrifuged at 5594 g for 15 min (Thermo Multifuge×3R). 50 μL of the supernatant from each well was transferred into a 96-well sample plate containing 50 μL of ultra pure water (Millipore, ZMQS50F01) and analyzed by LC/MS.

TABLE S2

| Structures | |
|---|---|
| Compound No. | Structure |
| 4 | 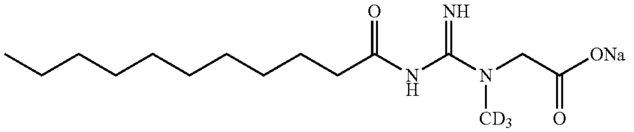 |
| 5 | 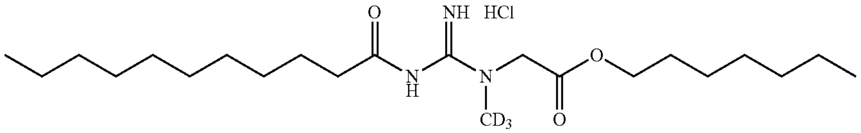 [SMILES: Cl ; [2H]C([2H])([2H])N(CC(=O)OCCCCCCC)C(=N)NC(=O)CCCCCCCCCC] |
| 8FB (free base) | 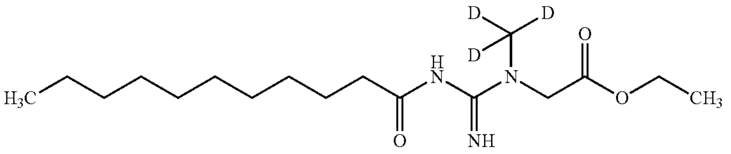 [SMILES: [2H]C([2H])([2H])N(CC(=O)OCC)C(=N)NC(=O)CCCCCCCCCC] |
| 10 | 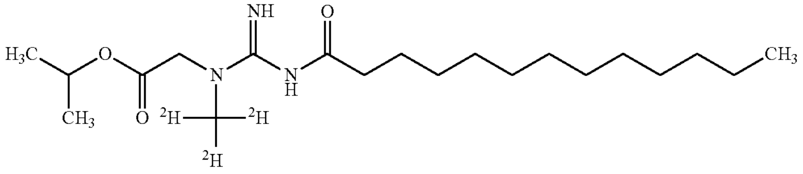 [SMILES: [2H]C([2H])([2H])N(CC(=O)OC(C)C)C(=N)NC(=O)CCCCCCCCCCCC] |
| 11 | 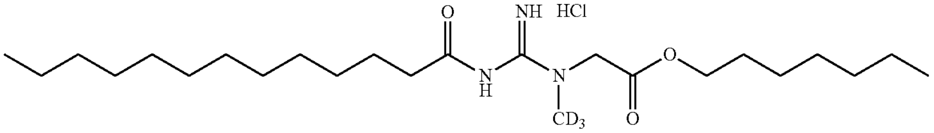 [SMILES: Cl ; [2H]C([2H])([2H])N(CC(=O)OCCCCCCC)C(=N)NC(=O)CCCCCCCCCCCC] |

TABLE S2-continued
| Structures | |
|---|---|
| Compound No. | Structure |
| 12 | 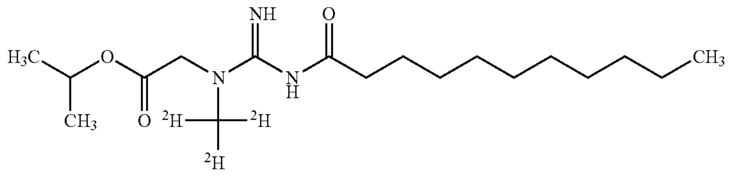 [SMILES: [2H]C([2H])([2H])N(CC(=O)OC(C)C)C(=N)NC(=O)CCCCCCCCCC] |
| 13 | 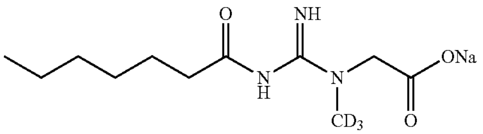 |
| 14 | 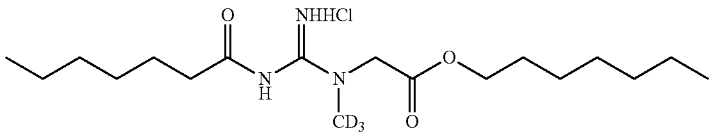 |
| 10-HCl | 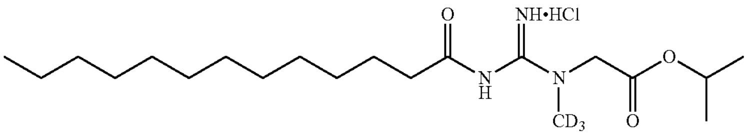 |
| 12-HCl | 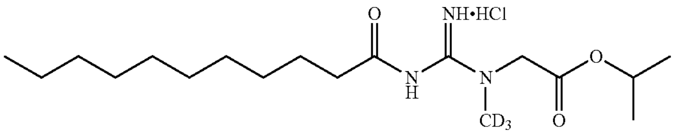 |
| 20 | 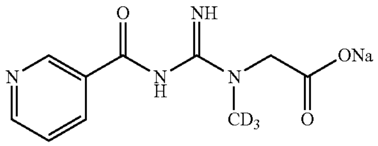 |
| 21 | 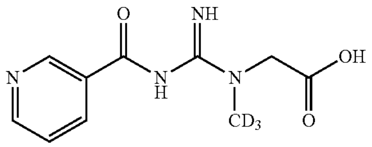 [SMILES: [2H]C([2H])([2H])N(CC(=O)O)C(=N)NC(=O)c1cccnc1] |
| 22 | 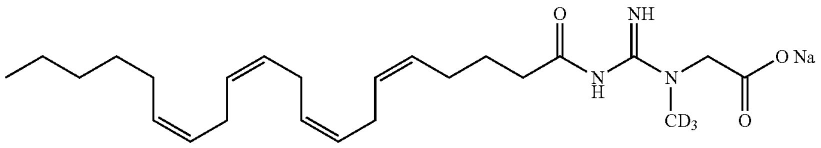 |
| 22-FB | 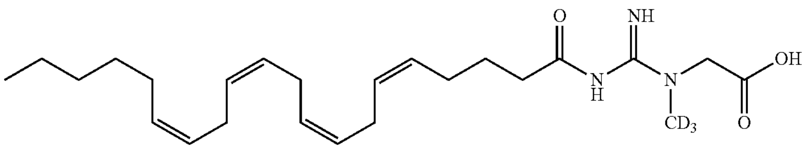 [SMILES: [2H]C([2H])([2H])N(CC(=O)O)C(=N)NC(=O)CCC/C=C\C/C=C\C/C=C\C/C=C\CCCCC] |

TABLE S2-continued
| Structures | |
|---|---|
| Compound No. | Structure |
| 23 | 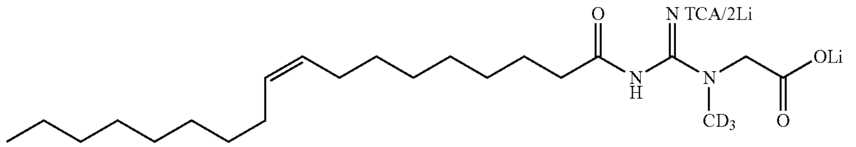 |
| 24 | 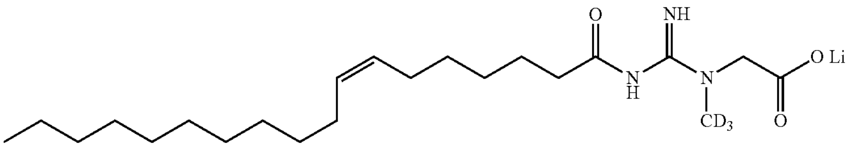 |
| 24-FB | 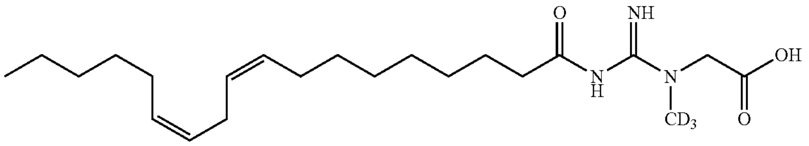 [SMILES: [2H]C([2H])([2H])N(CC(=O)O)C(=N)NC(=O)CCCCCCC/C=C\C/C=C\CCCCC] |
| 25 | 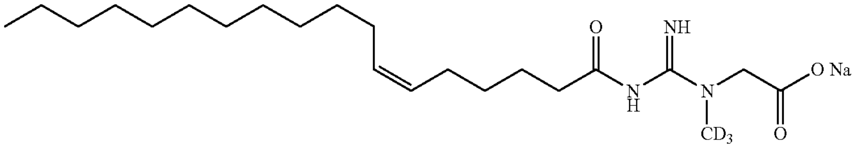 |
| 25-FB | 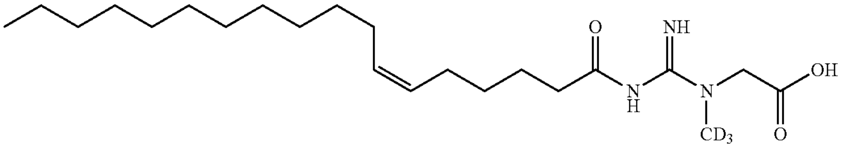 [SMILES: [2H]C([2H])([2H])N(CC(=O)O)C(=N)NC(=O)CCCC/C=C\CCCCCCCCCCC] |
| 26 | 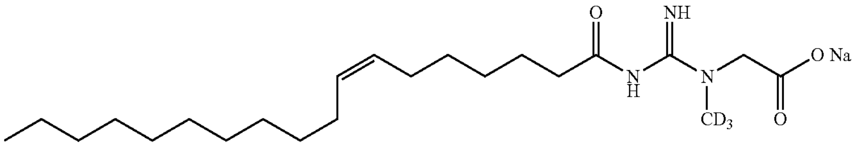 |
| 26-FB | 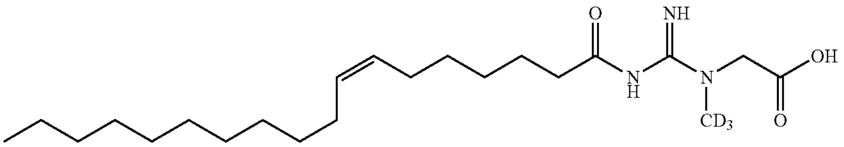 [SMILES: [2H]C([2H])([2H])N(CC(=O)O)C(=N)NC(=O)CCCCC/C=C\CCCCCCCCCC] |
| 27 | 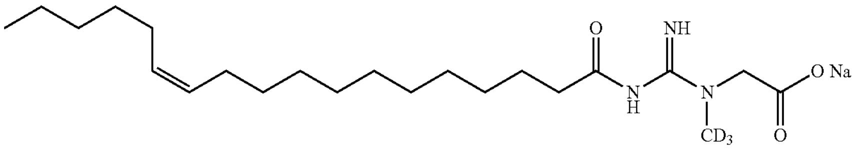 |
| 27-FB | 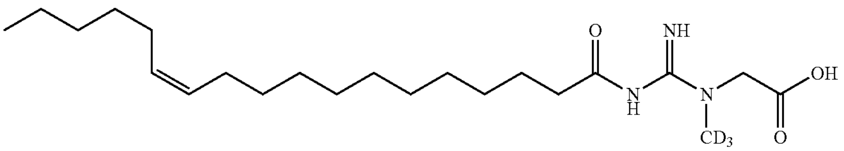 [SMILES: [2H]C([2H])([2H])N(CC(=O)O)C(=N)NC(=O)CCCCCCCCCC/C=C\CCCCC] |

TABLE S2-continued
| Structures | |
|---|---|
| Compound No. | Structure |
| 28 | 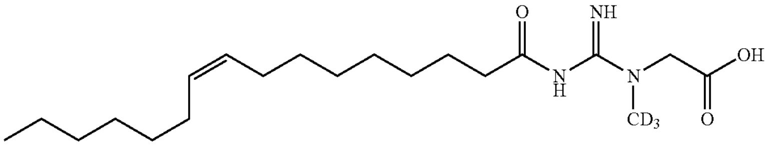 [SMILES: [2H]C([2H])([2H])N(CC(=O)O)C(=N)NC(=O)CCCCCCC/C=C\CCCCCC] |
| 29 | 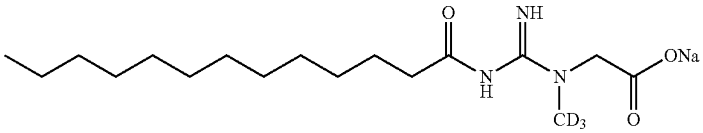 |
| 30 | 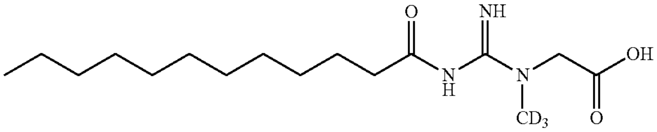 [SMILES: [2H]C([2H])([2H])N(CC(=O)O)C(=N)NC(=O)CCCCCCCCCCC] |
| 31 | 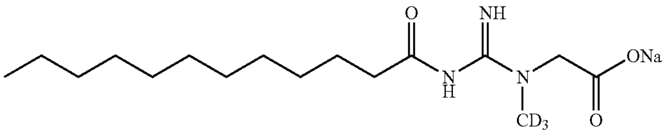 |
| 32 | 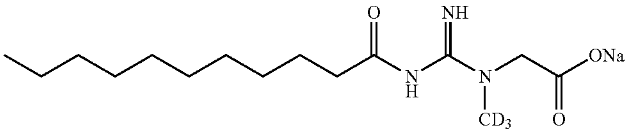 |
| 33 | 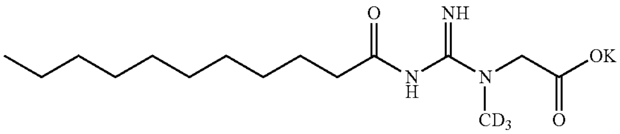 |
| 34 | 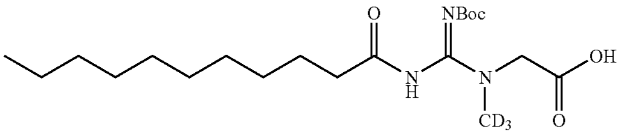 |
| 35 | 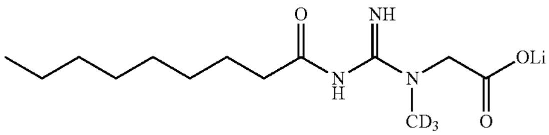 |
| 35-FB | 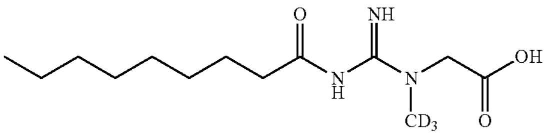 [SMILES: [2H]C([2H])([2H])N(CC(=O)O)C(=N)NC(=O)CCCCCCCC] |
| 36 | 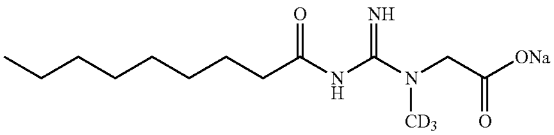 |

TABLE S2-continued
Structures
| Compound No. | Structure |
| --- | --- |
| 37 | 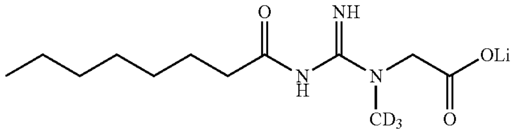 |
| 37-FB | 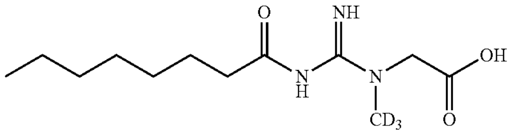 [SMILES: [2H]C([2H])([2H])N(CC(=O)O)C(=N)NC(=O)CCCCCCC] |
| 38 | 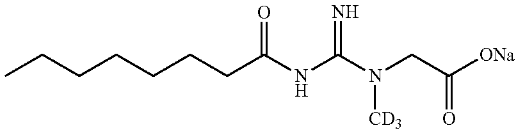 |
| 39 | 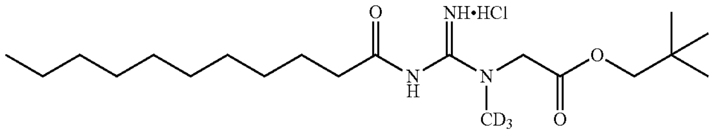 |
| 40 | 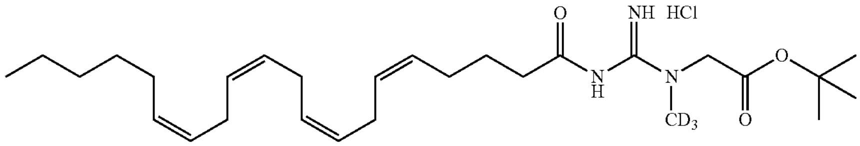 [SMILES: Cl ; [2H]C([2H])([2H])N(CC(=O)OC(C)(C)C)C(=N)NC(=O)CCC/C=C\C/C=C\C/C=C\C/C=C\CCCCC] |
| 41 | 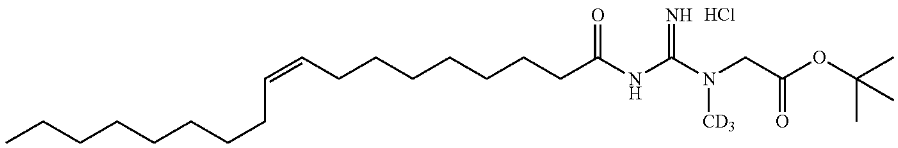 [SMILES: Cl ; [2H]C([2H])([2H])N(CC(=O)OC(C)(C)C)C(=N)NC(=O)CCCCCCC/C=C\CCCCCCCC] |
| 42 | 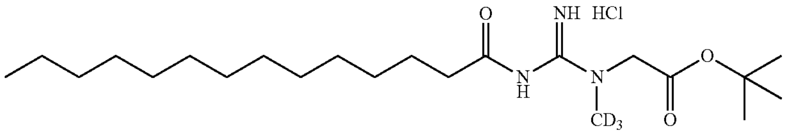 [SMILES: Cl ; [2H]C([2H])([2H])N(CC(=O)OC(C)(C)C)C(=N)NC(=O)CCCCCCCCCCCCC] |
| 43 | 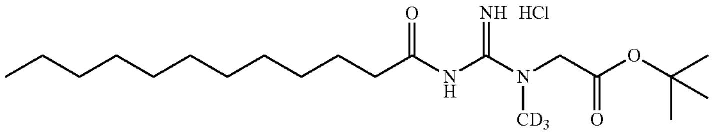 [SMILES: Cl ; [2H]C([2H])([2H])N(CC(=O)OC(C)(C)C)C(=N)NC(=O)CCCCCCCCCCC] |
| 44 | 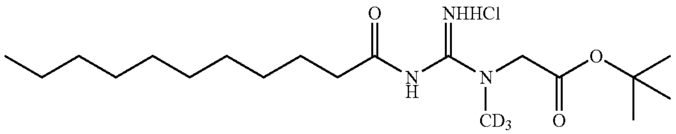 |
| 45 | 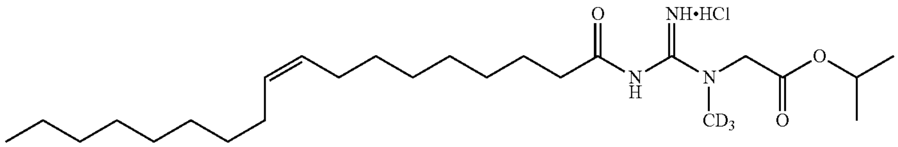 |

TABLE S2-continued

| Structures | |
|---|---|
| Compound No. | Structure |
| 46 | 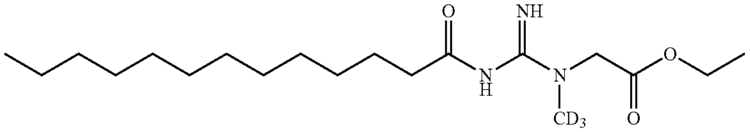 [SMILES: [2H]C([2H])([2H])N(CC(=O)OCC)C(=N)NC(=O)CCCCCCCCCCCC] |
| 47 | 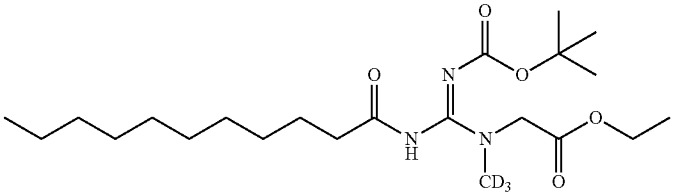 [SMILES: [2H]C([2H])([2H])N(CC(=O)OCC)/C(=N\C(=O)OC(C)(C)C)NC(=O)CCCCCCCCCC] |
| 48 | 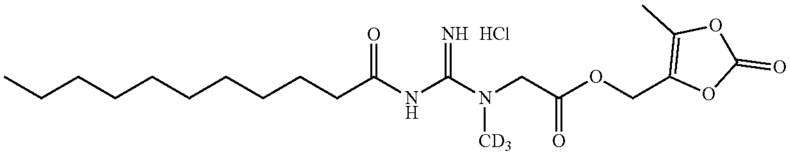 [SMILES: [2H]C([2H])([2H])N(CC(=O)OCc1oc(=O)oc1C)C(=N)NC(=O)CCCCCCCCCC ; Cl] |
| 49 | 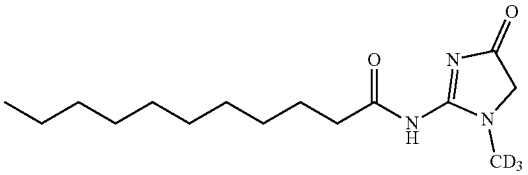 [SMILES: [2H]C([2H])([2H])N1CC(=O)N=C1NC(=O)CCCCCCCCCC] |
| 50 | 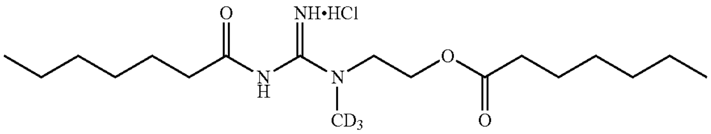 |
| 51 | 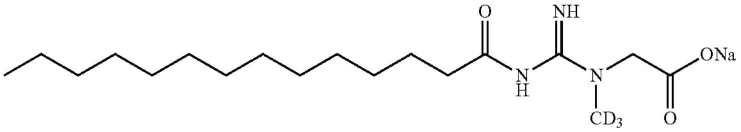 |

TABLE 2A

Stability of Creatine Prodrugs

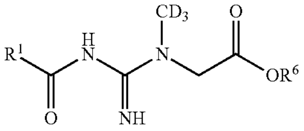

| | | | | | Plasma Stability | | Microsome Stability | | | Chemical Stability | |
|---|---|---|---|---|---|---|---|---|---|---|---|
| | | | | | Human | Mouse | Human | Mouse | PBS | SIF, no enzyme | SGF, no enzyme |
| Compd No. | R1**** | R | Salt* | Double Bond | $t_{1/2}$ (min) | $t_{1/2}$ (min) | $t_{1/2}$ (min) | $t_{1/2}$ (min) | % T0 at 2 hours at 37° C. | % T0 at 2 hours at 37° C. | % T0 at 2 hours at 37° C. |
| 20 | pyridyl | H | Na | 0 | >180 | >180 | >145 | >145 | 101 | NT | 78 |
| 21 | pyridyl | H | free | 0 | >180 | >180 | >145 | >145 | 105 | NT | 74 |
| 22 | C20 | H | Na | cis-5,8,11,14 | 130 | >180 | 24 | 9 | 35 | 86 | 30 |
| 23 | C18 | H | TCA/2 Li | cis-9 | 94 | >180 | 91 | 93 | 728 | 85 | 49 |
| 24 | C18 | H | Li | cis-9,12 | >180 | >180 | 78 | 82 | 150 | 74 | 39 |
| 25 | C18 | H | Na | cis-6 | >180 | >180 | >145 | >145 | 89 | NT | 72 |
| 26 | C18 | H | Na | cis-7 | >180 | >180 | 68 | >145 | 45 | NT | 95 |
| 27 | C18 | H | Na | cis-12 | >180 | >180 | 14 | 10 | 67 | NT | 96 |

TABLE 2A-continued

Stability of Creatine Prodrugs

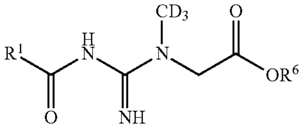

| Compd No. | $R^{1****}$ | R | Salt* | Double Bond | Plasma Stability Human $t_{1/2}$ (min) | Plasma Stability Mouse $t_{1/2}$ (min) | Microsome Stability Human $t_{1/2}$ (min) | Microsome Stability Mouse $t_{1/2}$ (min) | Chemical Stability PBS % T0 at 2 hours at 37° C. | Chemical Stability SIF, no enzyme % T0 at 2 hours at 37° C. | Chemical Stability SGF, no enzyme % T0 at 2 hours at 37° C. |
|---|---|---|---|---|---|---|---|---|---|---|---|
| 1 | C18 | H | Na | cis-9 | >180 | >180 | 133 | 83 | 76 | NT | 74 |
| 28 | C16 | H | Na | cis-9 | >180 | >180 | 90 | 84 | 51 | NT | 99 |
| 7 | C14 | H | Li | 0 | >180 | >180 | 46 | 121 | 90 | 77 | 63 |
| 51 | C14 | H | Na | 0 | NT | NT | NT | NT | NT | NT | NT |
| 29 | C13 | H | Na | 0 | >180 | >180 | 59 | 110 | 64 | NT | 91 |
| 30 | C12 | H | free | 0 | >180 | 162 | 94 | >145 | 145 | NT | 62 |
| 31 | C12 | H | Na | 0 | >180 | >180 | 59 | >145 | 98 | NT | 98 |
| 32 | C11 | H | Li | 0 | >180 | >180 | 110 | >145 | NT | NT | NT |
| 4 | C11 | H | Na | 0 | >180 | >180 | 68 | 87 | 69 | 61 | 94 |
| 33 | C11 | H | K | 0 | >180 | >180 | 72 | 106 | 85 | NT | 79 |
| 34 | C11 ($R^2$ = Boc) | H | free | 0 | >180 | >180 | >180 | 123 | NT | NT | NT |
| 35 | C 9 | H | Li | 0 | >180 | >180 | 65 | >145 | 116 | NT | 86 |
| 36 | C 9 | H | Na | 0 | >180 | >180 | 102 | >145 | 106 | NT | 99 |
| 37 | C 8 | H | Li | 0 | >180 | >180 | 114 | >145 | NT | NT | NT |
| 38 | C 8 | H | Na | 0 | >180 | >180 | >145 | >145 | 101 | NT | 99 |
| 13 | C 7 | H | Na | 0 | >180 | >180 | 647 | 912 | 97 | NT | 94 |
| 2 | C18 | ester, C 7 | HCl | cis-9 | <5 | <5 | 6 | 7 | 61 | NT | 81 |
| 11 | C13 | ester, C 7 | HCl | 0 | <5 | <5 | <5 | <5 | 42 | NT | 76 |
| 5 | C11 | ester, C 7 | HCl | 0 | 5 | <5 | <5 | <5 | 23 | NT | 73 |
| 14 | C 7 | ester, C 7 | HCl | 0 | NT | NT | NT | NT | NT | NT | 80 |
| 39 | C11 | ester, C 5 (neo-Pen) | HCl | 0 | <5 | <5 | <5 | <5 | 62 | NT | 103 |
| 39 | C11 | ester, C 5 (neo-Pen) | HCl | 0 | <5 | <5 | 6 | <5 | NT | NT | NT |
| 40 | C20 | ester, C 4 (t-butyl) | HCl | cis-5,8,11,14 | NT | NT | NT | NT | NT | NT | NT |
| 41 | C18 | ester, C 4 (t-butyl) | HCl | cis-9 | NT | NT | NT | NT | NT | NT | NT |
| 42 | C14 | ester, C 4 (t-butyl) | HCl | 0 | NT | NT | NT | NT | NT | NT | NT |
| 43 | C12 | ester, C 4 (t-butyl) | HCl | 0 | NT | NT | NT | NT | NT | NT | NT |
| 44 | C11 | ester, C 4 (t-butyl) | HCl | 0 | 100 | 8 | 9 | <5 | 42 | NT | 86 |
| 45 | C18 | ester, C 3 (i-Pr) | HCl | cis-9 | 22 | <5 | 96 | 63 | 54 | NT | 102 |
| 10-HCl | C13 | ester, C 3 (i-Pr) | HCl | 0 | 19 | <5 | 22 | 29 | 11 | 46 | 83 |
| 12-HCl | C11 | ester, C 3 (i-Pr) | HCl | 0 | <5 | <5 | <5 | <5 | 99 | NT | 117 |
| 46 | C13 | ester, C 2 | HCl | 0 | <5 | <5 | NT | NT | 0 | 45 | 111 |
| 8 | C11 | ester, C 2 | HCl | 0 | <5 | <5 | <5 | <5 | 0 | 17 | 117 |
| 47 | C11 ($R^2$ = Boc) | ester, C 2 | free | 0 | 169 | <5 | 16 | 5 | 55 | NT | 32 |
| 48 | C11 | dioxolanone | HCl | 0 | NT | NT | NT | NT | 97 | NT | 98 |
| 49 | C11 | creatinine | free | 0 | >180 | 47 | 24 | <5 | 87 | NT | 62 |
| 50 | C 7 | acetyl, C 7 | HCl | 0 | NT | NT | NT | NT | NT | NT | NT |
| 9 | C11 | acetyl | HCl | 0 | >180 | 33 | <5 | <5 | 0 | NT | 99 |

*$R^6$ when Na, Li, or K.

**Free = free base.

***NT = not tested.

****when $R^1$ is alkyl or alkenyl, the carbon count includes the carbonyl carbon to which $R^1$ is attached to.

TABLE 2B

Stability of Creatine Prodrugs

| Structure | Compound No. | Plasma Stability: Human $t_{1/2}$ (min) | Plasma Stability: Mouse $t_{1/2}$ (min) | Microsome Stability: Human $t_{1/2}$ (min) | Microsome Stability: Mouse $t_{1/2}$ (min) | Chemical Stability: PBS % T0 at 2 hours at 37° C. | Chemical Stability: SIF, no enzyme % T0 at 2 hours at 37° C. | Chemical Stability: SGF, no enzyme % T0 at 2 hours at 37° C. |
|---|---|---|---|---|---|---|---|---|
| See Table S2 | 8 | 0 | 0 | 0 | 0 | 0 | NT | 95 |
| See Table S2 | 44 | 100 | 8 | 9 | <5 | 107 | NT | 95 |
| 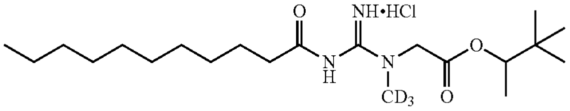 | 52 | 117 | <5 | <5 | <5 | 98 | NT | 98 |
| 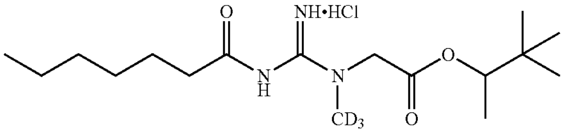 | 53 | 55 | <5 | <5 | <5 | 64 | NT | 91 |
| 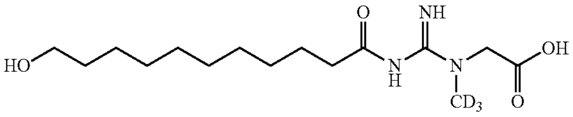 [SMILES: [2H]C([2H])([2H])N(CC(=O)O)C(=N)NC(=O)CCCCCCCCCCO] | 54 | >180 | >180 | >90 | >90 | 103 | NT | 102 |
| 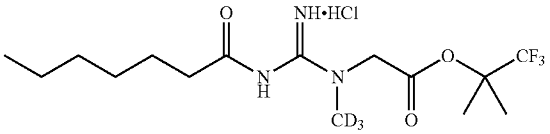 | 55 | 0 | 0 | 0 | 0 | 97 | NT | 94 |
| 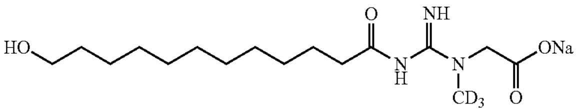 | 56 | >180 | >180 | >90 | >90 | 58 | NT | 81 |
| 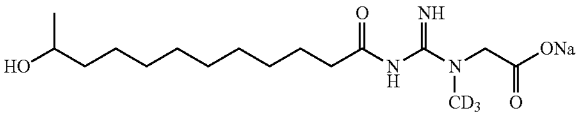 | 57 | >180 | >180 | >90 | >90 | 78 | NT | 89 |
| 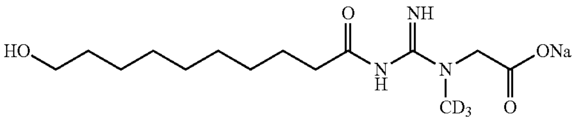 | 58 | >180 | >180 | >90 | >90 | NT | NT | NT |
| 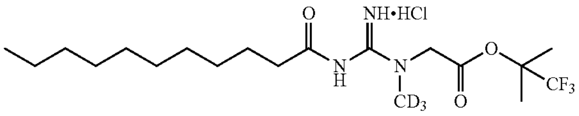 | 59 | 0 | 0 | 0 | 0 | 101 | NT | 30 |
| 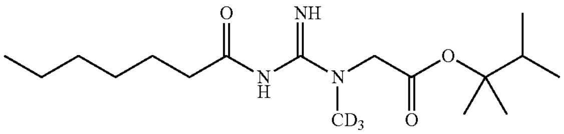 [SMILES: [2H]C([2H])([2H])N(CC(=O)OC(C)(C)C(C)C)C(=N)NC(=O)CCCCCC] | 60 | >180 | >180 | <5 | <5 | 101 | NT | 99 |
| 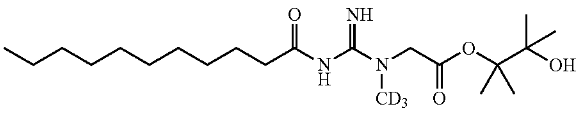 [SMILES: [2H]C([2H])([2H])N(CC(=O)OC(C)(C)C(C)(C)O)C(=N)NC(=O)CCCCCCCCCC] | 61 | <5 | <5 | <5 | <5 | 106 | NT | 99 |

TABLE 2B-continued

Stability of Creatine Prodrugs

| Structure | Compound No. | Plasma Stability Human $t_{1/2}$ (min) | Plasma Stability Mouse $t_{1/2}$ (min) | Microsome Stability Human $t_{1/2}$ (min) | Microsome Stability Mouse $t_{1/2}$ (min) | Chemical Stability PBS % T0 at 2 hours at 37° C. | Chemical Stability SIF, no enzyme % T0 at 2 hours at 37° C. | Chemical Stability SGF, no enzyme % T0 at 2 hours at 37° C. |
|---|---|---|---|---|---|---|---|---|
| 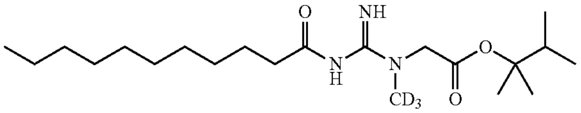 [SMILES: [2H]C([2H])([2H])N(CC(=O)OC(C)(C)C(C)C)C(=N)NC(=O)CCCCCCCCCC] | 62 | >180 | 76 | <5 | <5 | 62 | NT | 103 |
| 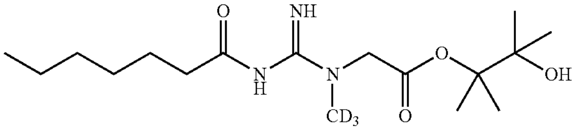 [SMILES: [2H]C([2H])([2H])N(CC(=O)OC(C)(C)C(C)(C)O)C(=N)NC(=O)CCCCCC] | 63 | <5 | <5 | <5 | <5 | 58 | NT | 101 |

TABLE 2C

Stability of Creatine Prodrugs

| Compound | Plasma Stability Human $t_{1/2}$ (min) | Plasma Stability Mouse $t_{1/2}$ (min) | Microsome Stability Human $t_{1/2}$ (min) | Microsome Stability Mouse $t_{1/2}$ (min) | Chemical Stability PBS % T0 at 2 hours at 37° C. | Chemical Stability SIF, no enzyme % T0 at 2 hours at 37° C. | Chemical Stability SGF, no enzyme % T0 at 2 hours at 37° C. |
|---|---|---|---|---|---|---|---|
| Compound 15 FA salt | 0 | 0 | NT | NT | NT | NT | NT |
| Compound K | 13 | 2 | NT | NT | NT | NT | NT |
| Compound Q | 10 | 1.3 | NT | NT | NT | NT | NT |
| Compound PP | 8 | 1.1 | NT | NT | NT | NT | NT |
| Compound L | 34 | 3 | 1.6 | 0.6 | NT | NT | NT |
| Compound U | 72 | 70 | NT | NT | NT | NT | NT |
| Compound BB | 9 | <2 | NT | NT | NT | NT | NT |
| Compound DD | 8.3 | <2 | NT | NT | NT | NT | NT |
| Compound SS | >90 | 0 | 0 | 0 | 0 | NT | 85 |
| Compound T | <2 | <2 | NT | NT | NT | NT | NT |
| Compound QQ | 0 | 0 | 9 | 4 | 85 | NT | 79 |
| Compound 15 | 0 | 0 | <5 | <5 | NT | NT | 97 |

Example 45: In Vitro Determination of Release of Creatine from Prodrugs ($d_3$-Creatine Release)

For assessment of the ability of prodrugs to release creatine, and to release creatine preferentially to unwanted cyclization to creatinine, $d_3$-labeled (deuterium labeled methyl group) prodrugs are incubated with brain homogenates (e.g., mouse, human) specially prepared to preserve FAAH activity or with rFAAH for direct cleavage study. The use of d3-labelled prodrugs is essential in order to distinguish prodrug-derived creatine (d3-creatine) from high concentrations of endogenous (non-labeled) creatine. Incubations (37° C.) are performed in 10 mM Tris, pH 7.4, 0.25M sucrose, 1 mM EDTA and 1 mM DTT for BH; 125 mM Tris, pH 9.0, 1 mM EDTA for rFAAH direct cleavage to optimize FAAH activity. Prodrugs are tested at final concentrations of 20 μM and 200 μM. Approximately 3-4 mg of homogenate is used for each reaction. Co-factor (NADPH) is included at a final concentration of 1 mM. FAAH activity is confirmed by conversion of 7-amino-4-methyl Coumarin-Arachidonamide to 7-amino-4-methyl Coumarin by fluorescent assay. Negative controls include incubations without brain homogenate/rFAAH (but with NADPH) or 65° C. heat inactivated brain homogenate/rFAAH to assess non-enzymatic prodrug cleavage under the conditions of the assay and FAAH inhibitor PF044578845 at the concentration of 1 μM. Prodrug incubations are prepared by addition of 8 μL of prodrug stock solution (500 or 5000 μM in DMSO or DMSO/methanol) to assay buffered, followed by addition of brain homogenate/rFAAH. At selected time points (e.g., 0, 30, 60 and 180 min) 45 μL aliquots are removed and the reactions are terminated by addition of 180 μL of ice-cold acetonitrile (80% ACN/20% water) stop solution. The samples are centrifuged at 15890×g for 10 minutes at 4° C., followed by transfer of the supernatants for storage at −20° C. pending LC-MS/MS analysis. Sample supernatants are analyzed by LC-MS/MS for determination of d3-prodrug, d3-creatine and d3-creatinine levels.

Deuterated creatine prodrugs were tested in 3 different in vitro assays to assess d3-creatine ($d_3$-Cr) release and cyclization to form d3-creatinine ($d_3$-Crn). These assays were 1) direct cleavage with recombinant human FAAH enzyme (rFAAH), 2) cleavage in mouse brain homogenates (MBH), and 3) human brain homogenates (HBH).

Creatine prodrug cleavage efficiency was determined by percentage of net $d_3$-Cr release in μM (positive reaction subtracted from negative control of no brain homogenate/rFAAH or inactivated brain homogenate/rFAAH) over nominal input concentration of 200 μM prodrug at 3 h. Propensity for creatinine cyclization was determined by percentage of $d_3$-Crn generated in μM in positive reaction over nominal input concentration of 200 μM prodrug at 3 h. See Tables 3A-3B.

Based on the in vitro results, creatine prodrugs of the present disclosure can be categorized into 2 groups. First group contains creatine prodrugs with fatty acid amide chains between C11 to C18 (at $R^1$ position in formula (I)) and with unmodified free COOH (at $R^3$ position in formula (I)) generally released significant amount of $d_3$-Cr (>23%) and minimal $d_3$-Crn cyclization. The second group contains creatine prodrugs with fatty acid amide chains of C20 or less than C9 or pyridyl and with COOH linked to aliphatic ester generally released small amount of $d_3$-Cr (Compound 8, 10-HCl, and 12-HCl, Table 3A) and predominantly cyclized into creatinine. These data are consistent with metabolic and chemical stability data in Tables 2A-2C.

In Vitro study of the linear creatine prodrugs (where $R^1$ and $R^6$ together do not form a ring), such as those shown in Tables 3A-3B, is instructional in assessing the development of efficacious macrocyclic creatine prodrugs (where $R^1$ and $R^6$ together forms a ring). Without being bound to any theory, the linear creatine prodrugs which shows high $d_3$-Cr release and minimize $d_3$-Crn cyclization can indicate that a corresponding macrocyclic creatine prodrug would be a good candidate for high in vivo creatine release (see Table 3B). A macrocyclic creatine prodrug that corresponds to a linear creatine prodrug is a macrocycle prodrug when cleaved at the ester would provide the linear creatine prodrug or closely related analogs (e.g., hydroxylated analogs) of the linear creatine prodrugs.

The linear creatine prodrugs are generally more stable than the corresponding macrocylic creatine prodrugs under in vitro rFAAH study conditions. Accordingly, the inventors can use the creatine release data obtained from the linear creatine prodrugs to guide development of the macrocyclic creatine prodrugs.

TABLE 3A

In vitro $d_3$-creatine ($d_3$-Cr) release and cyclization to form $d_3$-creatinine ($d_3$-Crn)

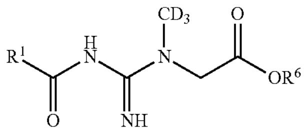

| Compd No. | $R^{1**}$ | $R^6$ | Salt | Double Bond in $R^1$ | Prodrug Cleavage (200 μM, 3 h) rFAAH net $d_3$-Cr release | rFAAH $d_3$-Crn release | Mouse BH net $d_3$-Cr release | Mouse BH $d_3$-Crn release | Human BH net $d_3$-Cr release | Human BH $d_3$-Crn release |
|---|---|---|---|---|---|---|---|---|---|---|
| 20 | pyridyl | H | Na | 0 | 0.0% | 0.4% | 0.0% | 1% | NT | NT |
| 21 | pyridyl | H | free | 0 | NT | NT | NT | NT | NT | NT |
| 22 | C20 | H | Na | cis-5,8,11,14 | 10.0% | 3.0% | NT | NT | 0.0% | 1.6% |
| 23 | C18 | H | TCA/2 Li | cis-9 | 80.3% | 3.2% | 29.0% | 2.5% | 43.5% | 2.0% |
| 24 | C18 | H | Li | cis-9,12 | 58.9% | 1.1% | NT | NT | 42.0% | 0.8% |
| 25 | C18 | H | Na | cis-6 | 46.8% | 0.3% | NT | NT | 33.0% | 0.3% |
| 26 | C18 | H | Na | cis-7 | 26.0% | 0.2% | NT | NT | 13.8% | 0.1% |
| 27 | C18 | H | Na | cis-12 | 5.3% | 0.1% | NT | NT | 1.9% | 0.0% |
| 1 | C18 | H | Na | cis-9 | 30.8% | 0.3% | NT | NT | 40.3% | 0.6% |
| 28 | C16 | H | Na | cis-9 | 37.3% | 0.3% | NT | NT | 45.3% | 0.5% |
| 7 | C14 | H | Li | 0 | 146.0% | 1.7% | NT | NT | 50.8% | 0.8% |
| 29 | C13 | H | Na | 0 | | | NT | NT | 141.6% | 2.0% |
| 30 | C12 | H | free | 0 | 45.1% | 7.5% | 18.0% | 8.7% | 36.0% | 7.3% |
| 31 | C12 | H | Na | 0 | NT | NT | NT | NT | 59.1% | 2.4% |
| 32 | C11 | H | Li | 0 | 28.7% | 0.9% | NT | NT | NT | NT |
| 4 | C11 | H | Na | 0 | 23.3% | 1.0% | 79.2% | 1% | 56.6% | 0.6% |
| 33 | C11 | H | K | 0 | NT | NT | NT | NT | 235.8% | 1.8% |
| 34 | C11 ($R^2$ = Boc) | H | free | 0 | NT | NT | NT | NT | NT | NT |
| 35 | C 9 | H | Li | 0 | 4.1% | 0.6% | NT | NT | 73.5% | 0.9% |
| 36 | C 9 | H | Na | 0 | NT | NT | NT | NT | NT | NT |
| 37 | C 8 | H | Li | 0 | 1.0% | 0.9% | NT | NT | NT | NT |
| 38 | C 8 | H | Na | 0 | NT | NT | NT | NT | NT | NT |
| 13 | C 7 | H | Na | 0 | NT | NT | NT | NT | 16.0% | 0.9% |
| 2 | C18 | ester, C7 | HCl | cis-9 | no | yes | NT | NT | 0.9% | 26.4% |
| 11 | C13 | ester, C7 | HCl | 0 | no | yes | NT | NT | 30.4% | 195.7% |
| 5 | C11 | ester, C7 | HCl | 0 | NT | NT | NT | NT | 41.2% | 258.0% |
| 14 | C 7 | ester, C7 | HCl | 0 | NT | NT | NT | NT | 6.4% | 76.9% |
| 39 | C11 | ester, C5 (neo-Pen) | HCl | 0 | NT | NT | NT | NT | 6.4% | 166.5% |
| 40 | C20 | ester, C4 (t-butyl) | HCl | cis-5,8,11,14 | NT | NT | NT | NT | NT | NT |
| 41 | C18 | ester, C4 (t-butyl) | HCl | cis-9 | NT | NT | NT | NT | NT | NT |

TABLE 3A-continued

In vitro $d_3$-creatine ($d_3$-Cr) release and cyclization to form $d_3$-creatinine ($d_3$-Crn)

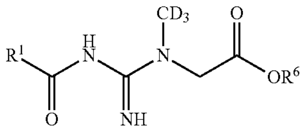

| Compd No. | $R^{1**}$ | $R^6$ | Salt | Double Bond in $R^1$ | Prodrug Cleavage (200 μM, 3 h) rFAAH net $d_3$-Cr release | rFAAH $d_3$-Crn release | Mouse BH net $d_3$-Cr release | Mouse BH $d_3$-Crn release | Human BH net $d_3$-Cr release | Human BH $d_3$-Crn release |
|---|---|---|---|---|---|---|---|---|---|---|
| 42 | C14 | ester, C4 (t-butyl) | HCl | 0 | NT | NT | NT | NT | NT | NT |
| 43 | C12 | ester, C4 (t-butyl) | HCl | 0 | NT | NT | NT | NT | NT | NT |
| 44 | C11 | ester, C4 (t-butyl) | HCl | 0 | NT | NT | NT | NT | NT | NT |
| 45 | C18 | ester, C3 (i-Pr) | HCl | cis-9 | no | yes | NT | NT | 0.4% | 22.0% |
| 10-HCl | C13 | ester, C3 (i-Pr) | HCl | 0 | 1.2% | 217.0% | NT | NT | 4.3% | 251.5% |
| 12-HCl | C11 | ester, C3 (i-Pr) | HCl | 0 | NT | NT | NT | NT | 2.9% | 265.7% |
| 46 | C13 | ester, C2 | HCl | 0 | 0.0% | 192.0% | NT | NT | 3.1% | 209.5% |
| 8 | C11 | ester, C2 | HCl | 0 | 0.0% | 77.9% | 2.4% | >50% | 4.9% | 100.0% |
| 47 | C11 ($R^2$ = Boc) | ester, C2 | free | 0 | NT | NT | NT | NT | 0.0% | 3.4% |
| 48 | C11 | dioxolanone | HCl | 0 | NT | NT | NT | NT | NT | NT |
| 49 | C11 | creatinine | free | 0 | NT | NT | NT | NT | 0.7% | 111.9% |
| 50 | C 7 | acetyl, C7 | HCl | 0 | NT | NT | NT | NT | NT | NT |
| 9 | C11 | acetyl | HCl | 0 | NT | NT | NT | NT | NT | NT |

*NT = not tested.

**$R^1$ is alkyl or alkenyl, the carbon count includes the carbonyl carbon to which $R^1$ is attached to

TABLE 3B

In vitro $d_3$-creatine ($d_3$-Cr) release

| Structure | Compound No. | Net % $d_3$-Cr Release (3 hours) | Corresponding Macrocycle Compound |
|---|---|---|---|
| 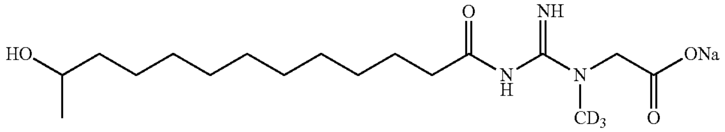 | 64 | 10 | M |
| See Table 2b | 56 | 5.8 | QQ |
| 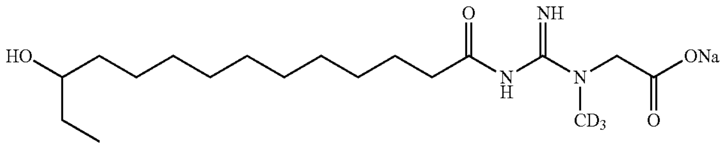 | 65 | 4.5 | N |
| 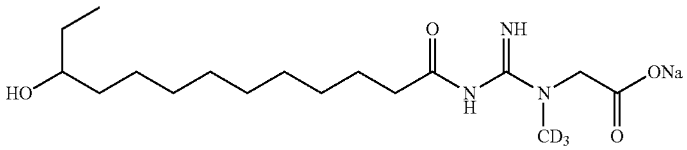 | 66 | 2 | L |
| 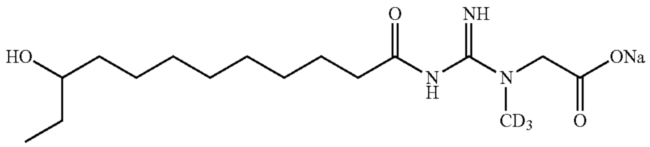 | 67 | 1.5 | O |

TABLE 3B-continued

In vitro $d_3$-creatine ($d_3$-Cr) release

| Structure | Compound No. | Net % $d_3$-Cr Release (3 hours) | Corresponding Macrocycle Compound |
|---|---|---|---|
| 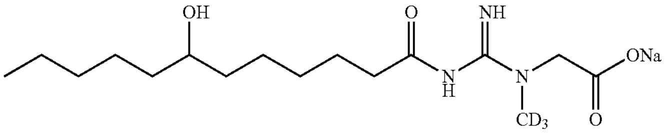 | 68 | 0.5 | FF |
| 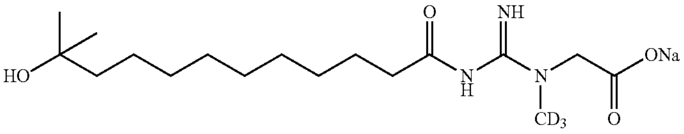 | 69 | 0.5 | U |
| See Table 2b | 54 | 0.25 | 15 |
| See Table 2b | 58 | 0 | SS |
| See Table 2b | 57 | 0 | K |
| 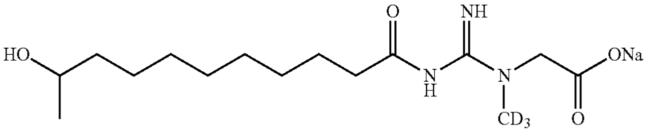 | 70 | 0 | P |
| 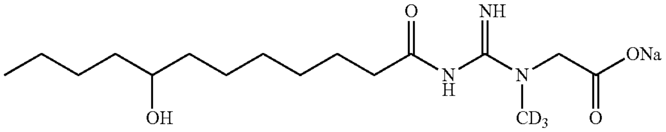 | 71 | 0 | CC |
| 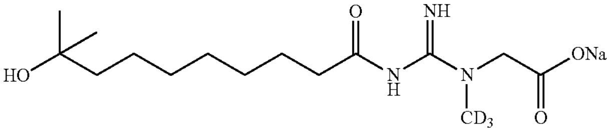 | 72 | 0 | X |
| 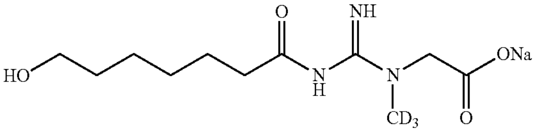 | 73 | 0 | EE |
| 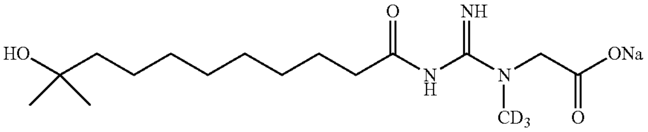 | 74 | 0 | HH |
| See Example 1 | Compound 1 (fee acid) Positive control | 59 | N/A |
| See Table S2 | Compound 4 (free acid) Positive control | 14 | N/A |

Example 46: In Vitro Creatine Prodrug Uptake and d3-Creatine Release in Cell Cultures Procedures for ARPE-19 Cells (Table 4A)

ARPE-19 cells (#CRL-2302) were obtained from ATCC and seeded at 350,000 cells/well in 6 well plates the day before uptake experiment. Creatine prodrugs will be dissolved in appropriate solvent (i.e. DMSO) at stock concentration of 5-10 mM and incubated in 2.4 mL serum-free medium (DMEM:F12 (ATCC: 30-2006) per well at final concentrations of 10 μM and 50 μM for 1 h and 6 h at 370 C/5% CO2. Morphological changes indicative of cell viability will be assessed by microscopes. In addition, prodrugs will be incubated in serum-free medium alone (cell-free) under the same conditions to determine chemical stability.

At the end of the incubation, supernatant will be collected from each well to assess prodrug recovery. Cells are then washed 3× with PBS. Plates, prodrugs in supernatant, prodrugs in serum-free medium are stored at −80° C. until harvest (within 5 days). On the day of extraction, 130 uL of lysis buffer (10 mM Tris pH 7.4) with EDTA-free protease inhibitors is added to each well and cells are removed using a cell scraper. Lysates are further homogenized using a handheld pestle and then centrifuged at 16,000 g, 40° C., for 10 minutes to collect cytosol fraction. Pellets will be stored at −80° C. until further analysis. A 4× volume of stop solution (80% ACN/20% water) will be added to the cytosol fraction, supernatant and medium. Samples will be centrifuged at 15,890 g (13,000 rpm) at 4° C. for 10 mins. Supernatant will be collected and stored at −80° C. within 5 days prior to LC-MS/MS analysis. Dosing solutions for each prodrug (10 μM) will be assayed to verify concentration. Cells alone with vehicle will serve as controls to assess background signal for LC-MS/MS. Two independent runs of experiment will be conducted.

Nine fatty acid amide creatine prodrugs were tested in human ARPE-19 cells to assess prodrug uptake and d3-Cr release inside the cells. 50 μM of prodrug was incubated in culture medium with the cells and the cells were harvested at 6 h. Quantitation of prodrugs, d-Cr (d3-creatine) and $d_3$-Crn ($d_3$-creatinine) in the cytosol fraction was corrected for total protein concentration. See Table 4A.

Fatty acid amide creatine prodrugs with free COOH showed uptake and d3-Cr release in ARPE-19 cells whereas pyridyl-Cr prodrug and fatty acid amide prodrugs with aliphatic ester linked to COOH group released small amount of d3-Cr, consistent with in vitro cleavage data for this sub-class of prodrugs.

TABLE 4A

In vitro Creatine Prodrug Uptake and d3-Creatine Release

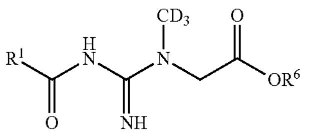

| Compd No. | $R^1$ | $R^6$ | Salt | Double Bond in $R^1$ | Cellular Uptake (50 μM, 6 h) ARPE-19 prodrug (nmol/mg protein) | $d_3$-Cr (nmol/mg protein) | $d_3$-Crn (nmol/mg protein) |
|---|---|---|---|---|---|---|---|
| 20 | pyridyl | H | Na | 0 | BQL | BQL | BQL |
| 23 | C18 | H | TCA/2 Li | cis-9 | 30.6 | 26.5 | <0.3 |
| 1 | C18 | H | Na | cis-9 | 24.8 | 23.5 | 0.77 |
| 7 | C14 | H | Li | 0 | 13.1 | 18.6 | <0.2 |
| 30 | C12 | H | free | 0 | 29.2 | 21.4 | <0.2 |
| 2 | C18 | ester, C7 | HCl | cis-9 | BQL | 0.5 | 1.0 |
| 11 | C13 | ester, C7 | HCl | 0 | BQL | 0.6 | 2.4 |
| 5 | C11 | ester, C7 | HCl | 0 | BQL | 1.6 | 8.4 |
| 45 | C18 | ester, C3 (i-Pr) | HCl | cis-9 | BQL | 0.74 | 1.03 |

Procedures for In Vitro Creatine Prodrug Uptake and d3-Creatine Release in Cell Cultures: Phenocell CrT Deficient Neurons (Table 4B)

Human neurons were obtained by differentiation of iPSC-derived neural stem cells for 14 days. The iPSCs were obtained from Phenocell Corporation. Neurons were cultured and differentiated to Day 10 and then frozen in liquid nitrogen. Neurons were thawed and replated at $1\times10^6$ per well of viable cells on poly-ornithine/laminin coated plates in 2 ml medium per well. Differentiation in complete Neurol medium with 2 ng/ml FGF2 was carried out for 4 additional days with a complete medium change (90% of medium) on Day 12. Activin A (20 ng/ml final conc.) was spiked into the cultures on Day 11 and Day 13. On day of the experiment (Day 14), prodrugs (50 μM) were be incubated with neurons for 2 hours at 37° C./5% $CO_2$ in complete Neurol medium with 2 ng/ml FGF2. In parallel, compounds were incubated in medium alone to assess chemical stability of parent prodrug and metabolites. At the end of the 2 hour incubation, supernatants were collected and frozen at −80° C. Neurons in 6 well plates were washed gently 3× with HBSS and frozen at −80° C. Cell lysates were obtained by addition of 130 μl/well 10 mM Tris pH 7.4 with complete Mini protease inhibitors and scraping of wells. Plates were kept on ice during processing. Lysates were homogenized by hand briefly with a green pestle in 1.5 ml centrifuge tubes and then vortexed at high speed for 5 seconds. Lysates were centrifuged at 13,000 g, 10 minutes, 4 C and supernatants (cytosol fraction) were transferred in a new tube. A crash solution constituted of 80% acetonitrile and 20% water with bucetin, d5-Cr (internal standard) was added at 4:1 volume to volume to 50 ul of all samples for a total volume of 250 μL. Then plate was spun at 4000 rpm, 10 minutes, 40° C. Samples were transferred to a new plate and frozen at −80° C. prior to analysis by LC-MS/MS (Table 4B).

TABLE 4B

In vitro Creatine Prodrug Uptake and d3-Creatine Release

| Study No. | Compound | Prodrug concentration in the cell cytosol (nmoles/mg protein) | $d_3$-Creatine concentration in the cell cytosol (nmoles/mg protein) | $d_3$-Creatinine concentration in the cell cytosol (nmoles/mg protein) |
|---|---|---|---|---|
| 1 | Compound 52 (10 μM) | 3.47 | 0.65 | 0.84 |
| 1 | Compound 52 (50 μM) | 12 | 2.9 | 29.6 |
| 1 | Compound 54 (10 μM) | BLOQ | BLOQ | BLOQ |
| 1 | Compound 54 (50 μM) | BLOQ | BLOQ | BLOQ |
| 2 | Compound 52 (50 μM) | 9.5 | 0.8 | 10.6 |
| 2 | Compound 15 (100 μM) | BLOQ | BLOQ | 9.5 |
| 2 | Compound 15 (500 μM) | BLOQ | 0.15 | 14.5 |
| 2 | Compound Q (100 μM) | BLOQ | 0.3 | 17.5 |
| 2 | Compound Q (500 μM) | BLOQ | 0.6 | 20 |
| 2 | Compound M (100 μM) | BLOQ | 0.2 | 8 |
| 2 | Compound M (500 μM) | BLOQ | 0.45 | 16 |
| 3 | Compound 52 (50 μM) | 0.51 | 2.84 | 8.82 |
| 3 | Compound U (50 μM) | 0.48 | BLOQ | 4.91 |
| 3 | Compound S (50 μM) | BLOQ | BLOQ | 5.93 |
| 3 | Compound V (50 μM) | BLOQ | BLOQ | 7.58 |
| 3 | Compound W (50 μM) | 0.44 | BLOQ | 7.21 |
| 3 | Compound EE (50 μM) | BLOQ | BLOQ | 0.49 |
| 3 | Compound HH (50 μM) | 0.088 | BLOQ | 0.98 |
| 3 | Compound X (50 μM) | BLOQ | BLOQ | 0.42 |

BLOQ = below limit of quantification

Examples 45 and 46 demonstrate evidence that a series of fatty acid amide creatine prodrugs can be cleaved and release $d_3$-Cr in vitro and transported into human cells.

Example 47: In Vivo Animal Studies

A creatine prodrug is administered as an intravenous bolus injection to groups of three to six adult male CD1 mice at an appropriate creatine prodrug dose equivalent per kg body weight. Animals are conscious at the time of the experiment. Blood samples (0.3 mL) are obtained via a jugular vein cannula at intervals over 8 hours following IV dosing. Blood is processed into plasma, then the plasma is immediately frozen at −80° C. until analyzed by LC-MS/MS. Samples may also be taken form the CSF or other appropriate biological fluid. Brains were collected and flash frozen immediately in liquid nitrogen. Brains were homogenized in 100 mM KPI buffer with a cocktail of anti-proteases on the same day as the sample preparation required for LC-MS/MS analysis.

Several prodrugs with either free COOH group and ester linkage and macrocycles were selected for IV dosing in animal study to assess PK and d3-Cr release in brain in vivo. Prodrugs were IV dosed in CrT KO mice at 10, 15, or 25 mg/kg in animal studies. Mouse brain homogenates (MBH) were prepared from brains collected from mice after dosing. Levels of prodrug, d3-Cr and d3-Crn were quantified in brain and expressed in brain concentration (for macrocycle prodrugs) or AUC (for linear prodrugs) over time. Very few prodrugs were detected in MBH. Surprisingly, FAA-Cr esters (Compounds 5, 8FB, 10-12, and 14CP4) dosing led to significant amount of both d3-Cr and d3-Crn in brains of CrT KO mice whereas FAA-Cr free acid prodrugs of the corresponding esters (Compounds 4 and 13) did not seem to cross BBB and thus no d3-Cr/d3-Crn detected in brains.

Co-administration of Compound 8 (HCl salt) and creatine transporter blocker, beta-guanidinopropionic acid (GPA) did not change the levels of d3-Cr in WT rat brains compared to dosing of Compound 8 alone, indicating that the uptake of Compound 8 was not dependent on the creatine transporter.

Collectively, the in vivo data demonstrated that FAA-Cr esters were capable of providing favorable d3-Cr/d3-Crn release ratio despite the fact that these compounds predominantly cyclized into d3-Crn in vitro. Interestingly, FAA-Cr esters with a total combined FAA chain and aliphatic ester chain length of C13 or C14 (Compounds 8, 12, and 14) generated higher levels of d3-Cr release compared to other FAA-Cr esters.

TABLE 5

In Vivo d3-Creatine Uptake in the Brain

| Compound | IV Dosing | Mouse | $AUC_{last}$ (h*ng/mL) prodrug | $d_3$-Cr | $d_3$-Crn |
|---|---|---|---|---|---|
| 10 | 10 mg/kg | CrT KO | BQL | 2620 | 2820 |
| 11 | 10 mg/kg | CrT KO | BQL | 2220 | 1840 |
| 4 | 10 mg/kg | CrT KO | BQL | BQL | BQL |
| 8 | 15 mg/kg | CrT KO | BQL | 7994 | NA |
| 12 | 10 mg/kg | CrT KO | BQL | 8210 | 9020 |
| 5 | 10 mg/kg | CrT KO | BQL | 2470 | 3850 |
| 13 | 10 mg/kg | CrT KO | BQL | BQL | BQL |
| 14 | 10 mg/kg | CrT KO | BQL | 6240 | 5310 |

*BQL (below quantitation limit): prodrug = 41.2 ng/mL; $d_3$-Cr = 13.7 ng/mL; $d_3$-Crn = 1.5 ng/mL Example 41 further provided data to support that fatty acid amide creatine prodrugs of the present disclosure, such as Compound 5, 8-FB, 10, 11, 12, 14 can release $d_3$-Cr in the brains of CrT KO mice. This is surprising given that the in vitro studies in Example 9 showed that ester compounds (Compounds 8, 10-HCl, and 12-HCl, Table 3) led to predominantly creatinine cyclization but apparently a favorable d3-Cr/d3-Crn ratio in vivo. Without being bound by any theory, the creatine prodrugs of the present disclosure designed to have enhanced cell membrane permeability independent of creatine transporter can more efficiently and effectively deliver and release creatine in the brain cells where it is needed the most.

Example 48: Creatine Delivery to CrT KO Mouse Brain Upon Treatment with Compound 15

Compound 15

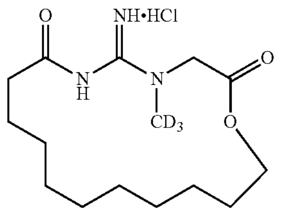

The plasma and brain concentrations of creatine and creatinine was measured in CrT KO mice upon treatment with compound 15 (FIG. 1). As shown by the FIG. 1, brain creatine (Cr) concentration was higher than the concentration in plasma. The ratio of $[\text{creatine}]_{Brain}$:$[\text{creatine}]_{Plasma}$ can be an useful parameter for a successful clinical development of creatine prodrugs for treating CTD and related conditions. Importantly, creatine levels were higher than creatinine (CRN) levels in mice treated with compound 15.

Example 49. d3-Creatine Delivery to Mouse Brain

Figure 3:
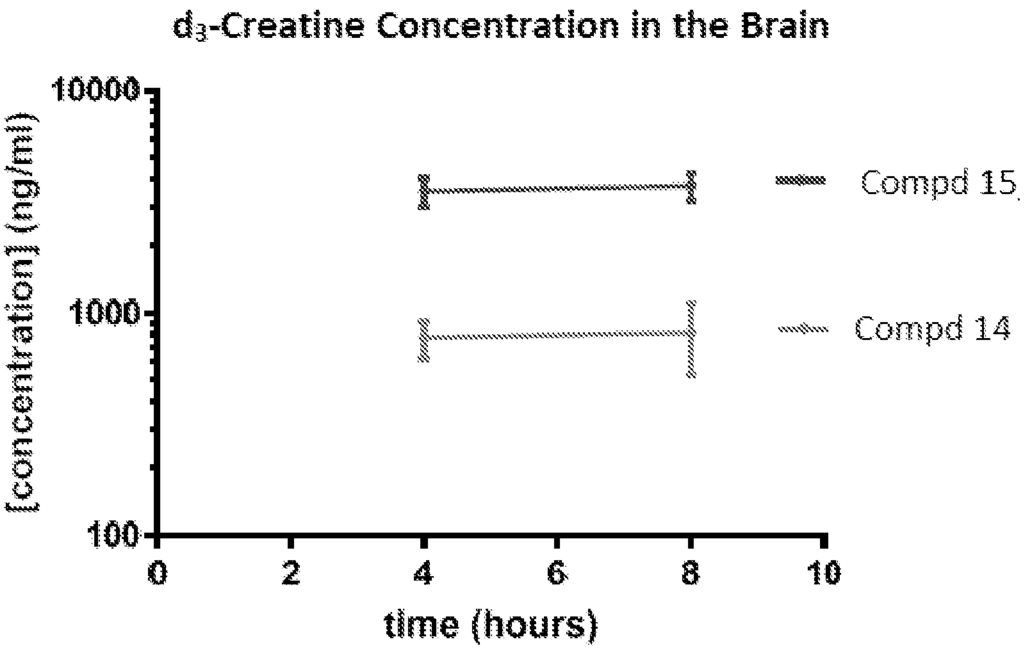
FIG. 3 shows the concentration of d3-creatine in the brain over time following 10 mg/kg IV dosing of compound 14 or compound 15 to mice.
Figure 4:
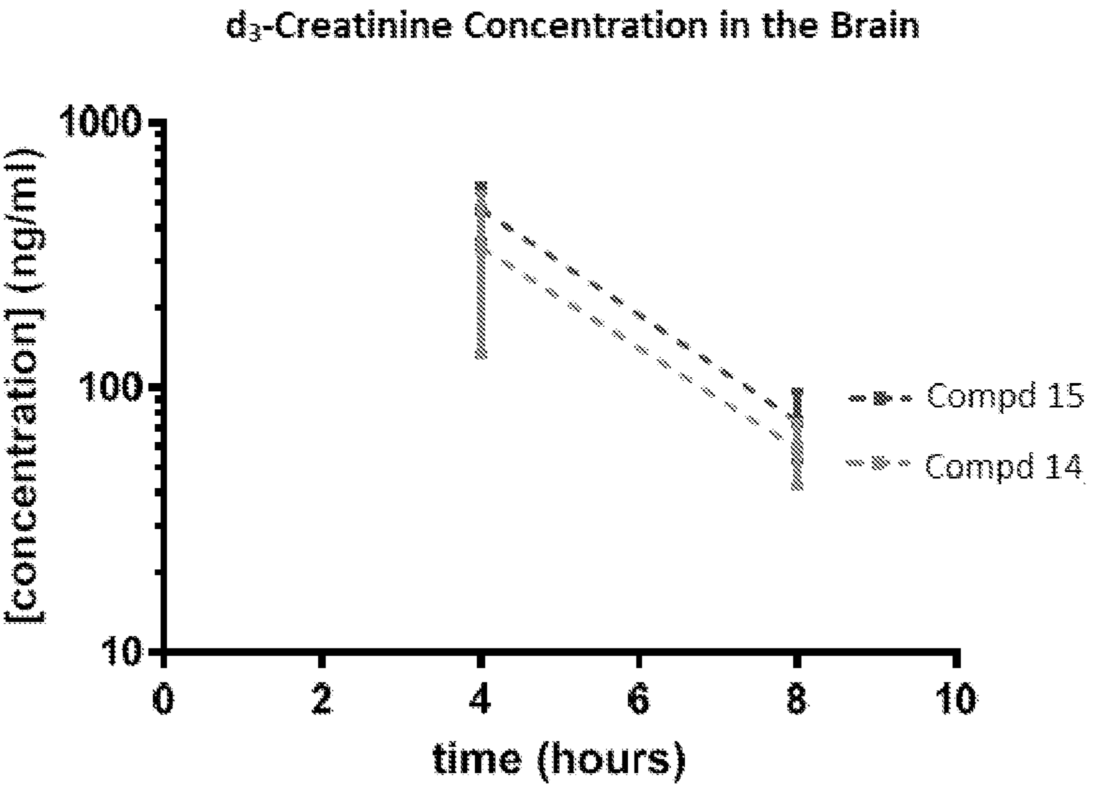
FIG. 4 shows the concentration of d3-creatinine in the brain over time following 10 mg/kg IV dosing of compound 14 or compound 15 to mice.

The brain concentrations of d3-creatine and d3-creatinine was measured in CrT KO mice following 10 mg/kg single dose IV bolus dose of compound 14 and 15 (FIGS. 3 and 4). As shown by FIG. 3, brain d3-creatine concentration was higher following administration of compound 15 compared to compound 14. Specifically, at 8 h after dosing, d3-creatine concentration in the brain was 4-folds greater for compound 15 (3729±523 ng/mL) compared to compound 14 (812±289 ng/mL)(FIG. 3). However, the brain concentration of d3-creatinine was not significantly different between compound 14 and compound 15 (FIG. 4), which is indicative of higher ratio of d3-creatine to d3-creatinine with compound 15 compared to compound 14. Without bound to any theory, the macrocyclic compound 15 prodrug reduces d3-creatine cyclization to d3-creatinine when compared to linear compound 14 prodrug.

The concentration of d3-creatine in CrT KO mice brain were also measured for other compounds disclosed in the present application as shown in Table 6. The concentrations of d3-creatine, d3-creatinine and creatine prodrugs are measured by LC-MS/MS. The brain sample is homogenized with 4×(weight to volume) of KPI 100 mM buffer containing anti-proteases and anti-phosphatases (if needed). 50 of brain homogenate is then de-proteinized using 4× volume/volume of a solution containing 80% acetonitrile and 20% water with bucetin, d5-Cr (internal standard). The plate is then spun at 4000 rpm, 10 minutes, 4° C. and samples are transferred to a new plate for bioanalysis. Each analyte in each sample was quantitated against a curve in matching biomatrix using an authentic standard.

TABLE 6 d3-Creatine Concentration in CrT KO Mice Brain

| Compound | Ring size | Branching | Concentration of d3-Cr (ng/ml) |
|---|---|---|---|
| Compound EE | C7 | No branch | 513 ± 16 |
| Compound FF | C7 | Pentyl Branch | BLOQ |
| Compound BB | C8 | No branch | 493 ± 49 |
| Compound CC | C8 | Butyl Branch | NT |
| Compound DD | C9 | No branch | 1386 ± 295 |
| Compound S | C9 | Methyl Branch | 2012 ± 96 |
| Compound V | C9 | Ethyl Branch | 595 ± 366 |
| Compound W | C9 | Propyl Branch | 254 ± 94 |
| Compound X | C9 | Dimethyl Branch | NT |
| Compound SS | C10 | No branch | 1233 ± 73 |
| Compound P | C10 | Methyl Branch | 736 ± 415 |
| Compound O | C10 | Ethyl Branch | 655 ± 87 |
| Compound HH | C10 | Dimethyl Branch | NT |
| Compound 15 | C11 | No branch | 3729 ± 522 |
| Compound K | C11 | Methyl Branch | 3047 ± 320 |
| Compound L | C11 | Ethyl Branch | 1100 ± 361 |
| Compound U | C11 | Dimethyl Branch | 868 ± 91 |
| Compound Q | C12 | No branch | 4393 ± 1117 |
| Compound M | C12 | Methyl Branch | 3365 |
| Compound N | C12 | Ethyl Branch | 1567 ± 57 |
| Compound GG | C12 | Dimethyl Branch | NT |
| Compound T | C13 | No branch | 3111 ± 72 |
| Compound VV | C18 | No branch | 780 ± 197 |
| Compound WW | C11 | Spiral cyclopentyl | 414 ± 30 |
| Compound UU | C11 | Spiral tetrahydrofuran | 224 ± 47 |
| Compound AA | C11 | Spiral cyclopropyl | 1030 ± 134 |

NT = not tested

The macrocycle prodrugs tested showed low or no amount of d3-creatinine in the brain at 8 h. Without being bound to any theory, these results show that the design of these prodrugs support the cleavage in favor of d3-creatine over cyclization (or results in reduction of cyclization).

Figure 2:
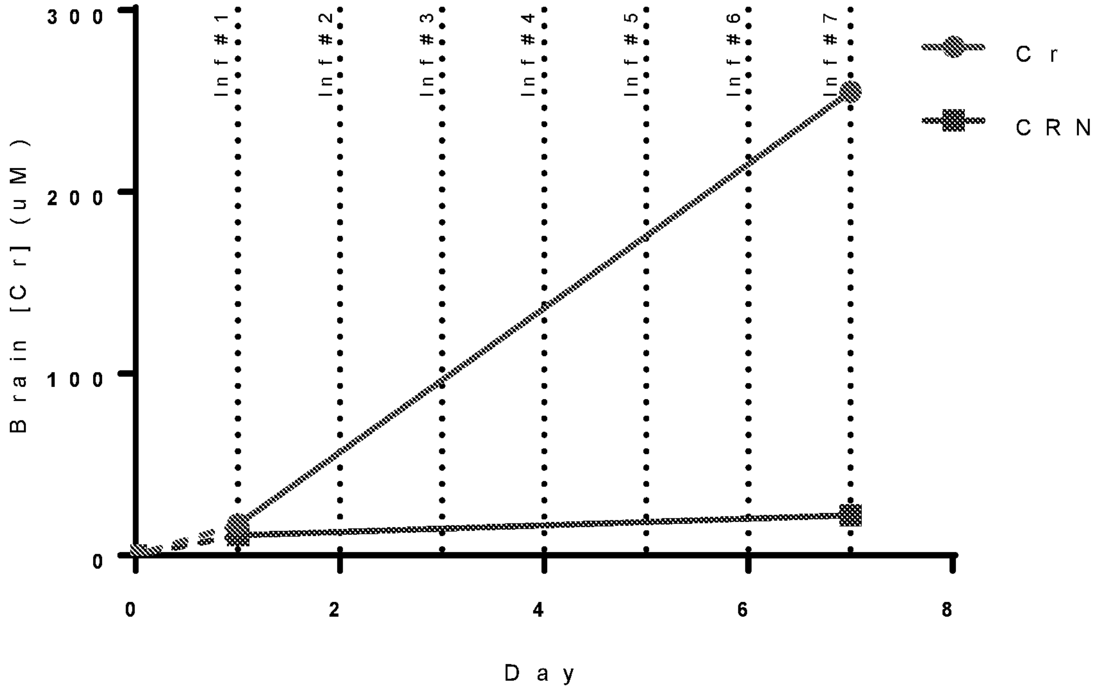
FIG. 2 is a graph of the data from a multi-dose study comparing d3-creatine and d3-creatinine levels in the brain of non-human primates, measured after a total of 7 infusions of compound 14 administered q.d. (once daily). Cr=d3-creatine; CRN=d3-creatinine.

Example 50: Repeat Dosing Study of Creatine Levels in the Brains of Non-Human Primates Non-human primate (NHP) brains were dosed with Compound 8 (120 mg/kg) and Compound 14 (18 mg/kg) over a seven day period (i.v. infusion provide q.d.). FIG. 2 shows that repeat administration dramatically increases d3-creatine (d3-Cr) levels in a linear manner and homogeneously in all brain regions tested. Moreover, the flat d3-creatine response suggests no significant loss of Compound 14 due to cyclization to d3-creatinine during the treatment period and no significant efflux out of the brain. Thus, without bound by any theory, Compound 14 can be useful as an option for overcoming CTD based on the enhancement of d3-creatine levels with minimal formation of undesired d3-creatinine (d3-CRN). Table 7 shows d3-Cr levels after 1 daily dose of infusion and after 7 daily doses of infusions of Compounds 8 and 14.

TABLE 7 d3-Creatine Concentration in NHP Brain

| Compound | Dose | After 1 daily dose of infusion (μM) | After 7 daily doses of infusions (μM) |
|---|---|---|---|
| Compound 14 | 18 mg/kg | 17 | 249 |
| Compound 8 | 120 mg/kg | 19 | 137 |

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the non-limiting exemplary methods and materials are described herein All publications and patent applications mentioned in the specification are indicative of the level of those skilled in the art to which this disclosure pertains. All publications and patent applications are herein incorporated by reference for all purposes to the same extent as if each individual publication or patent application was specifically and individually indicated to be incorporated by reference. Nothing herein is to be construed as an admission that the present disclosure is not entitled to antedate such publication by virtue of prior disclosure.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

What is claimed is:

1. A method for increasing creatine concentration in the brain of a subject in need thereof, comprising administering to the subject a therapeutically effective amount of a compound of Formula (I):

(I)

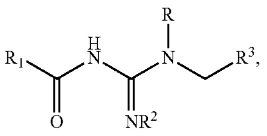

or a pharmaceutically acceptable salt or solvate thereof; wherein:

R is —$CH_3$, —$CH_2D$, —$CHD_2$, or —$CD_3$;

$R^2$ is hydrogen, —C(O)$NHR^5$, —C(O)$OR^5$, —C(O) (linear or branched alkyl), or —C(O) (linear or branched alkenyl);

$R^3$ is —C(O)$OR^6$;

$R^4$ is halogen, —OH, —$OR^5$, oxo, —$NH_2$, —$NHR^5$, —$N(R^5)_2$, —$NO_2$, —$CF_3$, —$C_1$-$C_6$ alkyl, or —$C_1$-$C_6$ haloalkyl;

$R^5$ is linear or branched alkyl;

$R^6$ and $R^1$ together is an alkylene group or an alkenylene group which with the atoms which they are each bonded to, forms a 12 to 25 membered ring, wherein 1, 2, 3, or 4 —$CH_2$-units making up the alkylene group or the alkenylene group is optionally replaced with a heteroatom selected from —O—, —S—, or —N—, provided that no adjacent —$CH_2$— is replaced;

wherein the alkylene group or the alkenylene group is optionally substituted with one or more $R^4$; and wherein, two $R^4$ on the same or adjacent carbon can form a 3 to 6 membered fused or spiro cycloalkyl ring or a 3 to 6 membered fused or spiro heterocyclic ring.

2. The method of claim 1, wherein:

a) R is —$CH_3$ or —$CD_3$; or b) $R^2$ is hydrogen.

3. The method of claim 1, wherein $R^6$ and $R^1$ together is an alkylene group or an alkenylene group which with the atoms which they are each bonded to, forms a 13 to 24 membered ring, wherein 1, 2, 3, or 4 —$CH_2$— units making up the alkylene group or the alkenylene group is optionally replaced with a heteroatom selected from —O—, —S—, or —N—, provided that no adjacent —$CH_2$— is replaced; wherein the alkylene group or the alkenylene group is optionally substituted with one or more $R^4$.

4. The method of claim 1, wherein the compound is a pharmaceutically acceptable salt selected from sodium salt, potassium salt, lithium salt, $Na_2PO_4H$ salt, hydrochloric acid salt, formic acid salt, trifluoroacetic acid salt, acetic acid salt or trichloroacetic acid/2 lithium salt.

5. The method of claim 1, wherein the compound has the structure of Formula (I-A):

(I-A)

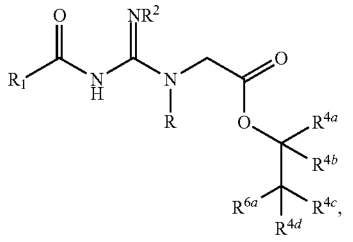

or a pharmaceutically acceptable salt or solvate thereof, wherein:

R is —$CH_3$, —$CH_2D$, —$CHD_2$, or —$CD_3$;

$R^2$ is hydrogen, —C(O) $NHR^5$, —C(O)$OR^5$, —C(O) (linear or branched alkyl), or —C(O) (linear or branched alkenyl);

$R^4$ is halogen, —OH, —$OR^5$, oxo, —$NH_2$, —$NHR^5$, —$N(R^5)_2$, —$NO_2$, —$CF_3$, —$C_1$-$C_6$ alkyl, or —$C_1$-$C_6$ haloalkyl;

$R^{4a}$, $R^{4b}$, $R^{4c}$, and $R^{4d}$, each independently, is H, halogen, —OH, —$OR^5$, oxo, —$NH_2$, —$NHR^5$, —$N(R^5)_2$, —$NO_2$, —$CF_3$, —$C_1$-$C_6$ alkyl, or —$C_1$-$C_6$ haloalkyl;

$R^5$ is linear or branched alkyl;

$R^{6a}$ and $R^1$ together is an alkylene group or an alkenylene group which with the atoms which they are each bonded to, forms a 12 to 25 membered ring, wherein 1, 2, 3, or 4 —$CH_2$-units making up the alkylene group or the alkenylene group is optionally replaced with a heteroatom selected from —O—, —S—, or —N—, provided that no adjacent —$CH_2$— is replaced;

wherein the alkylene group or the alkenylene group is optionally substituted with one or more $R^4$; and wherein, $R^{4a}$ and $R^{4b}$ or $R^{4c}$ and $R^{4d}$ together can form a 3 to 6 membered spiro cycloalkyl ring or a 3 to 6 membered spiro heterocyclic ring; or wherein $R^4$b and $R^4$c together can form a 3 to 6 membered fused cycloalkyl ring or a 3 to 6 membered fused heterocyclic ring.

6. The method of claim 5, wherein $R^{4a}$ is —$C_1$-$C_6$ alkyl and $R^{4b}$, $R^{4c}$, and $R^{4d}$ are each H.

7. The method of claim 1, wherein the compound has the structure of Formula (III-A)

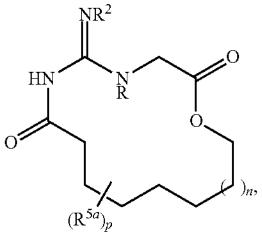

(III-A)

or a pharmaceutically acceptable salt or solvate thereof, wherein:

R is —$CH_3$, —$CH_2D$, —$CHD_2$, or —$CD_3$;

$R^2$ is hydrogen, —C(O) $NHR^5$, —C(O)$OR^5$, —C(O) (linear or branched alkyl), or —C(O) (linear or branched alkenyl);

$R^5$ is H or linear or branched alkyl;

$R^{5a}$ is halogen, —OH, —$OR^5$, oxo, —$NH_2$, —$NHR^5$, —$N(R^5)_2$, —$NO_2$, —$CF_3$, —$C_1$-$C_6$ alkyl, or —$C_1$-$C_6$ haloalkyl;

wherein, two $R^{5a}$ on the same or adjacent carbon can form a 3 to 6 membered fused or spiro cycloalkyl ring or a 3 to 6 membered fused or spiral heterocyclic ring;

n is 0, 1, 2, 3, 4, 5, 6, 7, 8, 9, 10, or 11; and p is 0, 1, 2, 3, 4, 5, 6, 7, or 8.

8. The method of claim 7, wherein R is —$CH_3$ or —$CD_3$.

9. The method of claim 7, wherein $R^2$ is H.

10. The method of claim 7, wherein n is 0, 1, 2, 3, 4, 5, 6, or 7.

11. The method of claim 7, wherein p is 0, 1, or 2.

12. The method of claim 7, wherein $R^{5a}$ is —$C_1$-$C_6$ alkyl.

13. The method of claim 1, wherein the compound is

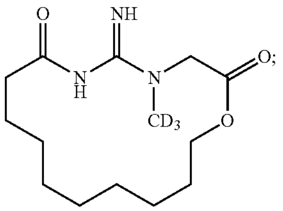

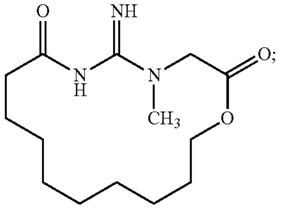

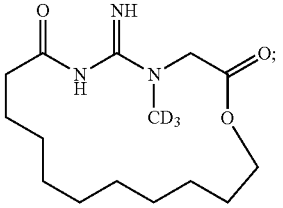

-continued

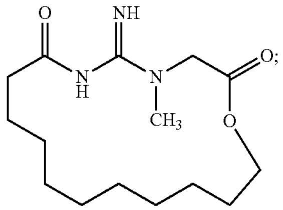

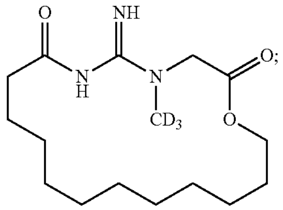

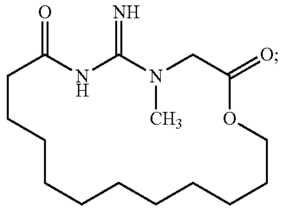

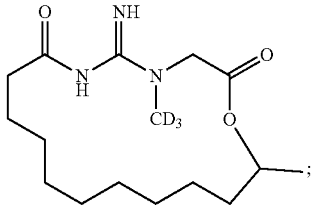

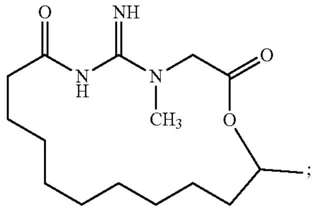

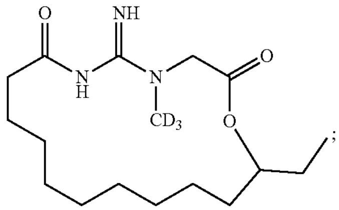

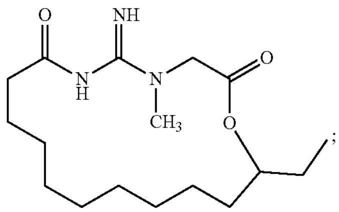

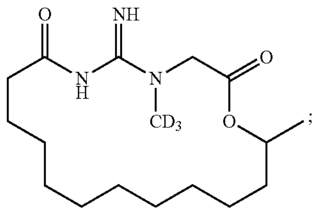

-continued
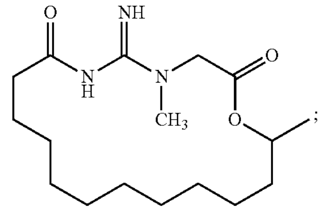
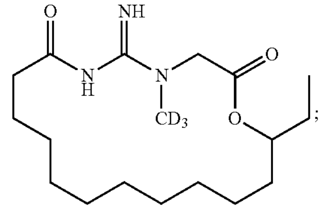
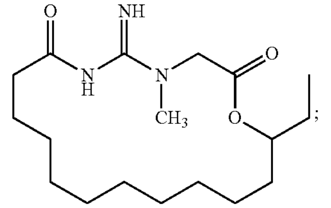
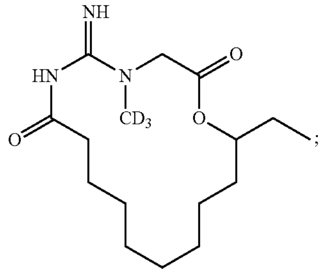
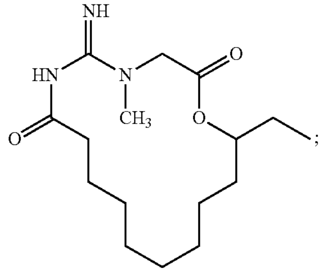
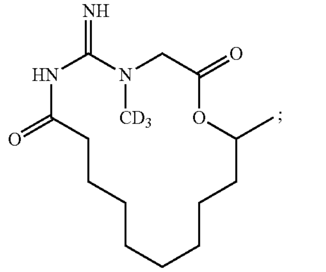
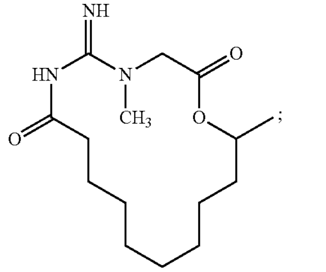
-continued
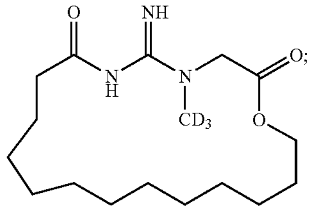
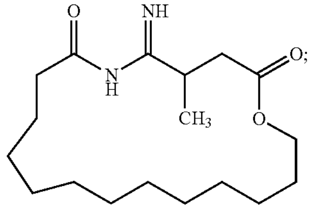
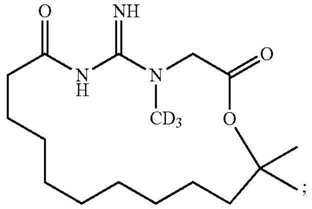
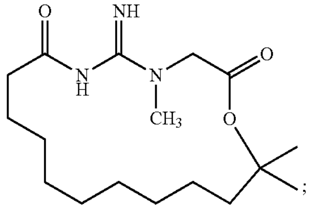
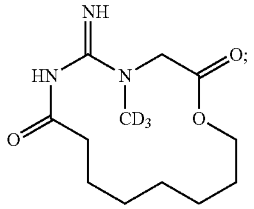
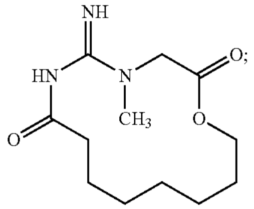
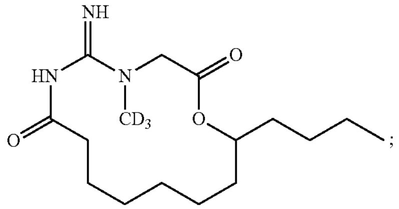
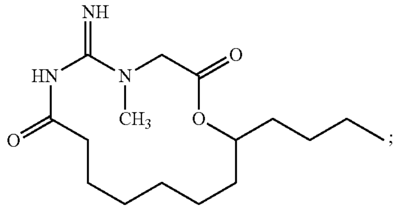
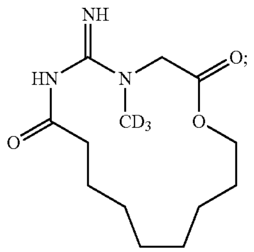
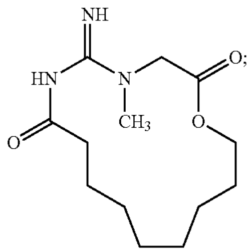

-continued
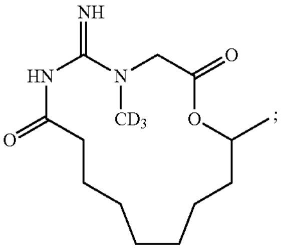
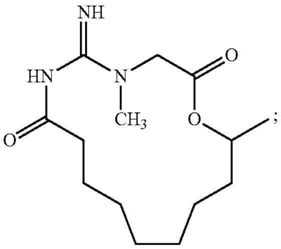
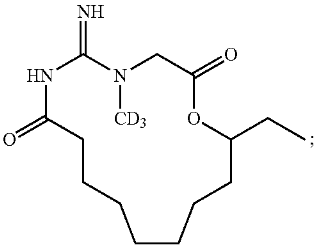
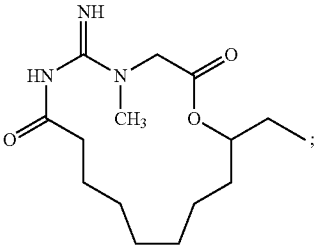
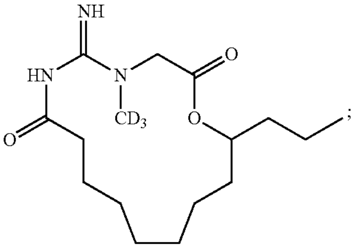
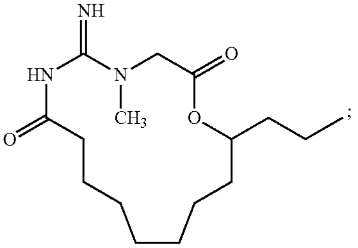
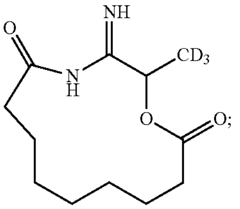
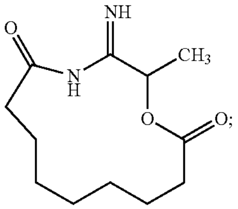
-continued
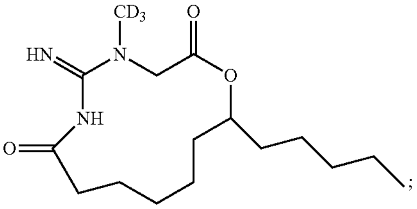
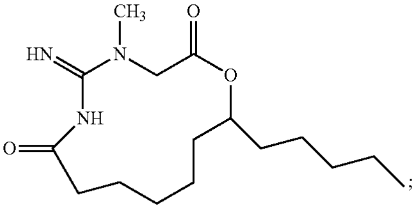
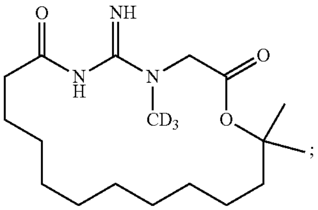
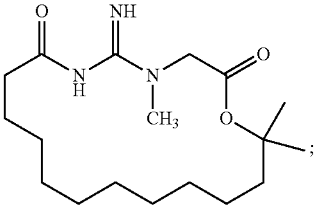
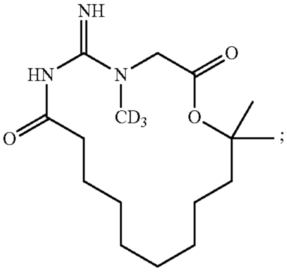
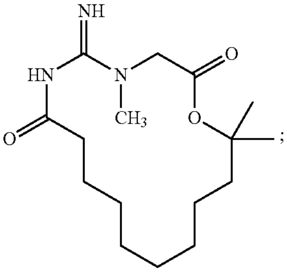
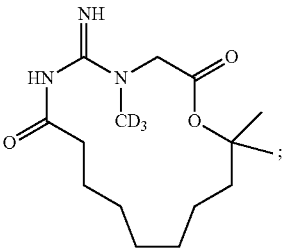

-continued
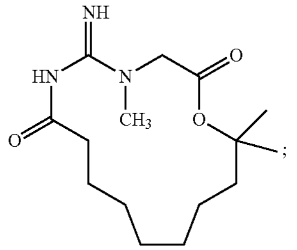
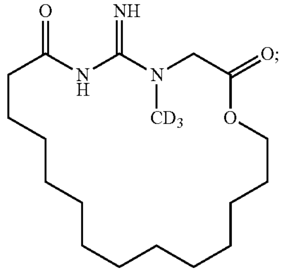
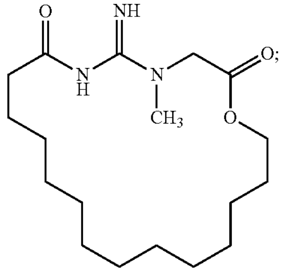
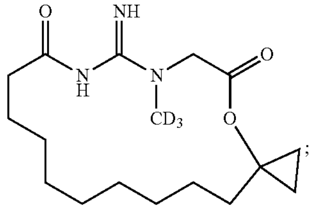
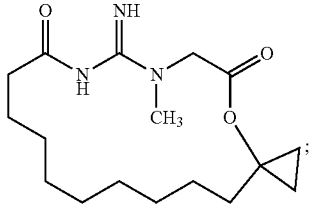
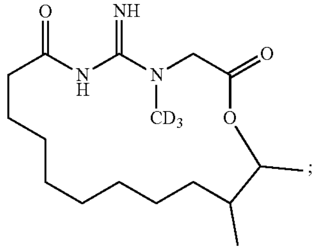
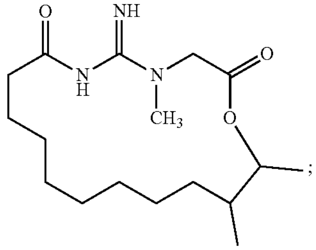
-continued
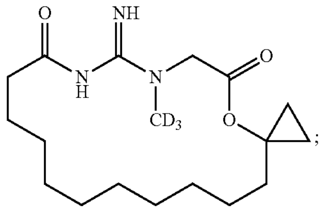
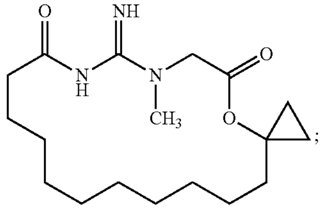
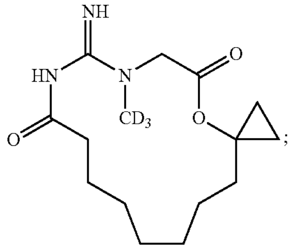
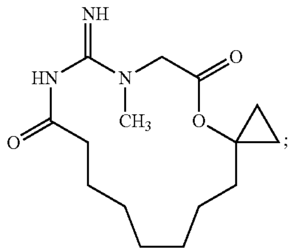
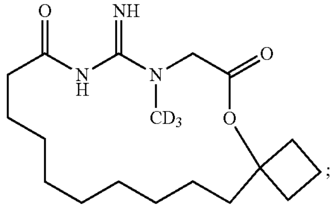
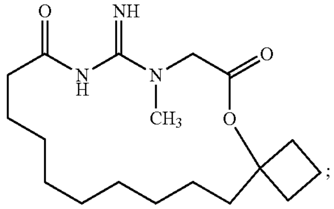
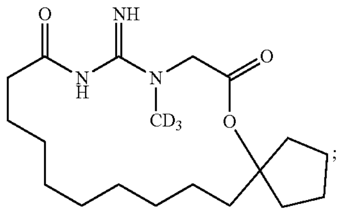

-continued
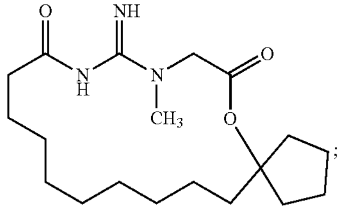
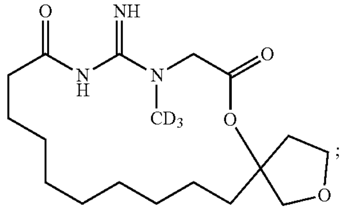
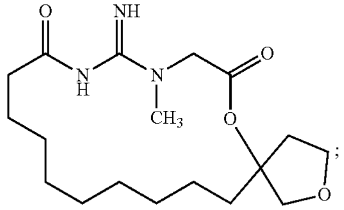
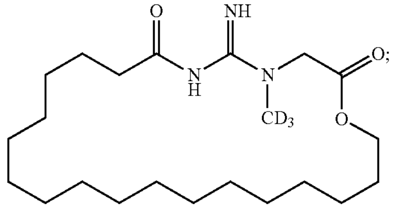
or
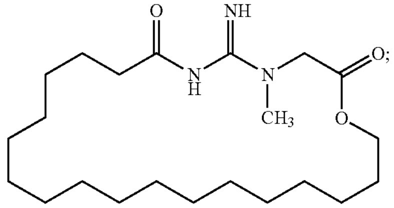
or a pharmaceutically acceptable salt thereof.
14. The method of claim 1, wherein the compound is
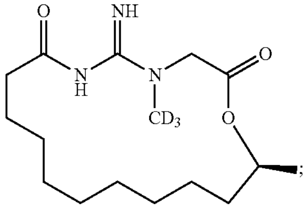
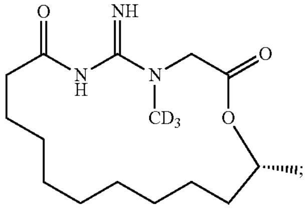
-continued
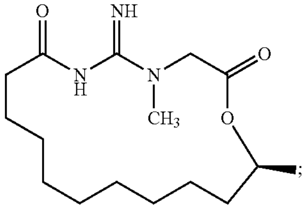
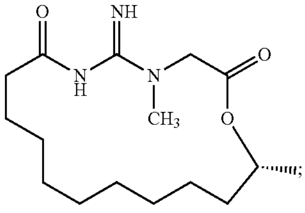
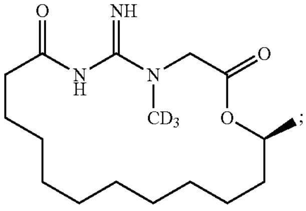
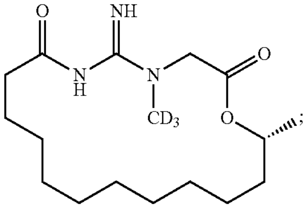
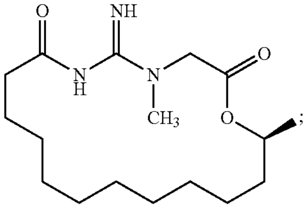
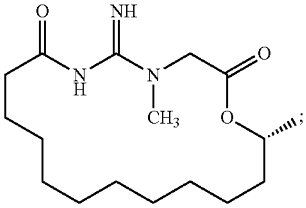
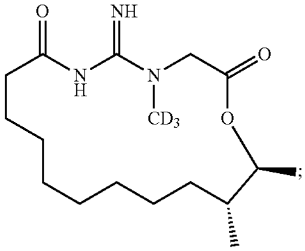

-continued
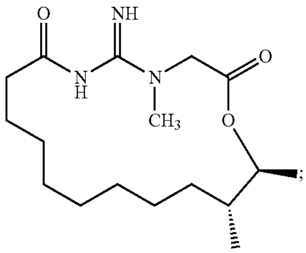
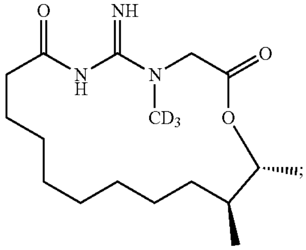
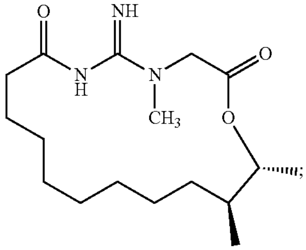
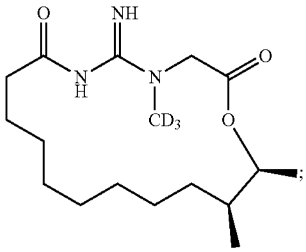
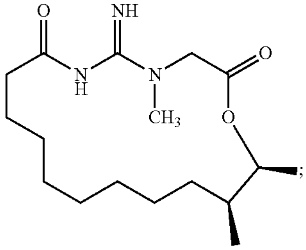
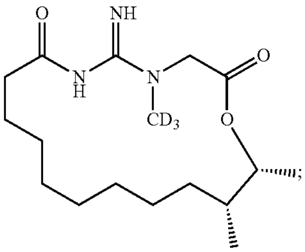 or
-continued
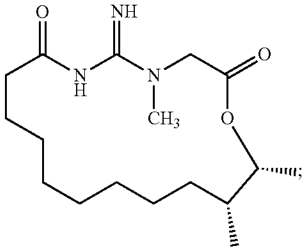
or a pharmaceutically acceptable salt thereof.
15. The method of claim 1, wherein the compound is
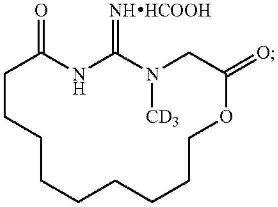
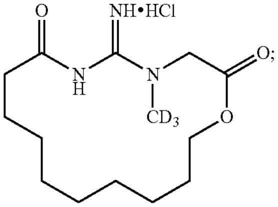
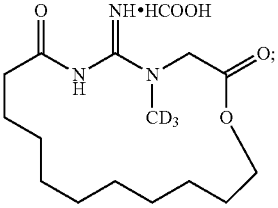
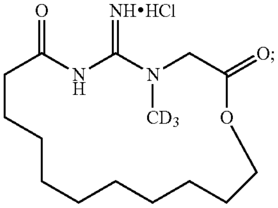
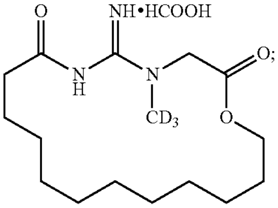
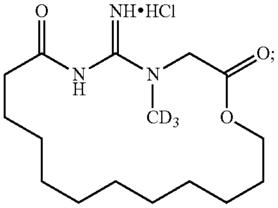
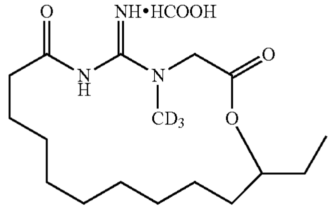
;
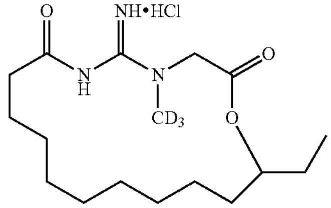
;
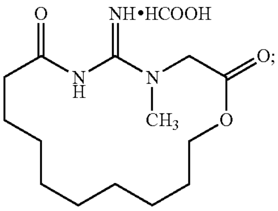
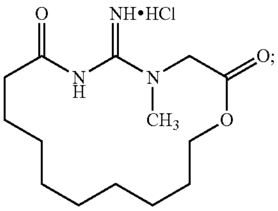

-continued
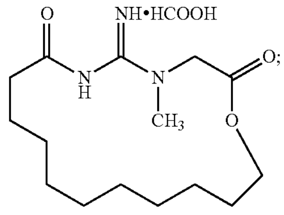
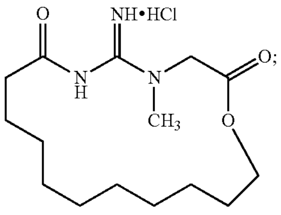
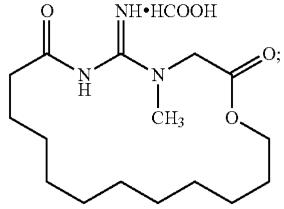
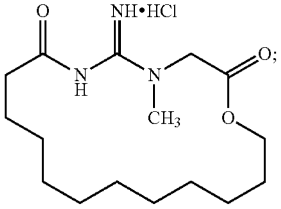
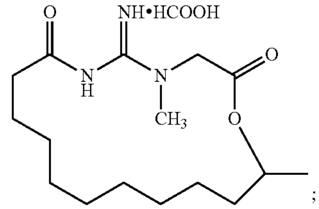
;
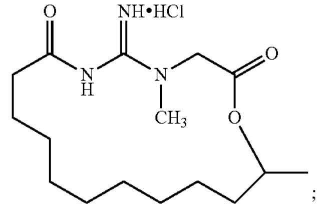
;
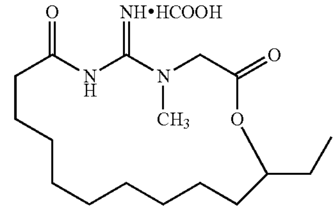
;
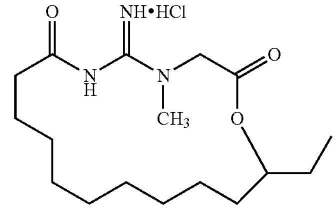
;
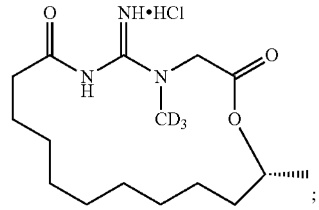
;
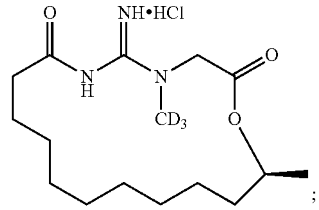
;
-continued
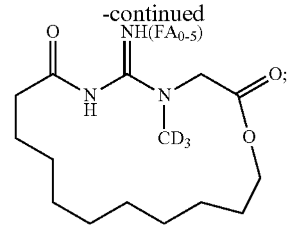
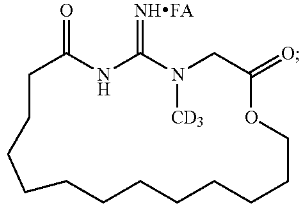
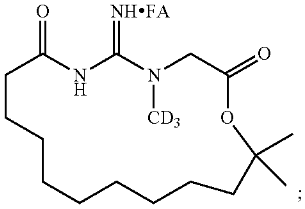
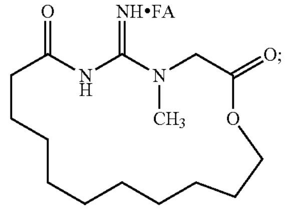
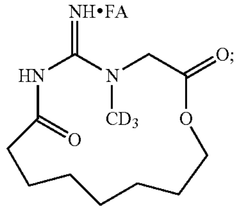
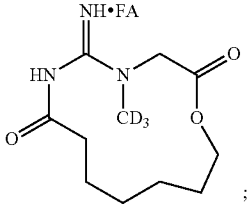
;
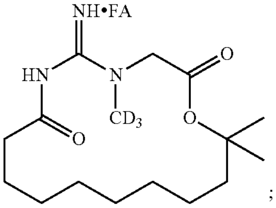
;
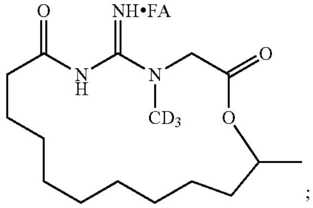
;
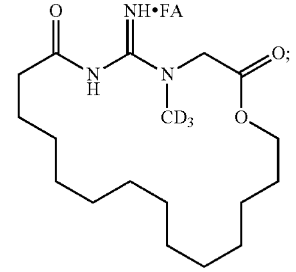
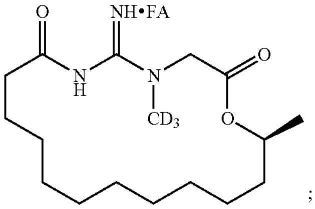
;

-continued
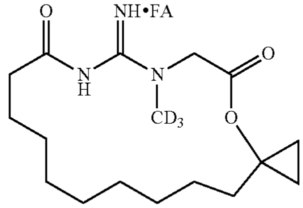
;
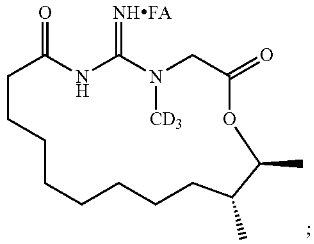
;
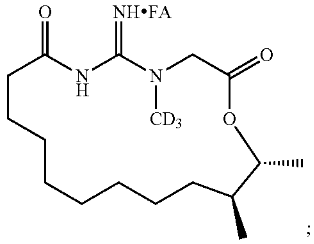
;
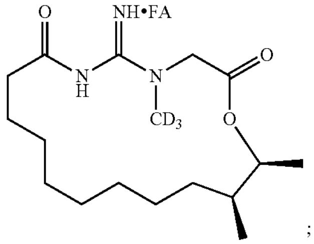
;
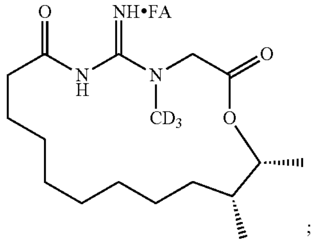
;
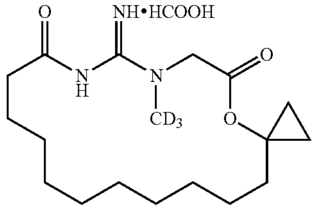
;
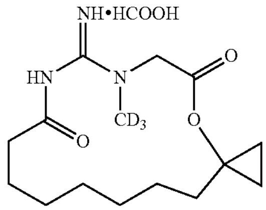
;
-continued
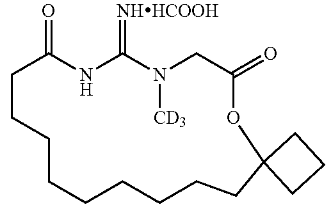
;
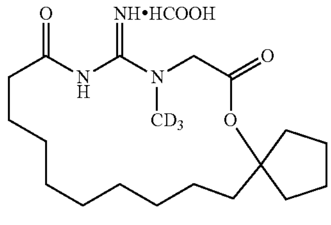
;
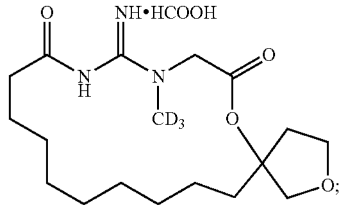
; or
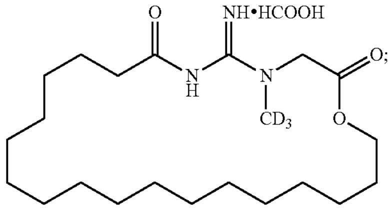
;
wherein FA is formic acid (HCOOH).
16. The method of claim 1, wherein the compound is
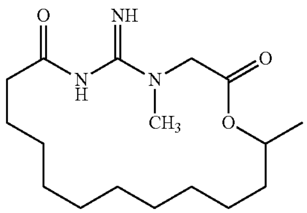
or
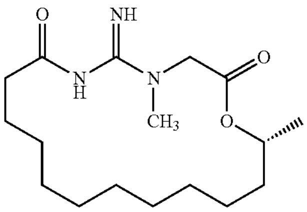
,
or a pharmaceutically acceptable salt thereof.

17. The method of claim 1, wherein the compound is a hydrochloric acid salt of
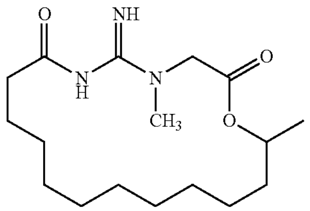
or
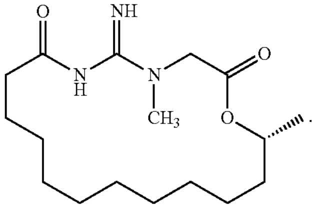
.
18. The method of claim 1, wherein the subject has a mutation in SLC6A8 gene.
* * * * *